United States Patent [19]
Ogawa et al.

[11] Patent Number: 5,976,146
[45] Date of Patent: Nov. 2, 1999

[54] SURGICAL OPERATION SYSTEM AND METHOD OF SECURING WORKING SPACE FOR SURGICAL OPERATION IN BODY

[75] Inventors: Akihisa Ogawa, Hachioji; Takahiro Kogasaka, Hino; Akio Nakada; Ryoichi Konou, both of Hachioji, all of Japan

[73] Assignee: Olympus Optical Co., Ltd., Tokyo, Japan

[21] Appl. No.: 09/095,848

[22] Filed: Jun. 11, 1998

[30] Foreign Application Priority Data

Jul. 11, 1997 [JP] Japan .................................. 9-186799
Dec. 5, 1997 [JP] Japan .................................. 9-335592

[51] Int. Cl.[6] ........................................................ A61F 5/00
[52] U.S. Cl. .......................... 606/86; 606/213; 604/174
[58] Field of Search .............................. 606/86, 87, 53, 606/91, 151–153, 213, 79, 164; 623/11, 12, 22; 604/174, 175, 176; 600/114

[56] References Cited

U.S. PATENT DOCUMENTS

| 4,545,374 | 10/1985 | Jacobson . |
| 4,799,785 | 1/1989 | Keates et al. . |
| 5,176,649 | 1/1993 | Wakabayashi . |
| 5,439,464 | 8/1995 | Shapiro . |
| 5,472,426 | 12/1995 | Bonati et al. . |

FOREIGN PATENT DOCUMENTS

| 0807415 A2 | 11/1997 | European Pat. Off. . |
| 2714285 | 6/1995 | France . |
| WO 97/34536 | 9/1997 | WIPO . |

*Primary Examiner*—Michael Buiz
*Assistant Examiner*—Lien Ngo
*Attorney, Agent, or Firm*—Frishauf, Holtz, Goodman, Langer & Chick, P.C.

[57] ABSTRACT

A surgical operation apparatus of this invention includes an operation sheath having a cavity securing portion that is inserted into vital tissue through the skin to secure a working cavity for a surgical operation in the body, and a sheet member that allows an operation tool to be inserted from outside the body into the cavity. The operation sheath is guided into the vital tissue by guide tools such as a dilator, a soft tube, and a mandrin.

49 Claims, 55 Drawing Sheets

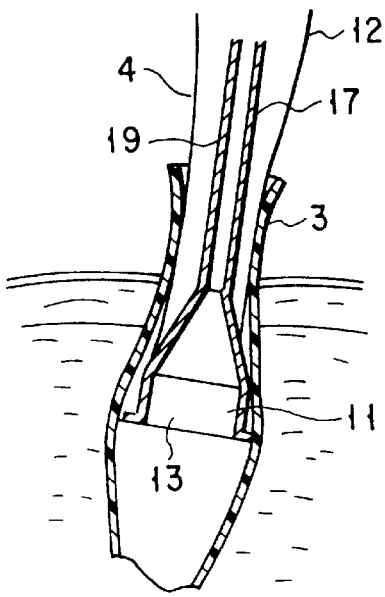
FIG. 6
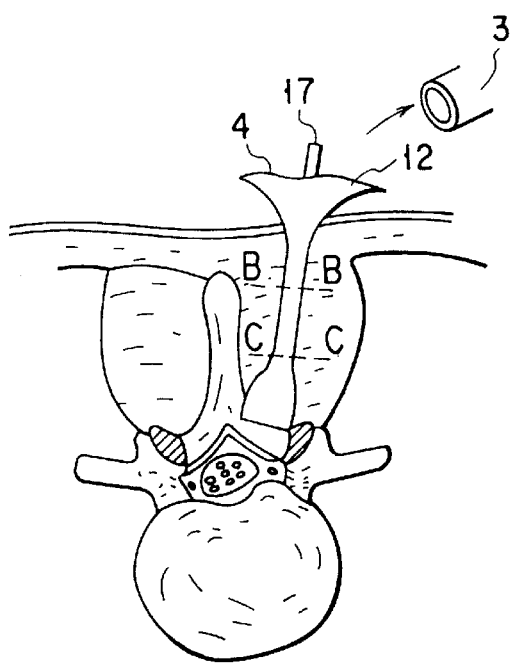
FIG. 7A
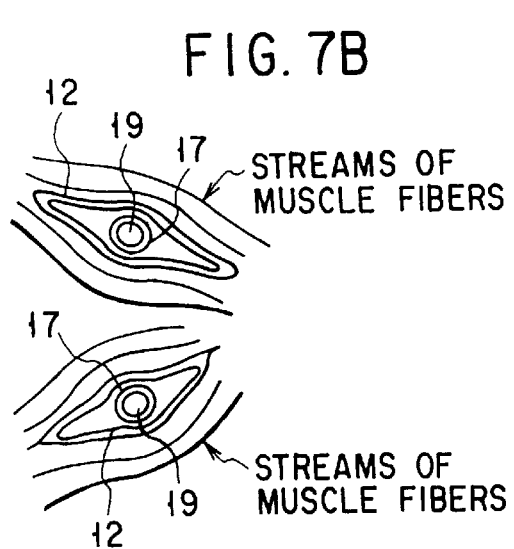
FIG. 7B
FIG. 7C

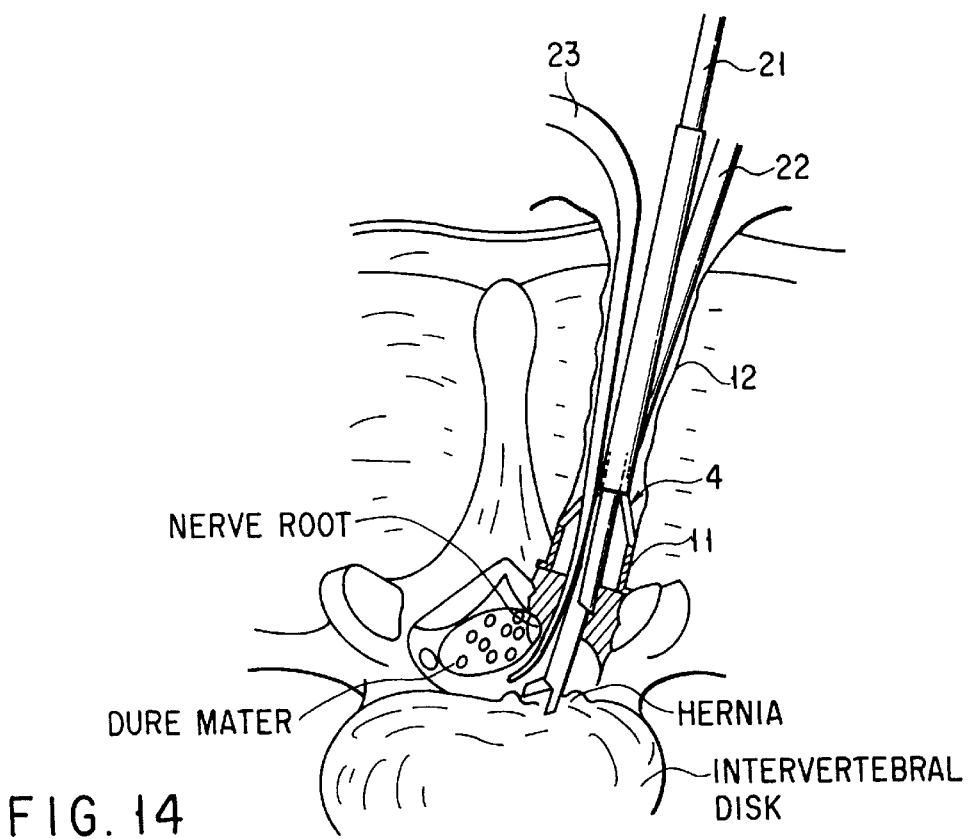
FIG. 14
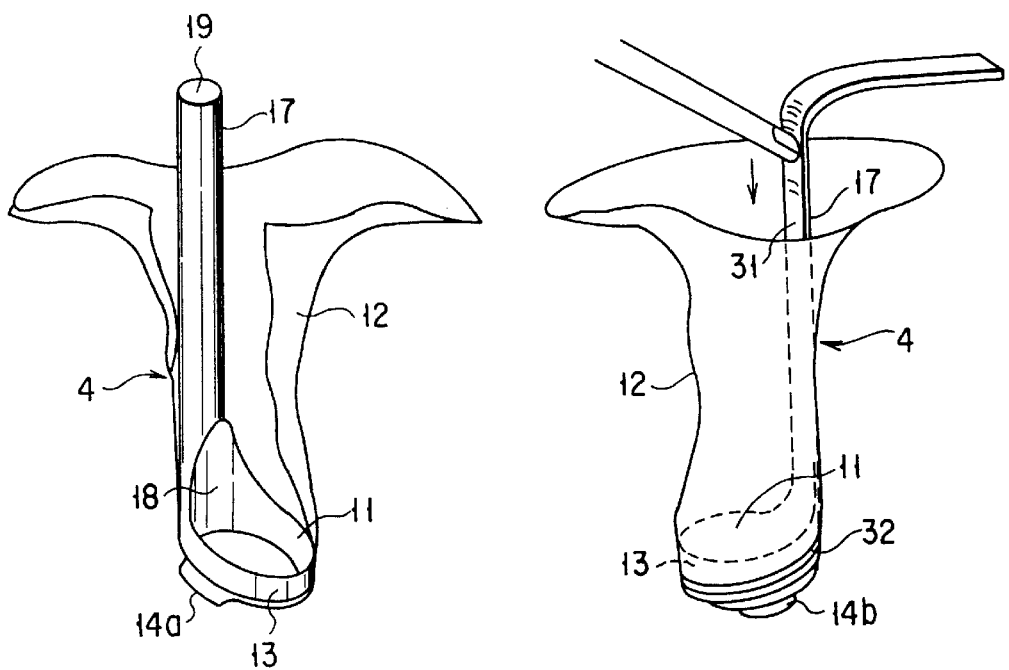
FIG. 15
FIG. 16

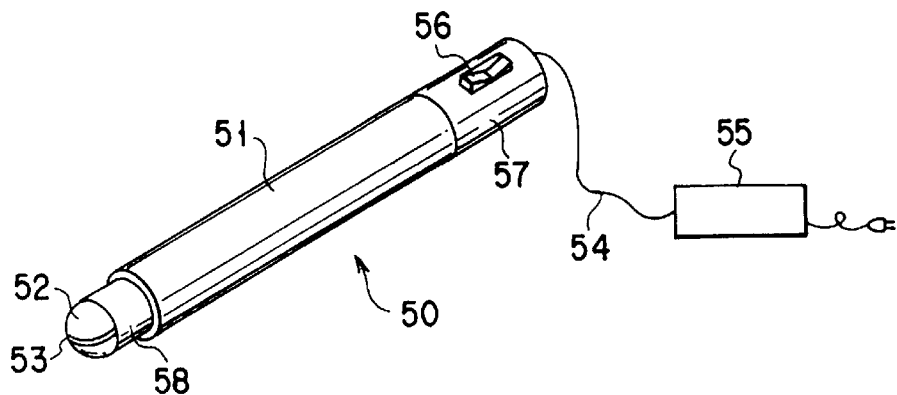
FIG. 27A
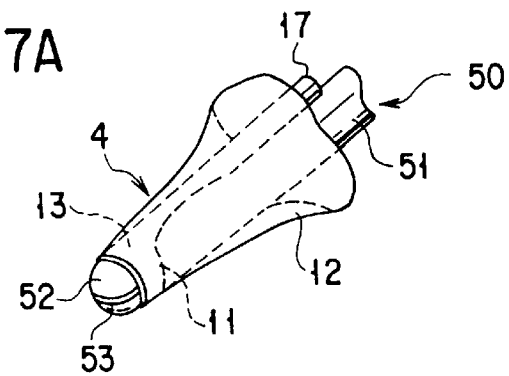
FIG. 27B
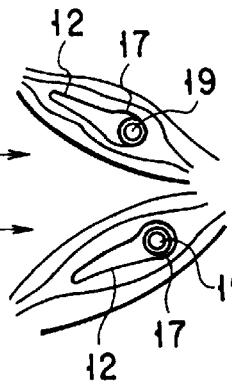
FIG. 28B
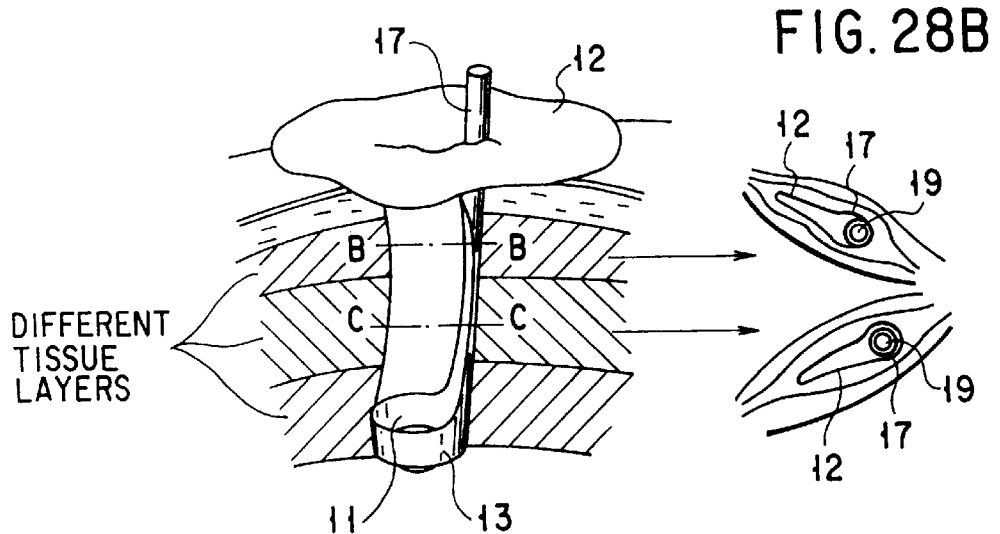
FIG. 28A
FIG. 28C

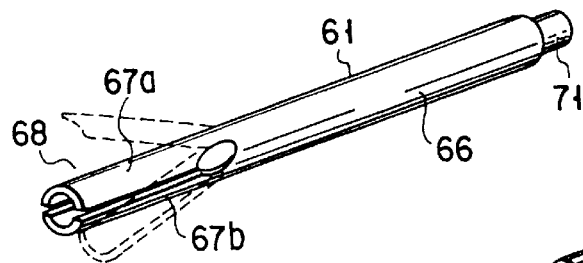
FIG. 29A
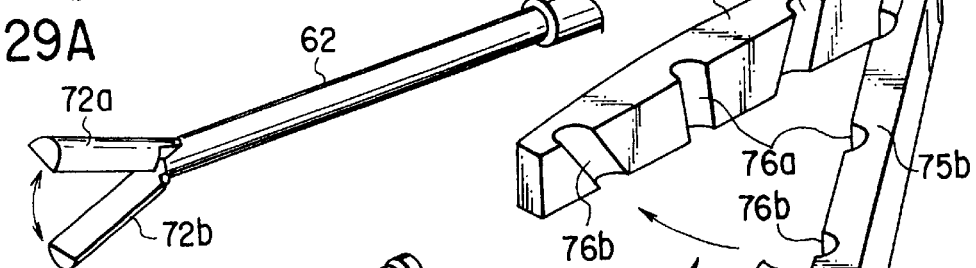
FIG. 29B
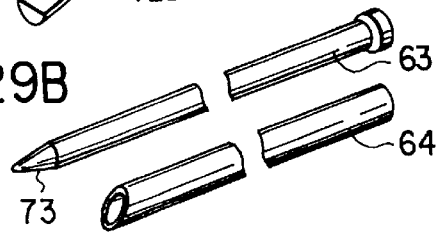
FIG. 29C
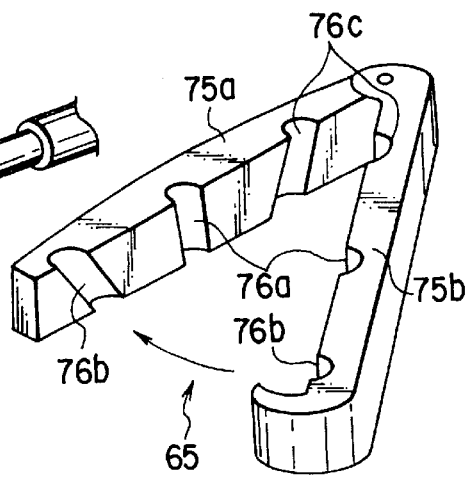
FIG. 29D
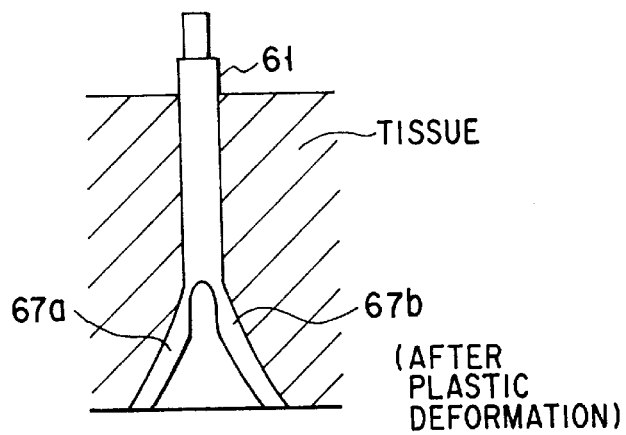
FIG. 30 (AFTER PLASTIC DEFORMATION)
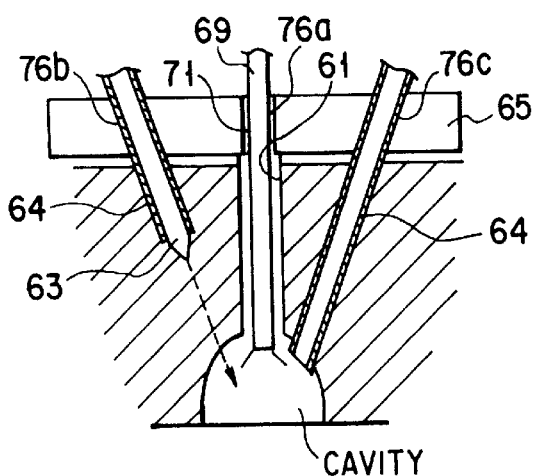
FIG. 31

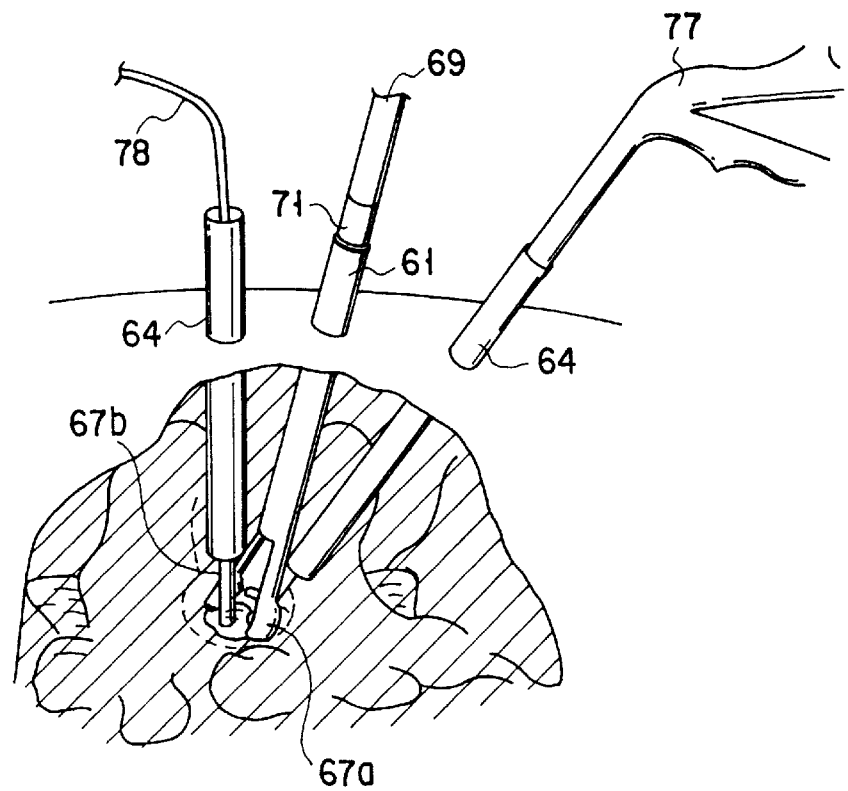
FIG. 32
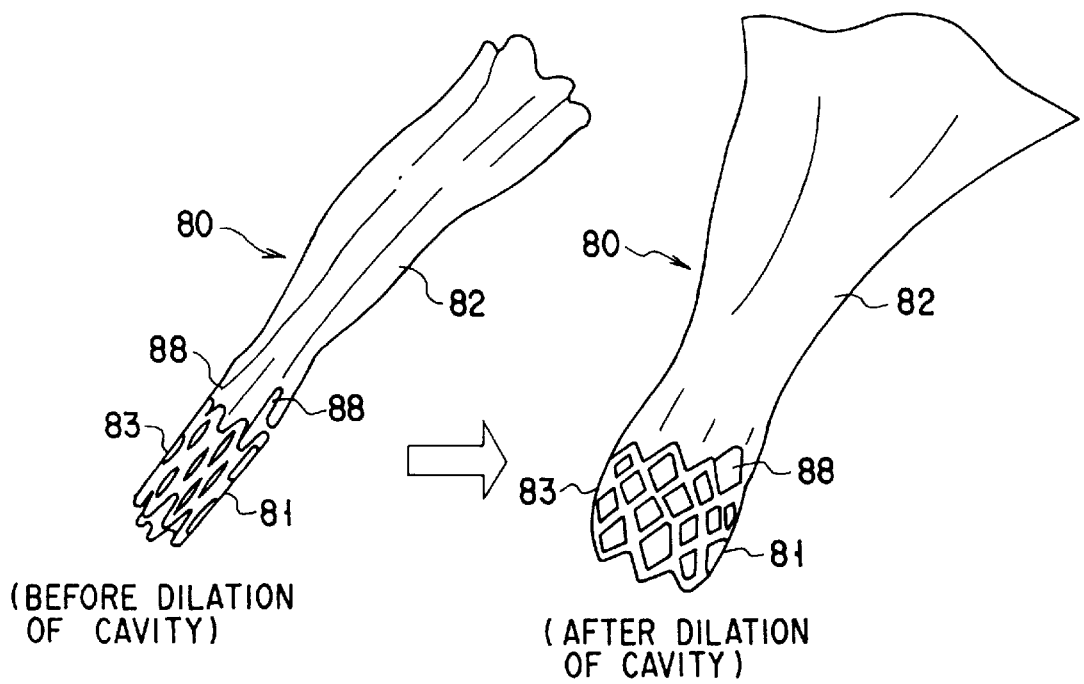
(BEFORE DILATION OF CAVITY)
FIG. 33A
(AFTER DILATION OF CAVITY)
FIG. 33B

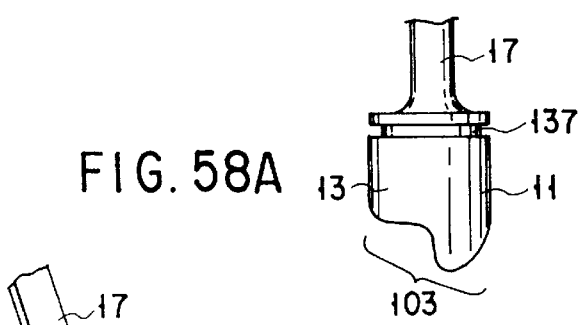
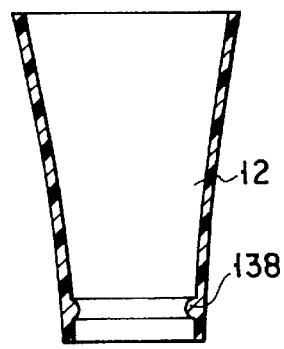
FIG. 58A
FIG. 58B
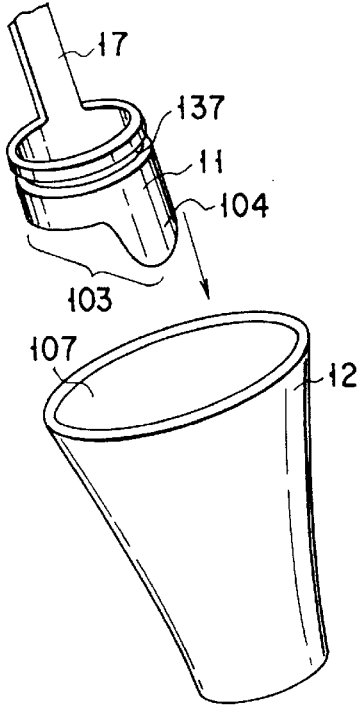
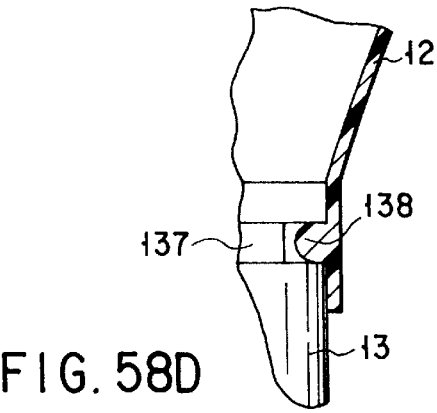
FIG. 58C
FIG. 58D
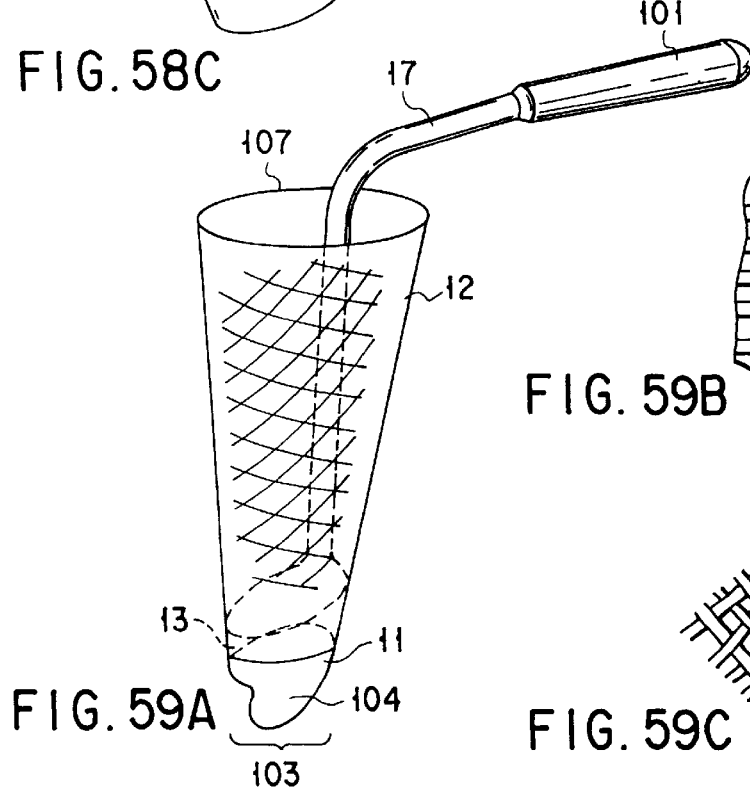
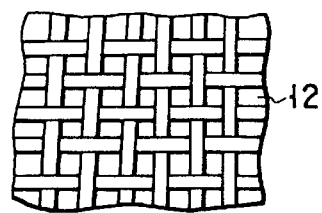
FIG. 59A
FIG. 59B
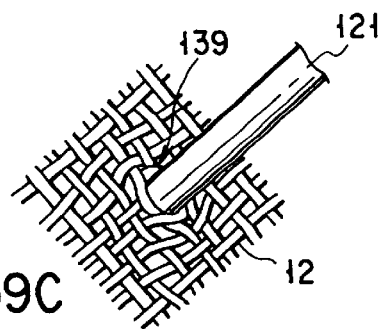
FIG. 59C

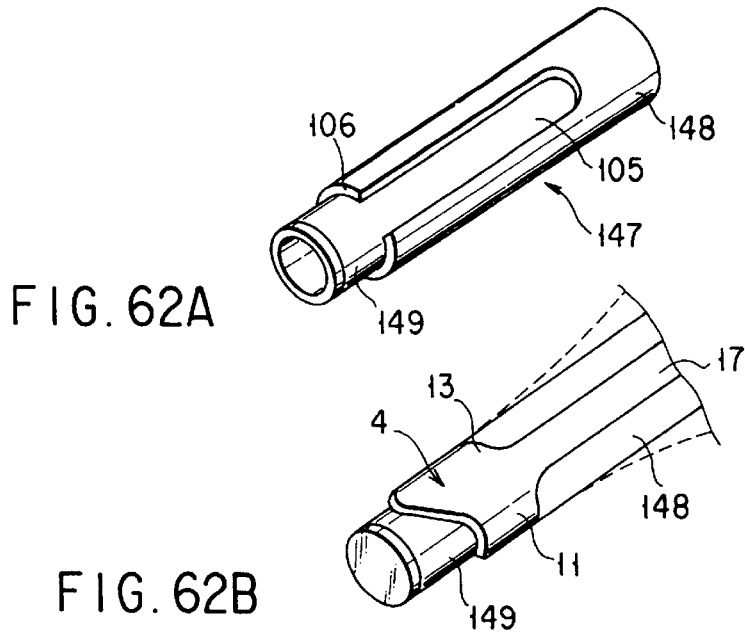
FIG. 62A
FIG. 62B
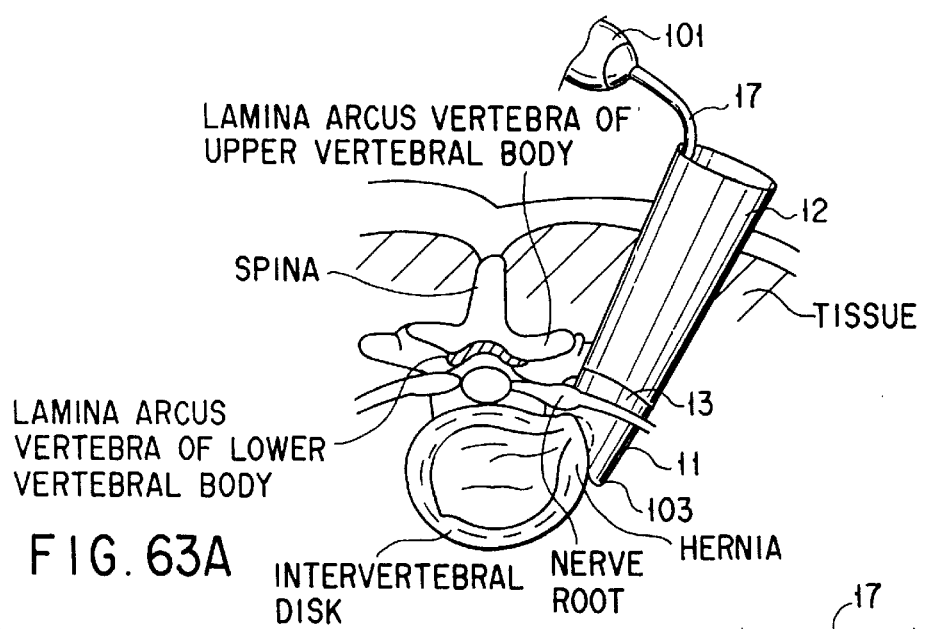
FIG. 63A
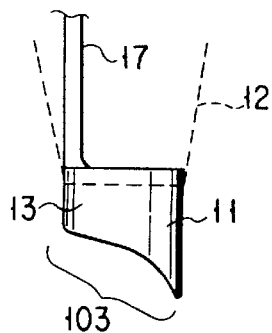
FIG. 63B
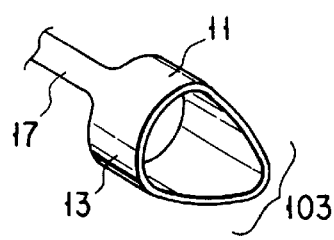
FIG. 63C
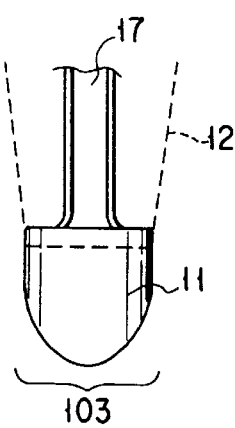
FIG. 63D

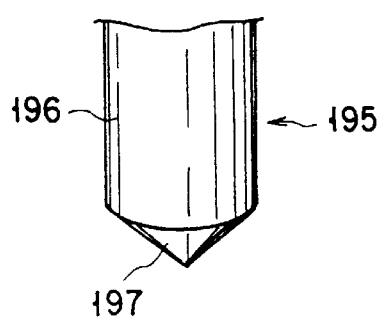
FIG. 72
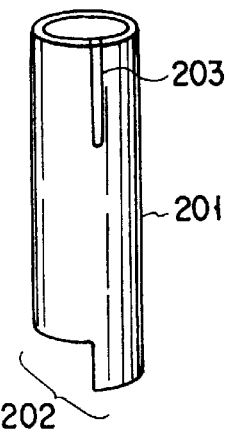
FIG. 73
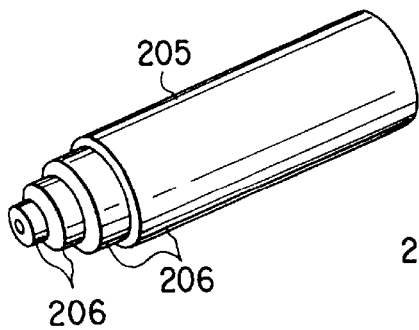
FIG. 74A
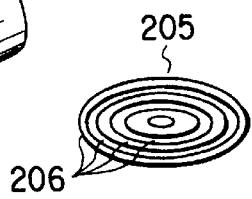
FIG. 74B
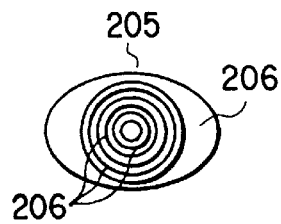
FIG. 74C
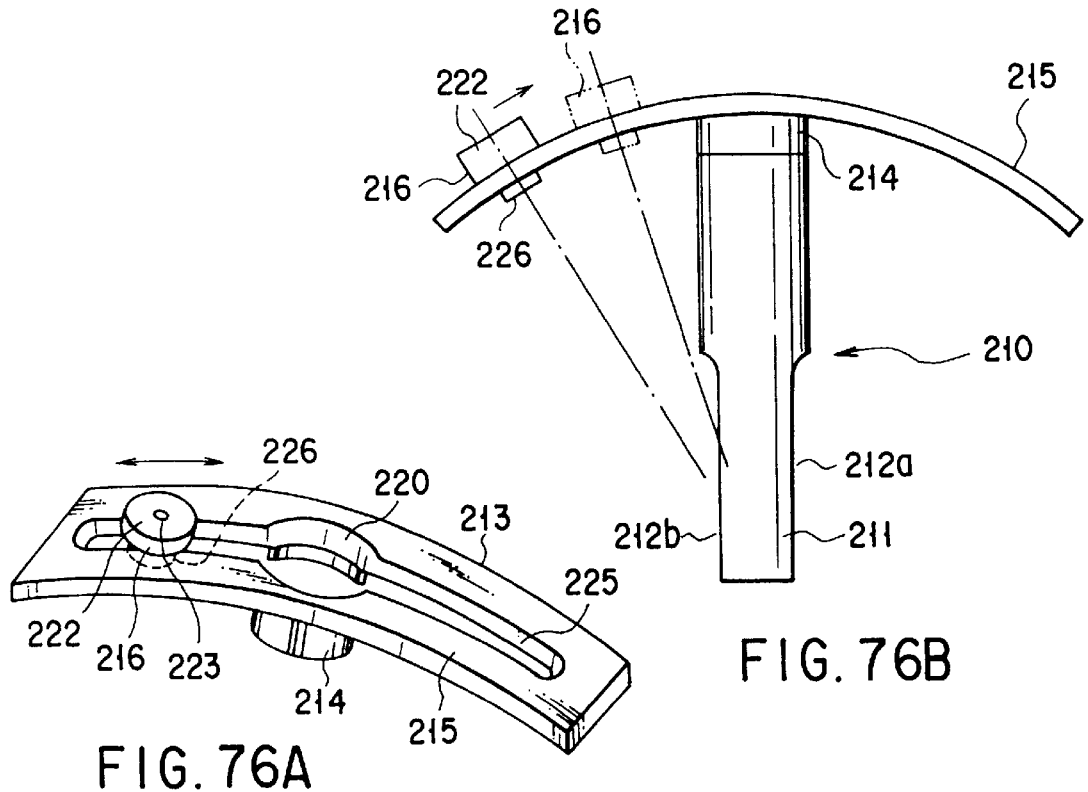
FIG. 76A
FIG. 76B

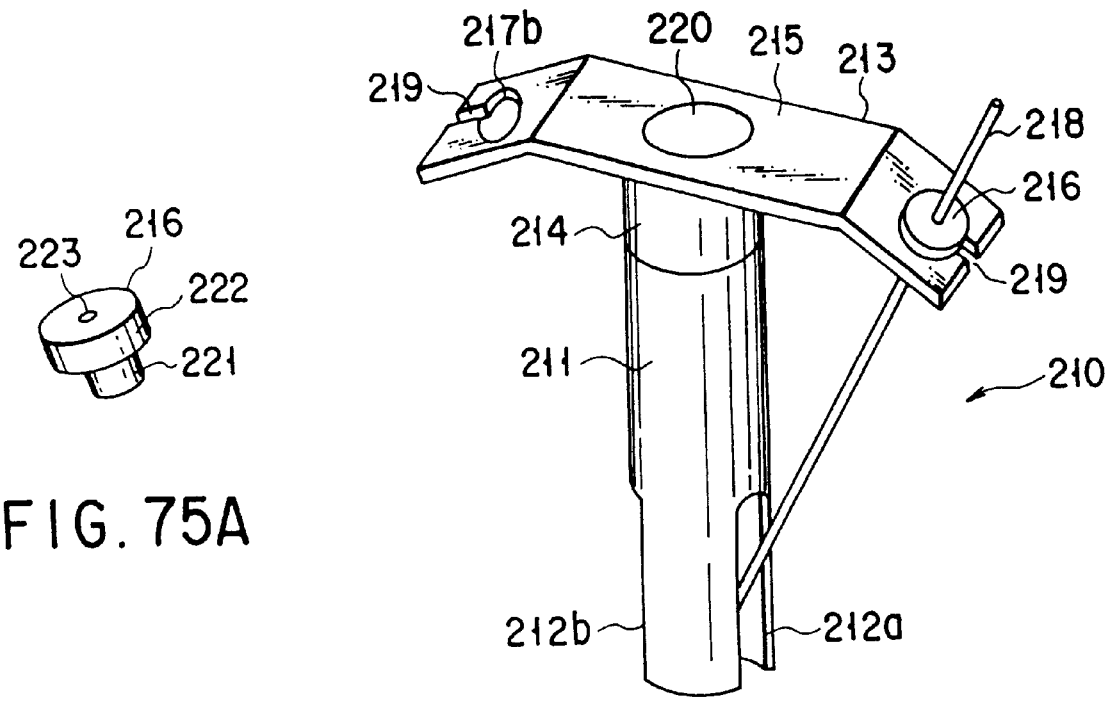
FIG. 75A
FIG. 75B
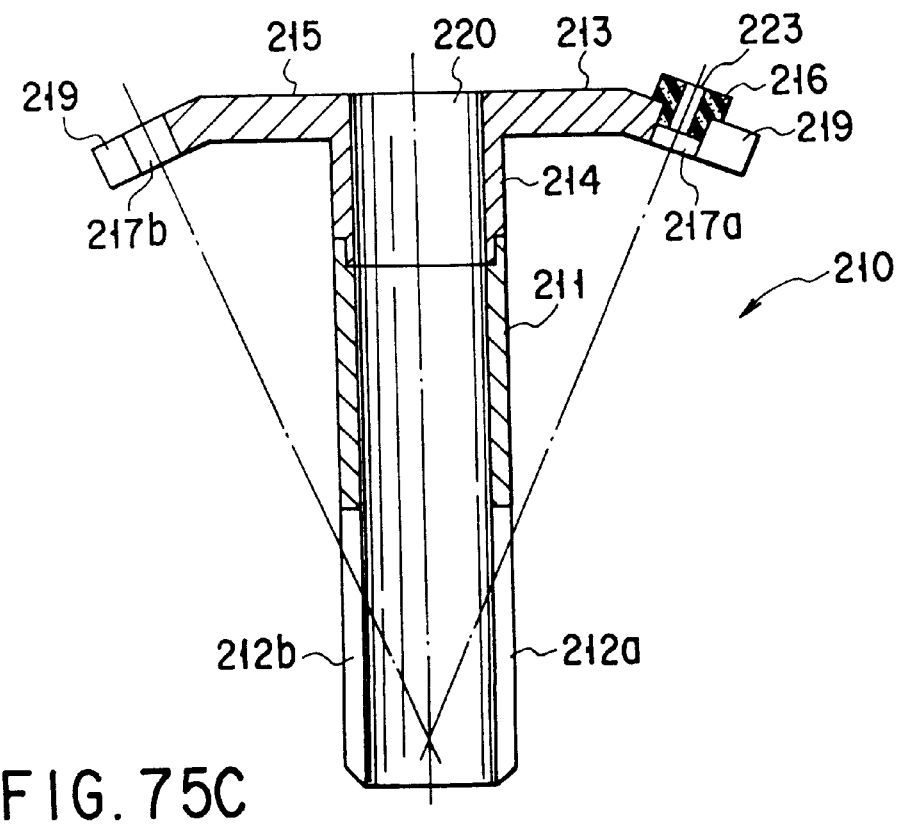
FIG. 75C

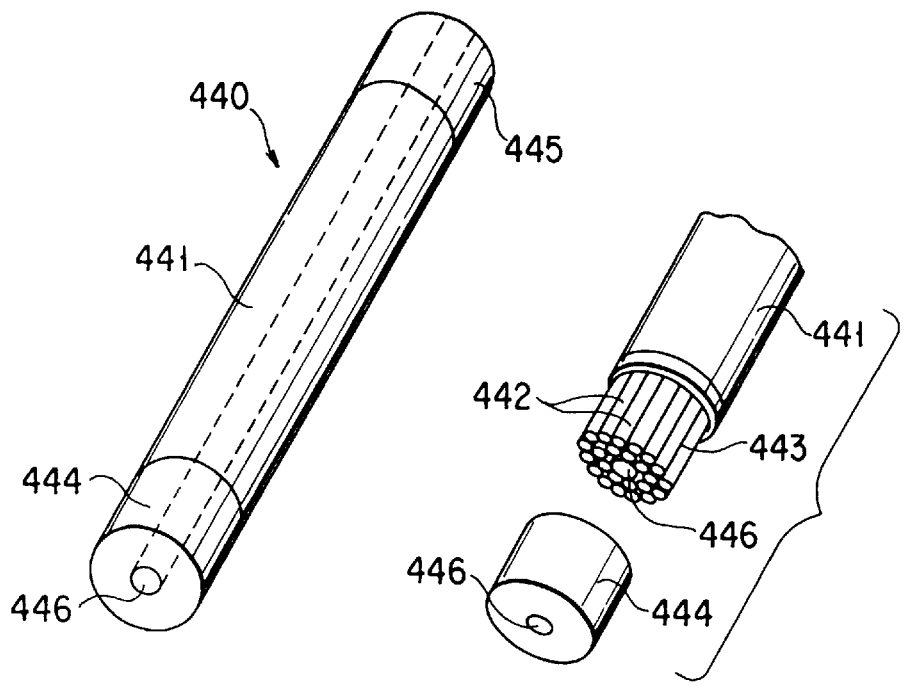
FIG. 103A    FIG. 103B
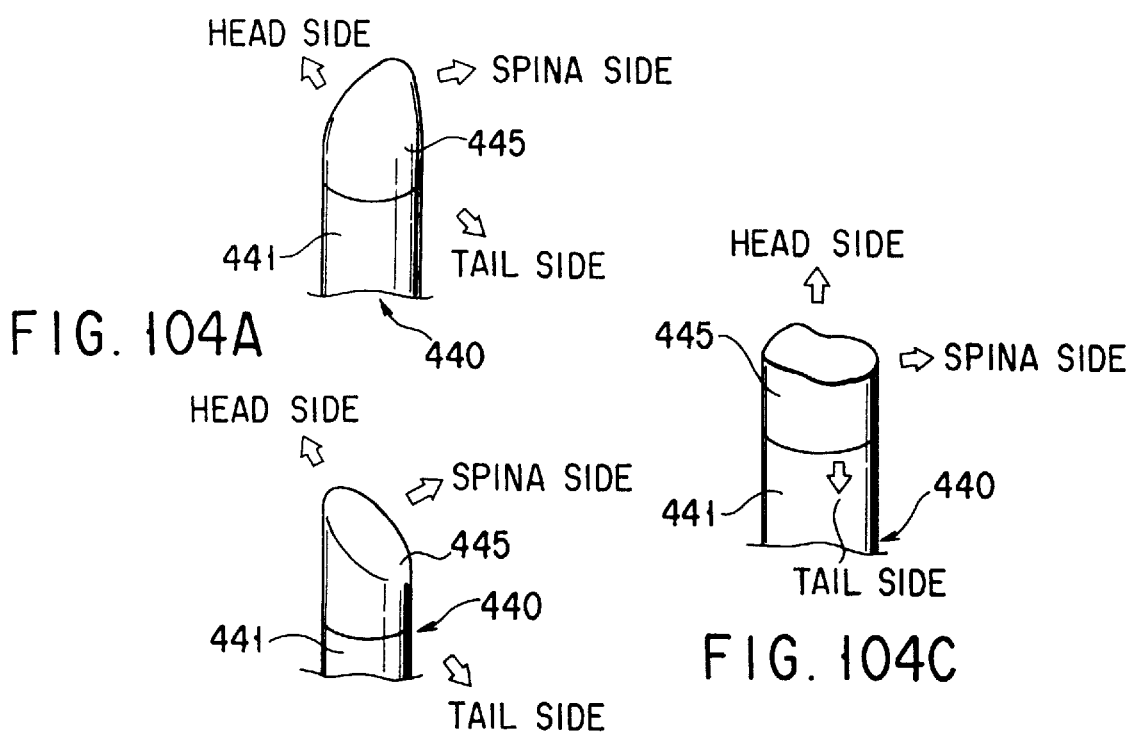
FIG. 104A
FIG. 104B
FIG. 104C

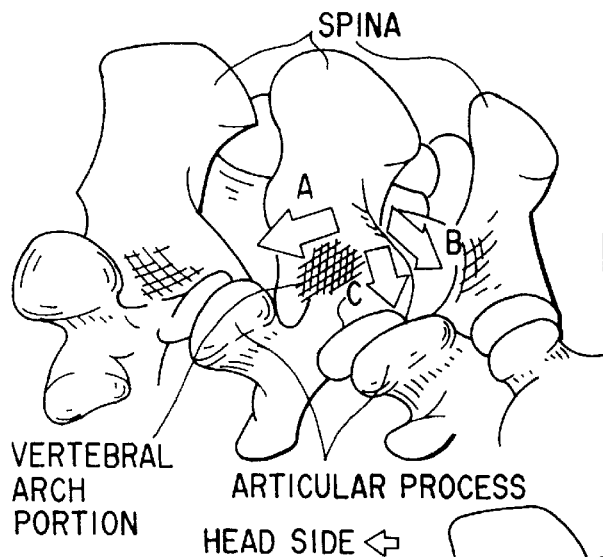
FIG. 105A
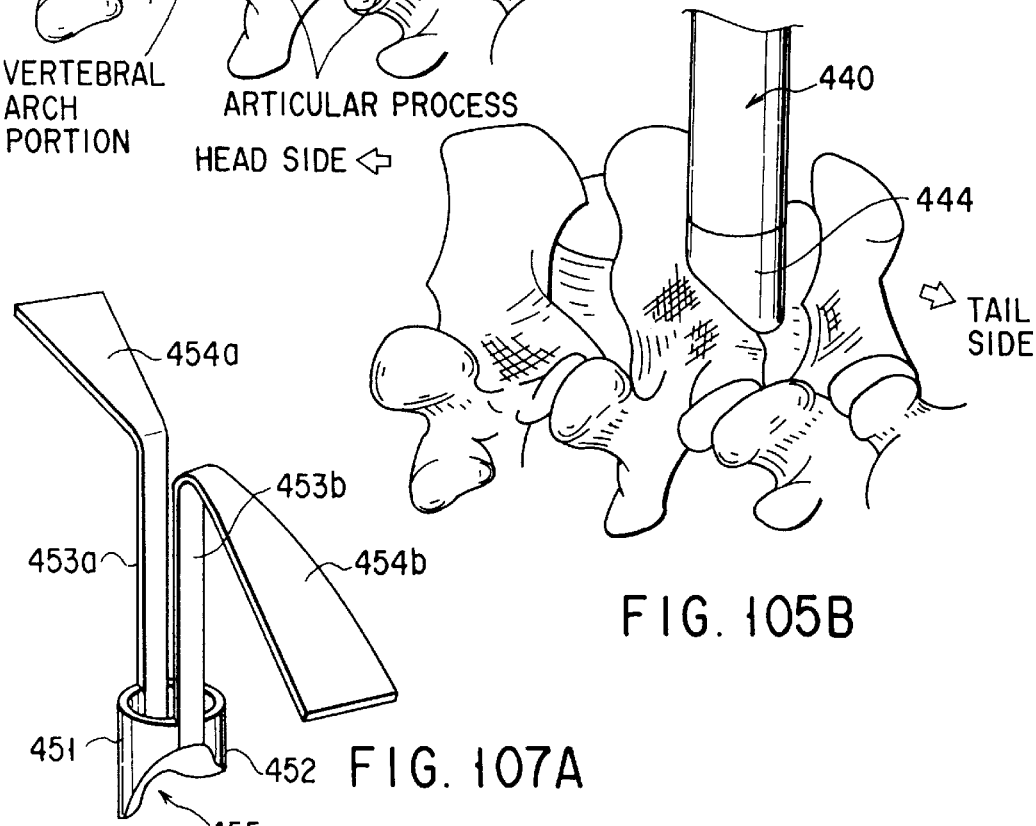
FIG. 105B
FIG. 107A
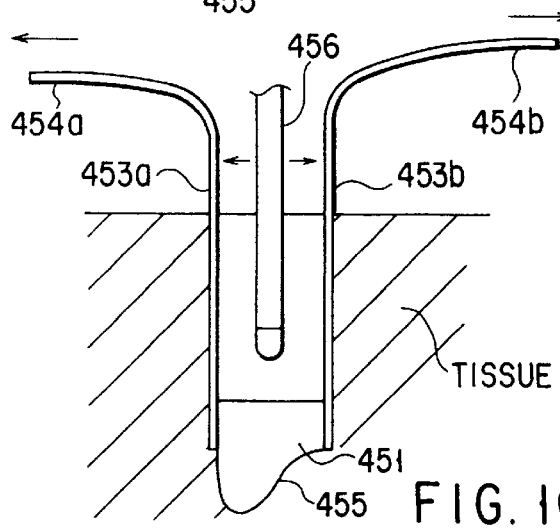
FIG. 107C
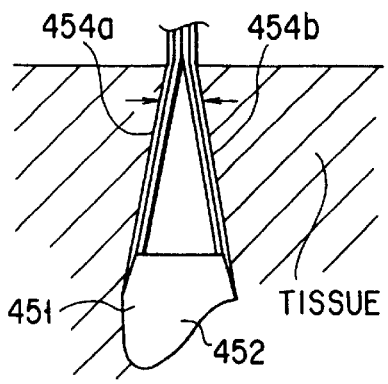
FIG. 107B

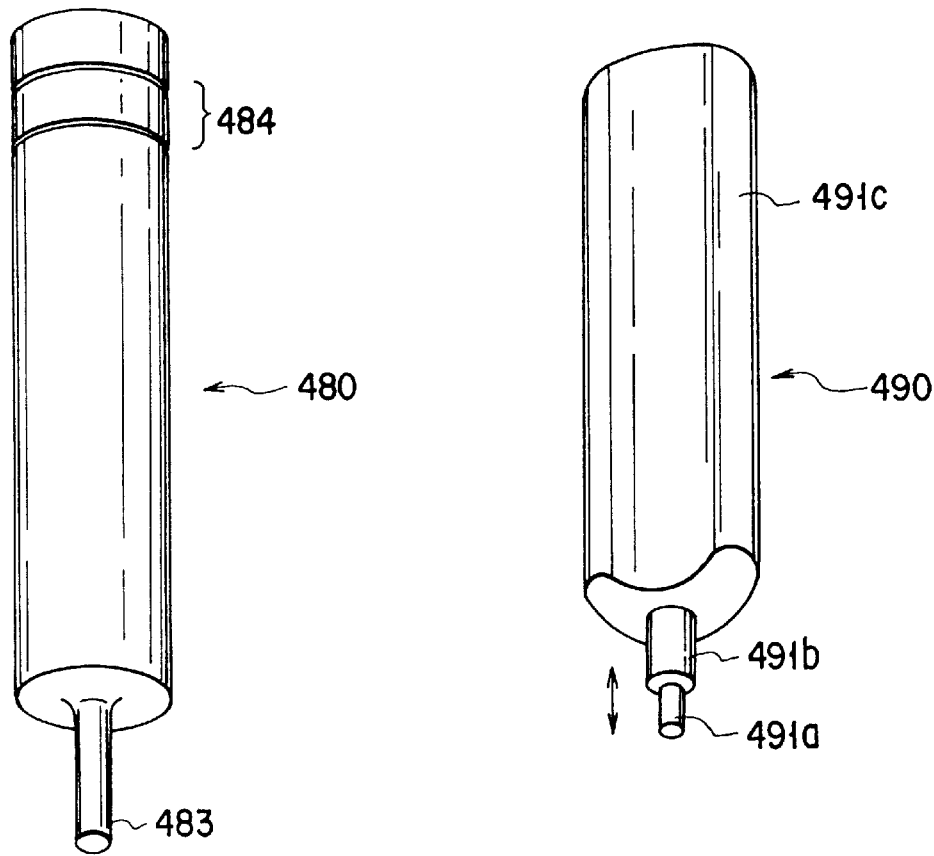
FIG. 112
FIG. 114
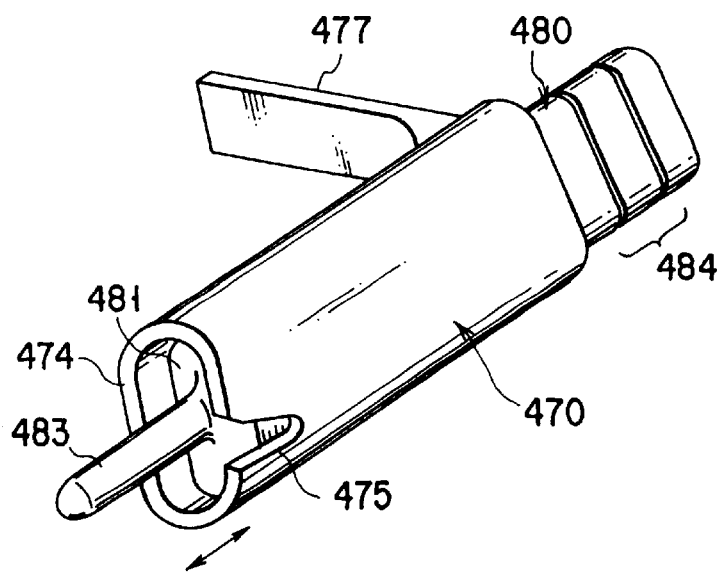
FIG. 113

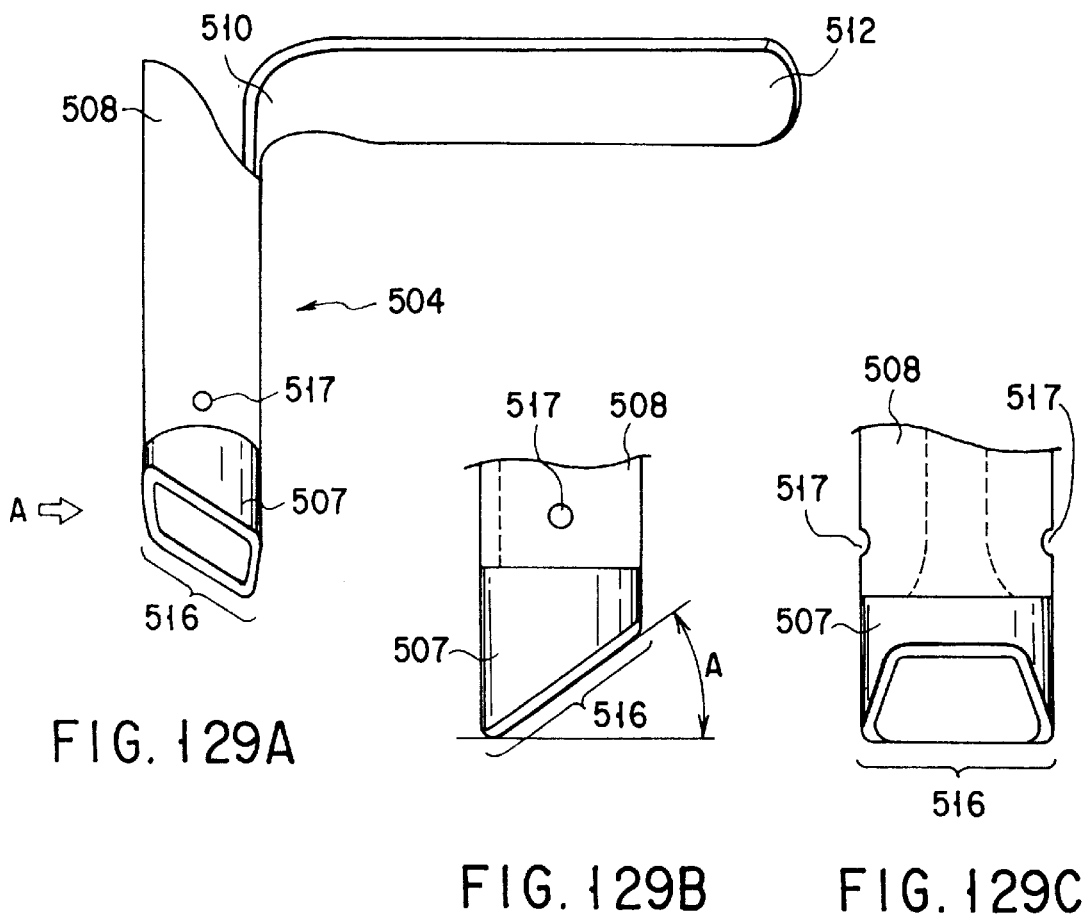
FIG. 129A  FIG. 129B  FIG. 129C
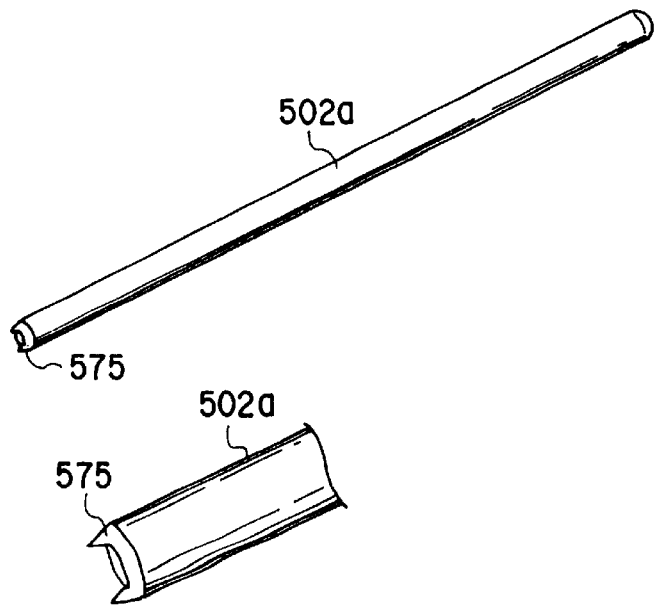
FIG. 130A
FIG. 130B

SURGICAL OPERATION SYSTEM AND METHOD OF SECURING WORKING SPACE FOR SURGICAL OPERATION IN BODY

BACKGROUND OF THE INVENTION

The present invention relates to a surgical operation system and method for percutaneously securing a cavity as a working space for a surgical operation in the body by using a cavity securing tool.

Recently, increasing numbers of operations in cavities in body tissues using endoscopes have been performed. The merit of such an operation is that a low invasive operation can be performed because a treatment is made with an approach to a cavity in the body through a small incision as compared with so-called open surgery in which a treatment is made with an approach to a target treatment site after a large incision is made in the tissue. However, one of the problems in endoscopic operations is that it is difficult to secure a good site of operation in the body.

For example, percutaneous lumbar discectomy is generally performed as follows. A median incision is made in the back of the patient to expose the back muscle. The back muscle is incised, and the incision in the back muscle is spread open by using a pushing element, thereby exposing the lumbar vertebrae. Part of the lamina of vertebral arch is removed to expose the yellow ligament having the nerve root. The yellow ligament is then incised, and the dura mater located therebelow is shifted to one side. The evagination portion of the hernia located on the rear side of the dura mater is removed. In a general conventional operation in which a median incision is made in the back of the patient, and a site of operation is exposed by using a pushing element, a lumbago occurs after the operation because a large incision is made in the dorsolumbar muscle, the dorsolumbar is separated from the bones, or the dorsolumbar muscle is pushed for a long period of time or with a strong force. In addition, pushing may cause unrecoverable damage to the back muscle.

Under the circumstances, as disclosed in U.S. Pat. No. 5,439,464, a technique of performing a back operation has been proposed. According to this technique, a plurality of cannulas are inserted from the back of the patient to positions near the spine. Physiological saline is then injected to a portion near the spine through one of the canulas to secure a working space with the pressure of the physiological saline. A hard mirror and a treatment tool are introduced through the remaining cannulas. After this process, an endoscopic operation is performed.

According to a general technique based on a so-called open surgery, an incision is made in the back to expose the back muscle, and the incision in the back muscle is spread open by a pushing element, thereby exposing the lumbar vertebrae. In this operation, pushing causes great damage to the back muscle. This may cause unrecoverable damage to the back muscle. In addition, an incision itself may cause great damage to the back muscle and the like.

In the technique of using a plurality of cannulas as in U.S. Pat. No. 5,439,464, damage to the back muscle by an incision and pushing is relatively small, but a sufficient visual field and a sufficient working space cannot be obtained.

BRIEF SUMMARY OF THE INVENTION

It is a first object of the present invention to provide a surgical operation system using a surgical operation cavity securing tool which can obtain a sufficient visual field and a sufficient working space to facilitate a low invasive surgical operation, even though pushing needs to be performed locally to a minimum necessary degree.

It is the second object of the present invention to provide a surgical operation system which can easily guide a surgical operation cavity securing tool to a region of surgical object.

It is the third object of the present invention to provide a low invasive surgical operation system which easily expose a region of surgical object and obtain a sufficient visual field and a sufficient working space, minimizing unnecessary tissue treatment before treatment on a region of surgical object.

The object of the present invention is achieved by the following means.

According to the present invention, there is provided a surgical operation apparatus comprising:
 a cavity securing tool including cavity securing means that is inserted into a living body through a skin to secure a working cavity in vital tissue and has a hole with an odd-shaped cross-section, and tool insertion channel means that allows a tool to be inserted into the cavity;
 an insertion tool for forming an insertion path for introducing said cavity securing tool into the vital tissue through the skin; and
 a cavity securing tool guide tool which has the same outer shape as the cross-sectional shape of the hole of the cavity securing means, on which said cavity securing tool can be fitted, and which can be fitted on said insertion tool.

In addition, according to the present invention, there is provided a surgical operation apparatus comprising a cavity securing tool including a cavity securing portion that is inserted into vital tissue through a skin to secure a working cavity for a surgical operation in a body, and a channel portion that allows an operation tool to be inserted from outside the body into the cavity, and a cavity securing tool guide tool having abrasion means formed on a distal end to abrade tissue from a bone, and a guide for guiding the cavity securing tool into the vital tissue.

In addition, according to the present invention, there is provided a surgical operation apparatus comprising:
 a cavity securing portion for securing a working cavity for a surgical operation in vital tissue; and
 a deformable tool insertion guide portion that communicates with a cavity secured by the cavity securing portion to cause the cavity to communicate with the outside of the body,
 wherein a surgical operation is performed upon insertion of an endoscope and an operation tool into the cavity secured by the cavity securing portion through the tool insertion guide portion, and the tool insertion guide portion comprises at least one deformable plate structure.

According to the present invention, there is provided a surgical operation system comprising:
 an endoscope serving as an observation means;
 a cavity securing tool including a cavity securing means that is inserted into vital tissue through a skin portion to secure a working space in the body, and a wall member having a hole for causing the cavity to communicate with the outside of the body, the wall member having at least a transparent portion;
 at least one port that is inserted into the vital tissue through another skin portion and guided to the cavity; and port insertion means for forming an insertion path for the port.

In addition, according to the present invention, there is provided a surgical operation system comprising:

an endoscope serving as observation means;

a cavity securing tool including cavity securing means that is inserted into vital tissue through a skin portion to secure a working space in the body, and a wall member having a hole for causing the cavity to communicate with the outside of the body;

at least one port that is inserted into the vital tissue through another skin portion and guided to the cavity; and port insertion means for forming an insertion path for the port, wherein the cavity securing tool and the port insertion means are made of titanium and can be observed by magnetic resonance imaging means (MRI).

Furthermore, according to the present invention, there is provided a surgical operation system comprising:

a cavity securing tool for securing a cavity in a region of surgical object; and cavity securing tool guide means having insertion position detection means that is arranged on a distal end to detect a position where the cavity securing tool is to be inserted, the guide means being used to insert the cavity securing tool into vital tissue.

According to the present invention, there is provided an endoscopic operation system comprising:

a cavity securing tool having a surface on a distal end which is brought into contact with a portion near a region of surgical object, the surface serving as a reference surface;

a cavity securing tool guide member having an indicator portion on a distal end which has a cross-sectional area smaller than that of the reference surface; and insertion position detection means for detecting an insertion position of the cavity securing tool by combining the cavity securing tool and the cavity securing tool guide member, wherein the cavity securing tool and the cavity securing tool guide member are arranged parallel to each other to be movable in a major axis direction, and a shape is detected from change amounts of the cavity securing tool and the cavity securing tool guide member.

Furthermore, according to the present invention, there is provided an endoscopic operation system comprising a cavity securing tool for securing a working cavity in tissue, the tool having engaging means to be engaged with a region of surgical object, cavity securing tool guide means serving as a guide for inserting the cavity securing tool into a body, and means for detecting an insertion position of the cavity securing tool by combining the cavity securing means and the cavity securing tool guide means, wherein the insertion position detection means is formed such that when the cavity securing tool is engaged with the region of surgical object, the sum of a protrusion amount of a bone portion into a cavity securing portion and a total length of the cavity securing tool guide means is almost equal to a total length of the cavity securing means, and detects the insertion position of the cavity securing means on the basis of coincidence between a proximal end of the cavity securing means and a proximal end of the cavity securing tool guide means.

Furthermore, according to the present invention, there is provided a treatment method using a system including a bone operation cavity securing tool that is inserted into tissue to form a working cavity, the tool having means for observing the cavity, tool insertion guide means through which a treatment tool is inserted, and engaging means having a distal end to be engaged with a posterior spine vertebral arch of a spine, and extracorporeal detection means for detecting a position of a region of surgical object, comprising the steps of:

(a) forming an insertion path in vital tissue at a predetermined position and angle;

(b) inserting the detecting means into the path and detecting the region of surgical object;

(c) inserting the bone operation cavity securing tool by using the detection means as a guide;

(d) engaging the bone operation cavity securing tool with the posterior spine vertebral arch;

(e) observing the cavity with the observation means; and (f) inserting a treatment tool into the tool insertion guide means, and performing a treatment on a bone under observation.

Moreover, according to the present invention, there is provided a treatment method using a system including a discectomy cavity securing tool that is inserted into tissue to treat a bone in a cavity securing with a distal end of the cavity securing tool, the tool having means for observing the cavity, tool insertion guide means through which a treatment tool is inserted, and engaging means having a distal end to be engaged with a posterior spine vertebral arch of a spine, and a discectomy cavity securing tool guide member, comprising the steps of:

(a) forming an insertion path in vital tissue at a predetermined position and angle;

(b) inserting the discectomy cavity securing tool guide member into the path, and abrading tissue around a region of surgical object with a distal end of the guide member;

(c) inserting the discectomy cavity securing tool, along the discectomy cavity securing tool guide member, into a place where abrasion is performed;

(d) engaging the discectomy cavity securing tool with the posterior spine vertebral arch;

(e) observing the cavity with the observation means; and (f) inserting a treatment tool into the tool insertion guide means, and performing a treatment on a bone under observation.

Additional object and advantages of the invention will be set forth in the description which follows, and in part will be obvious from the description, or may be learned by practice of the invention. The object and advantages of the invention may be realized and obtained by means of the instrumentalities and combinations particularly pointed out hereinbefore.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 6 is an anatomical chart showing a state in which an operation sheath is inserted into the tissue to the region of surgical object through the soft tube of the surgical operation cavity securing system according to the first embodiment;

FIGS. 7A to 7C are anatomical charts showing a state in which the operation sheath of the surgical operation cavity securing system according to the first embodiment is inserted into the tissue to the region of surgical object and indwelled therein;

FIG. 14 is a view for explaining the excision procedure using the surgical operation cavity securing system;

FIG. 15 is a perspective view showing an example of an operation sheath according to the second embodiment;

FIG. 16 is a perspective view showing another example of the operation sheath according to the second embodiment;

FIG. 27A is a perspective view showing a piercing tool according to the sixth embodiment;

FIG. 27B is a perspective view showing a state in which an operation sheath is fitted on the piercing tool;

FIG. 28A is a sectional view showing a state in which the operation sheath according to the sixth embodiment is inserted into tissue;

FIG. 28B is a sectional view taken along a line B—B in FIG. 28A;

FIG. 28C is a sectional view taken along a line C—C in FIG. 28A;

FIGS. 29A to 29D are perspective views showing the various tools belonging to a surgical operation cavity securing system according to the seventh embodiment;

FIG. 30 is a view for explaining a state in which the operation sheath is left in the tissue in the seventh embodiment;

FIG. 31 is a view for explaining a state of an operation using port guides in the seventh embodiment;

FIG. 32 is a view for explaining the overall state of the operation in the seventh embodiment;

FIGS. 33A and 33B are perspective views showing an operation sheath according to the eighth embodiment;

FIGS. 58A to 58D are views for explaining a cavity securing tool according to the 14th embodiment;

FIGS. 59A to 59C are views for explaining a cavity securing tool according to the 15th embodiment;

FIGS. 62A and 62B are views for explaining a pusher according to the 18th embodiment;

FIGS. 63A to 63D are views for explaining a cavity securing tool according to the 19th embodiment;

FIG. 72 is a view for explaining an insertion tool according to the 25th embodiment;

FIG. 73 is a view for explaining an insertion tool according to the 26th embodiment;

FIGS. 74A to 74C are views for explaining an insertion tool according to the 27th embodiment;

FIGS. 75A to 75C are views for explaining a port guide device according to the 28th embodiment;

FIGS. 76A and 76B are views for explaining a port guide device according to the 29th embodiment;

FIG. 101B is a bottom view of the cavity securing portion;

FIG. 102A is a perspective view showing the cavity securing portion of an operation sheath according to the 42nd embodiment;

FIG. 102B is a bottom view of the cavity securing portion;

FIG. 103A is a perspective view showing a search tool according to the 43rd embodiment;

FIG. 103B is an exploded perspective view showing the end portion of the search tool;

FIGS. 104A to 104C are views for explaining the function of the search tool according to the 43rd embodiment;

FIG. 105A is an anatomical chart of the spine as a treatment target viewed from the upper oblique side;

FIG. 105B is a view for explaining how the search tool is brought into contact with a portion of the spine;

FIG. 106 is a perspective view showing the tools belonging to a cavity securing tool system according to the 44th embodiment;

FIG. 107A is a perspective view showing a cavity securing tool according to the 45th embodiment;

FIGS. 107B and 107C are views for explaining how the cavity securing tool is used;

FIG. 108 is a perspective view showing an operation sheath according to the 46th embodiment;

Figure 110:
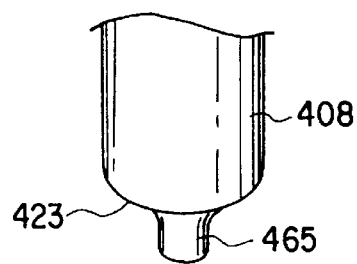
Figure 109A:
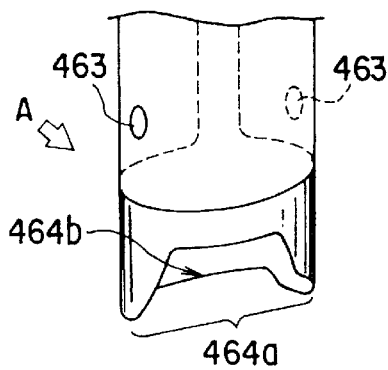
Figure 109B:
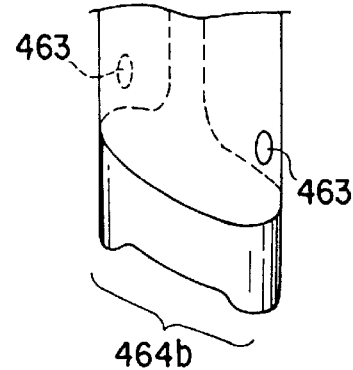
Figure 111A:
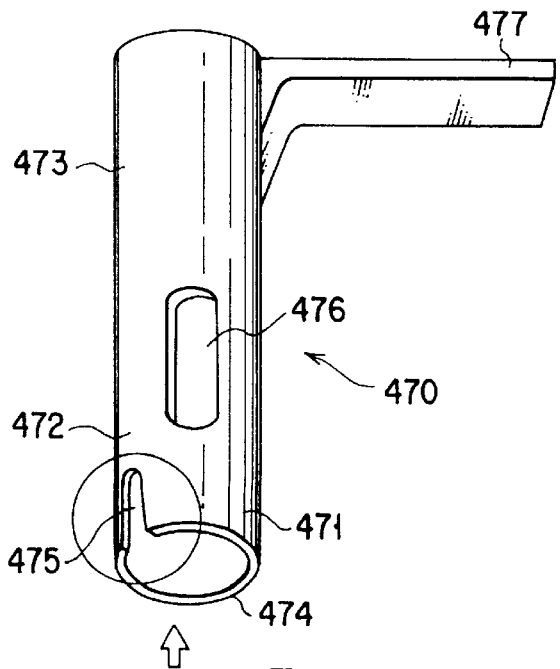
Figure 111B:
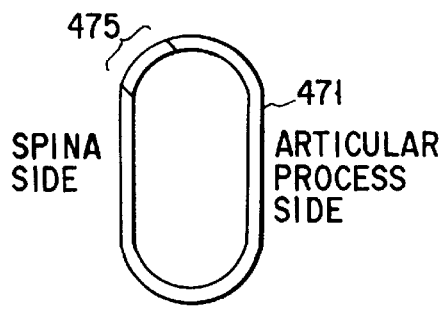
Figure 115:
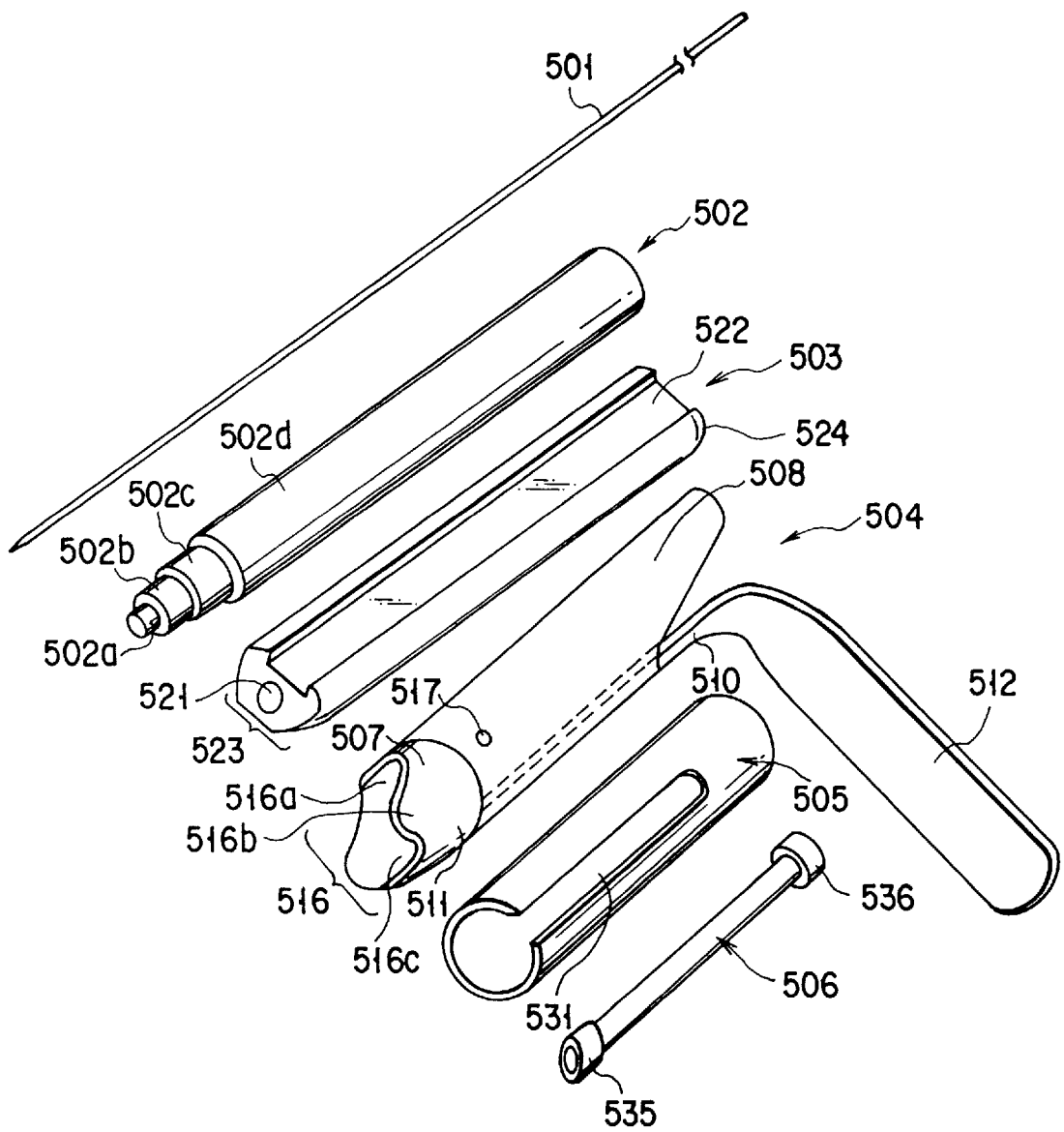
Figures 116A, 116B, 116C:
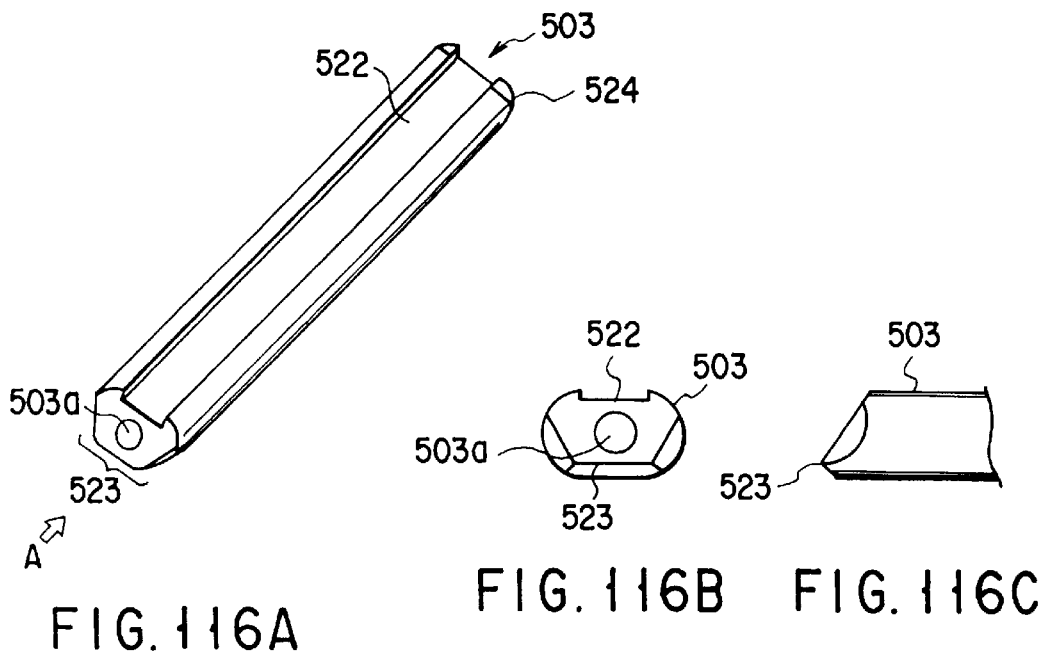
Figures 117A, 117B, 117C:
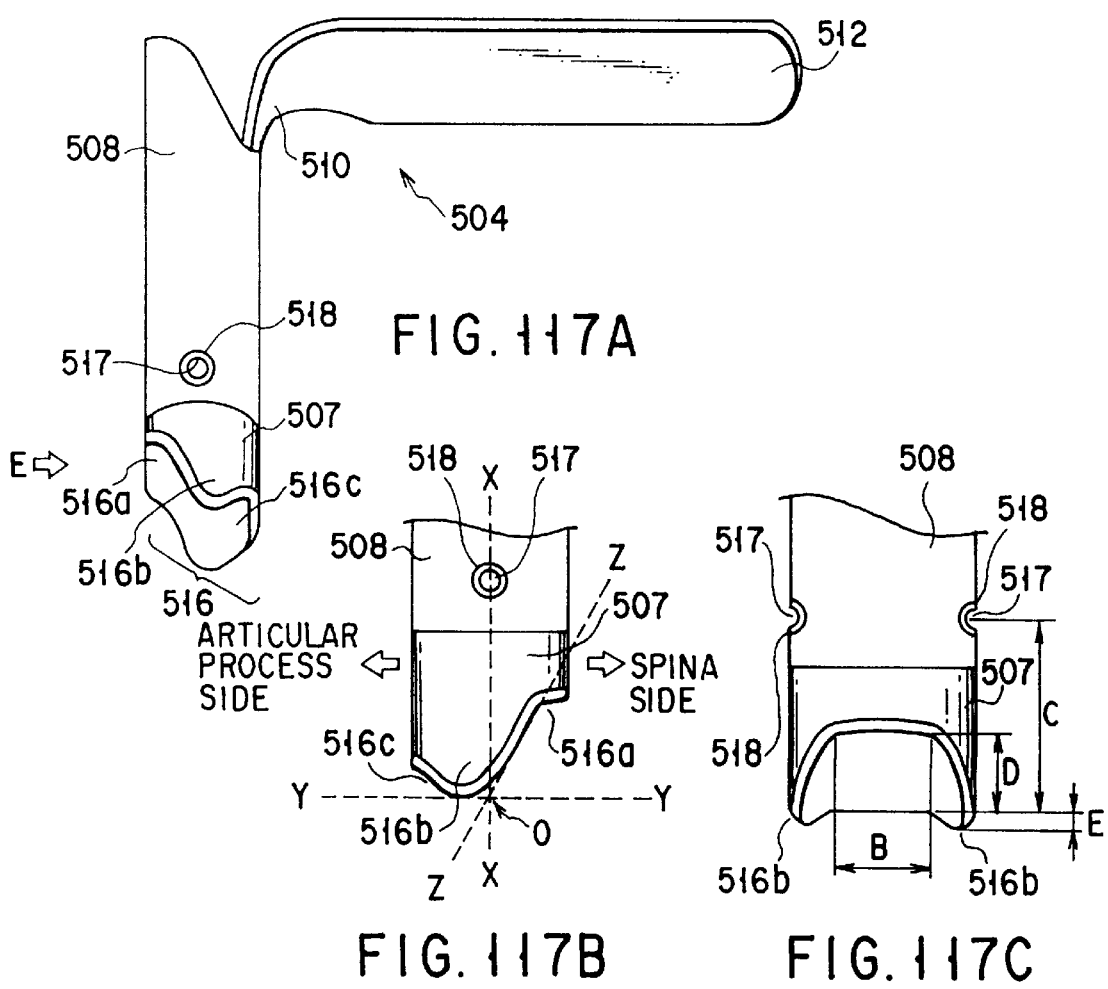
Figure 118A:
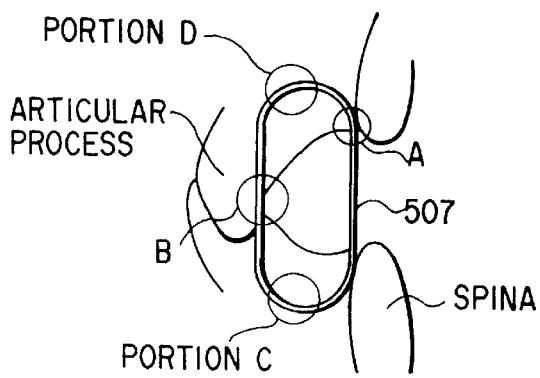
Figure 118B:
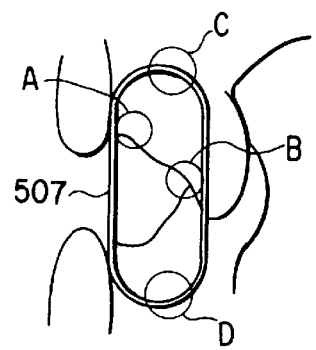
Figures 119A, 119B, 119C:
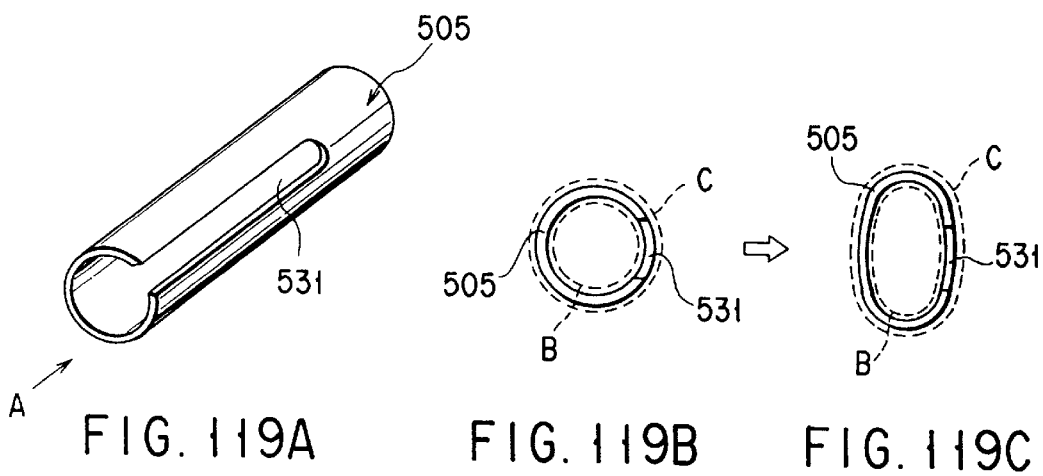
Figures 120A, 120B:
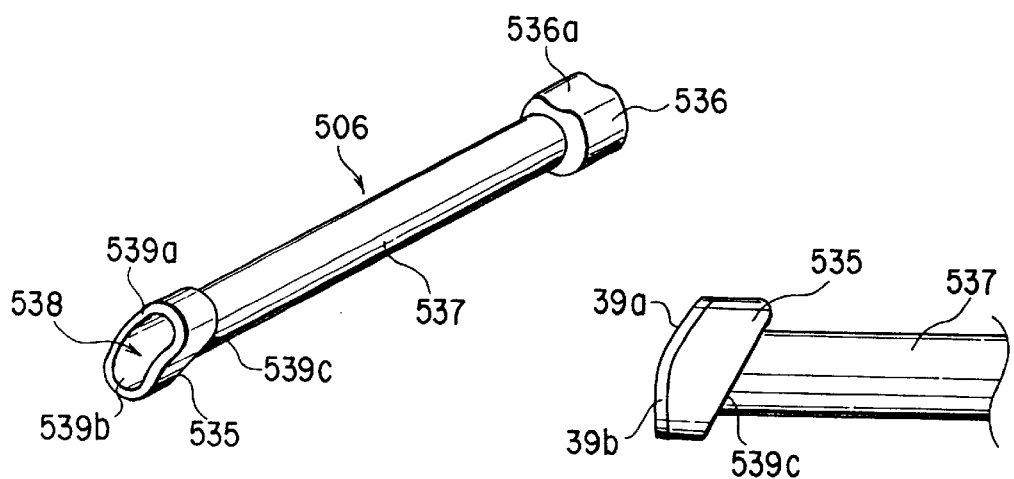
Figure 121:
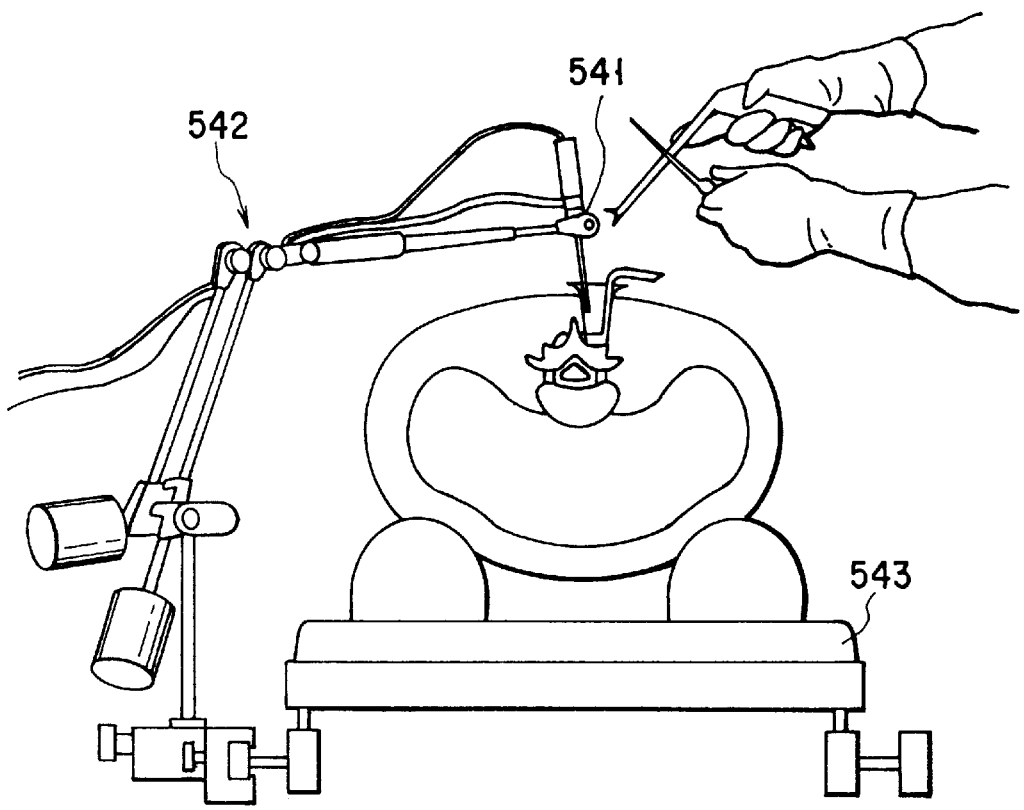
Figure 122:
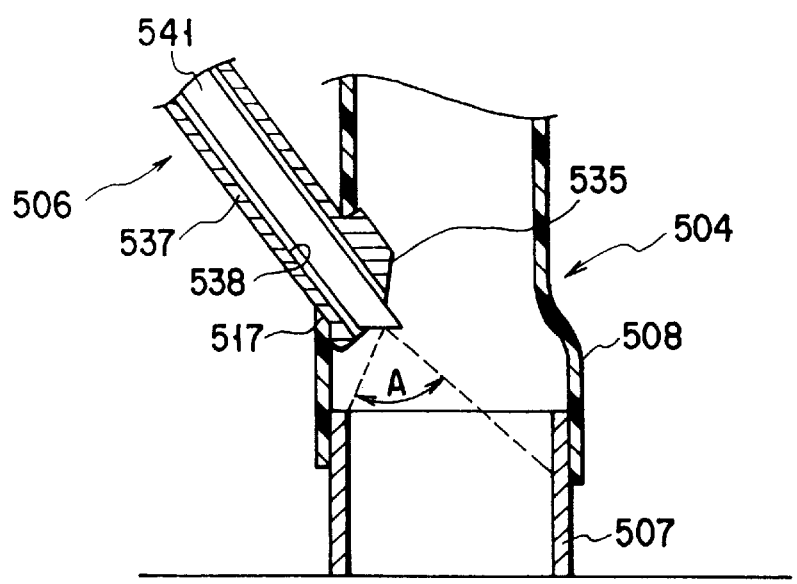
Figure 123:
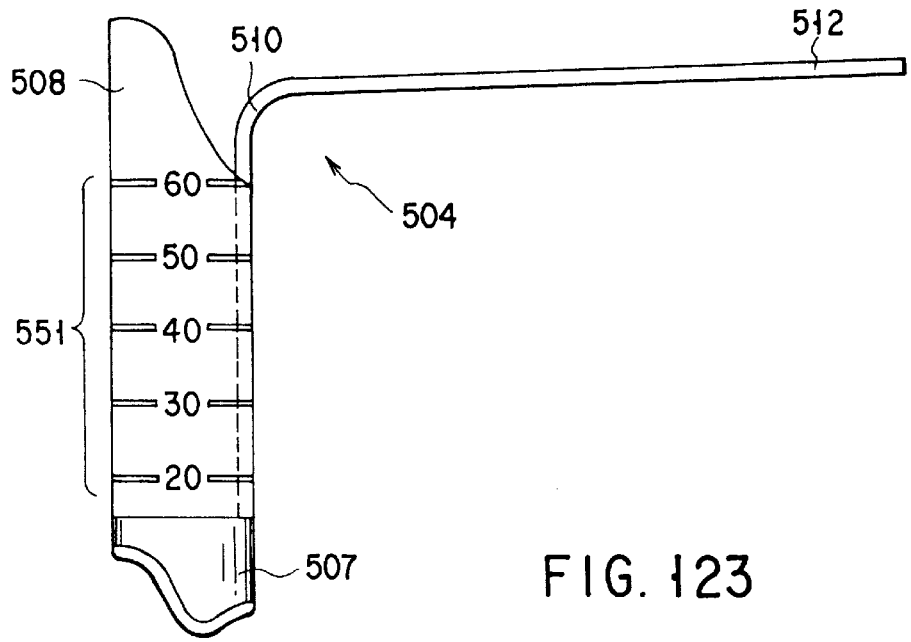
Figure 124:
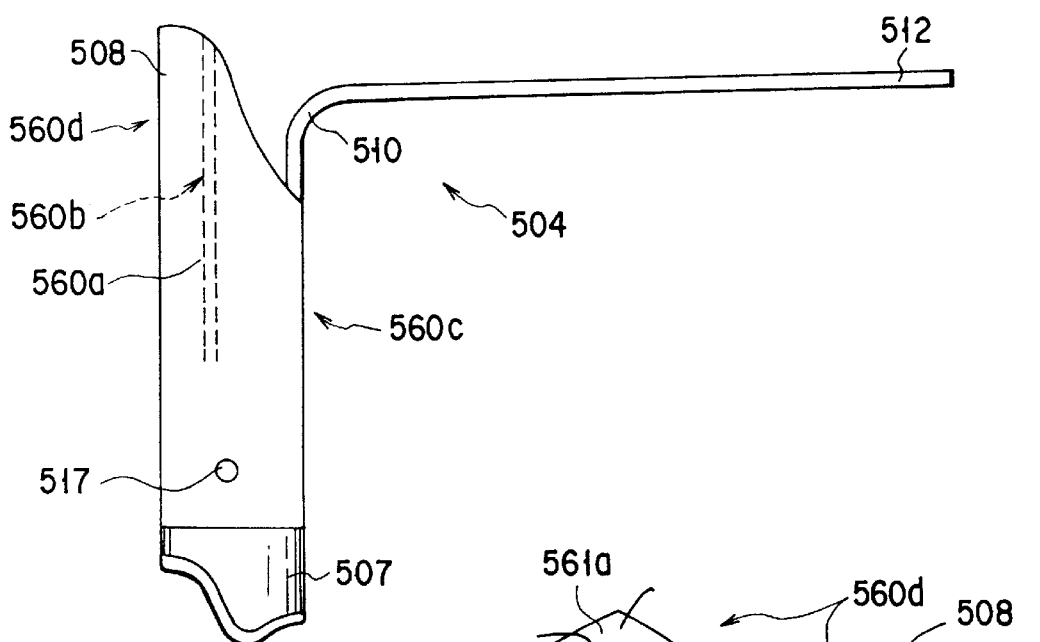
Figure 125:
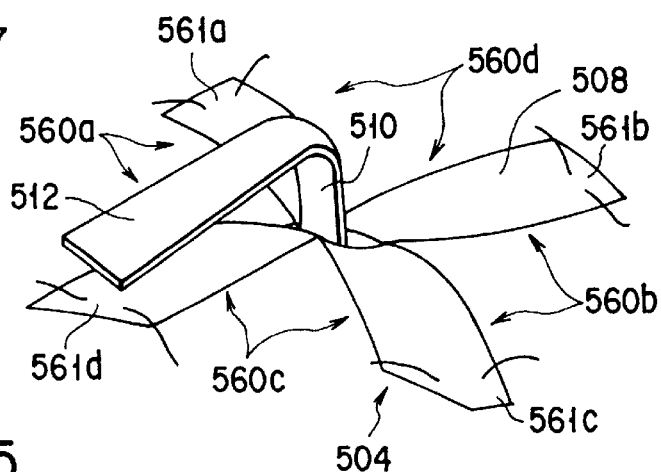
Figures 126A, 126B:
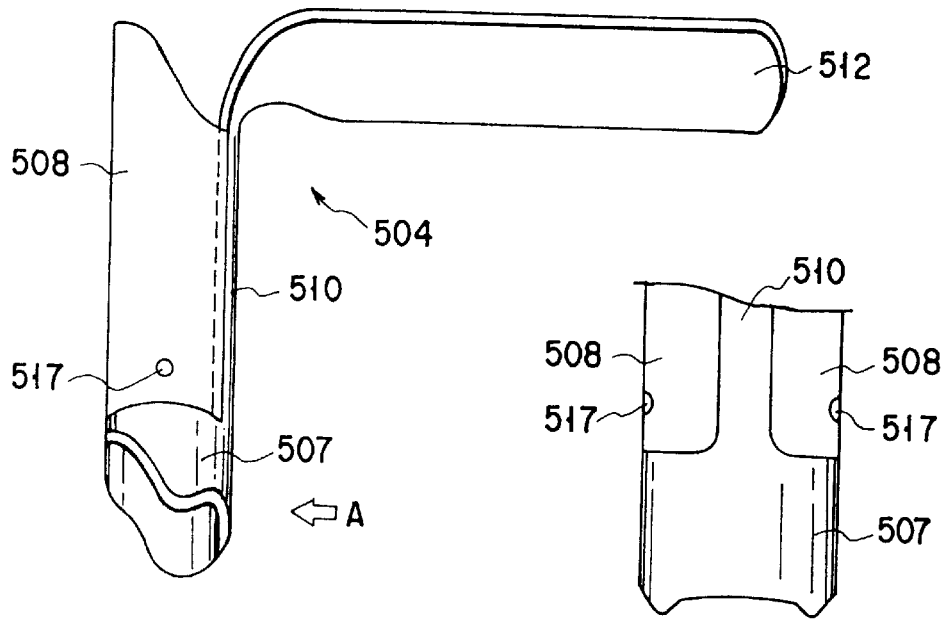
Figure 127:
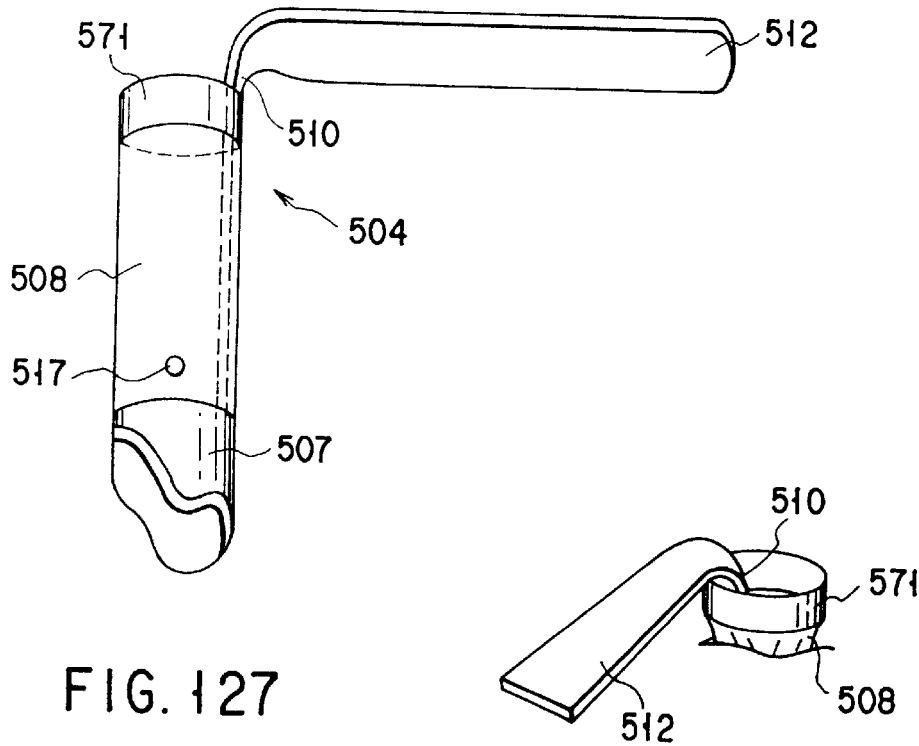
Figure 128:
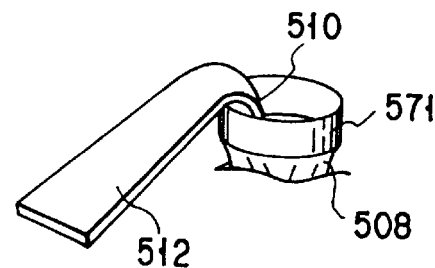
Figures 131A, 131B, 131C:
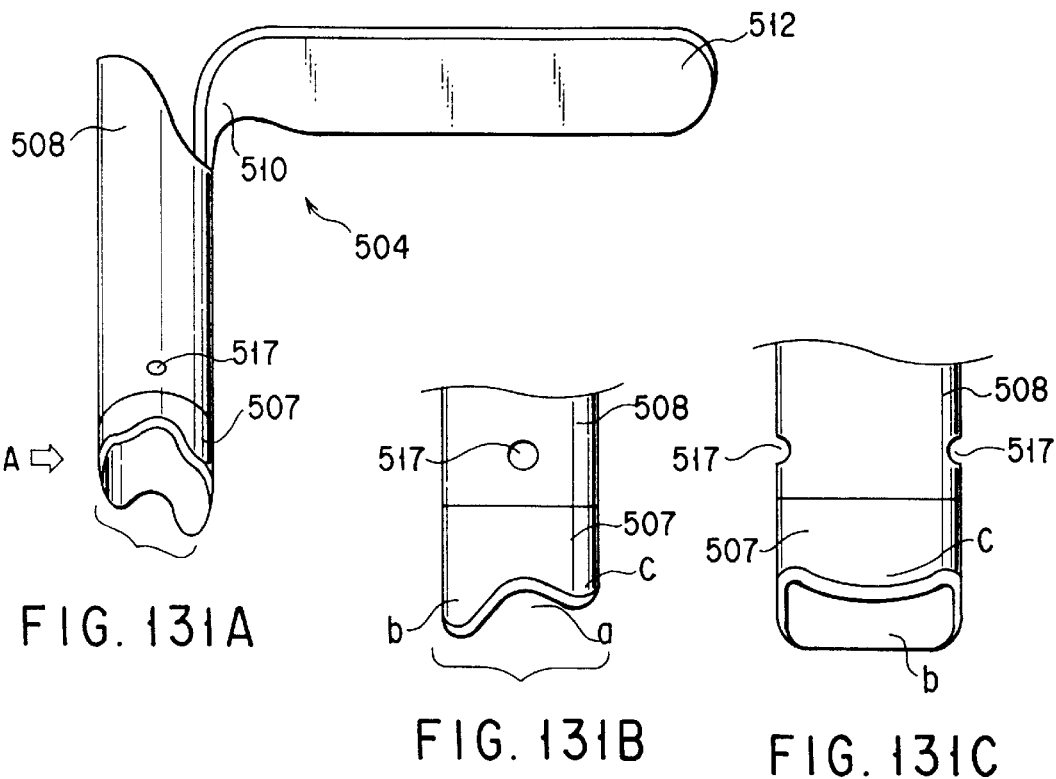
Figure 132:
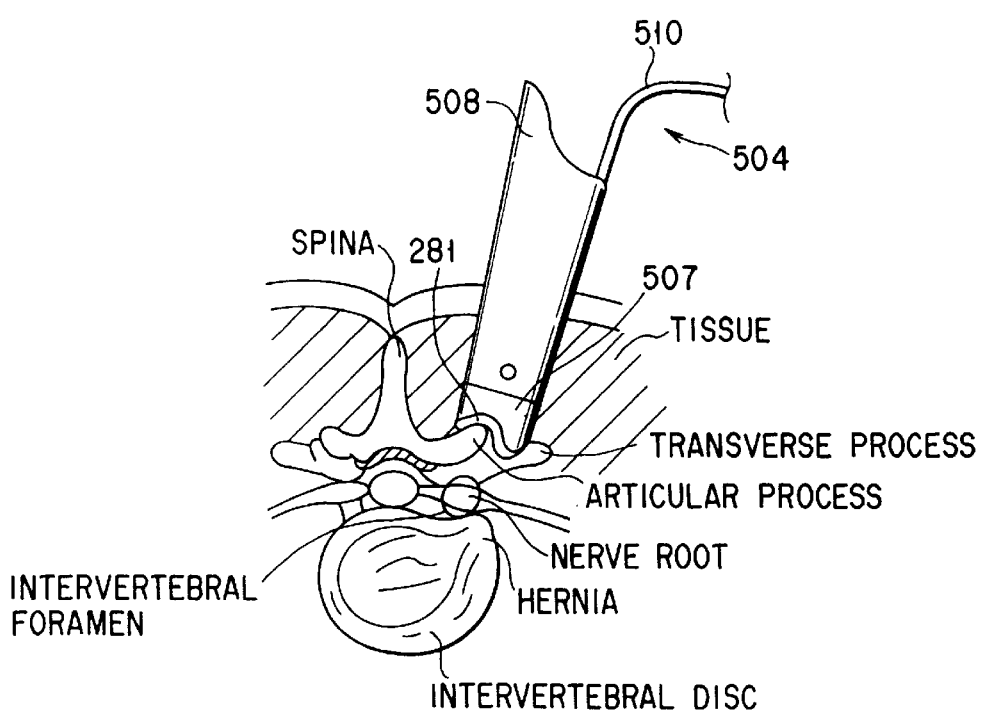

FIGS. 109A and 109B are perspective views showing an operation sheath according to the 47th embodiment;

FIG. 110 is a perspective view showing a mandrin according to the 48th embodiment;

FIG. 111A is a perspective view showing a cavity securing tool according to the 49th embodiment;

FIG. 111B is a bottom view of the cavity securing tool;

FIG. 112 is a perspective view showing an indicator member according to the 49th embodiment;

FIG. 113 is a perspective view showing a state in which the cavity securing tool and the indicator member according to the 49th embodiment are combined;

FIG. 114 is a perspective view showing a dilator for dilating a perforation in tissue according to the 49th embodiment;

FIG. 115 is a perspective view showing the tools belonging to a surgical operation cavity securing system according to the 50th embodiment;

FIG. 116A is a perspective view showing the mandrin of the system according to the 50th embodiment;

FIG. 116B is a view taken when the distal end of the mandrin is viewed from the direction of an arrow A in FIG. 116A;

FIG. 116C is a left side view of the distal end portion of the mandrin;

FIG. 117A is a perspective view showing an operation sheath according to the 50th embodiment;

FIG. 117B is a right side view showing the cavity securing portion of the operation sheath according to the 50th embodiment;

FIG. 117C is a view taken when the operation sheath according to the 50th embodiment is viewed from the direction of an arrow E in FIG. 117A;

FIG. 118A is a view for explaining how the operation sheath according to the 50th embodiment is used;

FIG. 118B is a view for explaining how the operation sheath according to the 50th embodiment is used;

FIG. 119A is a perspective view showing a pusher according to the 50th embodiment;

FIG. 119B is a view taken when the distal end of the pusher according to the 50th embodiment is viewed from the direction of an arrow A in FIG. 119A;

FIG. 119C is a view taken in the direction of the arrow A in FIG. 119A, showing another state of the distal end of the pusher according to the 50th embodiment;

FIG. 120A is a perspective view showing a port according to the 50th embodiment;

FIG. 120B is a left side view of the distal end portion of the port according to the 50th embodiment;

FIG. 121 is a view for explaining how the cavity securing system according to the 50th embodiment is used;

FIG. 122 is a view for explaining a treatment state in which a port is inserted into the operation sheath according to the 50th embodiment;

FIG. 123 is a left side view showing an operation sheath according to the 51st embodiment;

FIG. 124 is a left side view showing an operation sheath according to the 52nd embodiment;

FIG. 125 is a view for explaining how the operation sheath according to the 52nd embodiment is used;

FIG. 126A is a perspective view showing an operation sheath according to the 53rd embodiment;

FIG. 126B is a view taken when the cavity securing portion of the operation sheath according to the 53rd embodiment is viewed in the direction of an arrow A in FIG. 126A;

FIG. 127 is a perspective view showing an operation sheath according to the 54th embodiment;

FIG. 128 is a view for explaining how the operation sheath according to the 54th embodiment is used;

FIG. 129A is a perspective view showing an operation sheath according to the 55th embodiment;

FIG. 129B is a right side view of the cavity securing portion of the operation sheath according to the 55th embodiment;

FIG. 129C is a view taken when the operation sheath according to the 55th embodiment is viewed in the direction of an arrow A in FIG. 129A;

FIG. 130A is a perspective view showing a tube of a dilator which has the smallest diameter according to the 56th embodiment;

FIG. 130B is a perspective view showing the distal end portion of the tube having the smallest diameter according to the 56th embodiment;

FIG. 131A is a perspective view showing an operation sheath according to the 57th embodiment;

FIG. 131B is a right side view showing the cavity securing portion of the operation sheath according to the 57th embodiment;

FIG. 131C is a view taken when the operation sheath according to the 57th embodiment is viewed in the direction of an arrow A in FIG. 131A; and FIG. 132 is a view for explaining how an operation is performed by using the operation sheath according to the 57th embodiment.

DETAILED DESCRIPTION OF THE INVENTION

[First Embodiment]

The first embodiment of the present invention will be described with reference to FIGS. 1A to 14.

Figure 1A:
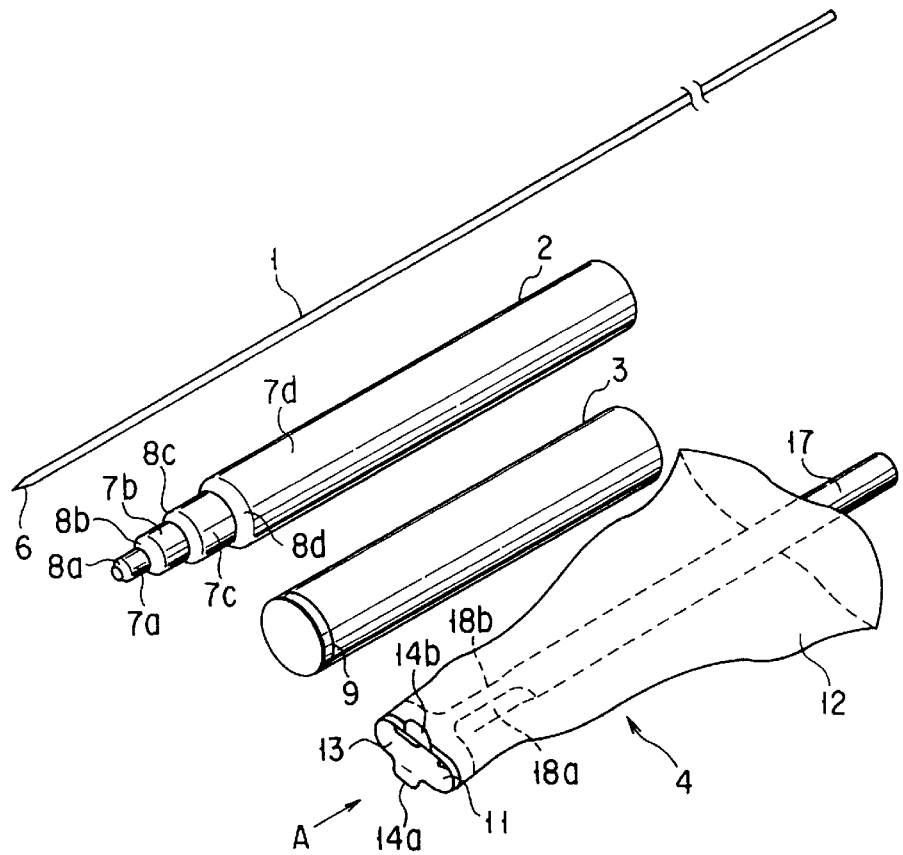
FIG. 1A is a perspective view showing the tools belonging to a surgical operation cavity securing system according to the first embodiment.

FIG. 1A shows the tools belonging to a surgical operation cavity securing system. Referring to FIG. 1A, reference numeral 1 denotes a guidewire; 2, a dilator serving as a tool to be inserted into the body; 3, a soft tube serving as a cavity securing tool guide; and 4, an operation sheath serving as a cavity securing tool.

The guidewire 1 is made of a hard material such as stainless steel and more specifically, a linear wire made of a material having the property of transmitting no X-rays. A perforating portion 6 is formed on the distal end of the guidewire 1.

The dilator 2 has a so-called extensible antenna type multi-tube structure having a plurality of tubes 7a to 7d fitted on each other. The tube 7a having the smallest diameter is fitted on the guidewire 1. The tube 7b having the next smallest diameter is fitted on the tube 7b. The tubes 7c and 7d having larger diameters are sequentially fitted on the preceding tubes, respectively, thereby securing a predetermined perforating diameter at the perforating position of the guidewire 1. The innermost tube 7a is fitted on the guidewire 1 to be slidable in a relatively tight state. The tube 7b is fitted on the tube 7a to be slidable in a relatively tight state. The tube 7c is fitted on the tube 7b to be slidable in a relatively tight state. The tube 7d is fitted on the tube 7c to be slidable in a relatively tight state. Chamfered portions 8a to 8d are respectively formed on the edges of the distal ends of the tubes 7a to 7d of the dilator 2.

The soft tube 3 serves s a guide means used to insert the operation sheath 4. For example, the soft tube 3 is a resin tube, which is flexible enough to deform in accordance with the outer shape of the operation sheath 4 to be inserted into a cavity as described later. The hole of the soft tube 3 has such a diameter that the soft tube 3 is fitted on the outermost tube 7d of the dilator 2 described above to be slidable in a relatively tight state. A chamfered portion 9 is formed on the edge of the distal end of the soft tube 3.

Figure 1B:
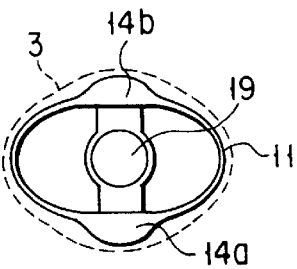
FIG. 1B is a view taken when the operation sheath of the system is viewed in the direction of an arrow A in FIG. 1A.

The operation sheath 4 serves as a cavity securing tool and includes a cavity securing portion as a cavity securing means 11 for securing a cavity in vital tissue and a soft tubular sheet member 12 as a soft tube member connected to the cavity securing means 11. The soft tubular sheet member 12 guides a tool through the hole and forms a communicating means to be used to insert the tool from the outside of the body into the cavity. The cavity securing means 11 has a belt-like cavity securing member, which is a hard ring-like member 13. As shown in FIG. 1B, the ring-like member 13 has a substantially oval (elliptic) shape. The ring-like member 13 serves as a cavity securing portion for securing a cavity as a working space for a surgical operation with the hole. A position holding means is formed on the outer wall of the cavity securing member. In this case, the position holding means is obtained by forming positioning folded portions 14a and 14b on two ends of the distal end of the ring-like member 13 in the minor axis direction. The positioning folded portions 14a and 14b are caught on tissue to reliably position the cavity securing means 11 at a predetermined position in the living body. In addition, the positioning folded portions 14a and 14b prevent tissue from entering the cavity and blocking the visual field. The ring-like member 13 is hard, but may be made of an elastically deformable material as long as it is strong enough to secure a working space.

The ring-like member 13 is out of round and odd-shaped. The outer circumference of the envelope of the ring-like member 13 including the positioning folded portions 14a and 14b is almost equal to the inner circumference of the soft tube 3. (see the dashed line in FIG. 1B). The outer circumference (circumference) of the envelope of the ring-like member 13 of the operation sheath 4, including the positioning folded portions 14a and 14b, may be slightly smaller than the inner circumference of the soft tube 3. The inner diameter of the soft tube 3 is set to be smaller than at least the maximum width of the ring-like member 13.

The soft tubular sheet member 12 is made of a soft sheet consisting of a resin such as polyurethane to have a funnel-like shape. In vital tissue, the soft tubular sheet member 12 easily deforms under the pressure from the tissue, and serves as a tool insertion deformable guide means for guiding, through the hole, a tool to the cavity formed by the cavity securing means 11. The edge of the small-diameter distal end of the soft tubular sheet member 12 is fitted/fixed on the outer surface of the ring-like member 13. The remaining portion of the soft tubular sheet member 12 has a skirt-like shape whose diameter gradually increases from the diameter of the fitted/fixed portion. The soft tubular sheet member 12 communicates with the hole of the ring-like member 13, and also forms a tool path communicating with the outside of the body during an operation. That is, the soft tubular sheet member 12 serves as a means for guiding, through the hole, a tool to the cavity formed by the cavity securing means 11, and also forms a tool insertion channel.

A tubular operating member 17 serving as an operating portion extends through the soft tubular sheet member 12. The distal end of the operating member 17 is coupled to the ring-like member 13 of the cavity securing means 11. The operating member 17 is made of a pipe member considerably thinner than the ring-like member 13. The distal end portion of the operating member 17 expands to the width of the ring-like member 13 in the minor axis direction and is integrally coupled to the two side end portions of the ring-like member 13 in the minor axis direction. Opening window portions 18a and 18b for treatment are notched in the two side portions of the expanding distal end portion of the operating member 17 in the major axis direction of the ring-like member 13. The hole of the ring-like member 13 of the cavity securing means 11 communicates with the inside of the soft tubular sheet member 12 through the opening window portions 18a and 18b. The hole of the operating member 17 forms a channel 19 directly communicating with the hole of the cavity securing means 11. The channel 19 of the operating member 17 also communicates with the hole of the cavity securing means 11 to form a tool guide means through which a tool such as a scope extends. The operating member 17 is coupled to the ring-like member 13 of the cavity securing means 11 to form an operating means for reliably positioning the cavity securing means 11 at a predetermined position in the living body.

Figure 2:
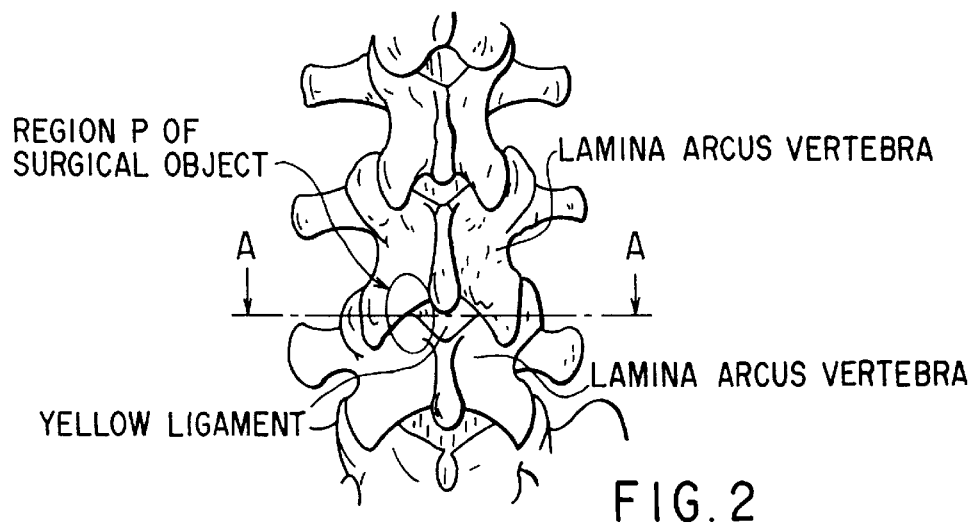
FIG. 2 is an anatomical chart of the human spine viewed from the back side.
Figure 3:
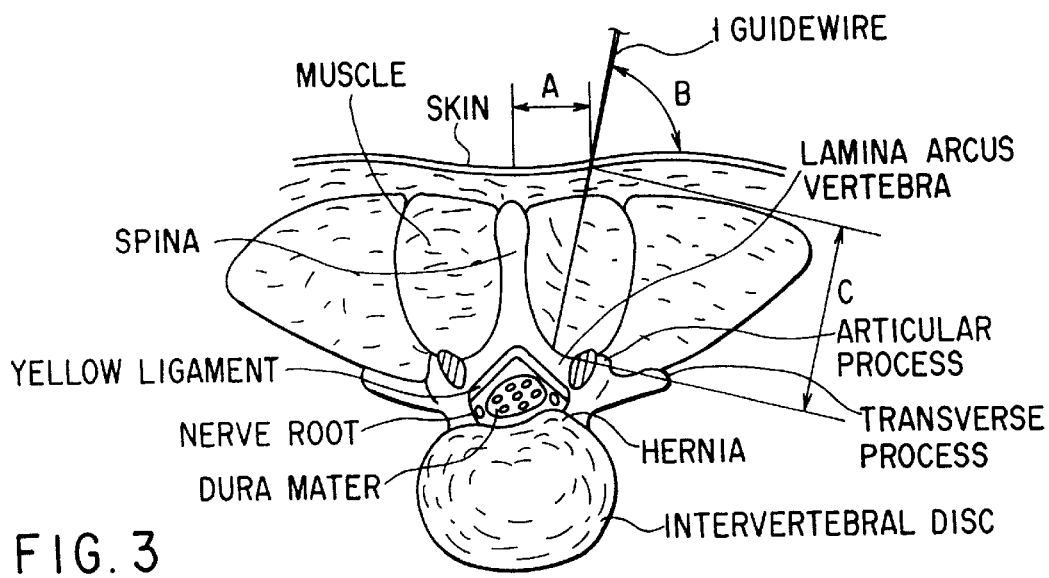
FIG. 3 is an anatomical chart taken along a line A—A in FIG. 2.

The function of this surgical operation cavity securing system in a method in which the system is applied to a surgical operation of accessing an intervertebral disc region from the back side of the human body and excising a hernia will be described next. FIG. 2 is an anatomical chart of the spine of the human body viewed from the back side. FIG. 3 is a sectional anatomical chart taken along a line A—A in FIG. 2.

As shown in FIG. 3, the operator inserts the guidewire 1 from the skin into the muscle, aiming at the center of a region P (see FIG. 2) of surgical object when viewed from the back side of the human body. At this time, the operator may make a small incision in the skin with a scalpel. The operator perforates the body and positions the guidewire 1 at a predetermined position in accordance with a distance A from the spina (or spinous process) to the perforating position, a perforating angle B, and a perforating depth C to the lamina arcus vertebra (or intervertebral disc) as shown in FIG. 3, which are obtained in advance from an X-ray image, a CT image, or the like obtained before the operation. After this perforating operation, the operator checks by X-ray fluoroscopy or the like whether the distal end of the guidewire 1 is properly located at the predetermined position. Note that perforating with the guidewire 1 may be performed under X-ray fluoroscopy.

Figure 4:
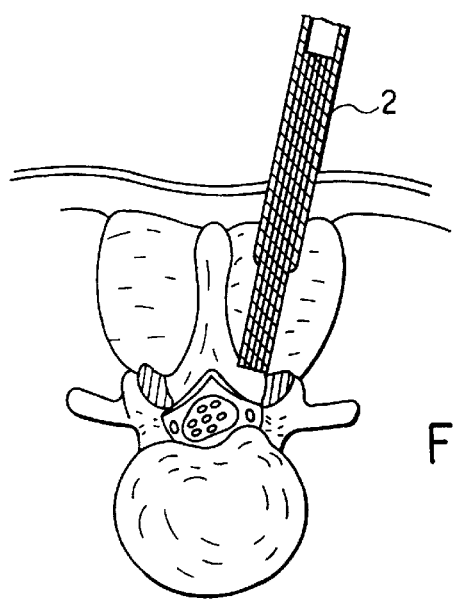
FIG. 4 is an anatomical chart showing a state in which the dilator of the surgical operation cavity securing system according to the first embodiment is inserted into tissue to a region of surgical object.
Figure 5:
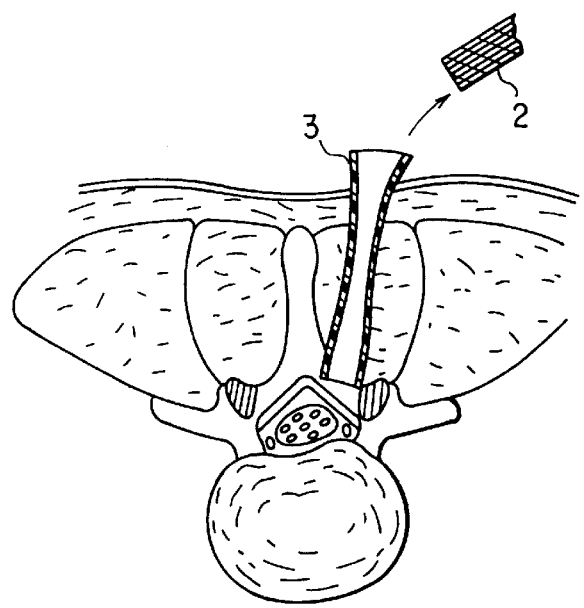
FIG. 5 is an anatomical chart showing a state in which the soft tube of the surgical operation cavity securing system according to the first embodiment is inserted into the tissue to the region of surgical object.

Subsequently, the first tube 7a is fitted on the inserted guidewire 1, and the distal end of the first tube 7a is inserted to the region P of surgical object of the tissue along the guidewire 1. Thereafter, the guidewire 1 is removed. As shown in FIG. 4, the thick tube 7b is fitted on the tube 7a having the smallest diameter, and the tubes 7c and 7d are sequentially fitted on the preceding tubes, respectively, thereby dilating the muscle to the outer diameter of the thick tube 7d. At this time, the muscle is dilated in the fiber direction of each layer, and is also torn and dilated along the fiber direction. The soft tube 3 is fitted on the thickest tube 7d of the dilator 2. The distal end of the soft tube 3 is inserted to the region P of surgical object. At this time, as shown in FIG. 5, only the dilator 2 is removed. As a result, the soft tube 3 is indwelled in the muscle.

As shown in FIG. 6, the operation sheath 4 is inserted into the body through the hole of the soft tube 3 as a guide means. The soft tube 3 is deformable. When, therefore, the soft tube 3 is indwelled in the muscle, the tube deforms to some degree under the pressure from the surrounding muscle. However, since the soft tube 3 is soft, the operation sheath 4 can be inserted into the body through the hole of the soft tube 3. If the soft tube 3 is resilient enough to leave a hole like the one shown in FIG. 5, insertion of the operation sheath 4 is facilitated.

When the operation sheath 4 is inserted into the body through the hole of the soft tube 3, the ring-like member 13 of the cavity securing means 11 of the operation sheath 4 does not deform, but the soft tube 3 so deforms as to conform to the outer shape of the ring-like member 13 including the folded portions 14a and 14b. That is, the ring-like member 13 including the folded portions 14a and 14b is inserted into the soft tube 3 in a tight state. In addition, since the soft tubular sheet member 12 is made of a soft sheet, the sheet member 12 is folded into a compact member when it is inserted. The sheet member 12 can be smoothly inserted into the soft tube 3.

When the ring-like member 13 of the operation sheath 4 is positioned to the region P of surgical object, only the soft tube 3 is removed. As a result, as shown in FIGS. 7A to 7C, the left soft tubular sheet member 12 is pressed by the surrounding muscle and clamped between the muscle layers torn in the fiber direction so as to be flattened. For example, FIG. 7B shows a cross-section taken along a line B—B in FIG. 7A, and FIG. 7C shows a cross-section taken along a line C—C in FIG. 7A. Since the folded portions 14a and 14b are locked to the muscle in the region P of surgical object, the ring-like member 13 of the cavity securing means 11 is reliably positioned and held. In addition, the folded portions 14a and 14b prevent tissue from entering the cavity held by the ring-like member 13, thereby securing a good visual field. The outer opening edge portion of the soft tubular sheet member 12 is kept expanded outside the body.

When the operation sheath 4 is dwelled in the muscle in the above manner, the cavity securing means 11 is positioned in the region P of surgical object to secure the cavity so as to form a working space in the region P. The soft tubular sheet member 12 forms a tool guide channel that causes the working space to communicate with the outside of the body. The channel 19 of the operating member 17 also forms a tool guide channel through which a tool extends to the working space. That is, the two channels constitute a tool guide means. Therefore, each portion of the tool guide means or a combination of the two portions is made more compact than the ring-like member 13 of the cavity securing means 11. For this reason, the tool guide means does not strongly push the muscle.

Figure 8A:
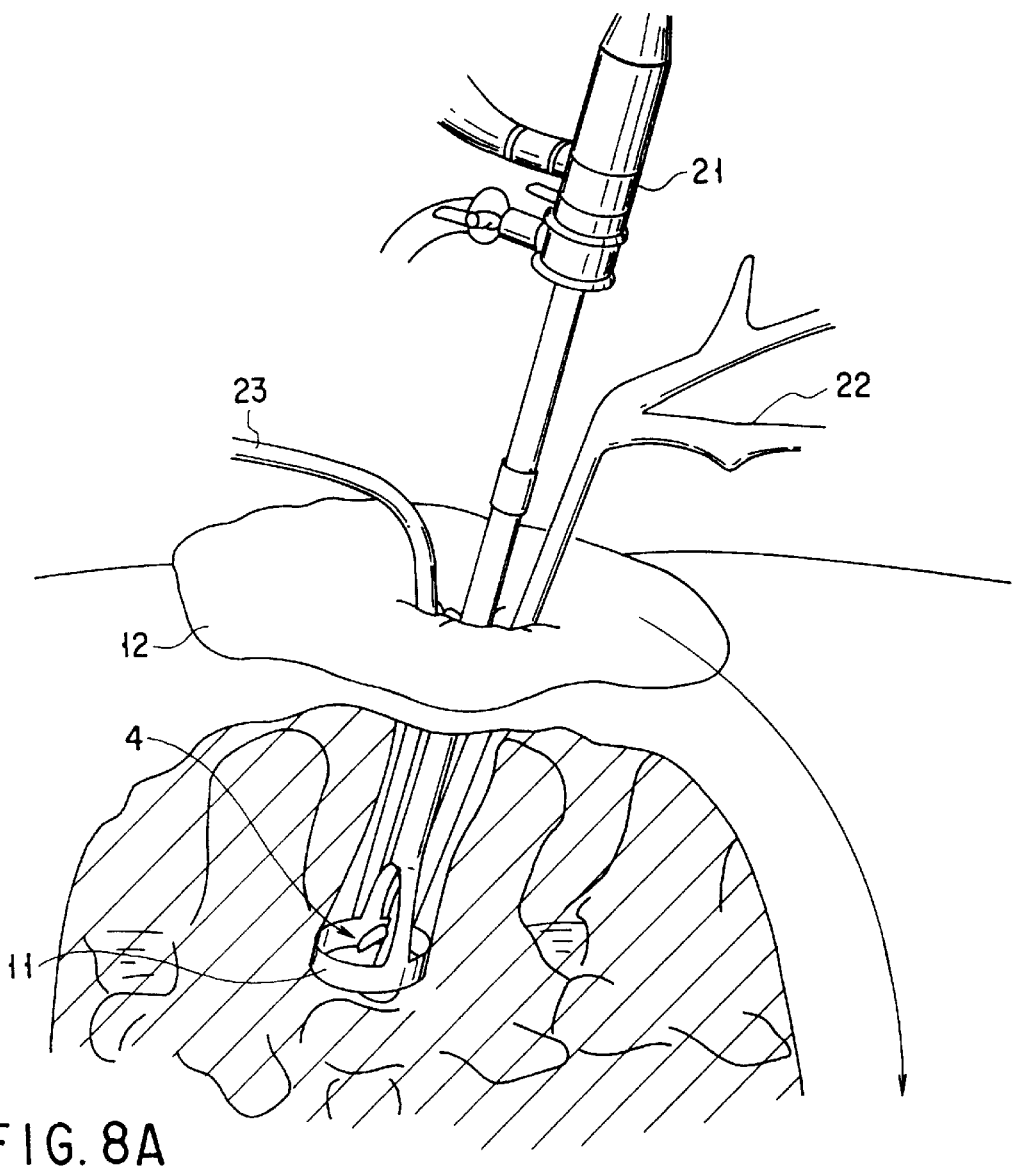
FIG. 8A is a view for explaining an operation state of the surgical operation cavity securing system according to the first embodiment.
Figure 8C:
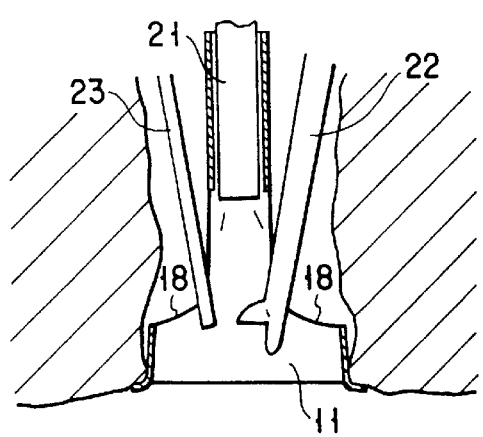
FIG. 8C is a view for explaining the state of a cavity in a working space.
Figure 8B:
FIG. 8B is a sectional view of a midway portion of the operation sheath.

FIG. 8A shows a state in which various tools inserted in the working area secured by the cavity securing means 11 through the soft tubular sheet member 12. In this case, a scope 21 with an irrigator is inserted through the insertion channel 19 of the operating member 17, and a curette 22 is inserted from one side of the opening of the flattened soft tubular sheet member 12. In addition, an aspirating pipe 23 is inserted from the other side of the opening of the flattened soft tubular sheet member 12. The respective tools are arranged in a line in the flattened soft tubular sheet member 12, as shown in FIG. 8B. The tools inserted from the two sides of the opening of the soft tubular sheet member 12 are inserted in the working space through the opening window portions 18a and 18b, as shown in FIG. 8C. In this case, since the soft tubular sheet member 12 does not restrict the movement of the tools, the tools can be obliquely inserted with ease, as shown in FIG. 8C. Therefore, the degree of freedom of the movement of tools is high, resulting in good operability. In addition, since the use of the soft sheet member allows insertion of a plurality of tools from one side, complicated operation can be efficiently performed. Note that when blood and the like collect in the working space, they can be drawn/discharged through the aspirating pipe 23.

When the approach angle to the site of operation is to be changed or the site of operation is to be slightly shifted, the position of the cavity securing means 11 with respect to the cavity in the tissue is changed to a given position by the operating member 17, and is held at the position. Since the scope 21 has the irrigator, a surgical operation may be performed while irrigation is performed with physiological saline or the like. With this operation, even if the site of operation bleeds, the site is washed, and the distal end of the scope 21 is not smeared with blood.

Figure 9:
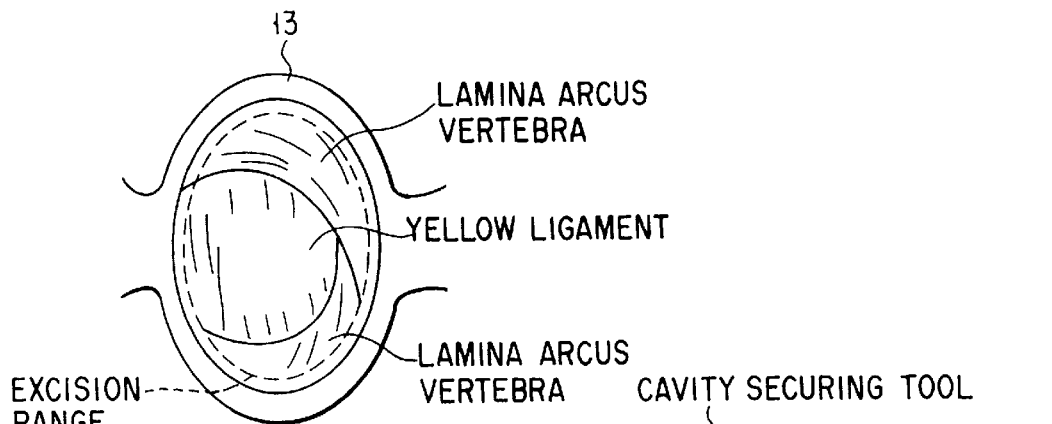
FIG. 9 is a view showing a visual field in which a working space in the region of surgical object secured by the operation sheath cavity securing means is observed with a scope.

FIG. 9 shows the visual field viewed when the working space in the region P of surgical object secured by the cavity securing means 11 is observed with the scope 21. The range indicated by the dashed line is an excision range.

Figure 10:
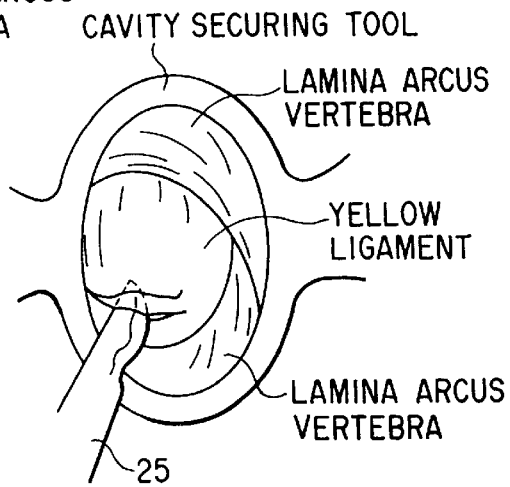
FIG. 10 is a view for explaining an excision procedure using the surgical operation cavity securing system.
Figure 11:
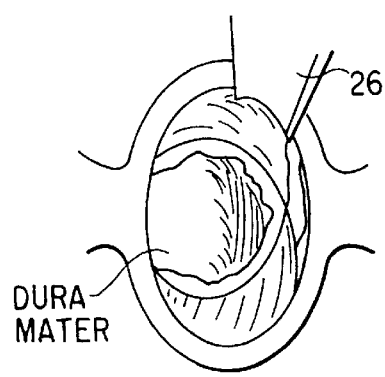
FIG. 11 is a view for explaining the excision procedure using the surgical operation cavity securing system.
Figure 12:
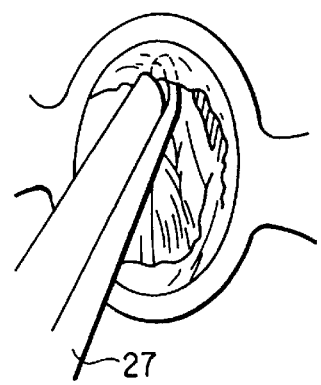
FIG. 12 is a view for explaining the excision procedure using the surgical operation cavity securing system.
Figure 13:
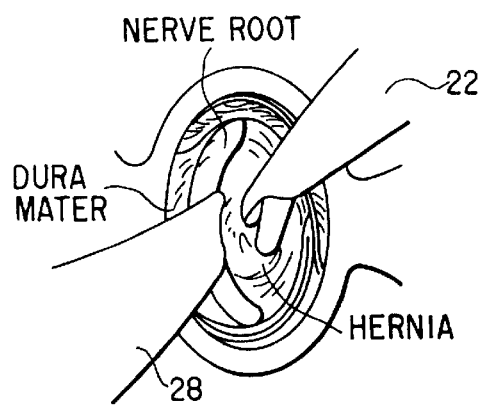
FIG. 13 is a view for explaining the excision procedure using the surgical operation cavity securing system.

An excision procedure will be described next. First of all, as shown in FIG. 10, the operator inserts a scalpel 25 into the site of operation through the soft tubular sheet member 12 and excises the yellow ligament. Thereafter, the operator removes the scalpel 25. As shown in FIG. 11, the operator inserts a drill or chisel 26 into the site to cut off the upper and lower lamina arcus vertebrae. In addition, as shown in FIG. 12, the operator cuts off the lamina arcus vertebra portion with a Kerison rongeur 27. As a result, the dura mater and the nerve root appear. As shown in FIGS. 13 and 14, the operator then inserts a nerve uncus 28 to move the dura mater and the nerve root altogether to one side, and excises the hernia of intervertebral disc with the curette 22 inserted from the other side. Alternatively, this operation may be performed by inserting a plurality of pairs of forceps from the same side.

Upon completion of this series of operations, the operator removes the operation sheath 4 from the body, and sutures the wound. The surgical operation is then complete.

Since the operation sheath 4 is constituted by the cavity securing means 11 and the soft tubular sheet member 12 communicating therewith, a working space having a necessary minimum size can be reliably ensured in only the region of surgical object in the living body by the ring-like member 13 of the cavity securing means 11. Since the soft tubular sheet member 12 does not push the muscle much, very little invasive effect is imposed on vital tissue. In addition, since the cavity securing means 11 is odd-shaped in accordance with the minimum necessary working space, only the necessary minimum area is occupied by the cavity securing means 11. As a result, the cavity securing means 11 does not push the tissue much. Therefore, pushing causes little damage to the back muscle, and unrecoverable damage to the back muscle can be avoided to a considerable extent. In addition, the amount of incision in the back muscle is small, and damage to the back muscle and the like can be reduced.

Furthermore, since the soft tube 3 serving as a guide means for guiding the odd-shaped ring-like member 13 is deformable, if the inner circumference of the soft tube 3 is set in accordance with the outer circumference of the ring-like member 13, the ring-like member 13 can be inserted. For this reason, the inner diameter of the soft tube 3 need not be set to be larger than the maximum diameter of the ring-like member 13 of the cavity securing means 11. The soft tube 3 can be thinned accordingly. The size of a perforation for the insertion of the soft tube 3 can be reduced. This also considerably reduces damage to the tissue.

Since the soft tubular sheet member 12 is made of a soft tube gradually expanding toward the outside of the body, a plurality of tools can be obliquely inserted into the soft tubular sheet member 12. In addition, since the soft tubular sheet member 12 is soft, the degree of freedom of the movement of the inserted tools is high, resulting in good operability. Even if, therefore, a plurality of tools are inserted at once, they do not interfere with each other. Furthermore, a plurality of tools can be inserted and used at once, resulting in convenience. Moreover, since the soft tubular sheet member 12 communicates with the cavity and serves as a guide for the insertion of a tool into the cavity, insertion/removal of tools is facilitated.

The operating member 17 extending to the outside of the body is placed as a position holding means in the operation sheath 4. The approach angle to a cavity, the position of the cavity, and the like can be set and changed through the operating member 17.

The operating member 17 is located in the center of a cavity, and the channel 19 is formed in the center of the operating member 17. When the scope 21 is inserted into the channel 19, tools such as forceps can be inserted from the two sides of the scope 21, the scope 21 hardly interferes with the tools located on the two sides, resulting in good operability.

The ring-like member 13 has the folded portions 14a and 14b as position holding means. These portions are caught on tissue to position the ring-like member 13. Once a cavity is secured, therefore, a positional shift from the cavity does not easily occur. In addition, the folded portions 14a and 14b prevent unnecessary tissue from entering the cavity, and hence can secure a necessary visual field and working space.

A path is formed within the body by the dilator 2 serving as an insertion tool, and the operation sheath 4 having a soft sheet is indwelled in the path. In forming a path by the dilator 2, a hole is formed by dilation without cutting the tissue, and the soft tubular sheet member 12 that does not push the tissue much is used. A very little invasive effect is therefore imposed on the tissue.

In this case, the soft tubular sheet member 12 need not be elastically extensible, but may be made of an elastic material.

In this system, when no tool insertion path is to be formed, a member like a port 64 in FIG. 29C (to be described later) may be inserted into a cavity upon penetration of a soft sheet through the tissue, and a tool may be inserted into the member. Alternatively, a tool may directly penetrate the soft sheet through the tissue along another path to be inserted into the cavity. Thereafter, an operation may be performed.

[Second Embodiment]

Figure 17:
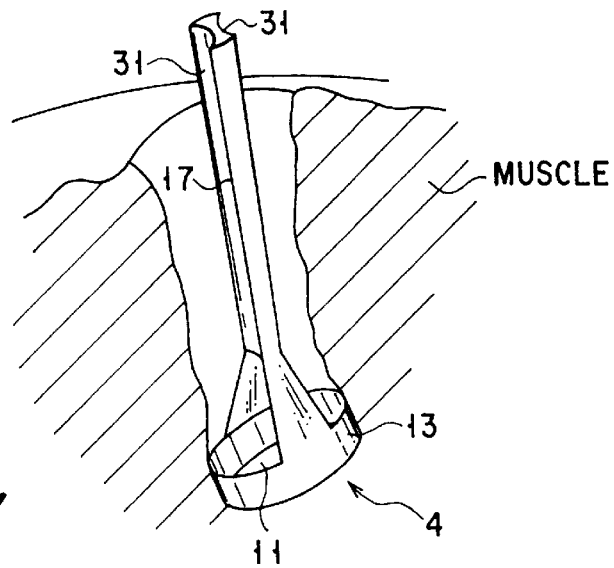
FIG. 17 is a perspective view showing still another example of the operation sheath according to the second embodiment.

The second embodiment of the present invention will be described with reference to FIGS. 15 to 17. The second embodiment includes modifications of the operating portion of the operation sheath 4 in the first embodiment described above. FIGS. 15 to 17 respectively show the different modifications.

In the modification shown in FIG. 15, an operating member 17 connected to a ring-like member 13 of a cavity securing means 11 is offset to one side of the ring-like member 13 in the major axis. An opening window portion 18 of an insertion channel 19 communicates with the hole of the cavity securing means 11. In this case, when a scope 21 is inserted into the channel 19, since the channel 19 is offset, a relatively large tool can be inserted into the cavity through a soft tubular sheet member 12.

In the modification shown in FIG. 16, the operating member 17 connected to the ring-like member 13 of the cavity securing means 11 is made of a plate-like member instead of a tubular member, and the position where the operating member 17 is connected to the ring-like member 13 of the cavity securing means 11 is offset to one side of the ring-like member 13 as in the above case. The operating member 17 has a tool guide surface 31 with a recess portion formed on the surface facing inward in the cavity securing means 11. FIG. 16 shows a state in which the operating member 17 is bent after it is inserted into the body. The soft tubular sheet member 12 is joined to the ring-like member 13 by binding the distal end portion of the member 12 fitted on the ring-like member 13 with a string 32. The joint portion with the string 32 may be coated with an adhesive to be hardened. A tool 33 is inserted into an operation sheath 4 along the guide surface 31 of the operating member 17. With this structure, the tool 33 can be easily and reliably introduced into the operation sheath 4.

In the modification shown in FIG. 17, the operating member 17 connected to the ring-like member 13 of the cavity securing means 11 is made of a plate-like member instead of a tubular member, and the position where the operating member 17 is connected to the ring-like member 13 of the cavity securing means 11 coincides with the center of the ring-like member 13. Tool guide surfaces 31 with recess portions are formed on the upper and lower surfaces of the plate-like operating member 17. In this case, since the operation sheath 4 has the operating member 17 serving as a tool guide means, the soft tubular sheet member 12 described above is not used. Obviously, however, the soft tubular sheet member 12 may be used.

In this embodiment as well, since the operating member 17 is smaller in size than the cavity securing means, tools can be easily inserted along the guide surfaces 31 without strongly pushing the muscle.

[Third Embodiment]

Figure 18:
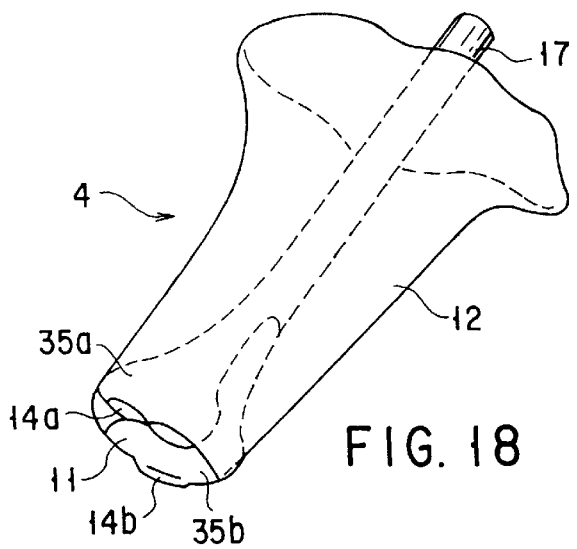
FIG. 18 is a perspective view showing an operation sheath according to the third embodiment.
Figure 19A:
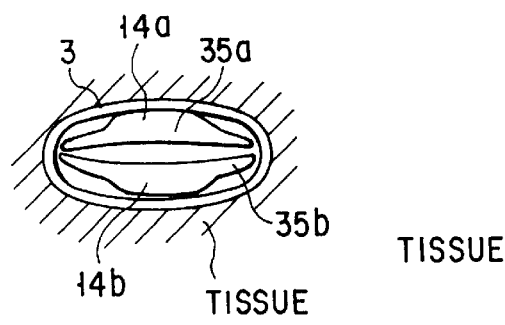
FIG. 19A is a cross-sectional view showing a state in the process of inserting the operation sheath according to the third embodiment into tissue.
Figure 19B:
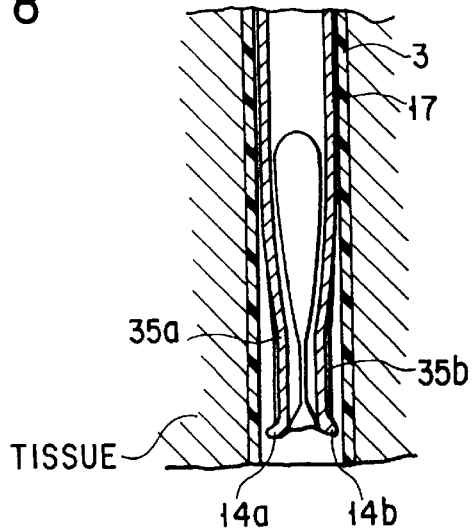
FIG. 19B is a longitudinal sectional view showing the same state.
Figure 20:
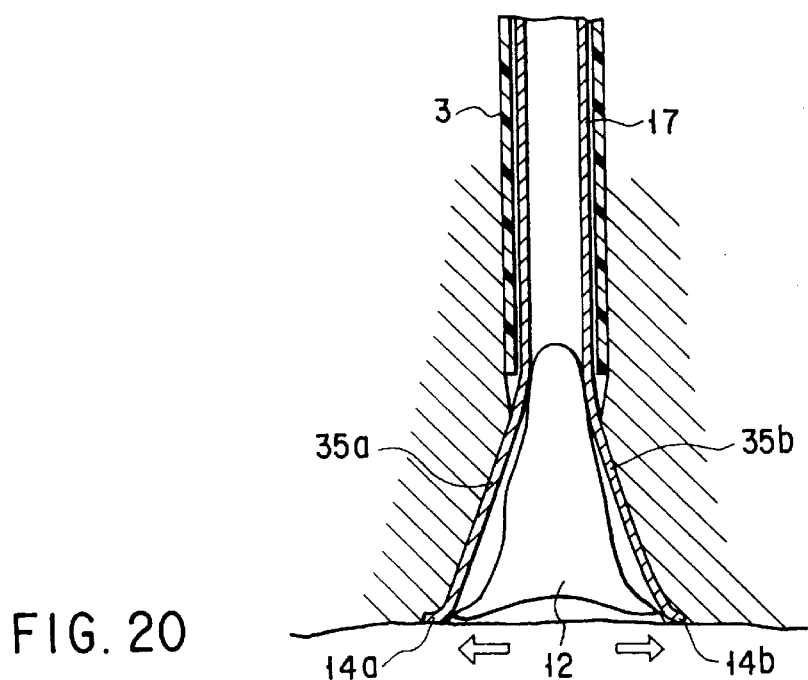
FIG. 20 is a cross-sectional view showing a state in the process of inserting the operation sheath according to the third embodiment is inserted into the tissue.

The third embodiment of the present invention will be described with reference to FIGS. 18 to 20. The third embodiment includes a modification of the cavity securing means 11 of the operation sheath 4 in the first embodiment described above. The third embodiment is identical to the first embodiment except for the cavity securing means 11. A cavity securing means 11 in this embodiment is constituted by two plate (or flap)-like members 35a and 35b that continuously extend from the distal end of an operating member 17 and oppose each other. The pair of leg-like members 35a and 35b constitute a cavity securing member. The plate-like members 35a and 35b are joined/bonded to the inner surface of the distal end portion of a soft tubular sheet member 12. Folded portions 14a and 14b are respectively formed on the distal ends of the plate-like members 35a and 35b. The pair of tongue-like members 35a and 35b are elastically formed to expand to at least the same degree as the shape of the ring-like member 13 described above.

An operation sheath 4 of this embodiment is used in the same manner as in the first embodiment. When, however, the operation sheath 4 is to be inserted into a soft tube 3, the gap between the two plate-like members 35a and 35b is narrowed, as shown in FIGS. 19A and 19B. When the plate-like members 35a and 35b reach the region of surgical object, and the guide soft tube 3 is pulled up, the plate-like members 35a and 35b elastically spread to dilate the tissue portion so as to secure a working space, as shown in FIG. 20. That is, the cavity securing means 11 serves both as a cavity securing means and a cavity dilating means.

According to this operation sheath 4, when the cavity securing member is to be inserted into the body, the plate-like members 35a and 35b constituting the cavity securing member can be inserted in a compact state. Both the operation sheath 4 and the soft tube 3 can be reduced in diameter, and hence the invasive effect on the vital tissue can be reduced. When this technique is applied to osteotomy, since the two plate portions spread to secure a cavity, the muscle on the surface of the bone can be retracted altogether.

[Fourth Embodiment]

The fourth embodiment of the present invention will be described with to FIGS. 21 to 24. The fourth embodiment includes a modification of the guide means for guiding the operation sheath 4.

Figure 21:
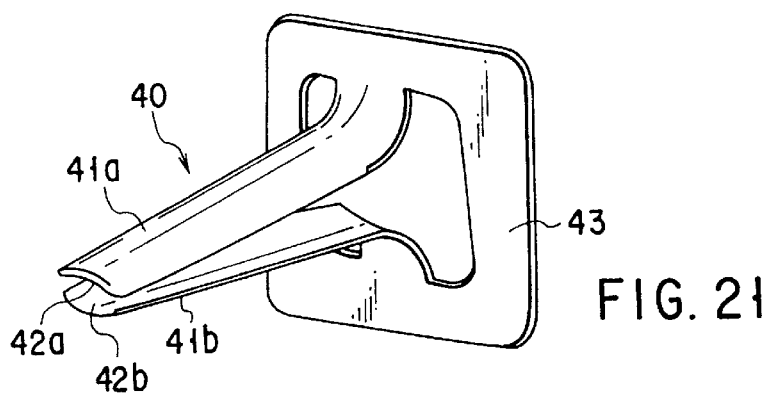
FIG. 21 is a perspective view showing a guide means for guiding the operation sheath according to the third embodiment.
Figure 22:
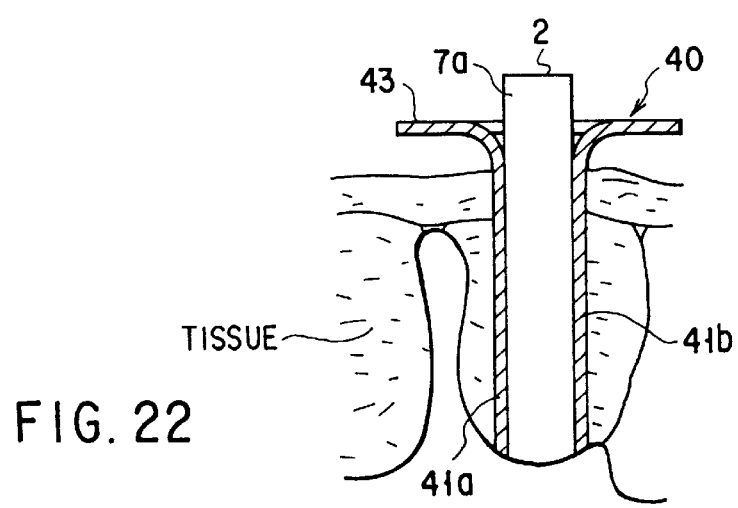
FIG. 22 is a sectional view showing how the guide means is used.

As shown in FIG. 21, a guide means 40 for guiding an operation sheath 4 is constituted by a pair of plate-like (or flap-like) guide members 41a and 41b opposing each other. Guide surfaces 42a and 42b are respectively formed on the opposing inner surfaces of the guide members 41a and 41b. Each of the guide surfaces 42a and 42b has an arcuated cross-section, and the envelope of each surface is cylindrical.

The guide members 41a and 41b are integrally formed with a rectangular ring-like board 43. The guide members 41a and 41b are normally biased by their own elasticity or the elasticity of the board 43 such that the gap between the distal end portions is narrowed, as shown in FIG. 21.

Figure 23:
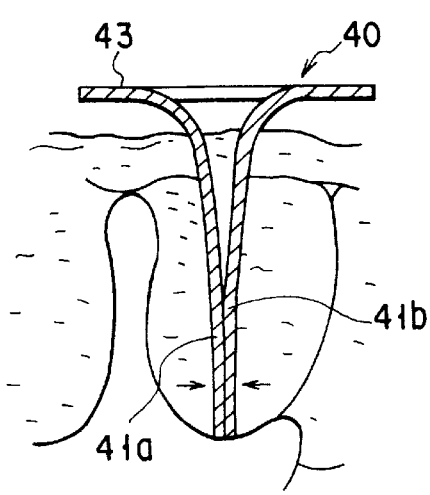
FIG. 23 is a sectional view showing how the guide means is used.
Figure 24:
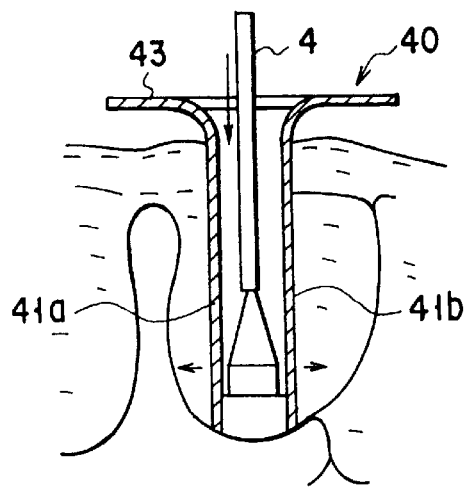
FIG. 24 is a sectional view showing how the guide means is used.

When this guide means 40 is to be used, the guide members 41a and 41b are spread and fitted on a last tube 7d of a dilator 2. The guide members 41a and 41b are then pushed and inserted into the tissue. Thereafter, the dilator 2 is removed. As a result, the guide members 41a and 41b are gathered together owing to the pressure from the tissue, as shown in FIG. 23. After this, as shown in FIG. 24, the operation sheath 4 described above is inserted between the guide members 41a and 41b and inserted along the guide surfaces 42a and 42b. The guide members 41a and 41b spread by a necessary amount in accordance with the size of the operation sheath 4, and guides the operation sheath 4 to a predetermined position in the living body while retracting the tissue. Thereafter, the guide members 41a and 41b are removed while the operation sheath 4 is left, and the same operation as described above is performed.

With the use of the guide means 40 in this embodiment, after the two guide surfaces 42a and 42b spread to retract the tissue such as the muscle on the surface of the bone altogether, the operation sheath 4 can be inserted and indwelled in the body. A clear visual field can therefore be obtained when the operation sheath 4 is inserted.

[Fifth Embodiment]

Figure 25A:
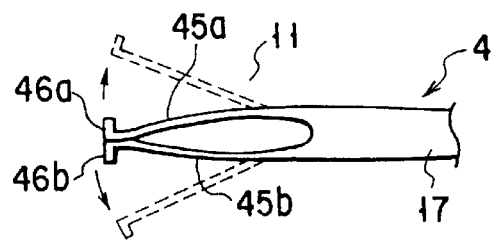
FIG. 25A is a side view showing the distal end portion of an operation sheath according to the fifth embodiment.
Figure 25B:
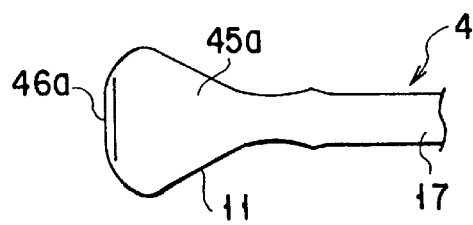
FIG. 25B is a plan view showing the distal end portion of the operation sheath.
Figure 26:
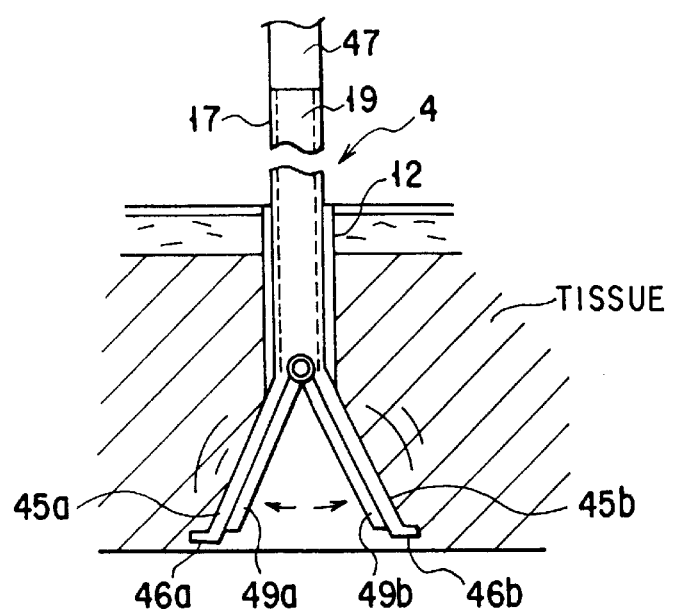
FIG. 26 is a view for explaining how the operation sheath according to the fifth embodiment is inserted into tissue.

The fifth embodiment of the present invention will be described with reference to FIGS. 25A to 26. The fifth embodiment includes a modification of the operation sheath 4 in the first embodiment described above. In this embodiment, a cavity securing means 11 of an operation sheath 4 is constituted by a pair of cavity securing plate-like members 45a and 45b facing each other and formed on the distal end of an operating member 17 made of a tubular member. As shown in FIG. 25B, each of the cavity securing plate-like members 45a and 45b has a width larger than the diameter of the operating member 17. Folded portions 46a and 46b extending in opposite directions are respectively formed on the distal ends of the cavity securing plate-like members 45a and 45b. Each of the cavity securing plate-like members 45a and 45b is made of a material capable of plastic deformation. Note that the distal end portions of the cavity securing plate-like members 45a and 45b are joined to the inner surface of the distal end of a soft tubular sheet member 12.

When the operation sheath 4 in this embodiment is to be used, the operation sheath 4 is inserted into vital tissue through a soft tube 3. When the cavity securing plate-like members 45a and 45b are positioned to a predetermined cavity securing site from the distal end of the soft tube 3, a cavity dilating tool 47 is inserted into the tissue through a channel 19 of the operating member 17 to spread the cavity securing plate-like members 45a and 45b. The spread cavity securing plate-like members 45a and 45b push/open the vital tissue, and undergo plastic deformation, thereby securing a working space inside the cavity securing plate-like members 45a and 45b, as shown in FIG. 26.

The cavity dilating tool 47 is obtained by forming a pair of operating pieces 49a and 49b, which spread laterally, on the distal end of an insertion member 48. The pair of operating pieces 49a and 49b are manually spread laterally to push/spread the cavity securing plate-like members 45a and 45b.

In this embodiment, the size of a working space can be adjusted. It suffices if the cavity securing plate-like members 45a and 45b are spread by a necessary amount.

19

[Sixth Embodiment]

The sixth embodiment of the present invention will be described with reference to FIGS. 27A to 28C. The sixth embodiment includes a piercing tool 50 in place of the dilator 2 in the first embodiment described above.

As shown in FIG. 27A, the piercing tool 50 has a cylindrical main insertion portion 51 having a scope channel formed inside. A hemispherical, transparent window member 52 is formed on the distal end portion of the main insertion portion 51. A fluoroscopic view of a portion ahead of the window member 52 can be obtained with a scope (not shown) inserted into the scope channel through the window member 52. A linear energizing portion 53 made of a conductive wire is formed on the outer surface of the window member 52, thus constituting an electric scalpel for incising perforated tissue. A high-frequency current is supplied from a high-frequency power supply 55 to the energizing portion 53 through a power cord 54 extending from the proximal end portion of the main insertion portion 51. A hand switch 56 for controlling energization is formed on the proximal end portion of the main insertion portion 51. A switch portion 57 may be detachably mounted on the main insertion portion 51. Alternatively, a foot switch may be used as a switch for controlling energization.

An operation sheath mount portion 58 is formed on the circumferential portion of the distal end of the main insertion portion 51. The operation sheath mount portion 58 is thinner than the remaining portion. The operation sheath mount portion 58 is inserted into the ring-like member 13 of the operation sheath 4 having the decentered operating member 17 in FIG. 15, thus mounting the operation sheath 4.

A case in which the operation sheath 4 is introduced into the region of surgical object by using the piercing tool 50 will be described next. First of all, as shown in FIG. 27B, the operation sheath 4 is mounted on the piercing tool 50 by fitting the ring-like member 13 on the operation sheath mount portion 58 of the piercing tool 50. The exposed window member 52 on the distal end of the piercing tool 50 is pushed into the muscle to perforate it. At this time, the energizing portion 53 is energized first to perforate the muscle. Once the window member 52 is inserted into the muscle, the muscular fiber is torn apart in the fiber direction by the window member 52 having the hemispherical, transparent outer surface, thereby allowing insertion of the piercing tool 50. Assume that the distal end of the piercing tool 50 reaches a different tissue layer and comes into contact with a hard tissue such as a fascia, and hence cannot be pushed into the tissue. In this case, the operator adjusts the direction of the energizing portion 53 to the fiber direction while observing the muscular fiber direction with a scope, and energizes the energizing portion 53 to incise the fascia or the like and perforate it. With this operation, the fascia is torn to allow insertion of the piercing tool 50 again. In this manner, the piercing tool 50 can be inserted to a predetermined depth through a plurality of different muscle layers. Since the piercing tool 50 is inserted without cutting the muscle, perforating operation causes little damage to the muscle. In addition, when the tissue bleeds in a perforating process, the bleeding can be stopped by supplying a high-frequency current to the energizing portion 53, i.e., performing a high-frequency coagulation process. In addition, the ligament tissue clinging to the surface of a bone may be incised by a high-frequency current. When the operation sheath 4 is inserted into the region of surgical object and indwelled therein, the piercing tool 50 is removed.

FIG. 28A shows a state in which the operation sheath 4 is successfully indwelled in the region of surgical object in this manner. In this state, a cavity as a working space is secured in the region of the treatment side by the ring-like member 13. A soft tubular sheet member 12 lies across different muscle layers. In this state, the soft tubular sheet member 12 is compressed by the surrounding muscle tissues and clamped between the muscle tissues torn in the fiber direction in the respective layers to be flattened. FIG. 28B shows a cross-section taken along a line B—B in FIG. 28A. FIG. 28C shows a cross-section taken along a line C—C in FIG. 28A. The muscular fibers are not therefore cut. In addition, since a soft sheet is placed on the muscular fibers, the pushing effect on the muscle is little. This further reduces damage to the muscle. In this method, tubes need not be repeatedly fitted on each other unlike in the method using the dilator 2 in the first embodiment.

This piercing tool 50 may be used in the following manner. First of all, the piercing tool 50 is inserted into the tissue independently of the soft tubular sheet member 12. The soft tube 3 is then fitted on the main insertion portion 51 in place of the dilator 2.

[Seventh Embodiment]

The seventh embodiment of the present invention will be described with reference to FIGS. 29A to 32. FIGS. 29A to 29D show the tools belonging to a surgical operation cavity securing system according to the seventh embodiment. Referring to FIG. 29A, reference numeral 61 denotes an operation sheath; 62, a cavity delating tool; 63, an inner wire; 64, a port; and 65, a port guide.

The operation sheath 61 is made of a pipe member 66 with a uniform diameter. A pair of split cavity securing pieces 67a and 67b opposing each other are formed on the distal end portion of the operation sheath 61. The cavity securing pieces 67a and 67b constitute a cavity securing means 68. As shown in FIG. 29A, the pair of cavity securing pieces 67a and 67b can be spread apart upon plastic deformation of the root portions of the cavity securing pieces 67a and 67b. The hole of the pipe member 66 forms a channel into which a scope 69 or the like is to be inserted. A fitting portion 71 is formed on the proximal end portion of the pipe member 66. A member of the port guide 65 constituted by small-diameter stepped portions is fitted on the fitting portion 71.

The cavity delating tool 62 can be inserted into the channel of the cavity securing means 68. A pair of operating pieces 72a and 72b that spread laterally are formed on the distal end of the cavity delating tool 62. The pair of operating pieces 72a and 72b are manually spread laterally to push/spread the cavity securing pieces 67a and 67b. Note that the number of cavity securing pieces is not limited to that described above.

The inner wire 63 can be tightly inserted into the channel of the cavity securing means 68. In addition, the inner wire 63 is inserted such that a perforating portion 73 on the distal end of the inner wire 63 protrudes from the distal end of the cavity securing means 68. The inner wire 63 can similarly be inserted and mounted in the pipe-like port 64.

The port guide 65 includes a pair of clamping members 75a and 75b. The pair of clamping members 75a and 75b are pivotally supported to be freely opened/closed. A reference guide hole 76a is formed in the inner surfaces of the clamping members 75a and 75b at a middle position. In addition, first and second guide holes 76b and 76c are formed on the two sides of the reference guide hole 76a. The operation sheath 61 can be clamped or the port 64 or the like can be guided through each of the reference guide hole 76a, the first guide hole 76b, and the second guide hole 76c that are formed when the pair of clamping members 75a and 75b are closed. The reference guide hole 76a is formed to be vertical to the port guide 65. The first and second guide holes 76b and 76c are inclined such that the center axes cross the extended line of the center axis of the reference guide hole 76a at one point. In addition, the extended lines connecting this point and the guide holes 76a, 76b, and 76c pass through the cavity securing means 68.

The function of the surgical operation cavity securing system of this embodiment. When the operation sheath 61 is to be inserted into the tissue, the inner wire 63 is inserted into the operation sheath 61. The perforating portion 73 is caused to protrude from the distal end of the closed cavity securing means 68. The perforating portion 73 is then inserted into the tissue such as muscle. When the cavity securing means 68 reaches the predetermined region of surgical object, the inner wire 63 is removed, and the cavity delating tool 62 is inserted instead. The pair of operating pieces 72a and 72b of the cavity delating tool 62 are manually spread to spread the cavity securing pieces 67a and 67b, thereby securing a cavity as a working space, as shown in FIG. 30.

The reference guide hole 76a of the port guide 65 is positioned and fitted on the fitting portion 71 of the operation sheath 61, and the port guide 65 is positioned to the operation sheath 61. At this time, the extended lines of the center axes of the first and second holes 76b and 76c of the port guide 65 are located at the center of the cavity formed by the cavity securing pieces 67a and 67b of the operation sheath 61.

A case in which the ports 64 are set by using the first and second guide holes 76b and 76c of the port guide 65 will be described. As indicated by the left side in FIG. 31, the port 64 in which the inner wire 63 is inserted is inserted into the tissue through the first guide hole 76b. As indicated by the left side in FIG. 31, the inner wire 63 is then positioned in the cavity formed by the operation sheath 61. In this manner, all the extended lines of the center axes of the reference guide hole 76a, the first guide hole 76b, and the second guide hole 76c of the port guide 65 are positioned in the cavity formed by the operation sheath 61. Thereafter, the guide members such as the inner wire 63 are removed, and tools are inserted into the cavity thorough the respective ports 64. The operator then performs an operation.

As shown in FIG. 32, therefore, various tools such as the scope 69, a curette 77, and other treatment tools 78 can be separately inserted into the tissue, and each tool can be positioned in the cavity secured/formed by the operation sheath 61.

In addition, since the respective tools are separately inserted into tissue through multiple holes, each insertion hole is small, and damage to the tissue is small. In addition, the pushing effect on the tissue is little, and hence damage to the tissue is small. Furthermore, since tools are inserted from separate positions, the tools do not so interfere with each other, resulting in good operability.

Since the operation sheath 61 in this embodiment requires only a small insertion hole, and forms a large cavity inside the sheath, a good site of operation can be obtained with a minimum invasive effect. In addition, according to this system, an operation sheath that elastically expands like the one shown in FIG. 18 can be used.

Note that the operation sheath 61 or the port 64 may be introduced into tissue by using a guide means like the soft tube 3 that is inserted in advance by using the inner wire or the dilator as in the first embodiment. In addition, the number of guide holes of the port guide 65 is not limited to three, and the port guide 65 may have two or four or more holes.

[Eighth Embodiment]

The eighth embodiment of the present invention will be described with reference to FIGS. 33A to 44. FIG. 33 shows an operation sheath 80 belonging to a surgical operation cavity securing system. The operation sheath 80 includes a cavity securing means 81 and a soft tubular sheet member 82 serving as a tool guide means connected thereto. The cavity securing means 81 is formed to be capable of plastic deformation using a ring-like member 83 made of a belt-like member having a mesh structure. It is conceivable that the ring-like member 83 may use one of the mesh structures shown in FIGS. 34A to 36B.

Figures 34A, 34B:
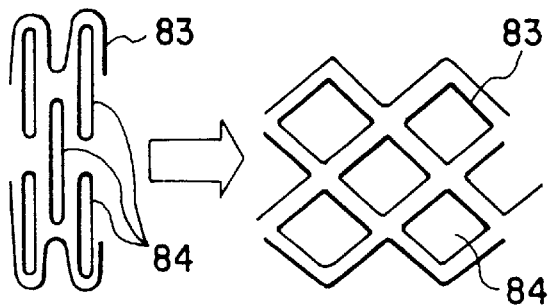
FIGS. 34A and 34B are perspective views showing an example of the ring-like member of the operation sheath according to the eighth embodiment.

FIGS. 34A and 34B show a notch structure having a plurality of slit-like notches 84 arranged in a staggered pattern. Owing to plastic deformation, either the compressed state shown in FIG. 34A or the expanded state shown in FIG. 34B can be held.

Figures 35A, 35B:
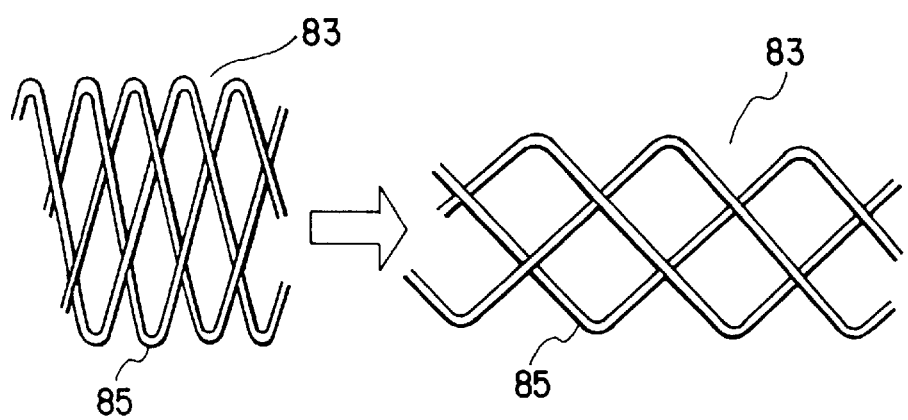
FIGS. 35A and 35B are perspective views showing another example of the ring-like member of the operation sheath according to the eighth embodiment.

FIGS. 35A and 35B show the structure obtained by weaving wire members 85. Owing to plastic deformation, either compressed state shown in FIG. 35A or the expanded state shown in FIG. 35B can be held.

Figures 36A, 36B:
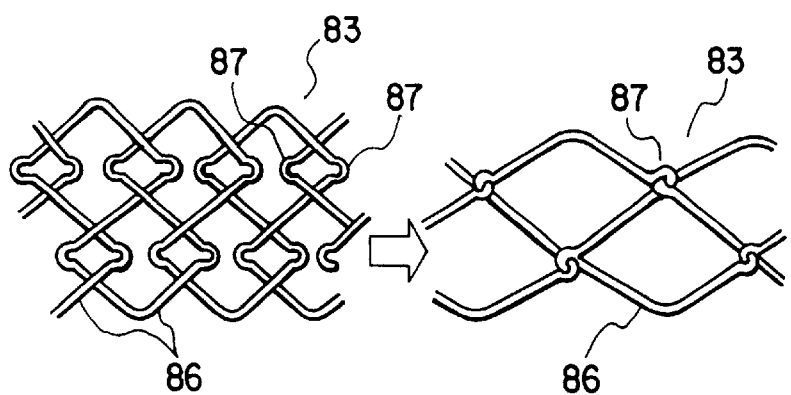
FIGS. 36A and 36B are perspective views showing still another example of the ring-like member of the operation sheath according to the eighth embodiment.

FIGS. 36A and 36B show the structure obtained by combining and weaving wire members 86. In this structure, lock portions 87 are formed at the intersections of the wire members 86. The structure is compressed while the lock portions 87 are unlocked, as shown in FIG. 36A, and is expanded while the lock portions 87 are locked, as shown in FIG. 36B. Although the wire members 86 themselves are not capable of plastic deformation, the respective states can be held as a whole.

Although not shown, the cavity securing means 81 may include a plate-like member having a circular or elliptic folded portion, or may include a substantially ring-like member having a portion with a mesh structure.

The soft tubular sheet member 82 serving as a tool guide means is similar to the soft tubular sheet member 12 in the first embodiment, and is used in a similar manner. The small-diameter portion of the distal end of the soft tubular sheet member 82 is connected to the ring-like member 83 of the cavity securing means 81. The hole of the soft tubular sheet member 82 communicates with the hole of the ring-like member 83. A plurality of tool introduction holes 88 are formed in the distal end portion of the soft tubular sheet member 82 to be adjacent to the ring-like member 83. Tools such as a scope 91 and a port 92 can be introduced into the hole of the cavity securing means 81 through the tool introduction holes 88.

Figure 37A:
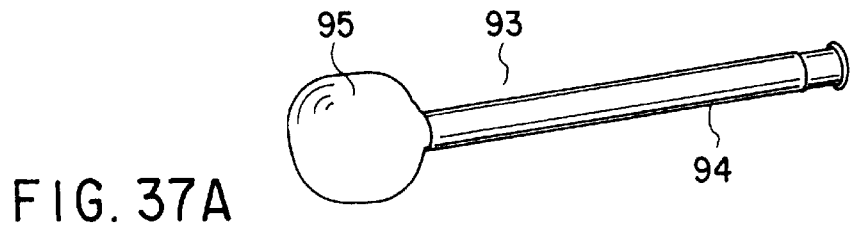
FIGS. 37A and 37B are perspective views showing a cavity dilating tool according to the eighth embodiment.
Figure 37B:
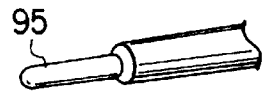
Figure 37C:
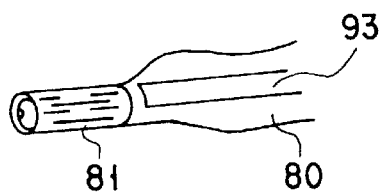
FIG. 37C is a perspective view showing a state in which the operation sheath is fitted on the cavity dilating tool.

FIGS. 37A to 37C show a cavity delating tool 93 as another tool belonging to the surgical operation cavity securing system. The cavity delating tool 93 includes an insertion tube 94 forming a tube path. A balloon 95 serving also as a mount portion on which the operation sheath 80 is to be mounted is formed on the distal end portion of the insertion tube 94. FIG. 37A shows the inflated state of the balloon 95. FIG. 37B shows the deflated state of the balloon 95. FIG. 37C shows a state in which the operation sheath 80 is mounted on the cavity delating tool 93.

Figures 38A, 38B:
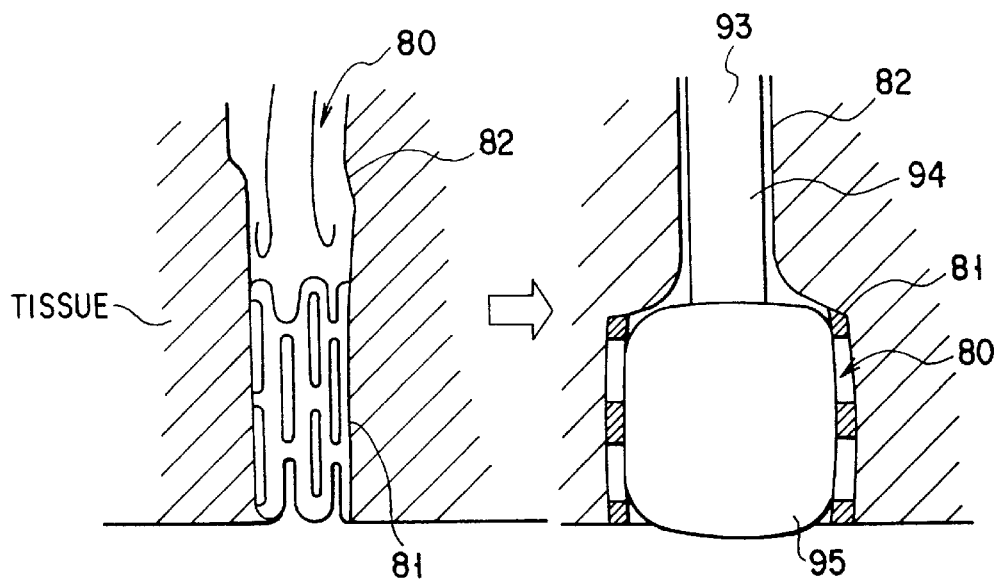
FIGS. 38A and 38B are views for explaining how the operation sheath according to the eighth embodiment is inserted into the tissue.

When the operation sheath 80 is to be used, the soft tube 3 in the first embodiment is inserted into tissue first, and the operation sheath 80 is then inserted into the tissue through the soft tube 3 as a guide. The cavity delating tool 93 having the deflated balloon 95 is inserted into the operation sheath 80 to prepare for insertion of the operation sheath 80 into tissue. A portion of the deflated balloon 95 is fitted in the compressed ring-like member 83, as shown FIG. 37C. The operation sheath 80 mounted on the cavity delating tool 93 is inserted into the soft tube 3, and the cavity securing means 81 of the operation sheath 80 is inserted to a predetermined position. When the cavity securing means 81 is located at the predetermined position, the soft tube 3 is removed. As a result, as shown in FIG. 38A, the operation sheath 80 is indwelled in the tissue. When a fluid is supplied into the balloon 95 through the tube path of the cavity delating tool 93 to inflate the balloon 95, the cavity securing means 81 is expanded more than the remaining portion, thereby securing a cavity inside the ring-like member 83 and forming a working space. Thereafter, the balloon 95 is deflated, and the cavity delating tool 93 is removed from the operation sheath 80. An operation similar to that in the first embodiment described above can be performed by using the operation sheath 80. In addition, in this case, recesses/projections are formed outside the mesh owing to the expanded mesh and the gaps between the mesh elements so as to form a position holding (positioning) means. The tissue is engaged with the recesses/projections to fix the operation sheath 80 to the tissue.

Figure 39:
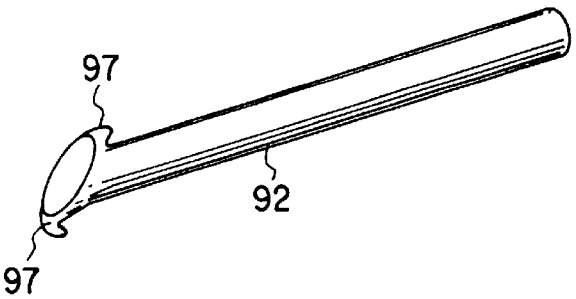
FIG. 39 is a perspective view showing a port according to the eighth embodiment.
Figure 40:
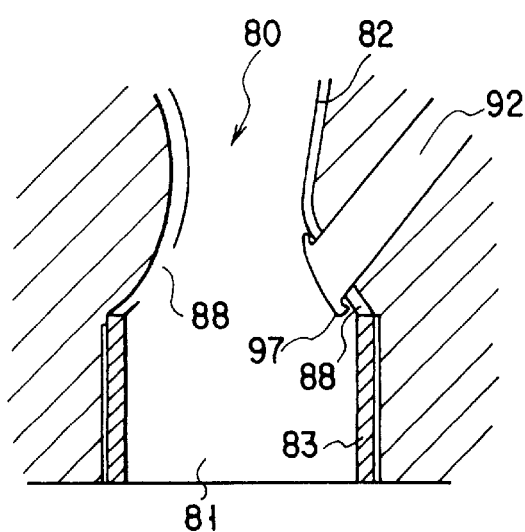
FIG. 40 is a sectional view showing a state in which the operation sheath and the port according to the eighth embodiment are inserted into the tissue.
Figure 42:
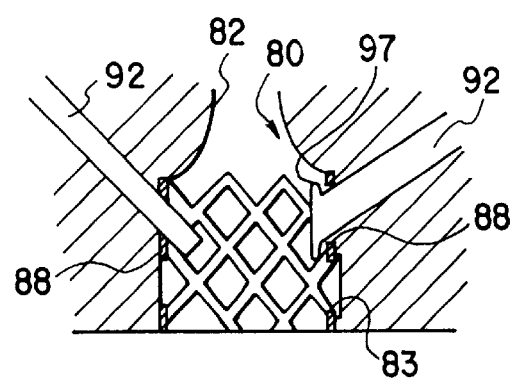
FIG. 42 is a view for explaining how an operation is performed upon insertion of the operation sheath and the port according to the eighth embodiment into the tissue.

Treatment like the one performed by the system having the porous structure in the seventh embodiment can be performed by using the operation sheath 80 of this embodiment. In this case, for example, the port 92 shown in FIG. 39 is used. Folded portions 97 are formed on the distal end of the port 92. As in the seventh embodiment, the port 92 is inserted into the tissue by using a dilator or an inner wire. The distal end of the port 92 is inserted into the tool introduction hole 88 of the operation sheath 80 that has been inserted and left in the tissue. The folded portions 97 are then locked to the tool introduction hole 88, as shown in FIG. 40. As a result, the port 92 communicates with the working space for the cavity secured by the cavity securing means 81 of the operation sheath 80. A tool can therefore be introduced into the working space secured by the operation sheath 80 through the cavity delating tool 62.

Figure 41:
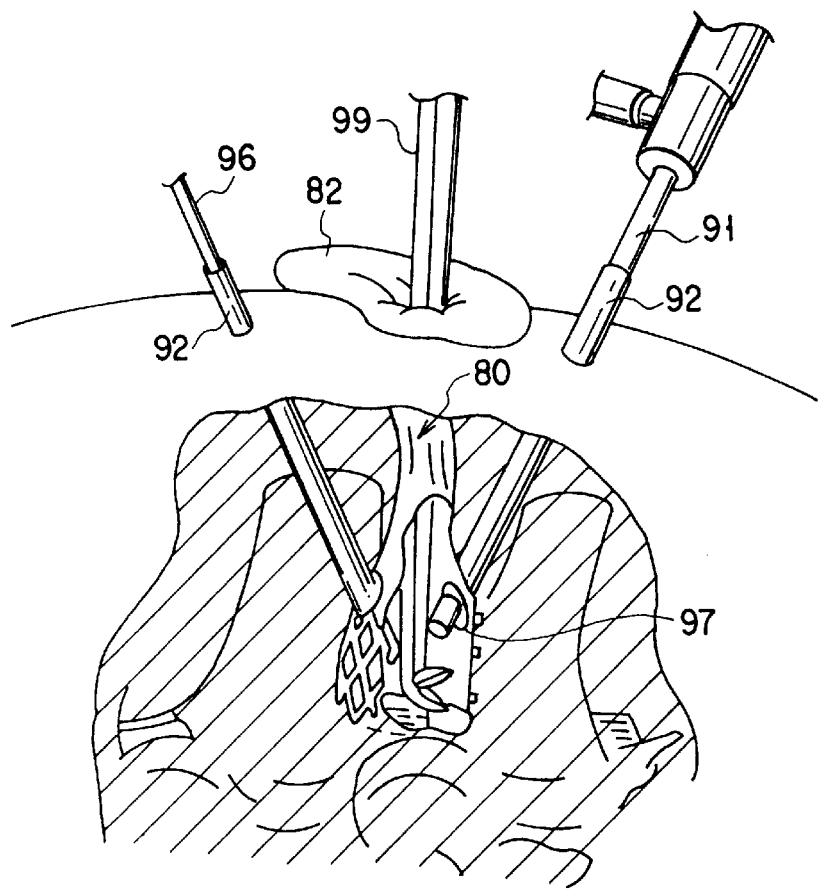
FIG. 41 is a view for explaining how an operation is performed upon insertion of the operation sheath and the port according to the eighth embodiment into the tissue.

FIG. 41 shows this state. Since the port 92 is a port through which the scope 91 or a treatment tool 96 is introduced to communicate with the operation sheath 80. Therefore, a tool 99 having a special shape can be introduced without the mediacy of the port 92, and the movement of even a tool that must be inclined for operation is not restricted, thereby improving operability.

After the operation, the operation sheath 80 is recovered. To do this, a soft tube may be fitted on the operation sheath 80 to remove the operation sheath 80 through the hole of the soft tube. Alternatively, forceps may be inserted along the outer surface of the operation sheath 80, and the expanded ring-like member 83 of the operation sheath 80 may be compressed so as to remove the operation sheath 80.

With the addition of a plurality of ports 92 requiring only small perforations, and the use of a cavity securing tool for delating a cavity, a low invasive operation can be performed with little interference between tools, good operability, and a satisfactory visual field. In addition, since the soft sheet is used as the operation sheath, the pushing effect on tissue can be minimized, realizing a low invasive operation. Furthermore, a tool having a special shape that cannot be inserted into the port 92 can be introduced into the soft operation sheath 80. Moreover, the movement of a tool is not restricted, thus further improving the operability.

The port 92 is locked to the operation sheath 80 with the lock portions to allow the channel to communicate with the cavity perfectly in terms of space. That is, the port 92 perfectly communicates with the cavity, and no tissue enters the cavity, thereby maintaining a good site of operation. In addition, a tool can be introduced into the cavity without fail.

Since the cavity securing means uses the member having the mesh structure, the expanded mesh elements hold the tissue throughout the circumferential portion. This reliably forms a cavity and forms a better visual field. Since recesses/projections are on the outer surfaces of the mesh elements owing to the mesh structure, the tissue is caught in these recesses/projections. As a result, the cavity securing means is positioned, and hence removal of the cavity securing means is prevented during an operation.

Figure 43:
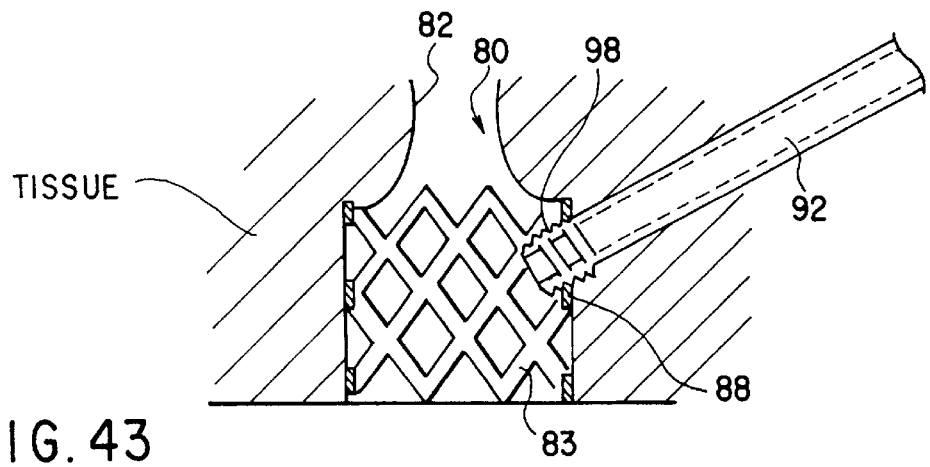
FIG. 43 is a view for explaining how an operation is performed upon insertion of the operation sheath and the port according to the eighth embodiment into the tissue.
Figure 44:
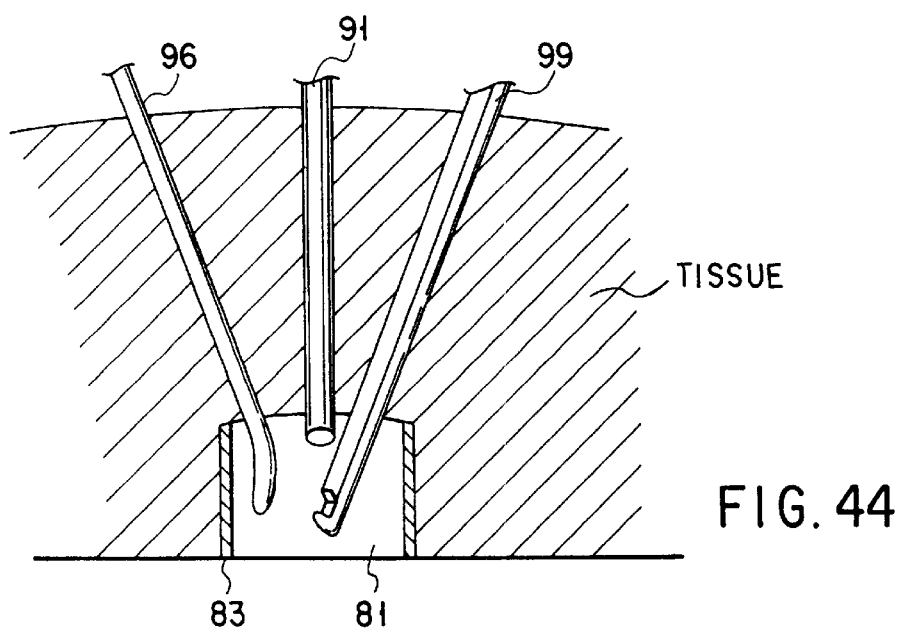
FIG. 44 is a view for explaining how an operation is performed upon insertion of the operation sheath and the port according to the eighth embodiment into the tissue.
Figure 45:
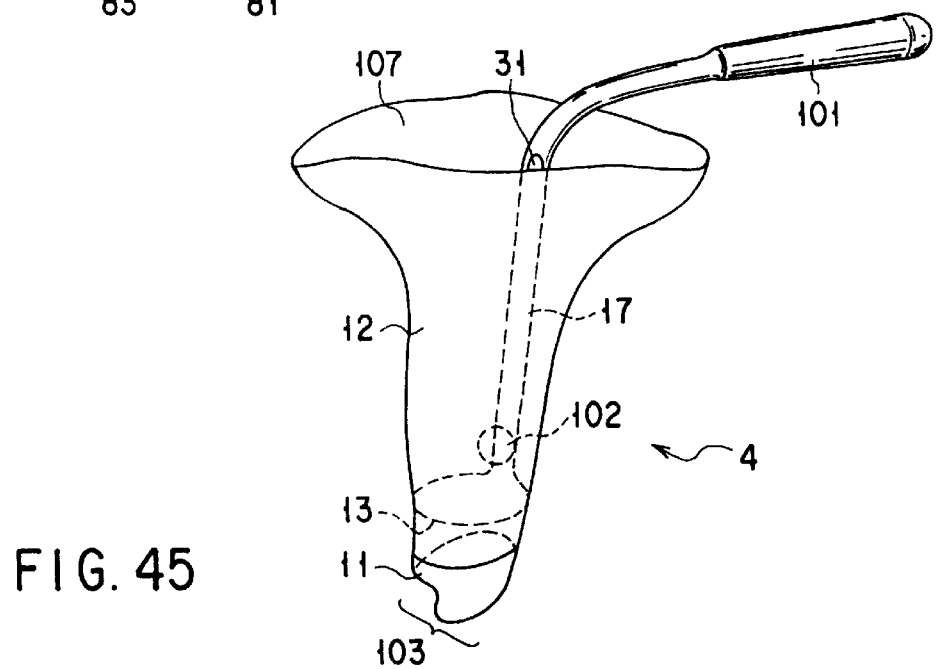
FIG. 45 is a perspective view showing an operation sheath according to the ninth embodiment.
Figure 46A:
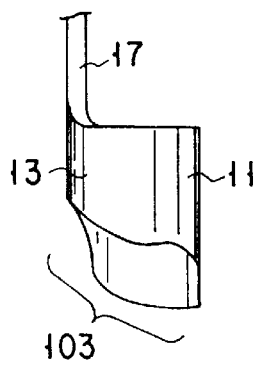
FIGS. 46A to 46D are views for explaining the cavity securing portion of the operation sheath according to the ninth embodiment.
Figure 46B:
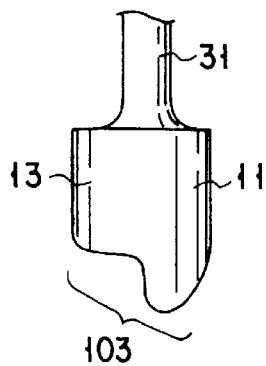
Figure 46C:
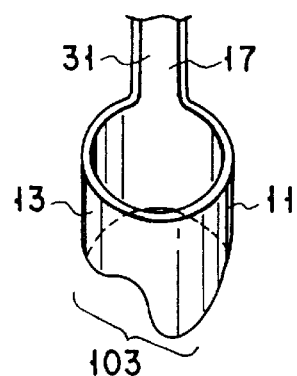
Figure 46D:
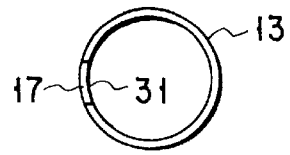

The port 92 is inserted into the tool introduction hole 88 of the operation sheath 80 to be connected thereto. However, a hole of the mesh of the ring-like member 83 of the cavity securing means 81 may be used as a tool insertion hole. In addition, a threaded portion 98 may be formed on the distal end portion of the port 92, and the threaded portion 98 may be threadably engaged with a hole of the mesh of the ring-like member 83, as shown in FIG. 43. FIG. 44 shows the operation sheath 80 in this embodiment from which the soft tubular sheet member 82 is omitted. That is, the operation sheath 80 has only the ring-like member 83 of the cavity securing means 81. In this case, the ring-like member 83 may be recovered after it is compressed by forceps. If, however, the ring-like member 83 is made of a vital absorbent material, the member can be indwelled in the tissue without being recovered.

Note that the interior of the soft tubular member of the operation sheath in each embodiment described above may be partitioned into a plurality of channels to allow tools to extend through the channels and to supply or discharge fluids such as blood and physiological saline through the channels.

The above description mainly concerns percutaneous lumbar discectomy. Obviously, however, the present invention can be applied to any operation in tissue, body cavities, and other sites, diagnoses, and the like.

[Ninth Embodiment]

The ninth embodiment of the present invention will be described with reference to FIGS. 45 to 51. In a surgical operation cavity securing system of the ninth embodiment, the operation sheath 4 shown in FIG. 16 in the second embodiment described above is partly modified. This embodiment further includes a pusher 100 serving as an insertion means for pushing the operation sheath 4 into tissue.

The operation sheath 4 in this embodiment differs from the one in the second embodiment in the following points. First, a round, rod-like gripping portion 101 is formed on the upper end portion of an operating member 17. The gripping portion 101 is bent toward the outside of the secured cavity. In this case, the gripping portion 101 is bent to the right, but may be bent in another direction outside the secured cavity in accordance with the use state of another tool or the like. A soft tubular sheet member 12 forms a tool insertion guide means for guiding a tool. A guide surface 31 for guiding a tool into the soft tubular sheet member 12 is formed on a portion of the operating member 17 which is located inside the soft tubular sheet member 12.

Second, an X-ray non-transmitting marking 102 is formed on the distal end portion of the soft tubular sheet member 12. This marking serves as a mark for allowing the operator to check the position where the soft tubular sheet member 12 is dwelled in the tissue by means of X-ray fluoroscopy or the like. The soft tubular sheet member 12 may not be transparent. However, this member is preferably transparent because the operator can visually check the surrounding condition.

Third, the distal end edge of a ring-like member 13 of a cavity securing means 11 is partly extended, as needed, to form the distal end edge of the ring-like member 13 into a shape conforming to the shape of a bone located around a place where a cavity for an operation is to be secured. With this extension of the ring-like member 13, an engaging portion 103 is formed, which serves as an engaging means that is brought into contact with the bone portion around the cavity securing site to be engaged with the bone portion. In this embodiment, the shape of the engaging portion 103 almost conforms to the shape of the bone portion including a portion between vertebral arches. More specifically, as shown in FIGS. 46A to 46D, the distal end of the cavity securing means 11 is shaped such that a portion corresponding to the position where the cavity securing means 11 comes into contact with the lower vertebral arch portion protrudes, and a portion corresponding to the spina is cut obliquely. In addition, a portion that comes into contact with the upper vertebral arch portion has a concave shape. Note that an illustration of the soft tubular sheet member 12 is omitted from FIGS. 46A to 46D. The ring-like member 13 has an inner diameter matching the largest outer diameter of the outer diameters of the tubes of a dilator 2.

Figure 47A:
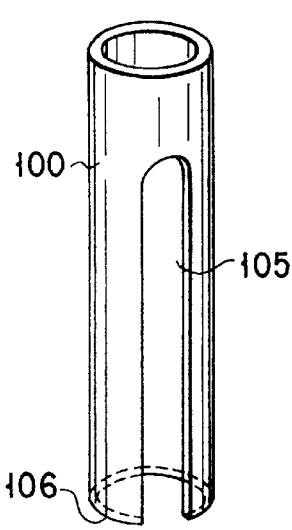
FIG. 47A is a perspective view showing a pusher according to the ninth embodiment.
Figure 47B:
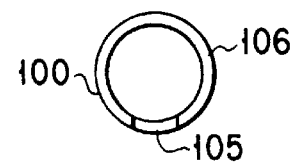
FIG. 47B is a bottom view of the pusher.
Figure 47C:
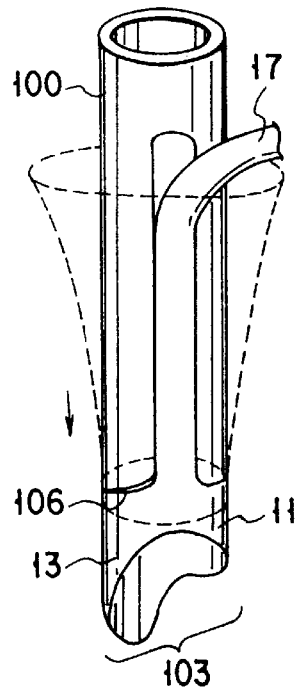
FIG. 47C is a view for explaining how the pusher is used.

The pusher 100 is made of a cylindrical member having an inner diameter matching the outer diameter of one of tubes 7a to 7d, of the dilator 2, which has the maximum diameter. The inner diameter of the pusher 100 is set to be equal to that of the ring-like member 13. The outer diameter of the pusher 100 is smaller than that of the ring-like member 13. As shown in FIG. 47A, a notched portion 105 is formed in a side surface portion of the pusher 100 to extend from a midway portion along the axial direction to open to the inner end edge. The linear portion of the operating member 17 of the operation sheath 4 is tightly fitted in the notched portion 105 without protrusion therefrom so as to engage the operating member 17. That is, the notched portion 105 serves as an engaging portion to be engaged with the operation sheath 4. In addition, the lower end of the pusher 100 serves as a press portion 106 that comes into tight contact with the upper end of the ring-like member 13 of the operation sheath 4.

The length of the pusher 100 is set such that the pusher 100 slightly protrudes from the proximal end of the tube 7d having the maximum outer diameter of the dilator 2 when the pusher 100 and the ring-like member 13 are fitted on the dilator 2 while the press portion 106 is in contact with the upper end of the ring-like member 13. In addition, the length of the pusher 100 is set such that the proximal end of the tube 7d of the dilator 2 coincides with the proximal end of the pusher 100 when the engaging portion 103 protrudes from the distal end of the dilator 2, comes into contact with a bone portion, and is engaged therewith. That is, when the proximal end of the tube 7d of the dilator 2 coincides with the proximal end of the pusher 100, the operator knows that the engaging portion 103 of the ring-like member 13 of the operation sheath 4 is engaged at a predetermined engaging position. The engaging portion 103 therefore indicates that a predetermined engaging state is obtained at a position and a depth that are suited for the bone shape of a target site, and also serves as a display means for the depth.

A case in which a surgical operation is performed to excise a hernia by using the system including the operation sheath 4 and the pusher 100 upon accessing the hernia from the back side will be described next. Since this operation is often performed by substantially the same procedure as that in the first embodiment described above, points different from the above method will be mainly described below.

Figure 48:
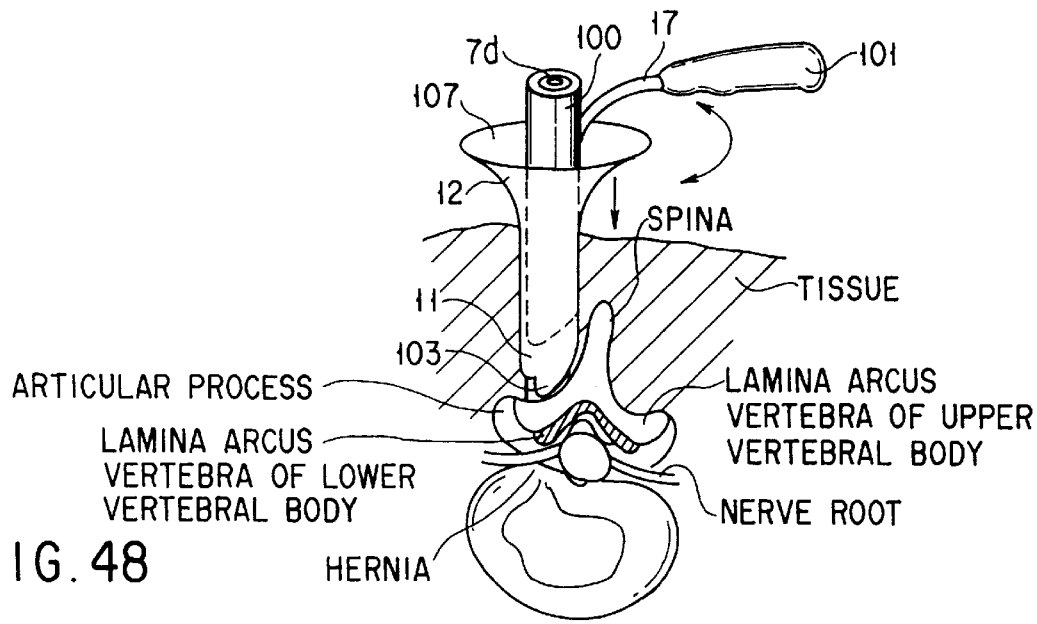
FIG. 48 is a view for explaining how the ninth embodiment is used.

After the tube 7d, of the dilator 2, which has the maximum diameter is inserted into the tissue, the operation sheath 4 is pushed into a region P of surgical object by using the pusher 100 without the soft tube 3. More specifically, the pusher 100 is inserted into the soft tubular sheet member 12 of the operation sheath 4, and the linear portion of the operating member 17 of the operation sheath 4 is fitted in the notched portion 105 of the pusher 100, thereby attaching the operating member 17 of the operation sheath 4 to the pusher 100 in the state shown in FIG. 47C. As shown in FIG. 48, the two members attached to each other are fitted on the tube 7d, of the dilator 2, which has the maximum diameter, and are slid and pushed into the tissue until the distal end of the cavity securing means 11 reaches the region of surgical object.

When the operation sheath 4 is inserted, since the outer diameter of the pusher 100 is smaller than that of the ring-like member 13, the pusher 100 does not rub against the soft tubular sheet member 12 strongly. Therefore, the soft tubular sheet member 12 does not easily break.

Figures 49A, 49B:
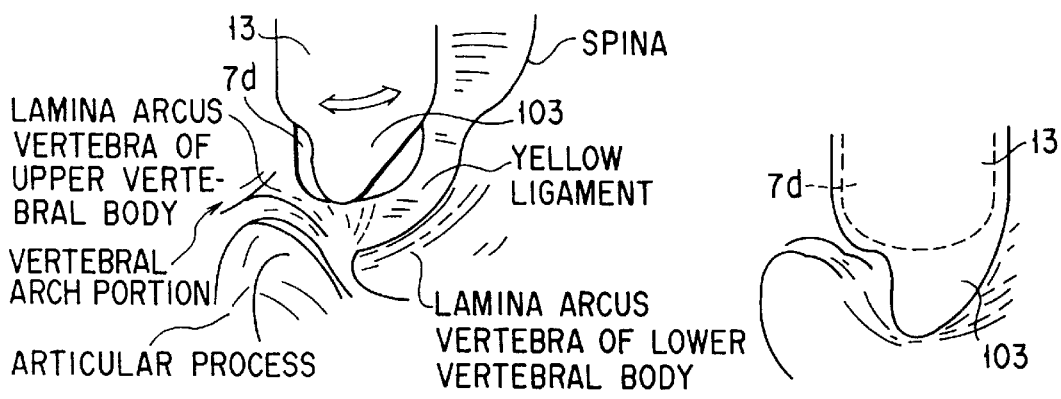
FIGS. 49A and 49B are views for explaining how the ninth embodiment is used.
Figures 50A, 50B:
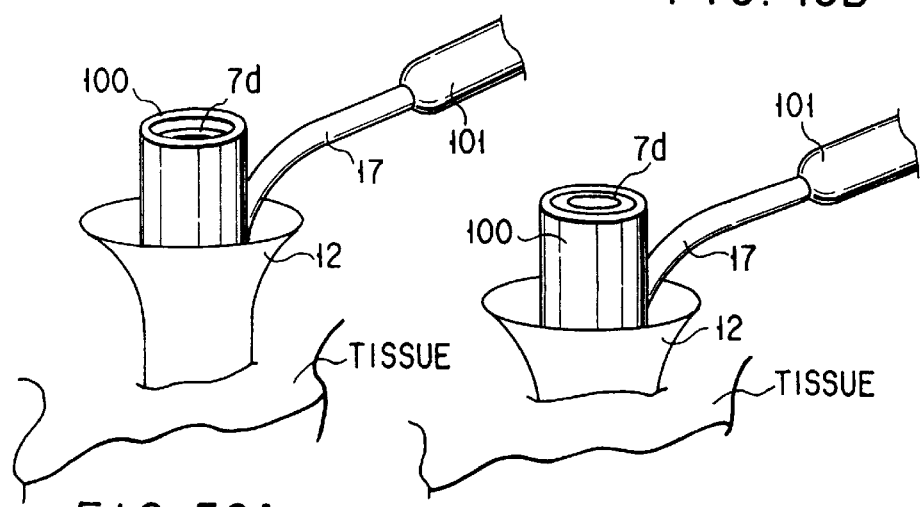
FIGS. 50A and 50B are views for explaining the positional relationship between the proximal end of the dilator and the proximal end of the pusher in the ninth embodiment.

When the engaging portion 103 of the ring-like member 13 of the cavity securing means 11 is not engaged with the bone portion at the predetermined engaging position, the proximal end edge of the tube 7d of the dilator 2 is inserted into the opening portion of the proximal end of the pusher 100, as shown in FIG. 50A. The operator sees this to know that a predetermined engaging state is not established. In this case, as shown in FIG. 49A, the engaging portion 103 is pushed to the deepest position by manually rotating the gripping portion 101 of the operating member 17 about the axis of the ring-like member 13 of the cavity securing means 11 or shifting the ring-like member 13. With this operation, the operator finds a position where the engaging portion 103 matches the bone shape in the region of surgical object and is engaged with the bone. That is, the operator holds the gripping portion 101 of the operating member 17 to find a position and depth at which the engaging portion 103 matches the bone shape at the target site. That is, the engaging portion 103 serves as a position detection means. As shown in FIG. 49B, at the position where the engaging portion 103 is engaged with the bone, the protrusion of the engaging portion 103 is inserted between the vertebral arches, and at the same time, almost the entire edge of the distal end of the ring-like member 13 of the cavity securing means 11 comes into contact with the bone portion around the cavity and is engaged therewith without any gap.

The proximal end of the tube 7d of the dilator 2 then coincides with the proximal end of the pusher 100, as shown in FIG. 50B. With this, the operator can know that the engaging portion 103 of the ring-like member 13 of the operation sheath 4 is engaged at the predetermined position and has reached the predetermined depth. Thereafter, the operator removes the pusher 100.

The engaging portion 103 of the cavity securing means 11 is engaged with the bone portion, and the entire surface of the cavity securing means 11 is brought into contact with the bone portion. Therefore, once a cavity for an operation is secured, no positional offset occurs. In addition, since almost the entire edge of the ring-like member 13 is engaged with the bone portion around the cavity, entrance of the tissue surrounding the ring-like member 13 into the cavity can be effectively prevented. A better visual field and working space required for an operation can therefore be secured.

Figure 51:
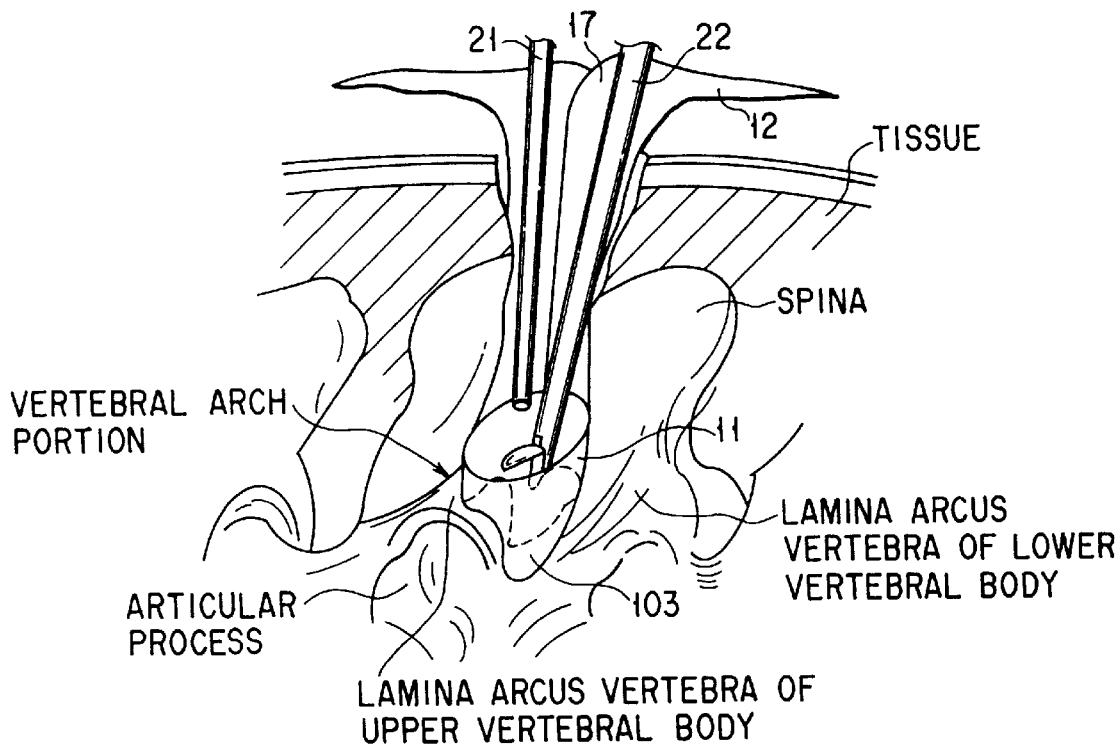
FIG. 51 is a view for explaining how the ninth embodiment is used.

After this, the operator inserts various tools into the working space through a tool insertion channel 107 of the operation sheath 4, and excises the hernia in the same manner as described above. FIG. 51 shows a case in which the operator is performing an operation upon insertion of a scope 21 and a curette 22 as an operating tool into the tool insertion channel 107 of the operation sheath 4.

In this embodiment, the pusher 100 is used in placed of the soft tube 3 as a guide means. However, the soft tube 3 may be used, and the operation sheath 4 and the pusher 100 may be inserted into the working space through the soft tube 3.

[10th Embodiment]

Figures 52A, 52B:
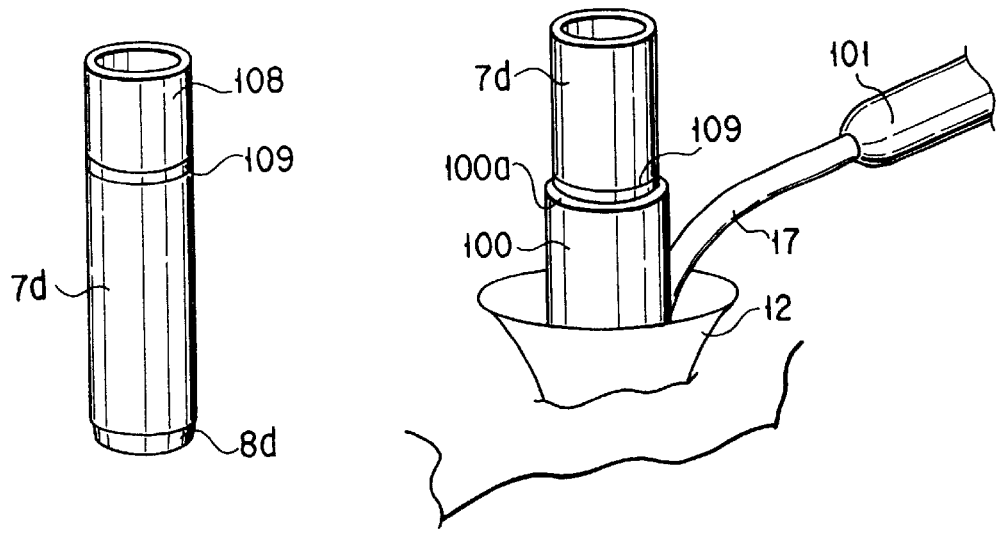
FIGS. 52A and 52B are views for explaining a dilator in the 10th embodiment.

The 10th embodiment of the present invention will be described with reference to FIGS. 52A and 52B. FIGS. 52A and 52B show a modification of the dilator in the ninth embodiment. The proximal end of a tube 7b of a dilator 2 is extended from the proximal end position of a pusher 100 by a sufficient length, and a position displaying marking portion 109 is formed on the outer surface of a proximal end extended portion 108 of the tube 7d, as shown in FIG. 52A. When a proximal end 100a of the pusher 100 is aligned with the marking portion 109 as shown in FIG. 52B, it indicates that an engaging portion 103 of a cavity securing means 11 is located at a proper insertion position where the engaging portion 103 is engaged with a bone in a region of surgical object.

[11th Embodiment]

Figure 53A:
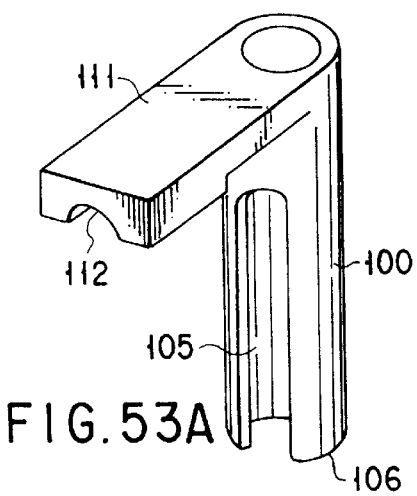
FIGS. 53A and 53B are views for explaining a pusher in the 11th embodiment.
Figure 53B:
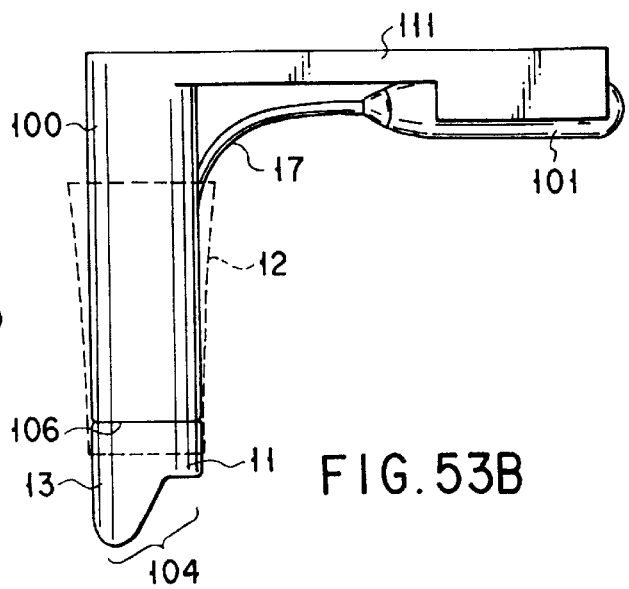

The 11th embodiment of the present invention will be described with reference to FIGS. 53A and 53B. The 11th embodiment includes a modification of the pusher 100 in the ninth and 10th embodiments. In this embodiment, a pusher 100 has an arm portion protruding from its upper end to one side. This arm portion serves as a gripping operating portion 111. A groove portion 112 is formed in a lower surface portion of the distal end portion of the gripping operating portion 111. The groove portion 112 serves as a lock means in which a gripping portion 101 of an operating member 17 of an operation sheath 4 is fitted to be engaged/held. A hole is formed in the upper end of the pusher 100. A tube 7b of a dilator 2 extends through this hole. This opening end serves as an indicator for indicating the relationship with the tube 7d of the dilator 2, as described above.

The pusher 100 in this embodiment used as follows. As shown in FIG. 53B, the operating member 17 of the operation sheath 4 is engaged with the pusher 100 to be coupled thereto. The operator then holds the gripping operating portion 111 of the pusher 100 with his/her hand, fits the operation sheath 4 on the tubes of the dilator 2, and pushes the operation sheath 4 into tissue, thereby inserting it into the tissue. At this time, force does not concentrate on the operating member 17 of the operation sheath 4 because the pusher 100 includes the groove portion 112 serving as a lock means for the gripping operating portion 111 and the operation sheath 4. For this reason, when a cavity securing tool is inserted into the body or engaged with a bone in a region of surgical object, the operating member 17 of the operation sheath 4 and a ring-like member 13 of a cavity securing means 11 are free from deformation and damage.

[12th Embodiment]

Figure 54:
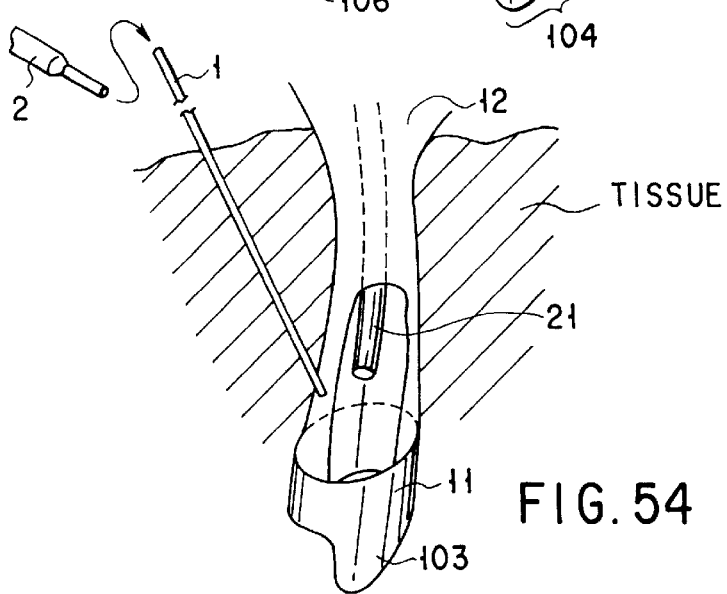
FIG. 54 is a view for explaining how an operation sheath and a dilator according to the 12th embodiment are used.
Figure 55:
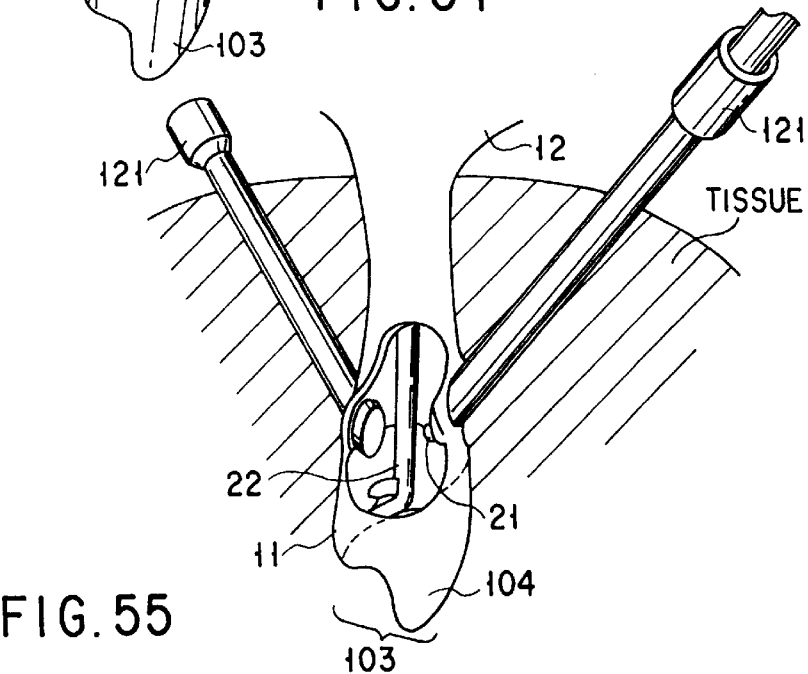
FIG. 55 is a view for explaining a state in which the operation sheath and ports according to the 12th embodiment are indwelled in the tissue.

The 12th embodiment of the present invention will be described with reference to FIGS. 54 and 55. The system of this embodiment includes a port 121 made of a cylindrical member and serving as a tool insertion means as well as the tool insertion channel 107 of the operation sheath 4 described above. This system is constituted by a guidewire 1, a dilator 2, and the port 121. The inner diameter of the hole of the port 121 is set such that the hole can be fitted on the tube having the largest diameter of the diameters of the tubes of the dilator 2, and an endoscope and other types of treatment tools can be inserted into the hole. Note that the distal end portion of the port 121 is cut obliquely.

The port 121 is set as follows. When the port 121 is required after the operation sheath 4 is set in the above method, the guidewire 1 is inserted into tissue from a side of the operation sheath 4 dwelled in the tissue toward a portion immediately above a ring-like member 13, and the distal end of the guidewire 1 pierces a soft tubular sheet member 12. Note that the soft tubular sheet member 12 is made of a material that the guidewire 1 can pierce.

At this time, an endoscope 21 is kept inserted in the soft tubular sheet member 12. In this state, a perforation is made in the wall of the soft tubular sheet member 12 from the outside with the guidewire 1. When the guidewire 1 is to pierce the soft tubular sheet member 12 under X-ray fluoroscopy, an X-ray non-transmitting marking 102 is preferably formed on the guidewire 1 to allow the operator to check whether the guidewire 1 is properly positioned. The operator may pierce the guidewire 1 into the soft tubular sheet member 12 while observing the guidewire 1 by MRI (Magnetic Resonance Imaging). In the latter case, the guidewire 1 is made of a material that allows observation by MRI.

Subsequently, the dilator 2 is fitted on the guidewire 1, and the perforation in the tissue as well as the hole in the wall of the soft tubular sheet member 12 are sequentially dilated. After the perforation is dilated by the dilator 2 to allow the port 121 to be inserted, the port 121 is fitted on the last tube of the dilator 2, and the port 121 is introduced into the extensible soft tubular sheet member 12. Thereafter, the dilator 2 is removed. As a result, as shown in FIG. 55, the distal end portion of the port 121 extends through the soft tubular sheet member 12 and is held therein, and the port 121 can be indwelled inside. In this case, since the soft tubular sheet member 12 behaves like an extensible rubber member and extends itself, the actual perforation is small. The distal end of the inserted port 121 is clamped by the elastic force of the soft tubular sheet member 12 to be coupled/fixed thereto. With this operation, the port 121 inserted from the outside of the body communicates with the cavity secured by a cavity securing means 11. In addition, the port 121 and the operation sheath 4 are coupled/fixed to each other by the elastic force of the soft tubular sheet member 12. This prevents muscle, blood, and the like from entering the cavity through the gap between the port 121 and the operation sheath 4 and interfering with a visual field or site of operation. Furthermore, since the port 121 and the soft tubular sheet member 12 are coupled/fixed to each other, a trocar does not easily come off, and a tool can be smoothly inserted into the cavity.

Note that an inner wire of a needle-like rod or a guidewire including a distal end means having a conical distal end and serving to make a perforation in a wall and a peripheral means for dilating the perforation in the wall may be used in place of the guidewire 1 and the dilator 2, as shown in FIG. 72 (to be described later).

An operation tool such as the scope 21 or a curette 22 can be inserted into the cavity region of surgical object secured by the cavity securing means 11 through the port 121 indwelled in the tissue. As shown in FIG. 55, a plurality of ports 121 may be extend through the soft tubular sheet member 12. In this case, each port 121 may serve as the overcoat tube of a trocar.

[13th Embodiment]

The 13th embodiment of the present invention will be described with reference to FIGS. 56A to 57B. This embodiment includes another example of the cavity securing tool. The tool insertion guide means of a cavity securing tool 130 is not a soft tubular sheet member but is constituted by a pair of arm portions 132a and 132b that coaxially and continuously extend from the upper end of a ring-like member 131 of the cavity securing means. That is, the arm portions 132a and 132b constitute a tool insertion guide means for introducing an operation tool along the inner surfaces of the respective arm portions serving as guide surfaces. The arm portions 132a and 132b face each other, and their inner surfaces are portions of a circumference surface coaxially continuous with the inner surface of the ring-like member 131. The arm portions 132a and 132b are relatively narrow and capable of elastic deformation such that the arm portions can come close to each other and separate from each other in the opposite directions, as indicated by the arrows in FIGS. 56A and 56B. Although a metal, a resin, or the like may be used to integrally form the ring-like member 131 and the arm portions 132a and 132b, the ring-like member 131 should be made of a relatively hard material while the arm portions 132a and 132b should be made of an elastic material.

As in the ninth embodiment, the ring-like member 131 of the cavity securing means has an engaging portion 132 with a shape conforming to the shape of a bone located around a region in which a working space is secured by the ring-like member 131. The engaging portion 132 forms an engaging means that comes into almost tight contact with the bone portion around the cavity securing site and is engaged with the bone portion.

As in the ninth embodiment, the 13th embodiment includes a pusher 133. The pusher 133 in this embodiment has a pair of engaging notched holes 134a and 134b in which the arm portions 132a and 132b are fitted.

Figure 56A:
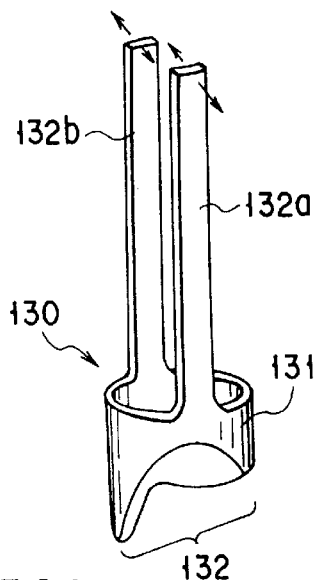
FIGS. 56A to 56D are views for explaining a cavity securing tool according to the 13th embodiment.
Figure 56B:
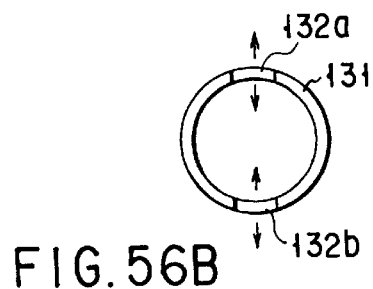
Figure 56C:
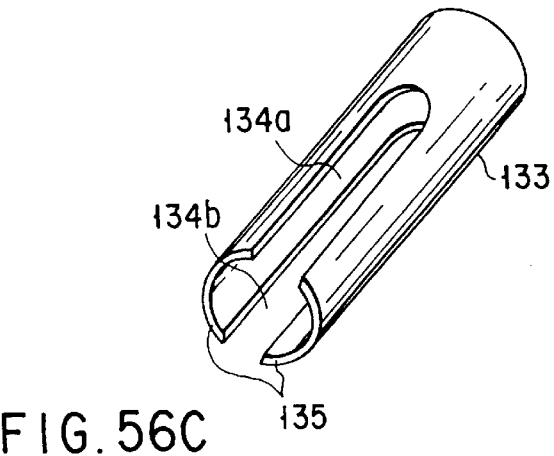
Figure 56D:
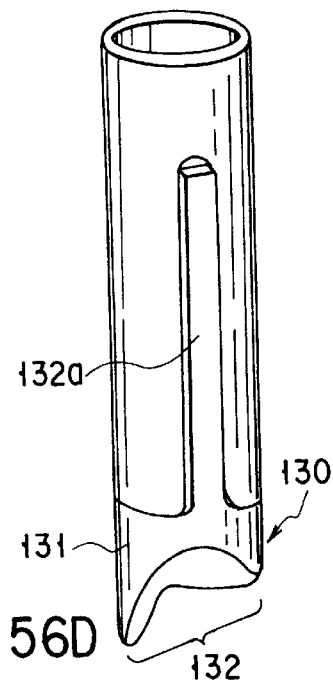

As shown in FIG. 56D, the arm portions 132a and 132b are respectively fitted in the engaging notched holes 134a and 134b of the pusher 133 to attach the cavity securing tool 130 to the pusher. 133. A lower end 135 of the pusher 133 is in contact with the upper end of the ring-like member 131 and engaged therewith.

Figure 57A:
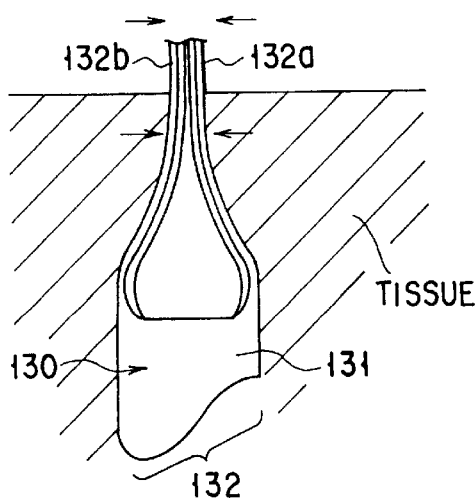
FIGS. 57A and 57B are views for explaining how the cavity securing tool according to the 13th embodiment is used.

In this state, as in the ninth embodiment, an insertion hole formed in tissue is dilated by the dilator, and the ring-like member 131 and the pusher 133 are fitted on the last tube of the dilator to be inserted into the tissue altogether. When the engaging portion 132 of the ring-like member 131 is engaged at a predetermined engaging position, the dilator and the pusher 133 are removed. As a result, the arm portions 132a and 132b deform and collapse due to the pressure from the tissue, and become flattened, as shown in FIG. 57A. Therefore, the arm portions 132a and 132b do not push the tissue, and hence cause no damage to the tissue.

Figure 57B:
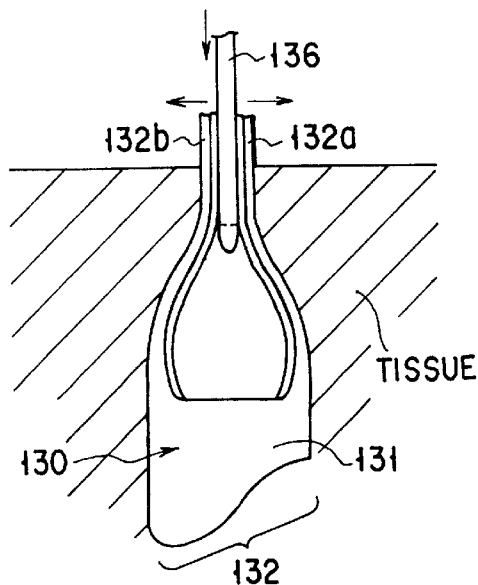

An operating tool 136 such as a scope or forceps is inserted into the cavity securing tool 130 in the following manner. As shown in FIG. 57B, the operating tool 136 is inserted between the arm portions 132a and 132b. The operating tool 136 is then introduced into the cavity for an operation through the inner surfaces of the arm portions 132a and 132b as guides. In this case, since the arm portions 132a and 132b spread minimally in accordance with the size of the operating tool 136 to be introduced and do not push the tissue, damage to the tissue is little.

In this embodiment, the number of arm portions 132a and 132b is two. However, the present invention is not limited to this. A plurality of arm portions or a plurality of combinations of arm portions facing each other may be formed.

[14th Embodiment]

The 14th embodiment of the present invention will be described with reference to FIGS. 58A to 58D. This embodiment includes still another example of the cavity securing tool. A cavity securing tool in the embodiment is designed such that a soft tubular sheet member 12 can be detachably mounted on a ring-like member 13 of a cavity securing means 11. The cavity securing tool of the 14th embodiment is the same as that of the ninth embodiment except for this.

This embodiment can be combined with another embodiment having the soft tubular sheet member 12.

As shown in FIG. 58A, a ring-like engaging groove 137 is formed in the outer surface of the ring-like member 13 throughout the entire circumference. In addition, as shown in FIG. 58B, a convex portion 138 is formed on the fitting inner surface portion of the soft tubular sheet member 12 throughout the entire circumference. The inner diameter of the convex portion 138 is smaller than the outer diameter of the ring-like member 13. The soft tubular sheet member 12 and the ring-like member 13 are coupled to each other as follows. As shown in FIGS. 58C and 58D, the convex portion 138 of the soft tubular sheet member 12 is fitted in the engaging groove 137 of the ring-like member 13 to be engaged therewith, thereby attaching the soft tubular sheet member 12 to the ring-like member 13. Although the convex portion 138 may be engaged with the engaging groove 137 with relative rigidity, relatively high elasticity is preferably provided for this engagement within the range in which a sufficient holding strength can be maintained. Since the convex portion 138 can be disengaged from the engaging groove 137 by applying a force larger than usual in the disengaging direction, the soft tubular sheet member 12 can be easily removed.

According to this structure, the ring-like member 13 as a cavity securing portion and the soft tubular sheet member 12 as a tool insertion guide means can be separated from each other. If, therefore, the soft tubular sheet member 12 is damaged when, for example, the soft tubular sheet member 12 is inserted into a port or the like, the soft tubular sheet member 12 may be used as a disposable member, while other members such as the ring-like member 13 can be reused. This realizes an economic system.

[15th Embodiment]

The 15th embodiment of the present invention will be described with reference to FIGS. 59A to 59C. In this embodiment, a soft tubular sheet member 12 of a cavity securing tool is made of a deformable sheet having a mesh structure. The 15th embodiment is the same as the ninth embodiment except for this. As a mesh structure, a structure obtained by weaving steel wires is conceivable. Each mesh element of the woven structure is smaller than the outer diameter of the port 121 in the 12th embodiment. If the soft tubular sheet member 12 has such a deformable mesh structure, a coupling portion 139 can be easily formed by only inserting the distal end of the guide port 121 using the above mesh element without perforating the soft tubular sheet member 12 with a guidewire 1 as in the 12th embodiment (see FIG. 59C). In addition, since the mesh element spreads in accordance with the size of the distal end of the port 121, the port 121 can be tightly engaged with the mesh element. Furthermore, since the sheet member is a deformable mesh structure, the structure collapses due the pressure from muscle and hence does not push the muscle.

[16th Embodiment]

Figure 60:
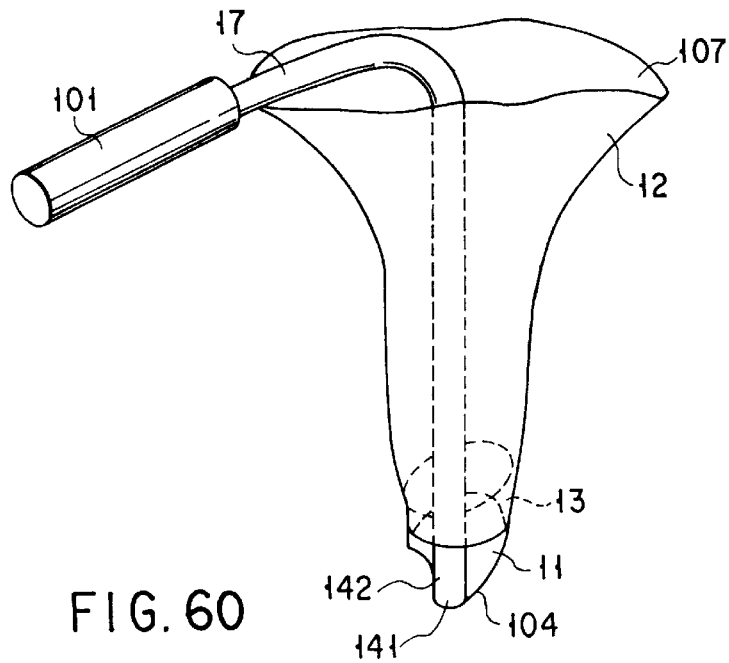
FIG. 60 is a perspective view showing a cavity securing tool according to the 16th embodiment.
Figure 61A:
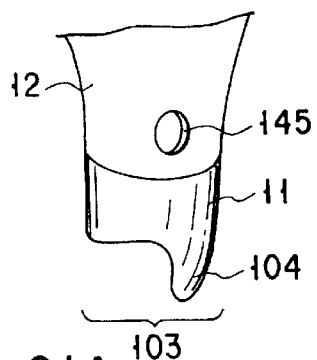
FIGS. 61A to 61D are views for explaining a means for coupling ports to a tubular sheet member in the 17th embodiment.
Figure 61B:
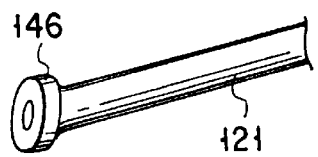
Figure 61C:
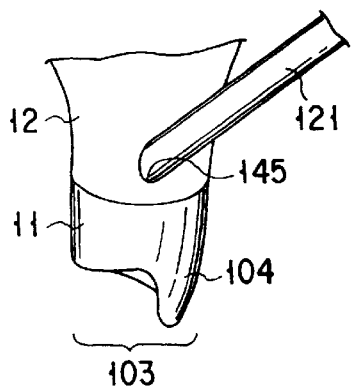
Figure 61D:
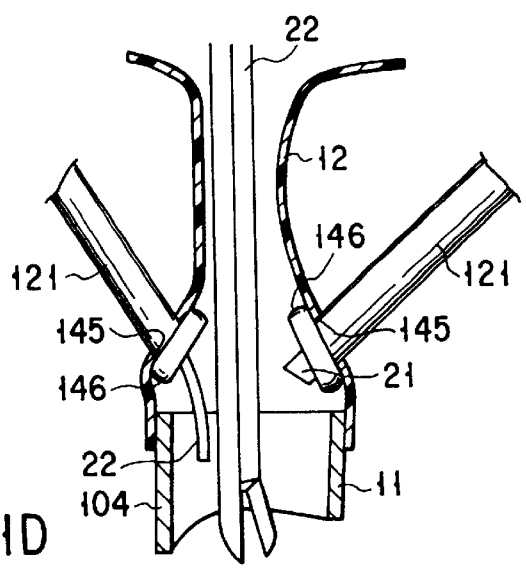

The 16th embodiment of the present invention will be described with reference to FIG. 60. A cavity securing tool in this embodiment differs from the one in the ninth embodiment in the following point. A gripping portion 101 bent from the upper end portion to the left side is formed on an operating member 17. A tissue peeling pushing uncus (spatula) 141 is formed on a tongue-like portion 104 of an engaging portion 103. This pushing uncus 141 can peel off tissue like muscle from a bone portion with which the engaging portion 103 is to be engaged. As the pushing uncus, a spatula-like member with a blade may be used. Alternatively, the pushing uncus 141 may be integrally formed on the tongue-like portion 104 or may be separately formed. The pushing uncus 141 is integrally and continuously formed with the operating member 17 through a thick portion 142. An operating force from the operating member 17 can therefore be directly transmitted to the pushing uncus 141. With this structure, tissue such as muscle can be peeled off from a bone portion, and the engaging portion 103 can be tightly fitted on the bone portion.

[17th Embodiment]

The 17th embodiment of the present invention will be described with reference to FIGS. 61A to 61D. This embodiment includes a modification of the means for coupling the port 121 to the soft tubular sheet member 12 in the 12th embodiment. One or a plurality of port insertion holes 145 are formed in a soft tubular sheet member 12 at the positions of port coupling portions. A concave/convex portion, e.g., a large-diameter collar (stop portion) 146, is formed on the distal end of a port 121 which is inserted into the port insertion hole 145. The diameter of the port insertion hole 145 is equal to or smaller than the outer diameter of the port 121 exclusive of the collar 146. The port 121 is introduced into the soft tubular sheet member 12 by using a guidewire or a dilator. The distal end of the port 121 then elastically spread the edge of the port insertion hole 145 and is inserted therein. When the port 121 is inserted into the port insertion hole 145, the large-diameter collar 146 is caught on the inner edge portion of the port insertion hole 145, thereby effectively preventing the port 121 from coming off the soft tubular sheet member 12.

[18th Embodiment]

The 18th embodiment of the present invention will be described with reference to FIGS. 62A and 62B. This embodiment includes a modification of the insertion means, i.e., the pusher 100, in the 12th embodiment. According to a pusher 147 in this embodiment, a cylindrical member 149 similar to a tube used in a dilator is inserted into a pusher member 148 having the same shape as that of the pusher 100, and these members are integrally formed. As shown in FIG. 62B, the cylindrical member 149 protrudes more to the distal end side than a press portion 106 of the pusher member 148, and a ring-like member 13 of an operation sheath 4 is tightly fitted on the distal end portion of the cylindrical member 149.

When a perforation is to be lastly dilated by the dilator, the pusher 147 is fitted on the last tube of the dilator and inserted into the tissue while the operation sheath 4 is attached to the cylindrical member 149 by fitting the ring-like member 13 on the distal end of the cylindrical member 149. This insertion means serves as the dilator and the pusher at once. Since the pusher member 148 is fitted on the cylindrical member 149 to be reinforced, a notched portion 105 for an operating member engaging means is formed in the pusher member 148. If, however, the pusher member 148 is used singly, this shape makes the member easily deform. In this embodiment, the pusher member 148 is free from abnormal deformation, and the degree of freedom in material design is high. Not that a relatively soft member may be used for this insertion means.

[19th Embodiment]

The 19th embodiment of the present invention will be described with reference to FIGS. 63A to 63D. A cavity securing tool in this embodiment differs from the one in each embodiment described above in the target (bone) portion. An engaging portion 103 formed on the edge of the distal end of a ring-like member (cavity securing portion) 13 of the cavity securing tool is shaped to be engaged with a bone portion around a side wall of a target intervertebral disc when the engaging portion 103 reaches it. More specifically, as shown in FIGS. 63B to 63D, the engaging portion 103 has a shape conforming to the shape of a vertebral body side surface bone including an intervertebral disc. In this access method, an access route is slightly closer to the abdomen side than the access route in the ninth embodiment. According to this embodiment, as shown in FIG. 63A, the cavity securing tool can be used for excision of the hernia of intervertebral disc which protrudes to one side. The 19th embodiment is the same as the ninth embodiment except for the above structure.

[20th Embodiment]

Figure 64A:
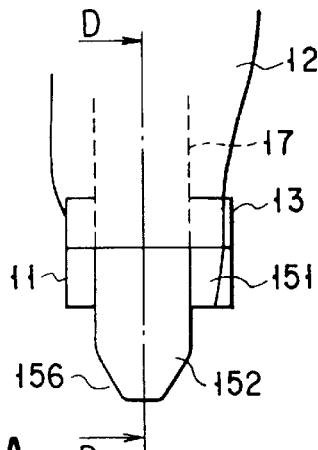
FIGS. 64A to 64D are views for explaining a cavity securing tool according to the 20th embodiment.
Figure 64C:
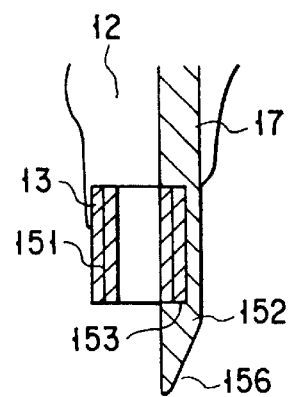
Figure 64B:
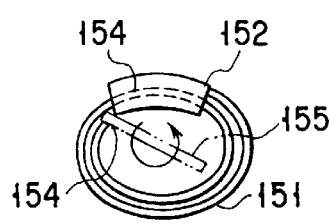
Figure 64D:
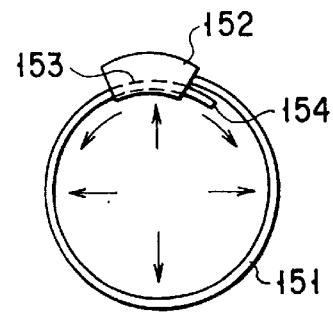

The 20th embodiment of the present invention will be described with reference to FIGS. 64A to 64D. This embodiment includes a modification of the ring-like member 13 of the cavity securing means. 11 in the ninth embodiment. A ring-like member 13 in the 20th embodiment is obtained by rounding a belt-like (plate-like) member 151 into a substantially cylindrical shape. One end of the belt-like member 151 is fixed in a groove 153 of a spatula-like pushing portion 152 formed on the lower end of an operating member 17. As shown in FIGS. 64A to 64C, the belt-like member 151 is initially wound into a whirring pattern with a small diameter. When, however, the operator pushes a moving end 154 with a plate-like operating tool 155 as shown in FIG. 64B, and spreads the belt-like member 151 wound into the swirling pattern as shown in FIG. 64D, the belt-like member 151 can be spread to a cylindrical shape having a diameter that allows normal use of the ring-like member 13.

The ring-like member 13 is inserted into the body to a region of surgical object while the belt-like member 151 is wound into the small-diameter shape. When the ring-like member 13 reaches the region of surgical object, the belt-like member 151 is spread. With this operation, damage to the tissue upon insertion of the cavity securing tool can be reduced, and a working space can be dilated.

The pushing portion 152 and the belt-like member 151 constitute an engaging means 156 that is engaged with a bone portion around a predetermined region of surgical object. As shown in FIG. 64A, the engaging means 156 has a symmetrical shape. For this reason, the horizontal orientation of the engaging means 156 does not change, and hence the engaging means 156 can be used for any types of members.

[21st Embodiment]

Figure 65:
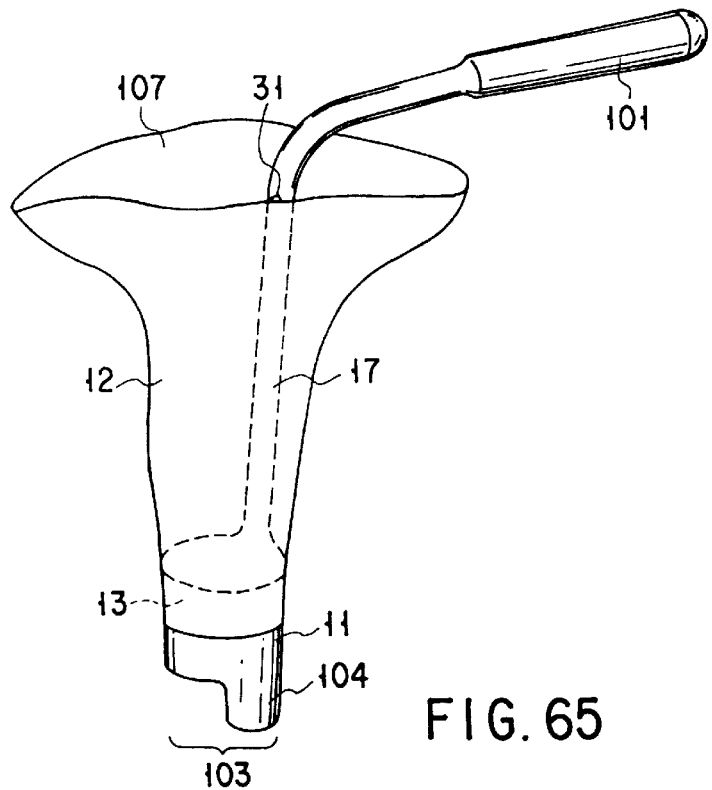
FIG. 65 is a view for explaining a cavity securing tool according to the 21st embodiment.
Figure 66A:
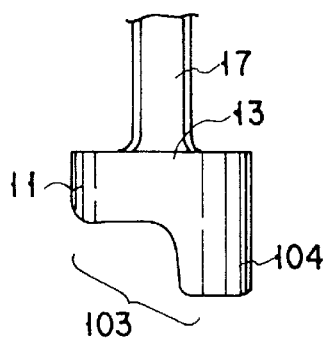
FIGS. 66A to 66D are view for explaining the engaging portion of the cavity securing tool according to the 21st embodiment.
Figure 66B:
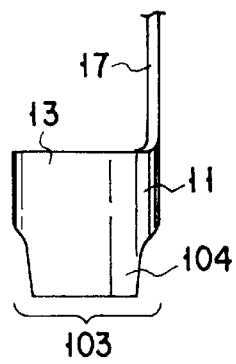
Figure 66C:
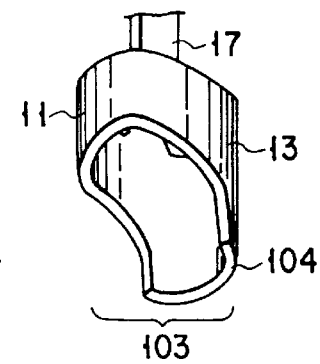
Figure 66D:

The 21st embodiment of the present invention will be described with reference to FIGS. 65 and 66. This embodiment is characterized in that a ring-like member 13 equivalent to the ring-like member 13 of the cavity securing means 11 of the operation sheath (cavity securing tool) 4 in the ninth embodiment described above has an elliptic shape instead of a perfect circular shape. The 21st is the same as the ninth embodiment except for this. As shown in FIG. 66, the ring-like member 13 has an elliptic shape, and the lower end edge of the ring-like member 13 is shaped in conformity of the shape of a bone portion located around a place where an operation cavity is to be secured, thereby forming an engaging portion 103 that is brought into contact with the bone portion around the cavity securing site and engaged therewith. Since the distal end of the engaging portion 103 has an elliptic shape, a wider visual field can be obtained in the vertical or horizontal direction with respect to the region of surgical object including the portion between vertebral arches than with an engaging portion having the same circumference as that of the engaging portion 103 and having a circular shape.

[22nd Embodiment]

The 22nd embodiment of the present invention will be described with reference to FIGS. 67A to 67D. As shown in FIG. 67D, a cavity securing tool 160 in this embodiment has a pair of pushing pieces 163 and 164 having different lengths and continuously formed as a cavity securing means on the distal end of a sheath portion 162 also serving as an operating portion. The pushing pieces 163 and 164 of the cavity securing portion are plate-like members, and can elastically spread through deformed arm portions 163a and 164a. The width of each of the pushing pieces 163 and 164 is larger than the sheath portion 162. The pushing pieces 163 and 164 differ in the lengths of the protruding portions. The protruding portion of the pushing piece 163 is longer than that of the pushing piece 164. Folded portions 166 and 167 protruding outward are formed on the distal ends of the pushing pieces 163 and 164. The distal end portions of the pushing pieces 163 and 164 constitute a means to be engaged with the vertebral arch portion of a positioning target portion.

Figure 67A:
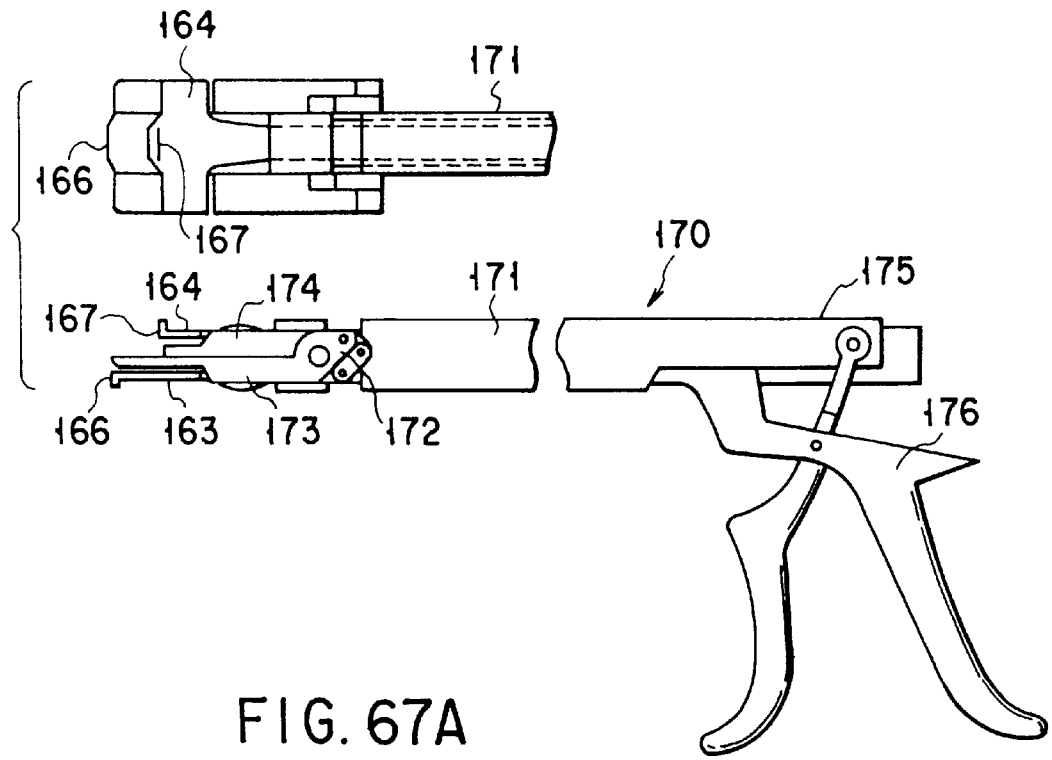
FIGS. 67A to 67D are views for explaining a cavity securing tool and a spreading tool according to the 22nd embodiment.
Figure 67B:
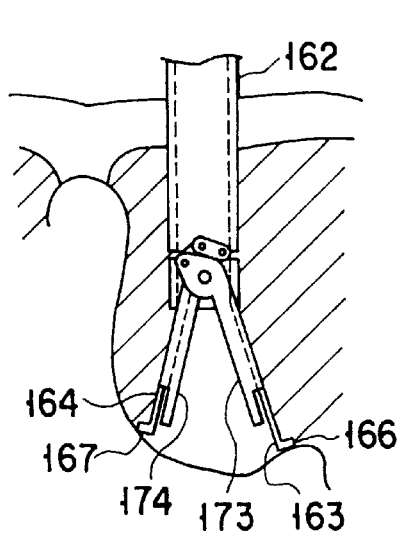
Figure 67C:
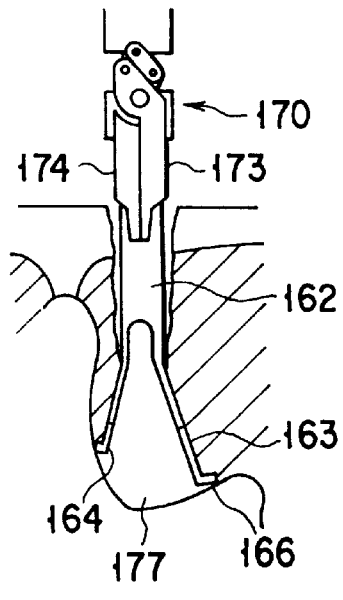
Figure 67D:
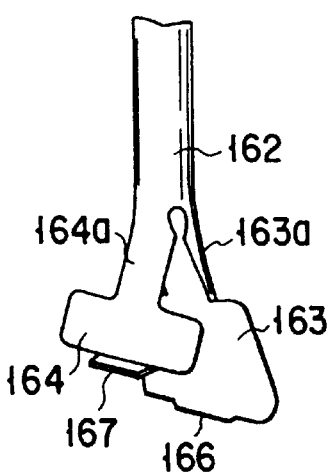

Referring to FIG. 67A, reference numeral 170 denotes a spreading tool for spreading the pushing pieces 163 and 164 of the cavity securing tool 160. Spreading elements 173 and 174 are attached to the distal end of a main insertion portion 171 through a link 172. The main insertion portion 171 can be inserted into the sheath portion 162. The spreading elements 173 and 174 can be spread by operating a handle 176 of an operating portion 175 which is formed on the proximal end side of the main insertion portion 171.

This cavity securing tool 160 is used as follows. The cavity securing tool 160 with the closed pushing pieces 163 and 164 is inserted into tissue by using an insertion tool such as a guidewire, a dilator, or a soft tube. When the cavity securing tool 160 is positioned in a region of surgical object, the spreading tool 170 is inserted into the sheath portion 162, and the spreading elements 173 and 174 are positioned to the inner surfaces of the pushing pieces 163 and 164. The spreading elements 173 and 174 are then spread to spread the pushing pieces 163 and 164 (see FIG. 67B). Thereafter, the spreading elements 173 and 174 are closed, and the spreading tool 170 is removed from the sheath portion 162 (see FIG. 67C).

The pushing pieces 163 and 164 of the cavity securing tool 160 are spread in the tissue to form a working space 177 in the region of surgical object. The distal ends of the pushing pieces 163 and 164 conform to the shape of the bone portion of the vertebral arch portion between the spina and the articular process to which the distal ends are to be positioned, and are locked to the bone portion.

[23rd Embodiment]

Figures 68A, 68B:
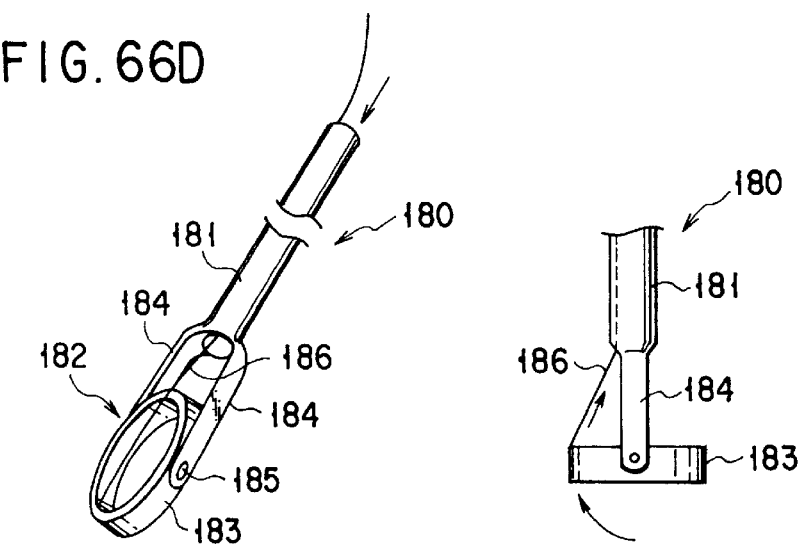
FIGS. 68A and 68B are views for explaining a cavity securing tool according to the 23rd embodiment.

The 23rd embodiment of the present invention will be described with reference to FIGS. 68A to 70B. As shown in FIGS. 68A and 68B, a cavity securing tool 180 in this embodiment has a cavity securing portion 182 on the distal end of a sheath portion 181. The cavity securing portion 182 includes a ring-like member 183. The ring-like member 183 is rotatably mounted on the cavity securing tool 180 through rotating shafts 185 attached to the distal ends of a pair of right and left support arms 184 extending from the distal end of the sheath portion 181.

Figure 69A:
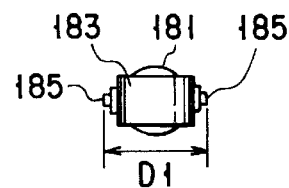
FIGS. 69A and 69B are views for explaining the cavity securing portion of the cavity securing tool according to the 23rd embodiment.
Figure 69B:
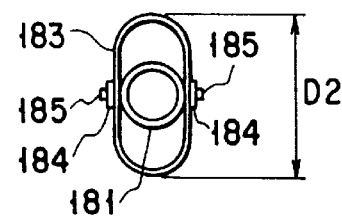

As shown in FIGS. 69A and 69B, the ring-like member 183 has an elliptic shape, and minor-axis-side portions of the ring-like member 183 are axially supported on the rotating shafts 185. With this structure, when the ring-like member 183 is set along the longitudinal direction of the sheath portion 181, the ring-like member 183 is elongated in the longitudinal direction of the sheath portion 181. The width of the ring-like member 183 is almost equal to the outer diameter of the sheath portion 181.

The distal end of a cavity securing portion operating wire 186 is connected to one end of the ring-like member 183 in the major axis direction. This wire 186 is guided to the proximal end side of the sheath portion 181 through the sheath portion 181. When the wire 186 is pulled, the ring-like member 183 rotates to be positioned in a direction perpendicular to the longitudinal direction of the sheath portion 181.

FIG. 69A shows a width D1 of the ring-like member 183 along the minor axis direction before the cavity securing portion 182 is rotated. The width D1 is the width of the ring-like member 183 when the cavity securing portion 182 is inserted into tissue. FIG. 69B shows a width D2 of the ring-like member 183 along the major axis direction after the cavity securing portion 182 is rotated. The width D2 is the maximum width of the ring-like member 183 when a cavity is to be secured.

Figure 70A:
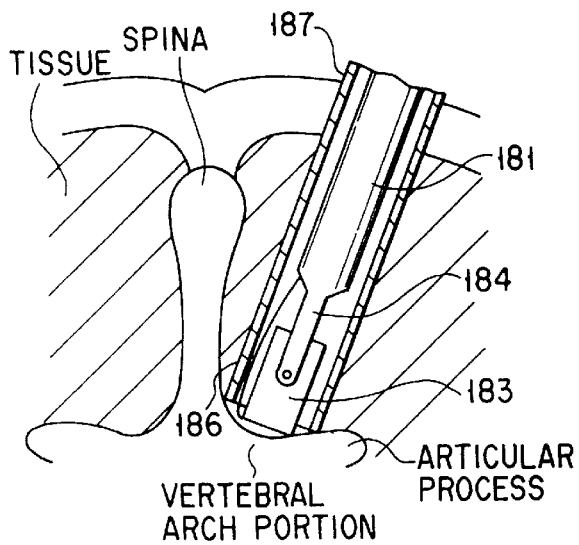
FIGS. 70A and 70B are views for explaining how the cavity securing tool according to the 23rd embodiment is used.
Figure 70B:
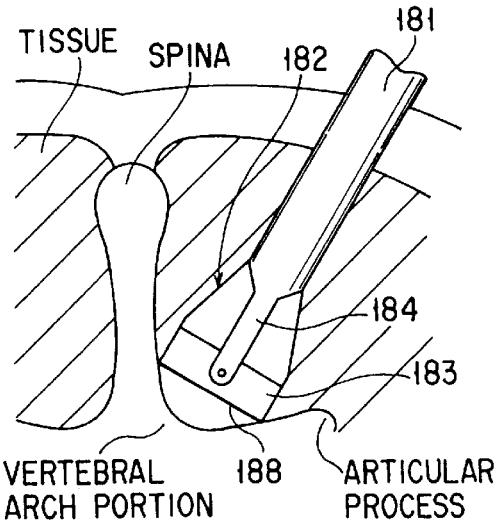

This cavity securing tool 180 is inserted into tissue as follows. As shown in FIG. 70A, for example, an insertion tool such as a dilator is used to form an insertion hole, and the cavity securing tool 180 is inserted to a region of surgical object by using a dilator tube 187 that is spread to a predetermined diameter or a member such as a soft tube like the one described before as a guide. After this insertion, the members such as the dilator, other than the cavity securing tool 180, are removed. As shown in FIG. 70B, the ring-like member 183 of the cavity securing portion 182 is rotated through 90° by a rotating means, and a working space 188 is formed in the region of surgical object by using the ring-like member 183. The support arm 184 extending from the distal end of the sheath portion 181 also contributes to cavity securing operation.

Note that an engaging means that is brought into contact with the bone portion around the cavity securing site and engaged therewith may be formed on the ring-like member 183 of the cavity securing portion 182.

According to this cavity securing tool 180, a large working space can be formed in a region of surgical object in tissue by forming a small insertion hole in the tissue.

[24th Embodiment]

Figure 71A:
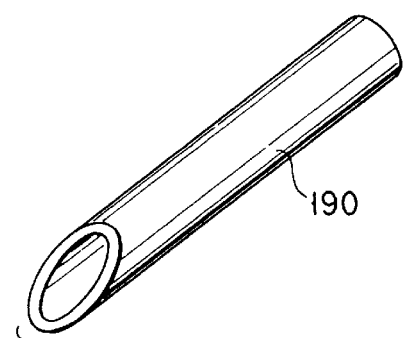
FIGS. 71A to 71C are views for explaining a dilator according to the 24th embodiment and how the dilator is used.
Figure 71B:
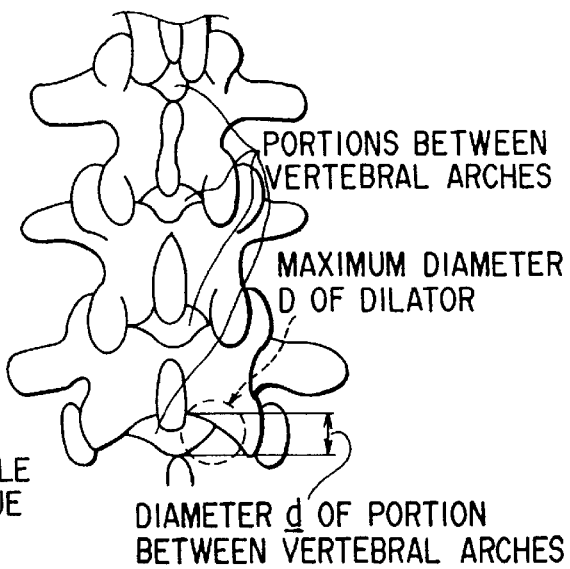
Figure 71C:
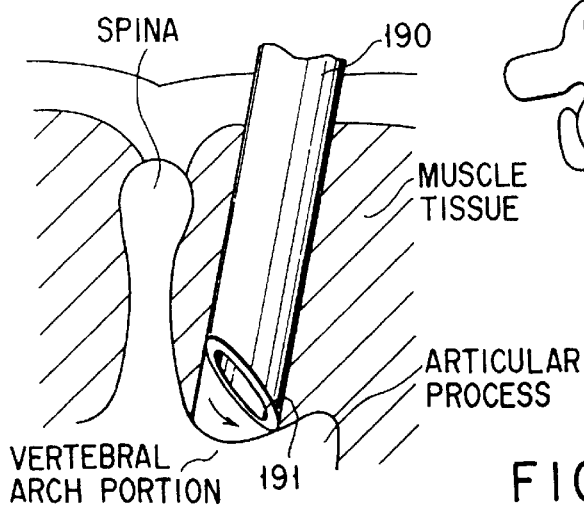

The 24th embodiment of the present invention will be described with reference to FIGS. 71A to 71C. This embodiment is associated with a tube 190 having the largest outer diameter of the outer diameters of the tubes of a dilator as an insertion tool used to form an insertion hole in tissue. The tube 190 guides a cavity securing tool. As shown in FIG. 70B, a sharp blade portion 191 is formed on the distal end of the tube 190 by obliquely cutting it. The tube 190 of the dilator, on which the sharp blade portion 191 is formed, has a diameter larger than that of a hole in the bone portion around a cavity securing site to which the tube 190 is to be applied. For example, the blade portion 191 is formed on the tube 190 having a diameter D larger than a diameter d of a portion 192 between vertebral arches. Although the diameter d of the portion 192 between vertebral arches differs among individuals, such differences can be known in advance by X-ray photography, MRI, or the like.

This tube 190 is used as follows. When an insertion hole formed in tissue is to be gradually dilated by using the respective tubes of the dilator, the tube 190 having the sharp blade portion 191 formed on its distal and having the diameter D larger than the diameter d of the portion 192 between vertebral arches is inserted into the insertion hole. As shown in FIG. 71C, the tissue clinging to the surface of the bone portion around the portion 192 between vertebral arches is abraded off by the blade portion 191. The diameter of the tube 190 is larger than the diameter d of the portion 192 between vertebral arches. This prevents the tube 190 from entering the portion 192 between vertebral arches and unnecessarily damaging other tissues. If a cavity securing tool is introduced after this processing, the cavity securing portion of the cavity securing tool can be brought into tight contact with the portion 192 between vertebral arches, and a good visual field can be obtained.

[25th Embodiment]

The 25th embodiment of the present invention will be described with reference to FIG. 72. This embodiment is associated with a dilator for an insertion tool which is used to formed an insertion hole in tissue. A dilator 195 is made of one needle-like member 196 and also serves as a guidewire. A perforating distal end 197 of the needle-like member 196 has a conical shape. The outer diameter of the dilator 195 is set to allow a cavity securing tool to be fitted on the dilator 195 and guided. According to this structure, when the perforating distal end 197 is pushed into a tissue surface, the dilator 195 can be inserted into the tissue, piercing the body. As a result, a dilated insertion hole can be formed at once. This operation is easy, and damage to the tissue is little as compared with a case in which a plurality of tubes fitted on each other like the dilator in the first embodiment are inserted. In addition, no guidewire needs to be inserted. A guidewire insertion hole may be formed in the center of the dilator 195, and a guidewire may be used.

[26th Embodiment]

The 26th embodiment of the present invention will be described with reference to FIG. 73. This embodiment is associated with a dilator used to form an insertion hole in tissue. According to this dilator, an engaging portion like the one described above, i.e., an engaging portion 202 having a shape conforming to the shape of a bone portion around a place where an operation cavity is to be secured, is formed on a tube having a diameter that allows a cavity securing tool to be fitted on the tube to be guided, normally a dilator tube 201 having the largest outer diameter. The engaging portion 202 is brought into contact with the bone portion around the cavity securing site and engaged therewith in conformity with the shape of the bone portion. An indicator 203 for indicating the position of the engaging portion 202 is marked on the outer surface of the proximal end portion of the dilator tube 201 in accordance with the position of the engaging portion 202.

The engaging portion 202 of the dilator tube 201 is engaged with the bone portion around the cavity securing site before a cavity securing tool is fitted on the dilator tube 201 and pushed into the tissue. With this operation, when a cavity securing tool having a bone portion engaging means like the one described above is to be used, the operator knows the engaging position, and hence can easily engage the cavity securing tool with the bone portion. In addition, since a proper engaging position is obtained from the dilator tube 201, and a cavity securing tool inserted afterward need not be unnecessarily moved. Therefore, damage to the tissue can be reduced.

[27th Embodiment]

The 27th embodiment of the present invention will be described with reference to FIGS. 74A to 74C. This embodiment is associated with a dilator as an insertion tool that is used to form an insertion hole in tissue. All tubes 206 of a dilator 205 or tubes following a given tube 206 have elliptic shapes. FIGS. 74A and 74B show the dilator 205 in which all the tubes 206 have elliptic shapes. FIG. 74C shows the dilator 205 in which only the tube 206 having the largest outer diameter is formed into an elliptic shape. According to this dilator 205, a flat insertion hole can be formed in tissue. In addition, a cavity securing tool having a flat cavity securing portion can be fitted on the dilator 205 and pushed into tissue. For example, the dilator 205 can be suitably used when a cavity securing tool including a ring-like member having an elliptic shape instead of a perfect circular shape, like the one in the 21st embodiment, is to be inserted into tissue.

[28th Embodiment]

The 28th embodiment of the present invention will be described with reference to FIGS. 75A to 75C. This embodiment is associated with a port guide device 210 for guiding a port to a target site. When an operation tool introduction port is to be used in addition to the insertion channel of an operation sheath as in the 12th embodiment, the port guide device 210 restricts the perforating position and direction of a guidewire for guiding a portion 121.

As shown in FIG. 75B, the port guide device 210 has a dilator tube 211, and a pair of side holes 212a and 212b are formed by notching opposing side wall portions of the outer surface of the lower end of the dilator tube 211. A first guide member 213 is detachably mounted on the upper end portion of the dilator tube 211.

The first guide member 213 has a central cylindrical portion 214 is fitted in and connected to the opening portion of the upper end of the dilator tube 211, and a plate-like arm portion 215 uniformly extending from the upper end of the central cylindrical portion 214 to the right and left. Guide holes 271a and 217b in which second guide members 216 are fitted are formed in the two end portions of the plate-like arm portion 215. Notches 219 that allow guidewires 218 to pass through are formed in the respective guide holes 217a and 217b. The inner diameter of the central cylindrical portion 214 is equal to that of the dilator tube 211. A hole 220 is coaxially formed in the central cylindrical portion 214.

As shown in FIG. 75A, the second guide member 216 includes a shaft portion 221 fitted in each of the guide holes 217a and 217b and a collar portion 222 formed on the upper end of the shaft portion 221. Only the shaft portion 221 is fitted in the guide hole 217 of the first guide member 213, and the collar portion 222 is locked to the first guide member 213, thereby the second guide member 216 thereon. A guidewire hole 223 through which the guidewire 218 extends is formed in the center of the second guide member 216.

As shown in FIG. 75C, the second guide members 216 are mounted in the guide holes 271a and 217b such that the axes of the guidewire holes 223 of the second guide members 216 coincide with the axes of the guide holes 271a and 217b. The respective axes coincide with each other on the axis of the dilator tube 211 and are located within the same plane. The axes of the guidewire holes 223 cross obliquely each other on the axis of the dilator tube 211 at acute angles with respect the axis of the dilator tube 211, and pass through the side holes 212a and 212b of the dilator tube 211.

This port guide device 210 is used as follows. The dilator tube 211 is used in place of the last tube of the dilator for forming an insertion hole in tissue, and a soft tube or an operation sheath used as a pusher is inserted into the tissue. Thereafter, the first guide member 213 is fitted and mounted on the proximal end portion of the dilator tube 211, and the second guide member or members 216 are fitted in one or both of the guide holes 271a and 217b while the dilator tube 211 is positioned. As shown in FIG. 75B, the guidewire 218 extends through the guidewire hole 223 of the second guide member 216 and is inserted from a side of the operation sheath into a soft tubular sheet member 12. After this perforating operation, the guidewire 218 is pulled out from the second guide member 216 along the axial direction, and is detached from the first guide member 213.

The first guide member 213 is then detached from the dilator tube 211. At this time, since the guidewire 218 passes through the notch 219, the guidewire 218 is not caught in the guide hole 217.

In this manner, the guidewire 218 can be inserted into tissue and a cavity at a proper position in a proper direction. A port like the one described above is inserted into the wall portion of the soft tubular sheet member 12 and coupled thereto and caused to communicate with a working space in a region of surgical object by using the inserted guidewire 218 as a guide. An operation tool can therefore be introduced from a side of the operation sheath into the working space through this port without the mediacy of the channel in the operation sheath. Therefore, a port can be introduced to a proper position in a treatment cavity, and a good visual field can always be obtained.

[29th Embodiment]

The 29th embodiment of the present invention will be described with reference to FIGS. 76A and 76B. This embodiment includes a modification of the port guide device 210 in the 28th embodiment.

A movement hole 225 is formed in a plate-like arm portion 215 of a first guide member 213 along its longitudinal direction. A second guide member 216 has collar portions 222 and 226 on the two ends of a shaft portion 221. The second guide member 216 is guided along the movement hole 225 while the plate-like arm portion 215 is clamped between the two ends of the second guide member 216. That is, the second guide member 216 is mounted on the plate-like arm portion 215 to be laterally movable while being fitted in the movement hole 225, as shown in FIGS. 76A and 76B.

The plate-like arm portion 215 is arcuated about the point where the above axes cross each other. The second guide member 216 can move along the movement hole 225 while being fitted therein. For this reason, the axis of the guidewire hole 223 of the second guide member 216 is always directed to the above point to pass therethrough. A hole 220 is formed in the center of the movement hole 225, and the movement hole 225 communicates with the hole 220. When the second guide member 216 is positioned in the hole 220, the second guide member 216 can be removed from the first guide member 213 through the hole 220.

According to the port guide device 210 in this embodiment, the position and inclination of the guidewire hole 223 can be selected by moving the second guide member 216 along the movement hole 225 of the first guide member 213. A perforating direction with respect to the axis of the dilator tube 211 can be selected. The same function/effect as those of the port guide device 210 in the above embodiment can be obtained except for this.

[30th Embodiment]

Figure 77A:
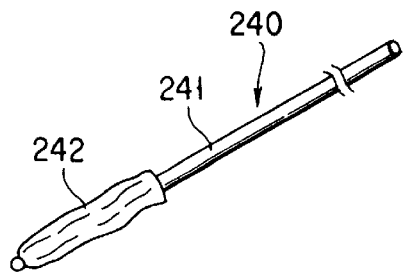
FIGS. 77A and 77B are views for explaining an insertion tool according to the 30th embodiment.
Figure 77B:
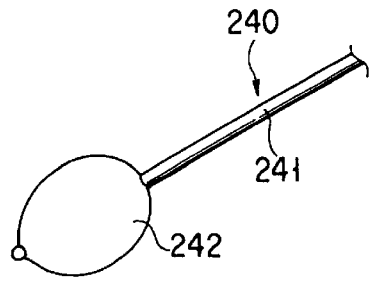

The 30th embodiment of the present invention will be described with reference to FIGS. 77A to 78B. This embodiment is associated with an insertion tool to be used in place of the above dilator. As shown in FIGS. 77A and 77B, an insertion tool 240 in the embodiment has a balloon 242 on the distal end portion of a tubular operating portion 241. The balloon 242 is inflated or deflated by supplying a fluid into the balloon 242 through the channel (not shown) formed in the operating portion 241. The balloon 242 is formed on the distal end portion of the operating portion 241 to be inflated in a substantially spherical shape.

Figure 78A:
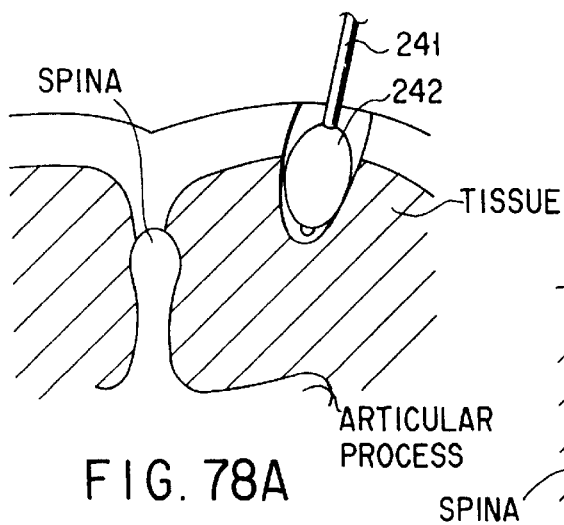
FIGS. 78A and 78B are views for explaining how the insertion tool according to the 30th embodiment is used.
Figure 78B:
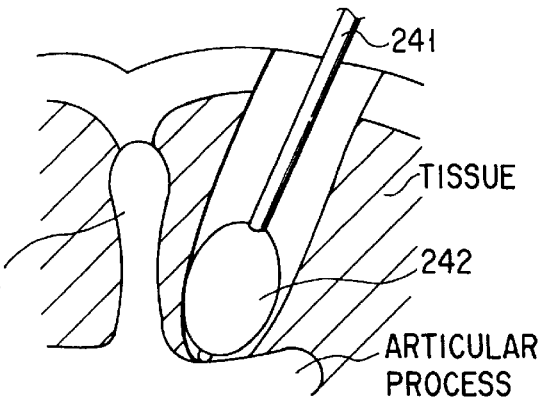

When an insertion hole is to be formed in tissue by using the insertion tool 240, the distal end of the operating portion 241 is brought into contact with the tissue surface and pushed toward a region of surgical object while the balloon 242 is inflated, as shown in FIG. 78A. As a result, as shown in FIG. 78B, the balloon 242 breaks through the body wall and enter the tissue to form a path through which a cavity securing tool is inserted.

After the path is formed by the insertion tool 240, the cavity securing tool is inserted as follows. Another guide tube such as a soft tube is inserted by using the tubular operating portion 241 as a guide, and the cavity securing tool is inserted through the guide tube. Alternatively, an auxiliary tool such as a soft tube or a pusher may be used to insert the cavity securing tool.

[31st Embodiment]

Figure 79A:
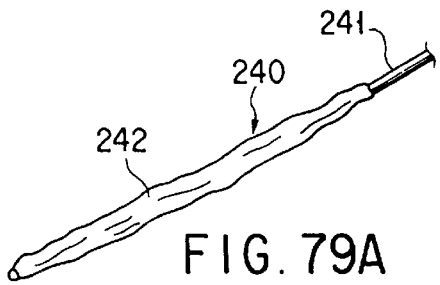
FIGS. 79A to 79C are views for explaining how an insertion tool according to the 31st embodiment is used.
Figure 79B:
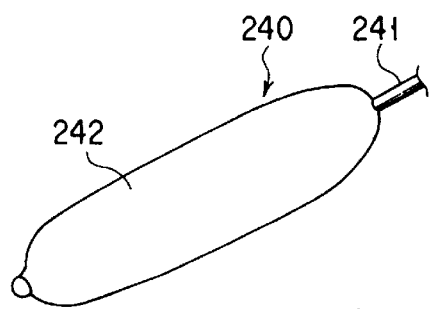
Figure 79C:
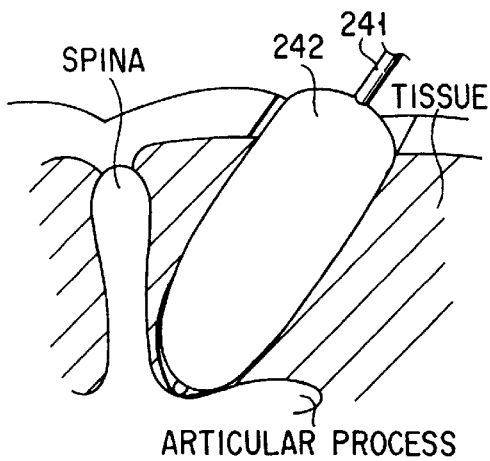

The 31st embodiment of the present invention will be described with reference to FIGS. 79A to 79C. This embodiment includes a modification of the insertion tool 240 described above. An insertion tool 240 of the embodiment has an elongated balloon 242 on an operating portion 241. The balloon 242 has a length almost equal to the length of the path to be formed in tissue. In this case, by using the outer surface of the inflated balloon 242, another guide tube such as a soft tube or a cavity securing tool can be directly inserted into the path. The 31st embodiment is the same as the 30th embodiment except for this.

[32nd Embodiment]

Figure 80:
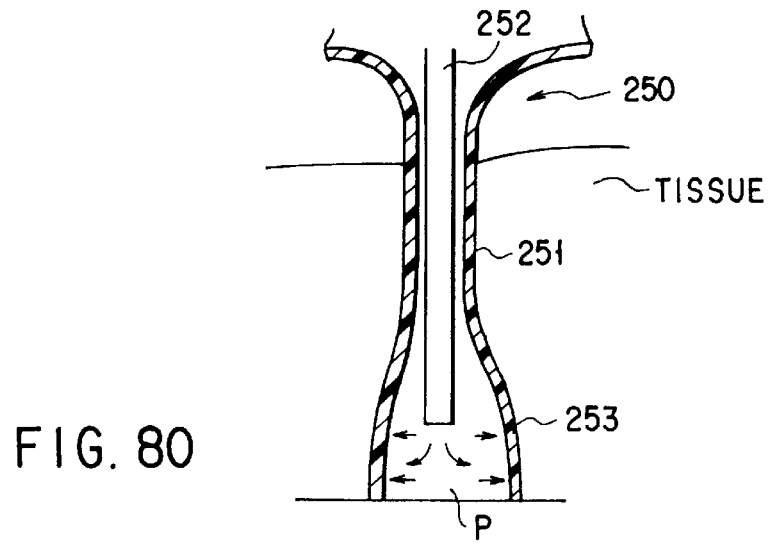
FIG. 80 is a view for explaining a cavity securing tool according to the 32nd embodiment.

The 32nd embodiment of the present invention will be described with reference to FIG. 80. A cavity securing tool 250 in this embodiment includes a tubular sheath 251 made of a deformable sheet member. This tubular sheath 251 forms a tool insertion guide means. For example, the cavity securing tool 250 is used as follows. First of all, tissue is perforated with an insertion tool such as a small-diameter guide tube or a tubular guidewire, and the tool is inserted into the body until the distal end of the tool reaches a region P of surgical object. The tubular sheath 251 is then narrowed, and a guide tube or tubular guidewire is inserted into the sheath to the region of surgical object. The distal end portion of the tubular sheath 251 is positioned in the region P of surgical object. Thereafter, only the guide tube or the tubular guidewire is pulled out. As shown in FIG. 80, a scope 252 is inserted into the indwelled tubular sheath 251. A liquid is supplied through the channel of the scope 252 to expand a cavity securing portion 253 on the distal end portion of the tubular sheath 251, thereby securing a working space in the region P of surgical object. The operator then performs an operation on a target site by introducing another operation tool through the tubular sheath 251 or the scope 252.

[33rd Embodiment]

Figure 81A:
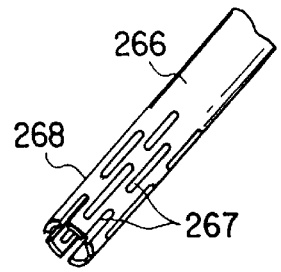
FIGS. 81A and 81B are views for explaining a cavity securing tool according to the 33rd embodiment.
Figure 81B:
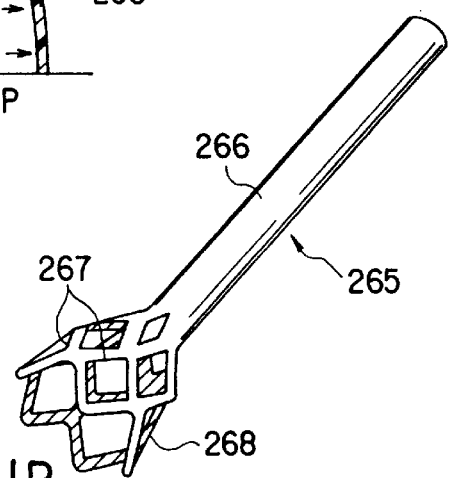

The 33rd embodiment of the present invention will be described with reference to FIGS. 81A and 81B. A cavity securing tool 265 in this embodiment has a guide portion 266 serving also as an operating portion, made of a pipe member which is relatively hard but deformable. As shown in FIG. 81A, a mesh is formed on the distal end portion of the guide portion 266 by forming a plurality of slit-like notches 267. With this structure, as shown in FIG. 81B, a cavity securing portion 268 capable of expanding by plastic deformation is formed.

When this cavity securing tool 265 is to be used, tissue is perforated with the guide portion 266 singly or by using a dilator or the like, and the cavity securing portion 268 is inserted to a region of surgical object, while the cavity securing portion 268 is kept narrowed, as shown in FIG.

81A. Thereafter, an expanding tool or a balloon is inserted into the guide portion 266, and the cavity securing portion 268 is expanded, as shown in FIG. 81B. With this operation, a working space is secured in the region of surgical object, and the operator introduces an operation tool through the guide portion 266 to perform an operation on a target site. That is, the cavity securing tool can be inserted to the region of surgical object through the small insertion hole, and a wide site of operation and a wide visual field can be obtained.

[34th Embodiment]

Figure 82A:
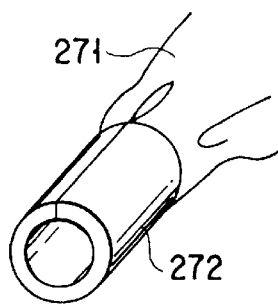
FIGS. 82A and 82B are view for explaining a cavity securing tool according to the 34th embodiment.

The 34th Embodiment of the present invention will be described with reference to FIG. 82. A cavity securing tool 270 in this embodiment includes a soft, deformable, tubular sheet member 271 and a cavity securing portion 272 formed on the distal end of the tubular sheet member 271. The cavity securing portion 272 is formed by winding a belt-like plate member into a single-layer tube. Note that the cavity securing portion 272 may be formed by winding the belt-like plate member into a multi-layer tube. The cavity securing portion 272 is narrowed when it is inserted into tissue, as shown in FIG. 82A.

Figure 82B:
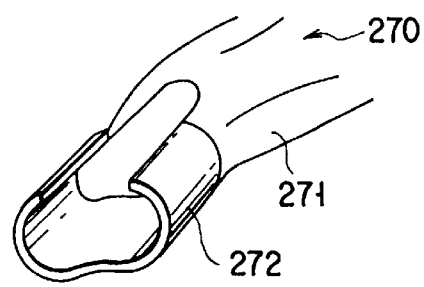

This cavity securing tool 270 can be introduced into tissue by, for example, the method in the first embodiment. After the cavity securing portion 272 is introduced/positioned in a region of surgical object, an expanding tool or a balloon is inserted into the cavity securing portion 272 through the tubular sheet member 271. The cavity securing portion 272 is then expanded by plastic deformation, as shown in FIG. 82B, to secure a working space in the region of surgical object. The operator introduces an operation tool into the working space and performs an operation on a target site. That is, the cavity securing tool can be inserted in the region of surgical object through the small insertion hole, and a wide site of operation and a wide visual field can be obtained.

[35th Embodiment]

Figure 83A:
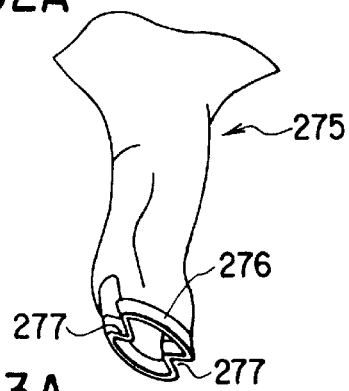
FIGS. 83A to 83C are view for explaining a cavity securing tool according to the 35th embodiment.
Figure 83B:
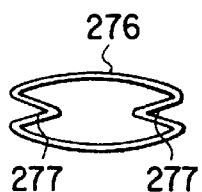
Figure 83C:
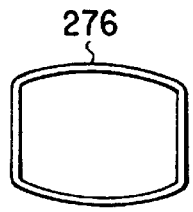

The 35th embodiment of the present invention will be described with reference to FIGS. 83A and 83B. This embodiment includes a modification of the cavity securing tool in the 34th embodiment. A cavity securing tool 275 includes a cavity securing portion 276 having tucked portions 277 on portions of a tubular member made of a belt-like plate material. With this structure, the cavity securing portion 276 is folded as shown in FIG. 83A, and is expanded into a substantially rectangular shape by elastic deformation as shown in FIG. 83B. A method of using this cavity securing tool is the same as that in the above embodiment.

[36th Embodiment]

The 36th embodiment of the present invention will be described with reference to FIGS. 84 and 85. In this embodiment, a cavity securing tool is applied to an operation in an abdominal cavity. More specifically, in the embodiment, an operation in an abdominal cavity is performed by using a cavity securing tool 290 that is almost identical to the cavity securing tool in the 33rd embodiment.

Figure 84:
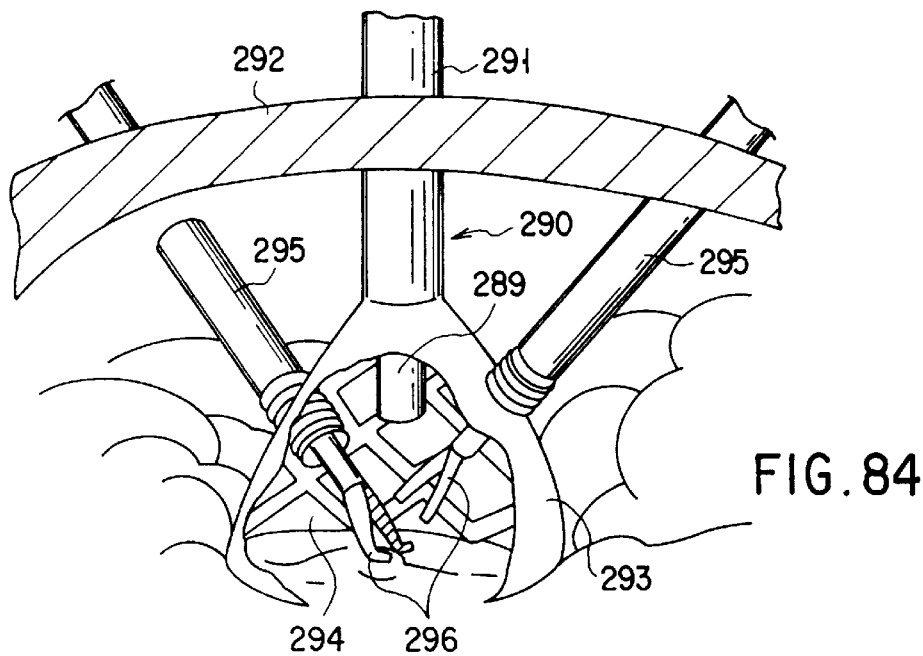
FIG. 84 is a view for explaining how a cavity securing tool according to the 36th embodiment is used.

FIG. 84 shows a state in which an abdominoscopic operation is being performed with the cavity securing tool 290. A guide portion 291 of the cavity securing tool 290, which also serves as an operating portion, extends through an abdominal wall 292, and a cavity securing portion 293 formed on the distal end portion of the guide portion 291 is expanded. A working space 294 is secured in a region of surgical object in the abdominal cavity by the expanded cavity securing portion 293. The distal end of a scope (abdominoscope) 289 is introduced into the working space 294 through the guide portion 291. In addition, the distal ends of ports 295 extending through the abdominal wall 292 are connected to mesh openings of the side wall of the cavity securing portion 293, and other operation tools 296 are introduced into the working space through the ports 295.

In an abdominoscopic operation, once the cavity securing tool 290 is placed in an abdominal cavity, pneumoperitoneum and a lifting operation or a pushing process for the organ in the abdominal cavity need not always be performed. In addition, an operation can be reliably and quickly performed after an operation cavity is secured.

Figure 85:
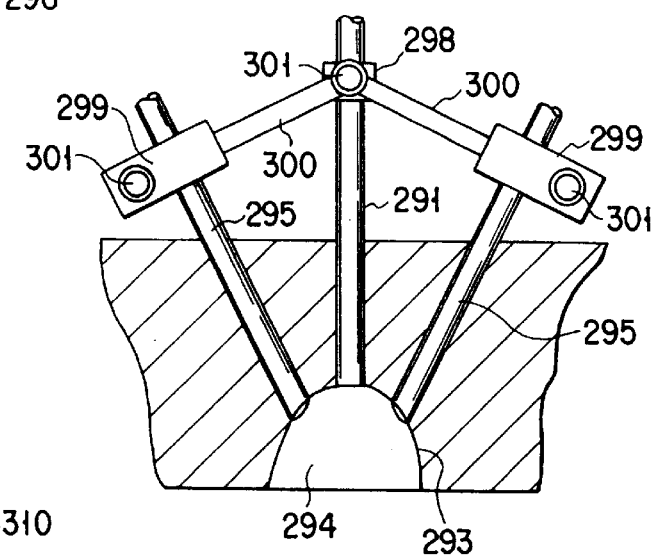
FIG. 85 is a view for explaining how a support tool according to the 36th embodiment is used.

The proximal end portions of the guide portion 291 and the ports 295 of the cavity securing tool 290, which are located outside the body, are supported by a support tool 297 in FIG. 85. The support tool 297 serves as a communicating means, outside the body, which allows the ports to communicate with the cavity secured in the body. The support tool 297 includes a first holding tube 298 for clamping and holding the guide portion 291 and second holding tubes 299 for clamping and holding the ports 295. The first holding tube 298 is coupled to the second holding tubes 299 through coupling members 300. In addition, the distance between each port 295 and the guide portion 291 of the cavity securing tool 290 and the angle of each port 295 with respect to the guide portion 291 can be adjusted. The first and second holding tubes 298 and 299 respectively have set screws 301. This support tool 297 can be applied to tools in other embodiments.

[37th Embodiment]

Figure 86A:
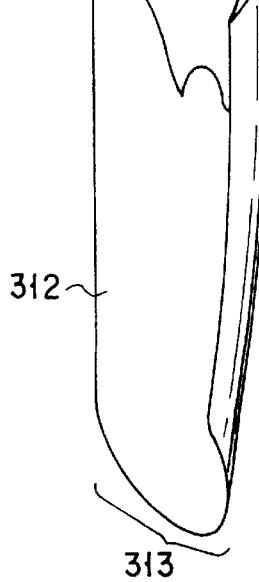
FIGS. 86A and 86B are views for explaining another cavity securing tool according to the 37th embodiment.
Figure 86B:
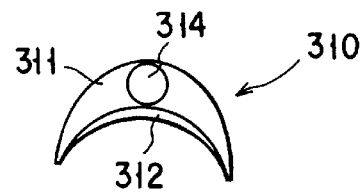

The 37th embodiment of the present invention will be described with reference to FIGS. 86A to 87C. This embodiment includes still another example of the cavity securing tool. As shown in FIG. 86A, a cavity securing tool 310 includes a spatula-like main body member 311 made of a relatively hard material. A gutter-like recess portion 312 is formed on a front surface portion of the main body member 311. The recess portion 312 forms a tool insertion guide channel, and a portion near the distal end portion of the recess portion 312 serves as a cavity securing means for securing a working space.

The distal end edge portion of the main body member 311 is formed into a relatively thin, arcuated portion and is also shaped in conformity with the shape of a bone around a site where a working space is to be secured. That is, this edge portion is formed into an engaging portion 313 that is brought into contact with a bone portion around a cavity securing site to be engaged therewith. A scope insertion opening 314 communicating with the recess portion 312 is formed in the proximal end portion of the main body member 311.

Figure 87A:
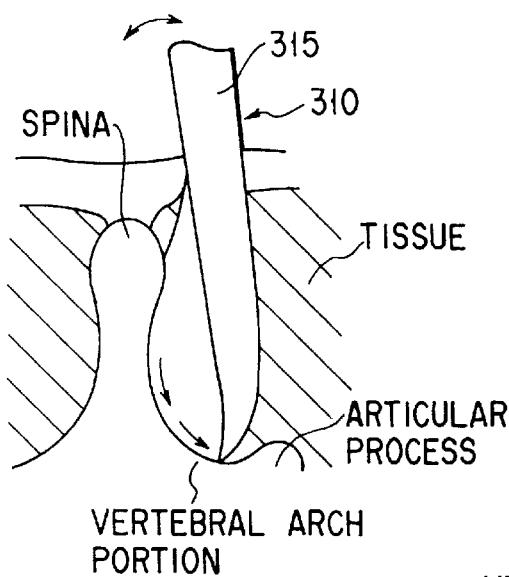
FIGS. 87A to 87C are views for explaining how the cavity securing tool according to the 37th embodiment is used.
Figure 87B:
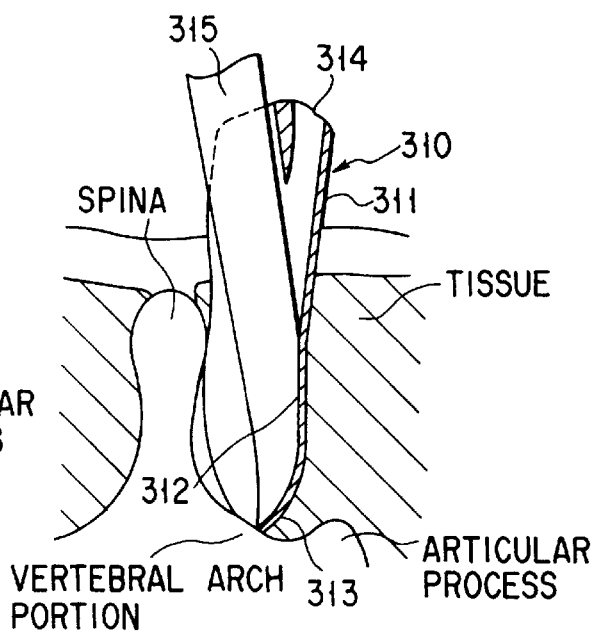
Figure 87C:
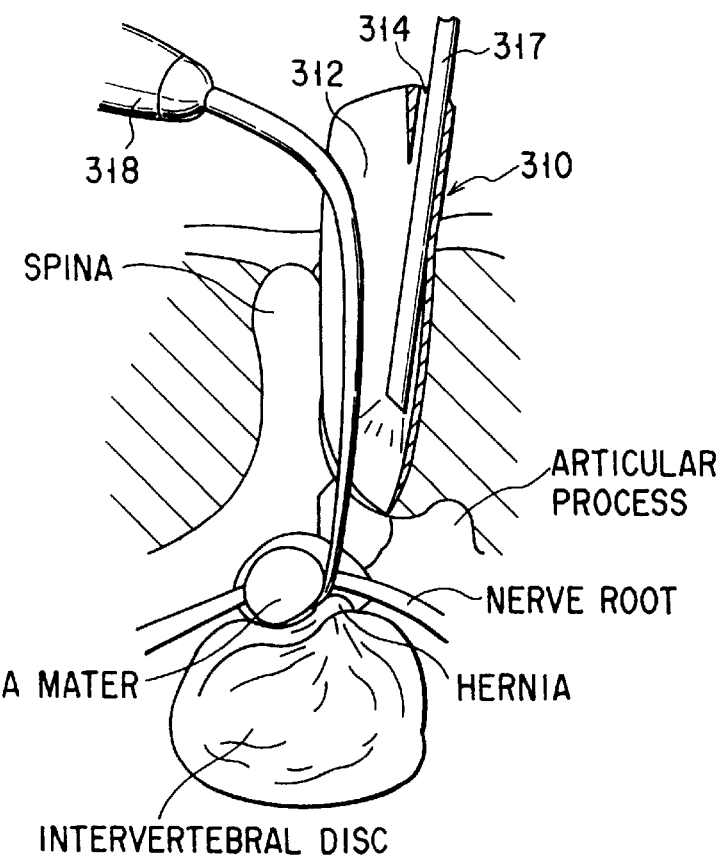

When this cavity securing tool 310 is to be used, another abrasion element 315 is inserted into tissue, and the surface of a bone portion between the spina and the vertebral arch portion is abraded with the blade portion of the abrasion element 315, thereby abrading the tissue off the bone portion, as shown in FIG. 87A. Subsequently, as shown in FIG. 87B, the cavity securing tool 310 is inserted into the tissue, along the back surface of the abrasion element 315, to a region of surgical object in which a working space is to be secured. The engaging portion 313 of the main body member 311 is engaged with the bone portion and positioned in accordance with the shape of the bone portion around the site in which a working space is to be secured. A scope 317 and an operation tool 318 are guided by the recess portion 312 of the cavity securing tool 310 positioned in this manner to be introduced into the secured working space secured in this manner. The operator then performs an operation. FIG. 87C shows a state in which the operation is being performed.

[38th Embodiment]

Figure 88:
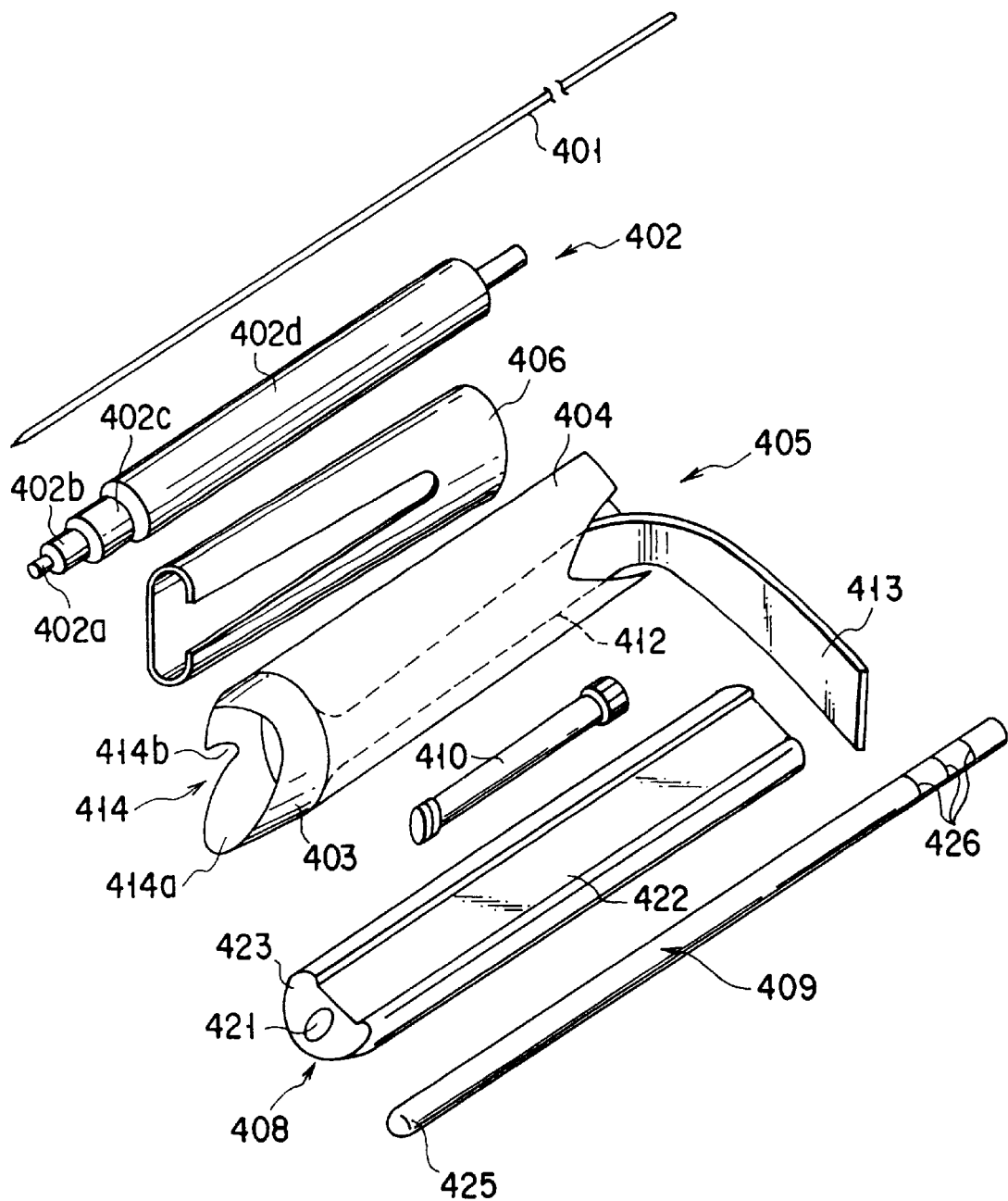
FIG. 88 is a perspective view showing the tools belonging to a cavity securing tool system according to the 38th embodiment.

The 38th embodiment of the present invention will be described with reference to FIGS. 88 to 98C. FIG. 88 shows various tools belonging to a cavity securing tool system. The cavity securing tool system includes a dilator 402 as an insertion tool, an operation sheath 405 having a cavity securing portion (cavity securing tool) 403 for securing a cavity on a treatment site and a cylindrical, soft sheet member 404 as an operation tool guide means, a pusher 406 for pushing the operation sheath 405 into the body, a mandrin 408 for guiding the insertion of the operation sheath 405, a rod-like probe 409 to be used in combination with the mandrin 408 to serve as a position detection means for searching for the position of an operation site, and a port 410.

The dilator 402 is a so-called multi-tube antenna type dilator in which a plurality of tubes 402a to 402d having different diameters are sequentially fitted on each other. The guidewire 401 can be inserted into the thinnest tube 402a. The guidewire 401 is the longest tool of all the tools. The distal end edges of the tubes 402a to 402d which are located on the insertion side are chamfered. The dilator 402 dilates a perforation formed by the guidewire 401 in such a manner that the thinnest tube 402a is fitted on the guidewire 401 inserted into the living body, and the tubes 402b to 402d are sequentially stacked on each other. Relatively thin tubes of the tubes 402a to 402d of the dilator 402, e.g., the tubes 402a and 402b are longer than the thicker tubes 402c and 402d. Of these long tubes, the tube 402b, for example, serves as an insertion guide means for the insertion of the mandrin 408 into vital tissue.

Figure 89A:
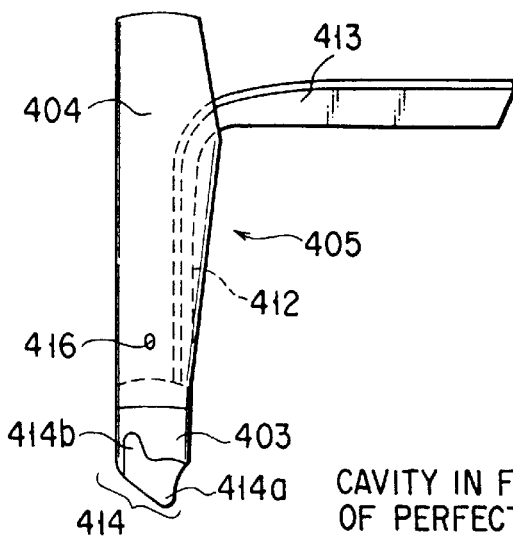
FIG. 89A is a side view of an operation sheath according to the 38th embodiment.

As shown in FIG. 89A, the operation sheath 405 includes the cavity securing portion 403 and the cylindrical, soft sheet member 404, as described above. A flat operating portion 412 extending outside the body through the soft sheet member 404 is contiguously formed on the cavity securing portion 403. The operating portion 412 is made of a plate-like (belt-like) member, located on the articular process side, and contiguous with the ring member of the cavity securing portion 403. The extended distal end portion of the operating portion 412 bends and protrudes to the articular process side. An operating gripping portion 413 is formed on this portion extending laterally. This flat operating portion 412 is tapered toward the distal end. The operating gripping portion 413 is wide to allow the operator to easily hold it when he/she manipulates it.

Figure 89B:
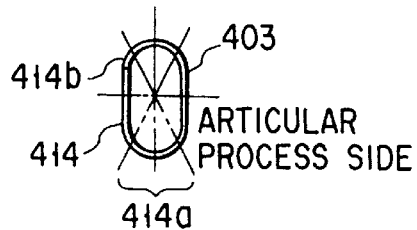
FIG. 89B is a bottom view of the cavity securing portion of the operation sheath.

The cavity securing portion 403 is made of a hard belt-like member to have an oval or elliptic, flat, ring-like shape. The distal end edge of this belt-like ring member is specially shaped to be engaged with a bone portion, that is, the distal end edge is formed into an engaging means 414 for the bone portion. As shown in FIG. 89B, the engaging means 414 includes a projection portion 414a located on the relatively tail side and a recess portion 414b located on the relatively head side of the spina side. With regards to the spine shown in FIG. 90A, the engaging means 414 has a contour shape conforming to the bone portion indicated by the dashed line in FIG. 90A, and is engaged with the bone portion.

Figure 90A:
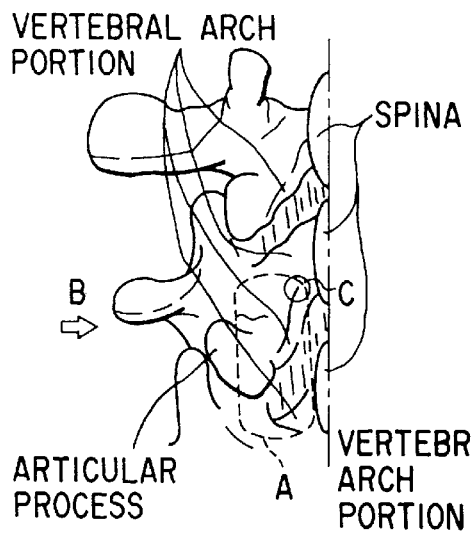
FIG. 90A is an anatomical chart of the spine in a surgical object viewed from the back side.
Figure 90B:
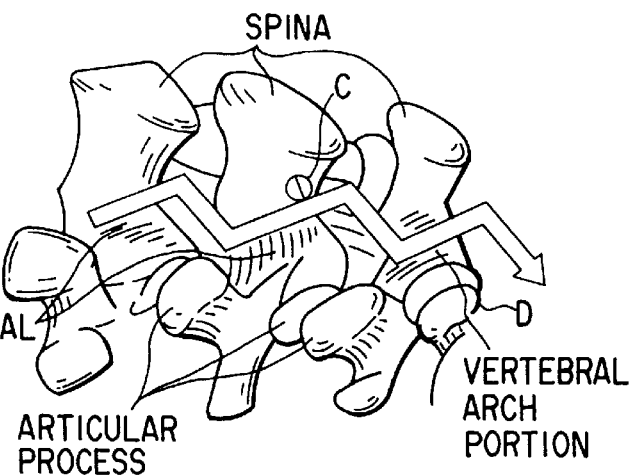
FIG. 90B is a perspective view of the spine.

Referring to FIG. 90A, a region A surrounded with the dashed line is a region of surgical object, and an inclined portion C between the spina and the vertebral arch portion is a portion to be engaged with the recess portion 414b of the engaging means 414. A relatively large indentation located on substantially the opposite side to the inclined portion C is a portion in/with which the projection portion 414a of the engaging means 414 is inserted/engaged. As shown in FIG. 90B, which is a view obtained when viewed from the direction of an arrow B in FIG. 90A, in general, the portions between vertebral arches greatly undulate, as indicated by an arrow D. In addition, the portions between the vertebral arches and the spinae have certain slopes.

Figure 89C:
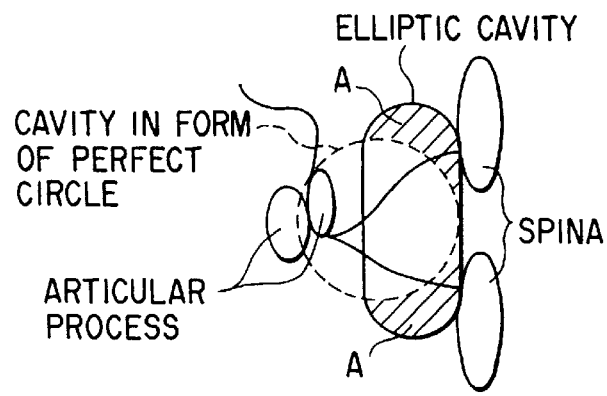
FIG. 89C is a view for explaining how the cavity securing portion to the 38th embodiment.

The hole of the cavity securing portion 403 of the operation sheath 405 has an oval or elliptic cross-section, i.e., a flat cross-section. The circumference of the cavity securing portion 403 is almost equal to that of the cavity securing portion in the form of a perfect circle in the previous embodiment. For this reason, as shown in FIG. 89B, the treatment cavity is longer than that in the previous embodiment. The reasons why such an elliptic cavity is formed will be described below. A treatment in an operation often proceeds from the portion between vertebral arches to the head and tail sides. In this case, the region of surgical object is a region elongated in the head/tail direction (the region indicated by the dashed line in FIG. 90A). If, therefore, the circumference of the cavity securing portion is set to be equal to that of a cavity securing portion in the form of a perfect circle, and the hole of the cavity securing portion is made elliptic or oval, a larger treatment region can be covered in the hole with substantially the same pushing effect as that given by the cavity securing portion in the form of a perfect circle. In addition, as shown in FIG. 89C, the cavity in the form of a perfect circle comes into contact with the spinae, and hence cannot be moved to the spina side. For this reason, the treatment region A cannot be fully covered in the cavity. In contrast to this, the oval or elliptic cavity can cover a larger part of the treatment region A than the cavity in the form of a perfect circle. In addition, if the vertebral arch between an articular process and a spina is narrow (which differs among individuals or depending on the vertebral body level), the region of surgical object cannot be positioned in substantially the center of the cavity in the form of a perfect circle in some case. In contrast to this, since the elliptic or oval cavity is short in the minor axis direction, no unnecessary portion enters the cavity, and the region of surgical object can be positioned in substantially the center of the cavity. For the above reasons, when the circumference of an elliptic cavity is made equal to that of a cavity in the form of a perfect circle, the region of surgical object can be efficiently covered in the cavity with substantially the same pushing effect as that given by the cavity in the form of a perfect circle.

The cavity securing portion 403 has the projection portion 414a and the recess portion 414b which serve as an engaging means for a bone. The recess portion 414b is shaped in conformity with the slope from a vertebral arch portion to a spina. This slope is steep in some person or depending on the vertebral body level. If the cavity securing portion 403 has no recess portion serving as an engaging means for a spina, the cavity securing portion 403 comes into contact with the slope. When the cavity securing portion 403 is pushed inside, the portion moves toward the articular process along the slope. As a result, the region of surgical object cannot be positioned in the cavity. In contrast to this, in this embodiment, since the recess portion 414b of the cavity securing portion 403, which serves as an engaging means and is located on the spina side, is fitted on the slope, even if the slope is steep, the region of surgical object can be positioned in the cavity. In addition, since the slope is fitted in the recess portion 414b when the sheath is inserted, the cavity securing portion 403 can be easily positioned. Furthermore, the projection portion 414a and the recess portion 414b serving as an engaging means almost conform to the shape of a portion around the treatment site to prevent unnecessary muscle tissue from entering the cavity.

As described above, since the cavity securing portion 403 has the projection portion 414a and the recess portion 414b, which serve as an engaging means for the elliptic hole and a bone, a region of surgical object can be efficiently caught and indwelled in the hole. Even if, therefore, the vertebral arch portion is narrow and the slope is steep, which depends on individuals or the vertebral body level, a good cavity can be held. Obviously, the cavity securing portion 403 can be used without posing no problem even if the vertebral arch is wide and the slope is not very steep. For this reason, the belt-like ring member of the cavity securing portion 403 is not limited to an oval or elliptic shape, and an odd-shaped ring member such as a rectangular or round rhomboid ring member can be used.

The soft sheet member 404 of the operation sheath 405 is flexible enough to be easily collapsed by the pressure from surrounding tissue when it is indwelled in the tissue. The soft sheet member 404 is made of a transparent material that allows the operator to see the movement of tissue or a tool located outside a cavity from the cavity side with an endoscope. In addition, an antireflection means such as a means using a satin material is preferably applied to at least the inner surface of the operation sheath 405 in a region positioned in vital tissue. Furthermore, one or a plurality of port coupling holes 416 in which the distal end portion of ports 410 can be inserted are formed in part of the wall of the soft sheet member 404. The soft sheet member 404 may have a flared shape that spreads outward in the form of a funnel.

Figures 91A, 91B:
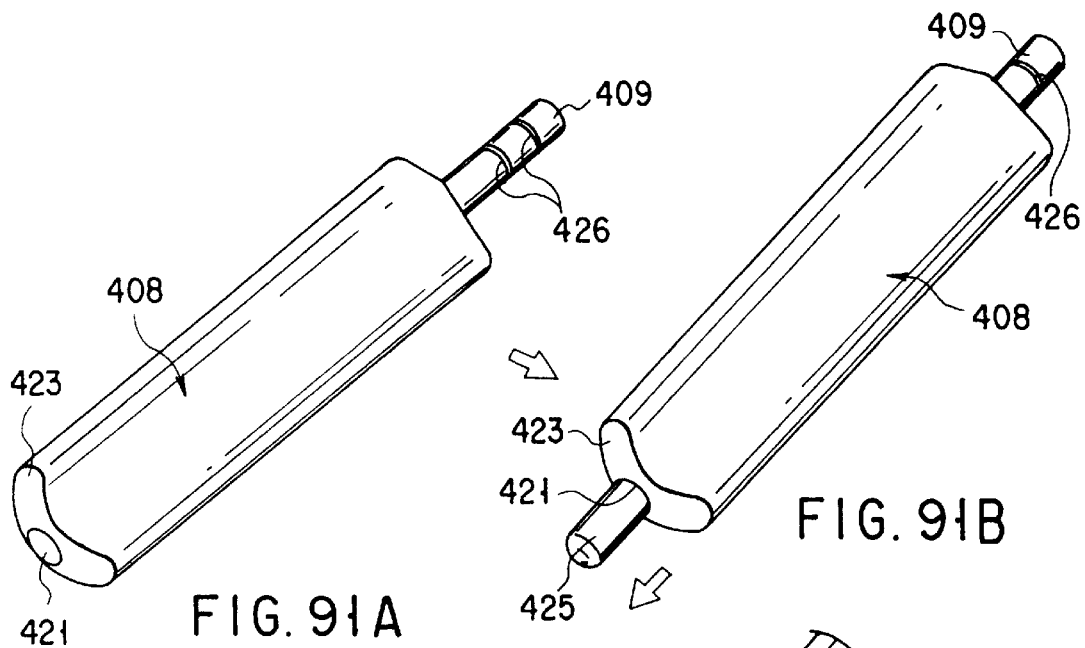
FIGS. 91A to 91C are views for explaining a mandrin and a probe in the 38th embodiment.

The outer surface of the mandrin 408 is almost tightly fitted to the inner surface of the cavity securing portion 403. Obviously, the cross-section of the mandrin 408 has the same flat shape, e.g., oval or elliptic shape, as that of the cavity securing portion 403. As shown in FIG. 91A, an insertion hole 421 is formed in the center of the mandrin 408 to extend therethrough along the axial direction. The insertion hole 421 is formed to allow the tube 402b, of the long tubes 402a and 402b, which has a larger diameter to be relatively tightly fitted therein, and to allow the probe 409 for searching for the insertion position of the mandrin 408 to extend therethrough. Note that the insertion hole 421 need not be formed in the center of the mandrin 408, and may be formed at a position decentered from the center in the major axis direction of an oval cross-section. An operating portion relief groove 422 serving also as a guide for fitting the operating portion 412 is formed in the outer surface of the mandrin 408. The distal end face of the mandrin 408 is formed into a smooth curved surface. The thickness of the mandrin. 408 is set such that the mandrin 408 is not fitted in the portion between vertebral arches (the hole between vertebral arches) and locked to a bone portion. The distal end face of the mandrin 408 serves as a reference surface 423 to be used when the shape of a site of operation is to be detected from outside the body with the probe 409.

As shown in FIG. 91B, the probe 409 extends through the insertion hole 421 of the mandrin 408. The distal end portion of the probe 409 serves as a detecting portion 425 protruding from the reference surface 423 of the mandrin 408. A position indicator 426 consisting of lines is marked on the other end portion of the probe 409. The position indicator 426 indicates the protrusion amount of the detecting portion 425 protruding from the reference surface 423 of the mandrin 408, i.e., the insertion depth of the probe 409. That is, the position indicator 426 indicates the insertion depth of the probe 409 protruding from the reference surface 423 of the mandrin 408. With this depth, the depth of the site of operation can be detected. The position indicator 426 serves as an extracorporeal detection means for externally detecting the shape of an insertion site at which the distal end of the mandrin 408 is positioned.

Note that the above indicator 426 can be made of a proper combination of different colors, lines, and the like.

A procedure in a surgical operation method of excising a hernia by accessing it from the back side using the cavity securing tool system of this embodiment will be described next. First of all, as in the first and ninth embodiments, a perforation is formed from the skin into the muscle toward a region of surgical object with the guidewire 401, the distal end of the guidewire 401 is inserted the proximal end portion of a spina. This position is checked by X-ray fluoroscopy or the like. The dilator 402 is then fitted on the guidewire 401. The tubes 402a to 402d of the dilator 402 are sequentially fitted on each other to dilate the tissue around the portion perforated with the guidewire 401 so as to dilate the perforation. The guidewire 401 is pulled out immediately after the thinnest tube 401a is inserted. After a necessary number of tubes, i.e., the tubes 402a to 402d, of the dilator 402 are inserted, for example, the tubes 402c and 402d are pulled out while the tubes 402a and 402b are left.

The mandrin 408 is pushed into the tissue by using the tube 402b as a guide while adjustment is made to insert the long tubes 402a and 402b of the dilator 402 into the insertion hole 421 of the mandrin 408. Since the perforation to be accessed has been dilated by the dilator 402, even the relatively thick mandrin 408 having an odd-shaped cross-section can be easily inserted into the perforation.

Figure 92A:
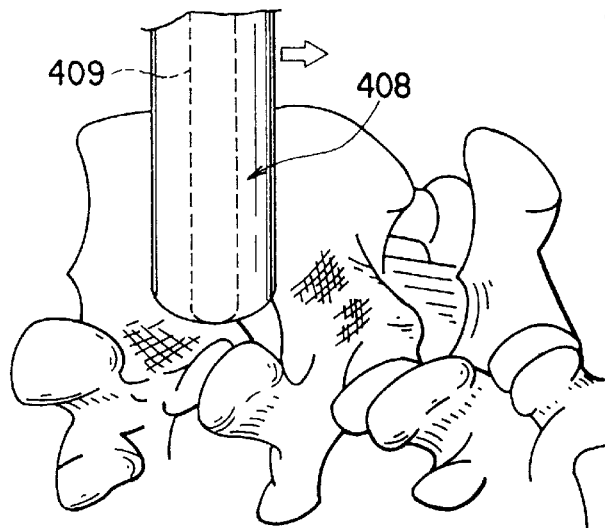
FIGS. 92A and 92B are views for explaining how the mandrin and the probe in the 38th embodiment are used.
Figure 92B:
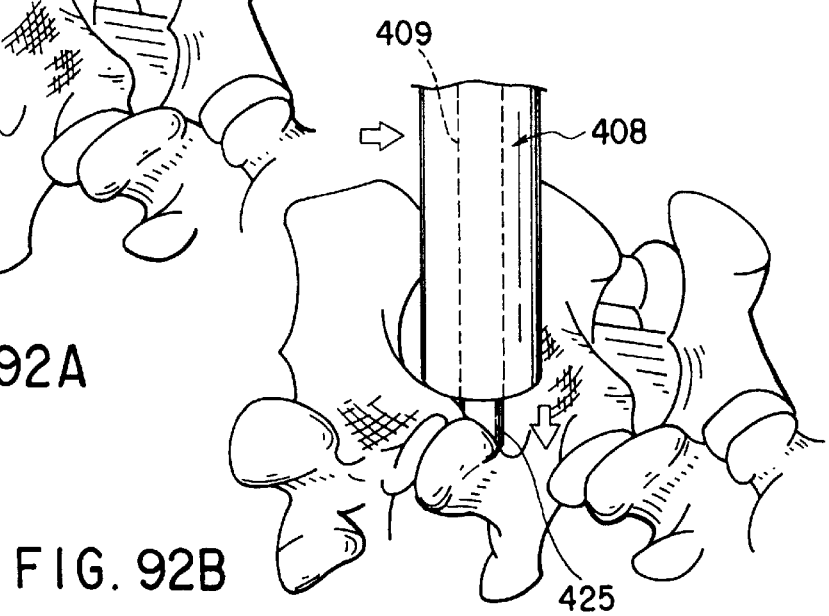
Figure 93A:
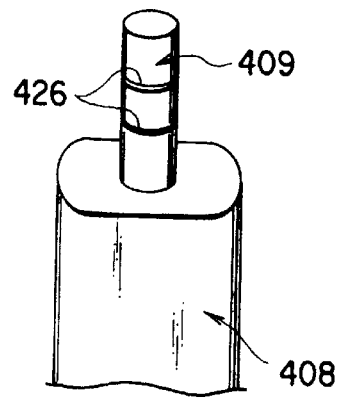
FIGS. 93A and 93B are views for explaining the state of an indicator when position detection is performed by using the mandrin and the probe in the 38th embodiment.
Figure 93B:
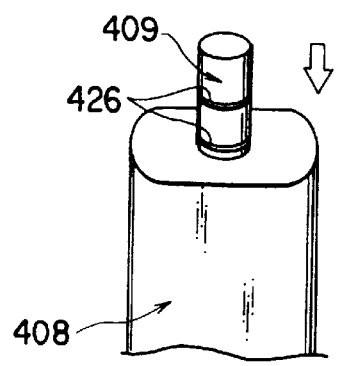

Subsequently, the long tubes 402a and 402b of the dilator 402 are pulled out from the insertion hole 421 of the mandrin 408, and the probe 409 is inserted into the insertion hole 421 instead. Since the long tubes 402a and 402b of the dilator 402 and the probe 409 are longer than the mandrin 408, they can be easily manipulated. As shown in FIGS. 92A and 92B, the operator searches for a target surgical object by using the probe 409 extending through the mandrin 408. More specifically, the operator pierces the detecting portion 425 on the distal end of the probe 409 from the reference surface 423 of the mandrin 408, and searches the portion between vertebral arches with the detecting portion 425. By repeatedly inserting the detecting portion 425 of the probe 409, the operator searches for a position where the detecting portion 425 enters the hole portion between the vertebral arches relatively deep. The operator can easily know from outside the body on the basis of the position of the position indicator 426 that the probe 409 is inserted into the hole portion between the vertebral arches relatively deep. More specifically, the protrusion amount of the detecting portion 425 of the probe 409 from the reference surface 423 of the mandrin 408 is known from the position of the indicator 426 with respect to the proximal end face of the mandrin 408, thereby allowing the operator to check the shape and position of the region of surgical object. FIG. 93A shows the indicator 426 before the position of the portion between the vertebral arches is detected. FIG. 93B shows the indicator 426 after the position of the portion of the vertebral arches is detected.

When the position of the portion between the vertebral arches is detected by the probe 409 in this manner, the mandrin 408 also follows the movement of the probe 409, and the reference surface 423 on the distal end of the mandrin 408 is positioned to the region of surgical object. The diameter of the mandrin 408 is larger than that of the hole between the vertebral arches, and the reference surface 423 is a relatively large surface. For this reason, the mandrin 408 is safely positioned without entering the portion between the vertebral arches. In this manner, the mandrin 408 can be easily positioned to the treatment site, and the reference surface 423 of the mandrin 408 can be reliably positioned to a predetermined treatment site.

Figure 97A:
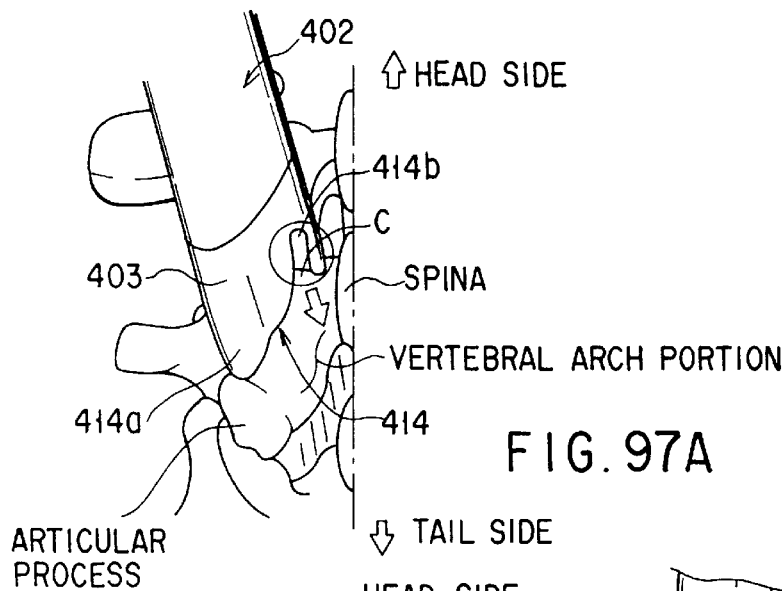
FIGS. 97A to 97C are views for explaining how the operation sheath in the 38th embodiment is used.
Figure 97B:
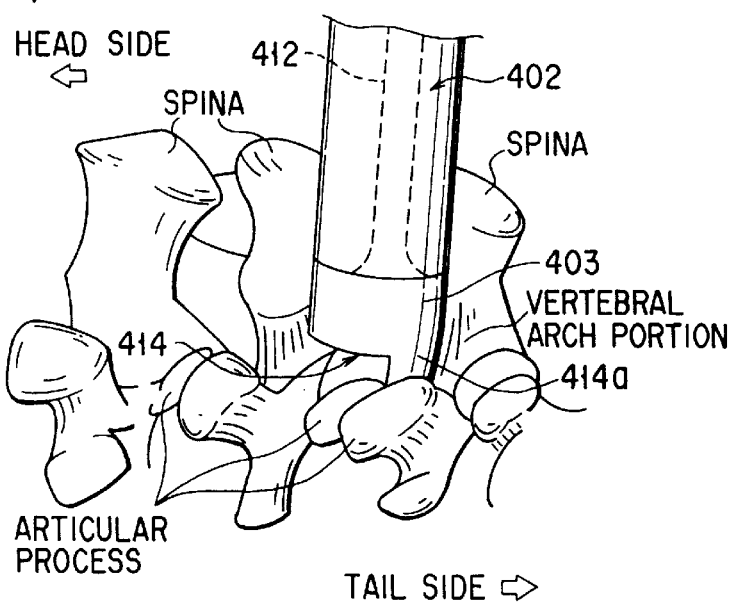
Figure 97C:
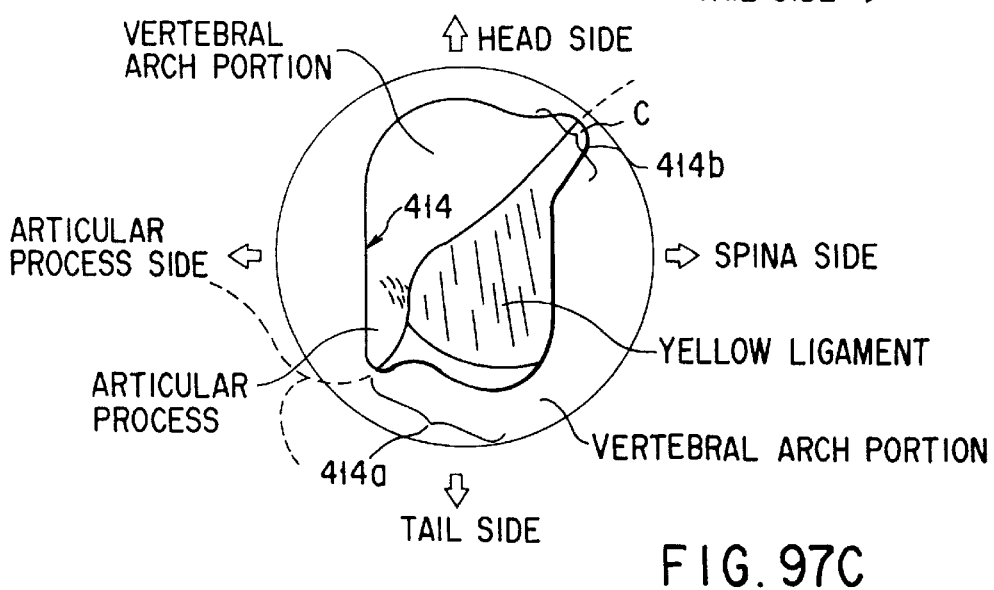

When the mandrin 408 is positioned, the probe 409 is pulled out while the mandrin 408 is left. As in the ninth embodiment, the pusher 406 is inserted into the operation sheath 405 outside the body, and these members are then fitted on the mandrin 408. The operation sheath 405 is inserted to the deepest possible position by using the mandrin 408 as a guide. When the proximal end of the mandrin 408 and the proximal end of the pusher 406 coincide with each other, the operator determines that the operation sheath 405 has been inserted to the deepest possible position. As shown in FIGS. 97A and 97B, the engaging means 414 of the cavity securing portion 403 is engaged with the bone portion around the treatment site. Since the engaging means 414 of the cavity securing portion 403 is shaped in conformity with the shape of the bone portion around the place where an operation cavity is to be secured, the cavity securing portion 403 can be accurately and reliably engaged with the predetermined site. The cavity securing portion 403 of the operation sheath 405 can be indwelled at a proper position by combining the means for detecting the position of surgical object using the probe 409 with the step of leaving the operation sheath 405 in the body by using the mandrin 408 as a guide which is introduced to a proper position by the position detection means.

Figure 91C:
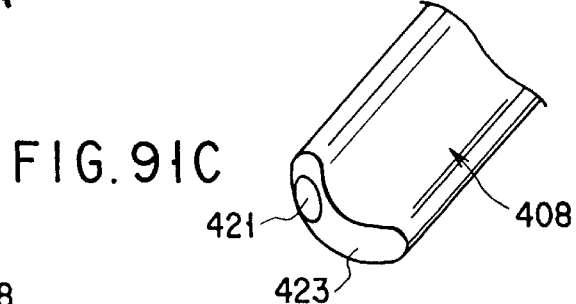

Note that the insertion hole 421 may not be formed in the center of the mandrin 408, as shown FIG. 91C. For example, as shown in FIG. 91C, when the insertion hole 421 is offset downward, the mandrin 408 can be shifted to the head side and located thereon. As a result, the operation sheath 405 inserted along the mandrin 408 is also positioned on the head side. That is, if one of a plurality of mandrins 408 having insertion holes 421 formed at different positions is properly selected and used in accordance with the state of an operation site such as a vertebral arch portion or the difference among individuals, the operation sheath 405 can be guided to a more proper position along the mandrin 408.

Figure 96A:
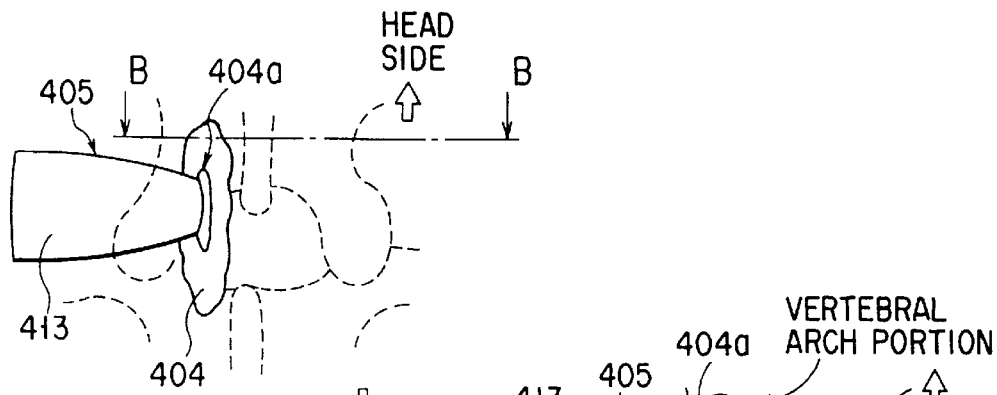
FIGS. 96A and 96B are views for explaining how the operation sheath is used.
Figure 96B:
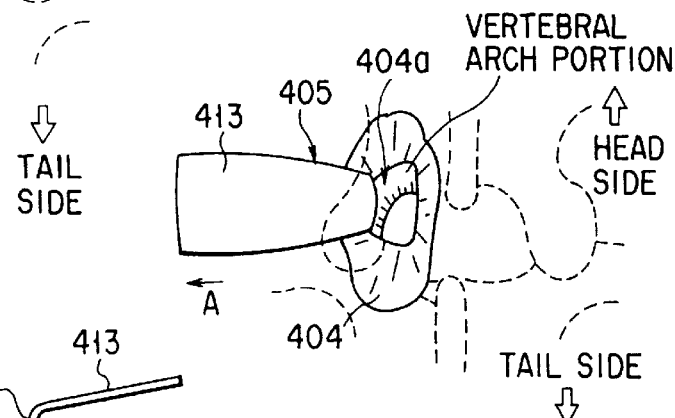
Figure 96C:
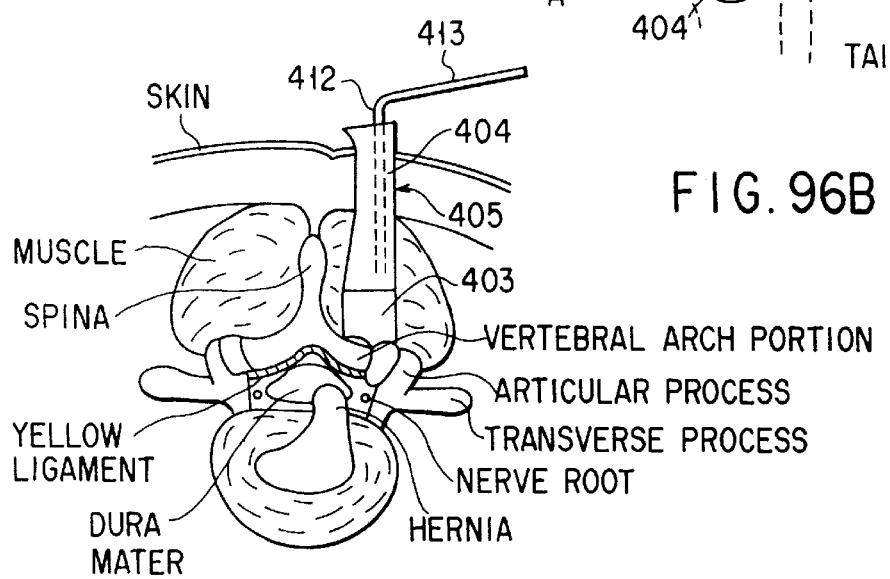
FIGS. 96C and 96D are sectional views taken along a line B—B in FIG. 96A.
Figure 96D:
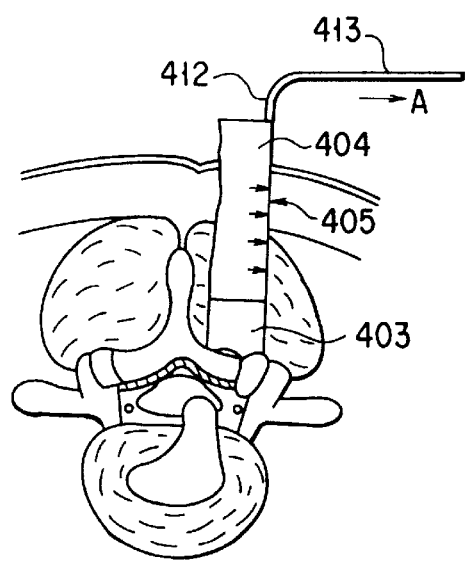

After the operation sheath 405 is positioned in the operation region in the body, the pusher 406 is pulled out. FIG. 96C shows the state of the visual field obtained by observation in the cavity securing portion 403 with an endoscope. As shown in FIG. 96A, the soft sheet member 404 is compressed by the pressure from the surrounding muscle immediately after the pusher 406 is pulled out. For this reason, the operation sheath 405 causes no damage to the surrounding tissue. In addition, since the operating portion 412 is positioned on the articular process side, and the operating gripping portion 413 bends and extends toward the articular process side, the operating portion 412 does not easily interfere with a treatment tool when it is inserted into the operation sheath 405 as compared with a case in which the operating gripping portion 413 is positioned on the spina side. As shown in FIG. 96B, therefore, if the operating portion 412 is pulled to the articular process side in the direction of an arrow A to open a treatment tool insertion opening 404a of the soft sheet member 404, interference with a treatment tool when it is inserted can be minimized, thus allowing the treatment tool to be easily inserted.

In addition, the operator is standing on a side of the patient lying with his/her face down, and is located in a direction almost perpendicular to the head/tail direction of the patient. For this reason, the operator operates treatment tools (including the endoscope) from the head/tail direction of the patient. Therefore, there is little interference between the operating portion and the treatment tools.

Figure 94:
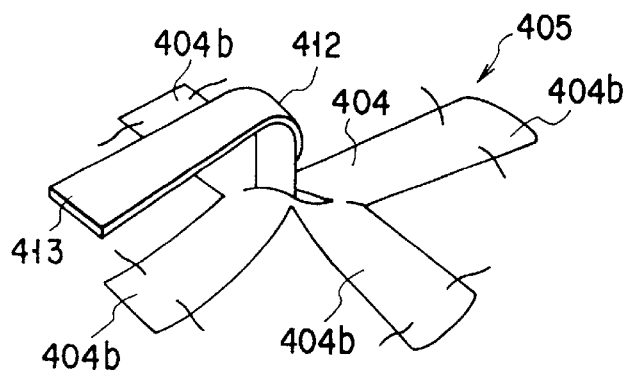
FIG. 94 is a view for explaining the state of the portion of the operation sheath which is located outside the body in the 38th embodiment.
Figure 95:
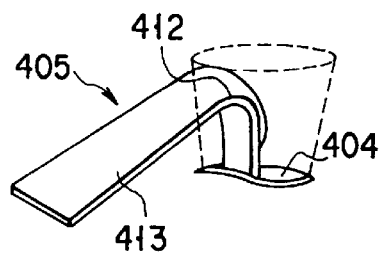
FIG. 95 is a view for explaining the state of the portion of the operation sheath which is located outside the body in the 38th embodiment.

If the exposed portion of the soft sheet member 404 which is located outside the body interferes with an operation, a plurality of incisions are made in the exposed portion to divide it into a plurality of tongue-like portions 404b, as shown in FIG. 94. These tongue-like portions 404b may be stitched onto the skin of the body or fixed thereto with an adhesive tape. Alternatively, as shown in FIG. 95, the exposed portion of the soft sheet member 404 may be cut.

The subsequent treatments and the like are the same as those in the other embodiments. When a tool is to be caused to approach a region of surgical object from a side of the soft sheet member 404, the operator pierces the guidewire 401 into tissue, and inserts the distal end of the guidewire 401 into the port coupling hole 416. In this case, since the distal end of the guidewire 401 can be observed with an endoscope 427 inserted into the soft sheet member 404, the distal end of the guidewire 401 can be easily and reliably guided. The dilator 402 is fitted on the guidewire 401, and a path extending into the cavity securing portion 403 is formed while the guidewire 401 is observed with the endoscope inserted into the soft sheet member 404. The port 410 can be introduced into the operation sheath 405 by using the dilator 402 as a guide. As a result, the port 410 is engaged with the soft sheet member 404. The operator can insert a treatment tool through the port 410 and perform a treatment.

Figure 98A:
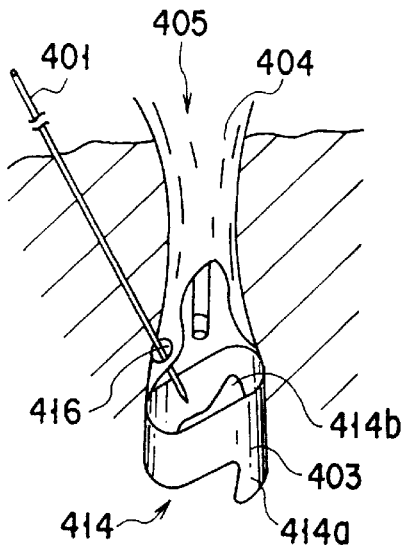
FIGS. 98A to 98C are views for explaining a modification of the operation sheath according to the 38th embodiment.
Figure 98B:
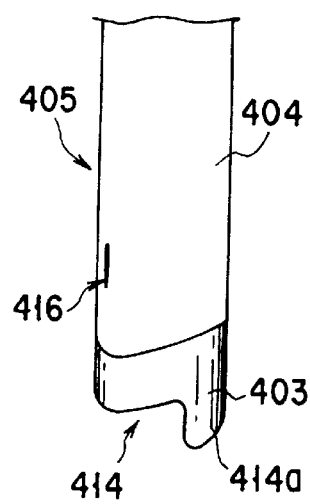
Figure 98C:
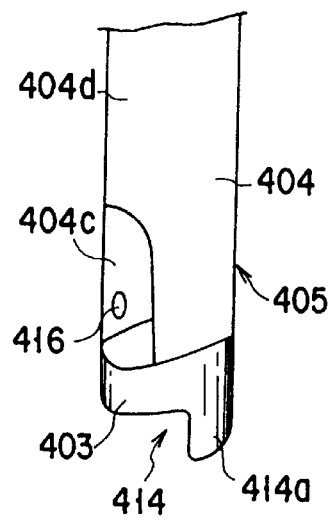

As the port coupling hole 416, a slit-like hole like the one shown in FIG. 98B may be used. A slit-like hole is easy to form. As shown in FIG. 98C, only a portion 404c surrounding the port coupling hole 416 may be made transparent, while a remaining portion 404d may be made opaque. When an opaque portion is formed on the soft sheet member 404, no tissue can be seen through the opaque portion to prevent reflection of light. In addition, a satisfactory antireflection means such as a means using a satin material can be easily applied to the inner surface of the opaque portion.

[39th Embodiment]

Figure 99A:
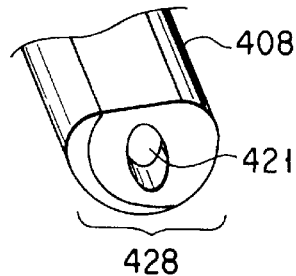
FIG. 99A is a perspective view showing the distal end portion of a mandrin according to the 39th embodiment.
Figure 99B:
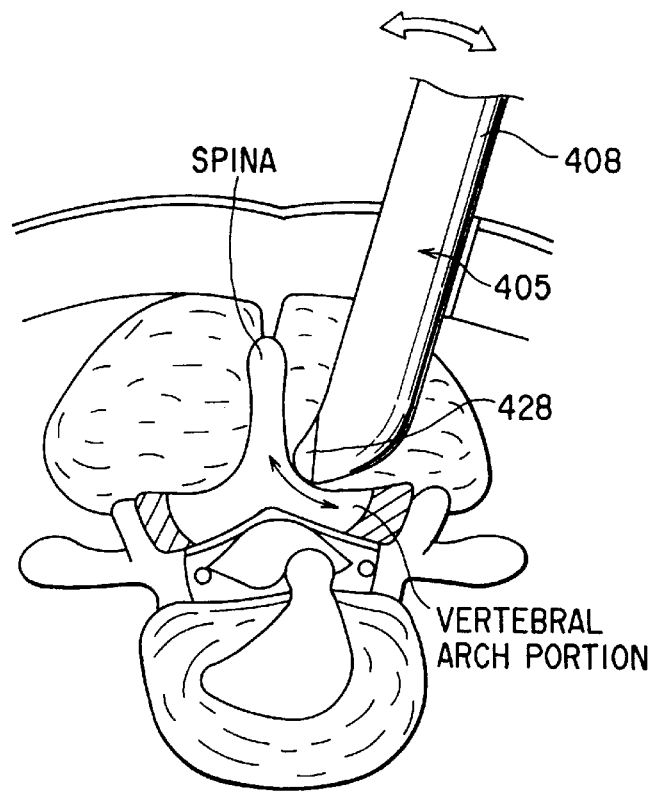
FIG. 99B is a view for explaining how the mandrin is used.

The 39th embodiment of the present invention will be described with reference to FIGS. 99A and 99B. In this embodiment, as shown in FIG. 99A, a sharp portion 428 is formed on a portion of the distal end edge of a mandrin 408 so as not to impair the function of an engaging means 414 for a bone. This mandrin 408 is used as follows. After the mandrin 408 is inserted into the body as in the above embodiment, tissue such as muscle clinging to a vertebral arch portion is abraded off by using the sharp portion 428 of the mandrin 408, as shown in FIG. 99B, before an operation sheath 405 is introduced. As described previously, the size of the distal end portion of the mandrin 408 is set such that the distal end does not enter the portion between vertebral arches (hole between vertebral arches). This therefore prevents the mandrin 408 from accidently entering the portion between the vertebral arches and damaging the tissue or the like on an unnecessary portion.

The operator can intuitively know the position of the mandrin 408 by abrading tissue such as muscle clinging to a vertebral arch portion with the mandrin 408. In addition, the operator can easily position the operation sheath 405 and can clearly observe a site of operation after the sheath is indwelled by clearly abrading the tissue off. If this process is not performed, since muscle is clinging to a bone in the region of surgical object after the operation sheath 405 is indwelled, the operator must cut the tissue with an electric scalpel and remove it with the forceps. That is, a cumbersome process is required to expose the bone portion around the treatment site. In contrast to this, in this embodiment, the above process is relatively simplified, and hence an operation is considerably facilitated.

[40th Embodiment]

Figures 100A, 100B:
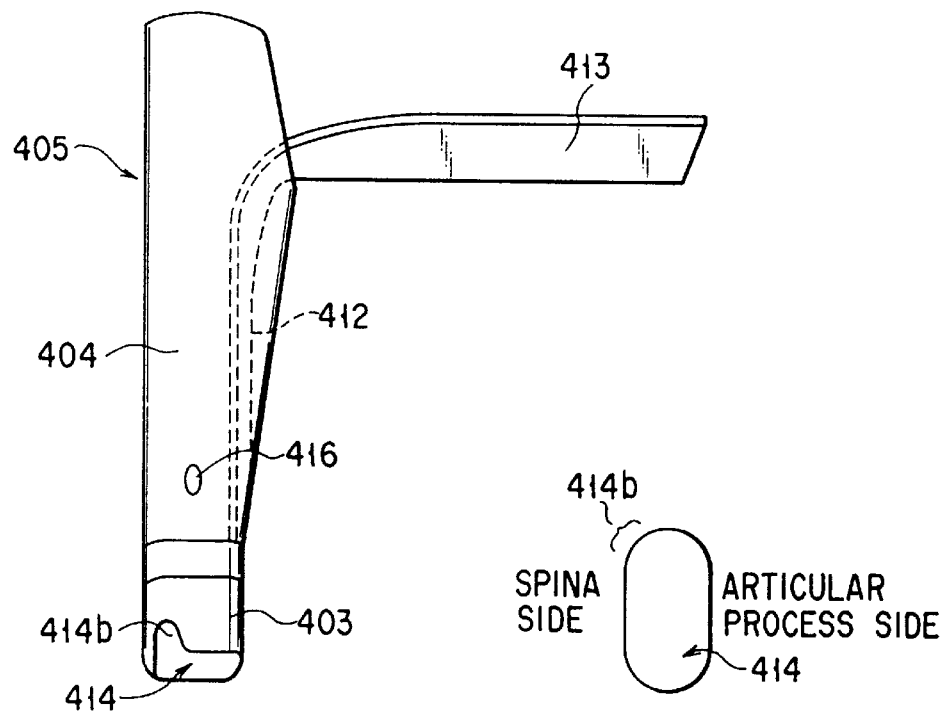
FIG. 100A is a perspective view showing an operation sheath according to the 40th embodiment.
FIG. 100B is a bottom view of the cavity securing portion of the operation sheath.

The 40th embodiment of the present invention will be described with reference to FIGS. 100A and 100B. This embodiment includes a modification of the operation sheath 405. An engaging means 414 of a cavity securing portion 403 of an operation sheath 405 has no projection portion 414a, and the distal end edge of the cavity securing portion 403 is flat. The engaging means 414 has a recess portion 414b at a position corresponding to a spina. The operation sheath 405 is the same as that in the 38th embodiment except for the above structure.

Since the engaging means 414 has no projection portion 414a, the cavity securing portion 403 of the operation sheath 405 can be shifted to the tail side after the cavity securing portion 403 is temporarily inserted. If the engaging means 414 has the projection portion 414a, the projection portion 414a comes into contact with a vertebral arch portion, and the cavity securing portion 403 can hardly be shifted to the tail side. Since the operation sheath 405 in this embodiment does not have the projection portion 414a that interferes with the above movement, the operation sheath 405 can be smoothly moved toward the tail side. The operator can therefore know the state of a portion around an operation site by observing a wide region around the operation site moving the operation sheath 405, and can easily check the site of operation.

[41st Embodiment]

Figure 101A:
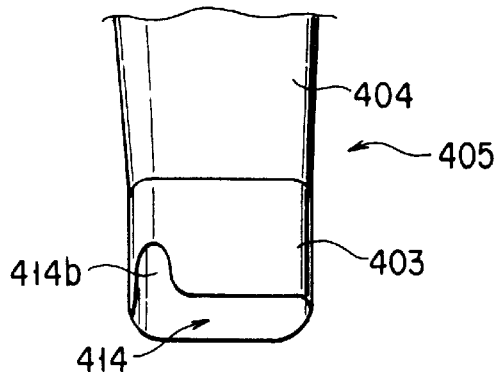
FIG. 101A is a perspective view showing the cavity securing portion of an operation sheath according to the 41st embodiment.
Figure 101B:
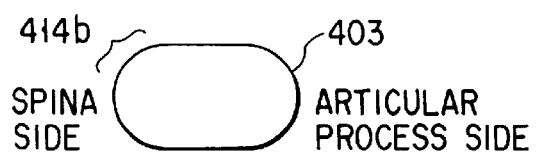

The 41st embodiment of the present invention will be described with reference to FIGS. 101A and 101B. The ring-like member forming the cavity securing portion 403 of the operation sheath 405 in the 38th embodiment has the flat shape elongated in the head/tail direction. The ring-like member of a cavity securing portion 403 in the 41st embodiment has a flat shape elongated in the lateral direction. That is, the ring-like member of the cavity securing portion 403 has a flat shape elongated toward the spina side and the articular process side. With this shape, a laterally wide view of an articular process portion can be obtained to allow the operator to easily check the region of the bone to be excised. This facilitates an operation.

In addition, the cavity securing portion 403 in this embodiment has only a recess portion 414b to be engaged with an inclined portion extending from a spina to a vertebral arch portion. However, the cavity securing portion 403 may have a projection portion 414a as in the 38th embodiment.

[42nd Embodiment]

Figure 102A:
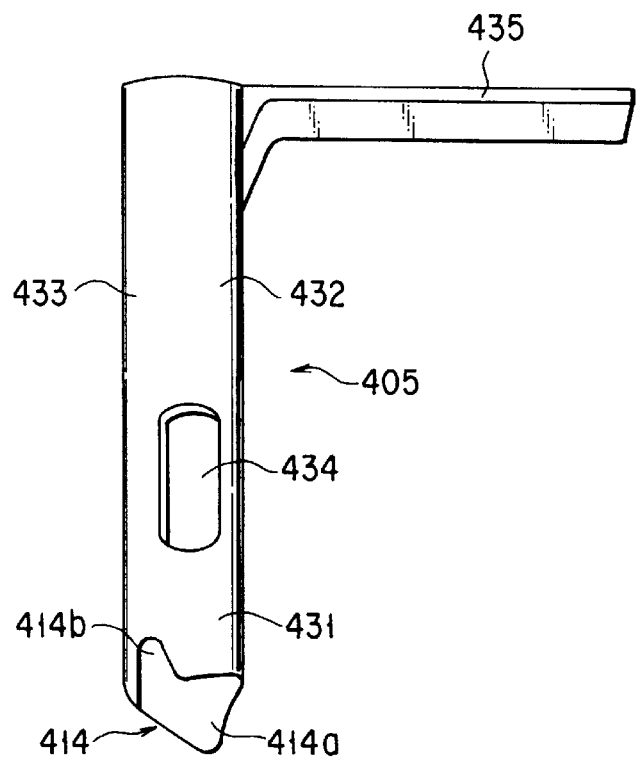
Figure 102B:
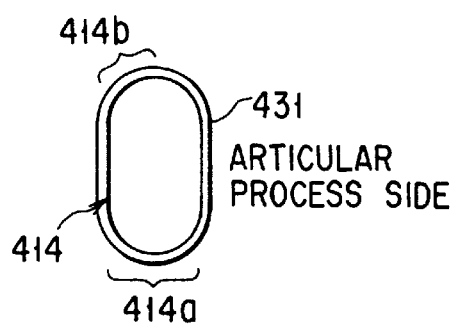

The 42nd embodiment of the present invention will be described with reference to FIGS. 102A and 102B. An operation sheath 405 in this embodiment is obtained by integrating a cavity securing portion 431 and a tool guide portion 432 into one hard sheath 433. The cavity securing portion 431 has a flat cross-section, e.g., an elliptic or oval cross-section, as in the above embodiments. An engaging means 414 to be engaged with a bone is formed on the distal end edge of the cavity securing portion 431. A port insertion hole (port insertion portion) 434 is formed in a side wall of the tool guide portion 432. An operating gripping portion 435 extending toward the articular process side is formed continuously with the upper end portion of the tool guide portion 432.

The operation sheath 405 is also inserted into the body by using a dilator 402 and a mandrin 408. The mandrin 408 is pulled out, and an operation tool is introduced into the body instead. The operator then performs an operation. In this embodiment, since the cavity securing portion on the distal end of the operation sheath is elliptic and has the engaging means for a bone, the region of surgical object can be efficiently secured as in the case of the sheath described previously. In addition, since a tool can be inserted into the cavity securing tool through the hole formed in its side wall, interference between tools can be reduced.

[43rd Embodiment]

The 43rd embodiment of the present invention will be described with reference to FIGS. 103A to 105B. In the 38th embodiment, the position detection means for searching for a site of operation is constituted by the mandrin 408 and the probe 409. In the 43rd embodiment, as a position detection means, a search tool 440 having the following structure is used. The search tool 440 has a pipe-like main body 441. A pipe bundle 443 formed by orderly bundling a plurality of wire members 442 consisting of a fiber material and having the same length is housed in the main body 441. Cap-like soft portions 444 and 445 are attached to the two ends of the main body 441. The respective end portions of the pipe bundle 443 are covered with the corresponding soft portions 444 and 445. The respective end portions of the pipe bundle 443 are tightly covered with the corresponding soft portions 444 and 445 in contact with their inner surfaces. The wire members 442 may be hollow or solid members. The respective wire members 442 are housed in the main body 441 to be independently movable in the axial direction. With this structure, when one soft portion 444 of the search tool 440 is pushed and deformed, the respective wire members 442 independently move in the axial direction in accordance with the deformation of the soft portion 444 so as to push the other soft portion 445 from the inside. As a result, the other soft portion 445 deforms into a shape corresponding to the shape of one soft portion 444. That is, the outer shapes of one soft portion 444 and the other soft portion 445 of the search tool 440 maintain inverted transfer shapes having identical recess/projection patterns. The shape of one soft portion 444 is reflected in the shape of the other soft portion 445. That is, these portions constitute a reflection means. A through hole 446 in which a guide member is inserted is formed in the center of the search tool 440.

When one soft portion 444 of the search tool 440 is pressed against an arbitrary portion of the undulating spine portion shown in FIGS. 105A and 150B, the shape of the portion appears as the outer shape of the other soft portion 445.

When, for example, one soft portion 444 of the search tool 440 is pressed against portions A, B, and C of the spine shown in FIG. 105A, shapes corresponding to the shapes of the portions A, B, and C appear on the other soft portion 445. FIG. 104A shows the transfer shape corresponding to the shape of the portion A. FIG. 104B shows the transfer shape corresponding to the shape of the portion B. FIG. 104C shows the transfer shape corresponding to the shape of the portion C.

In the above-described operation, the search tool 440 is used as follows. After a dilator 402 is inserted into the body, the dilator 402 is pulled out, and the search tool 440 is inserted into the resultant perforation. Alternatively, a proper one of tubes 402a to 402d of the dilator 402 is left, and the left tube is inserted into the hole 446 to insert the search tool 440 into the body. The operator searches for a site of operation with the search tool 440. When the site of operation is found, the operator can insert the operation sheath 405 into the body by fitting the operation sheath 405 on the dilator 402. Note that the search tool 440 may not have the hole 446.

[44th Embodiment]

Figure 106:
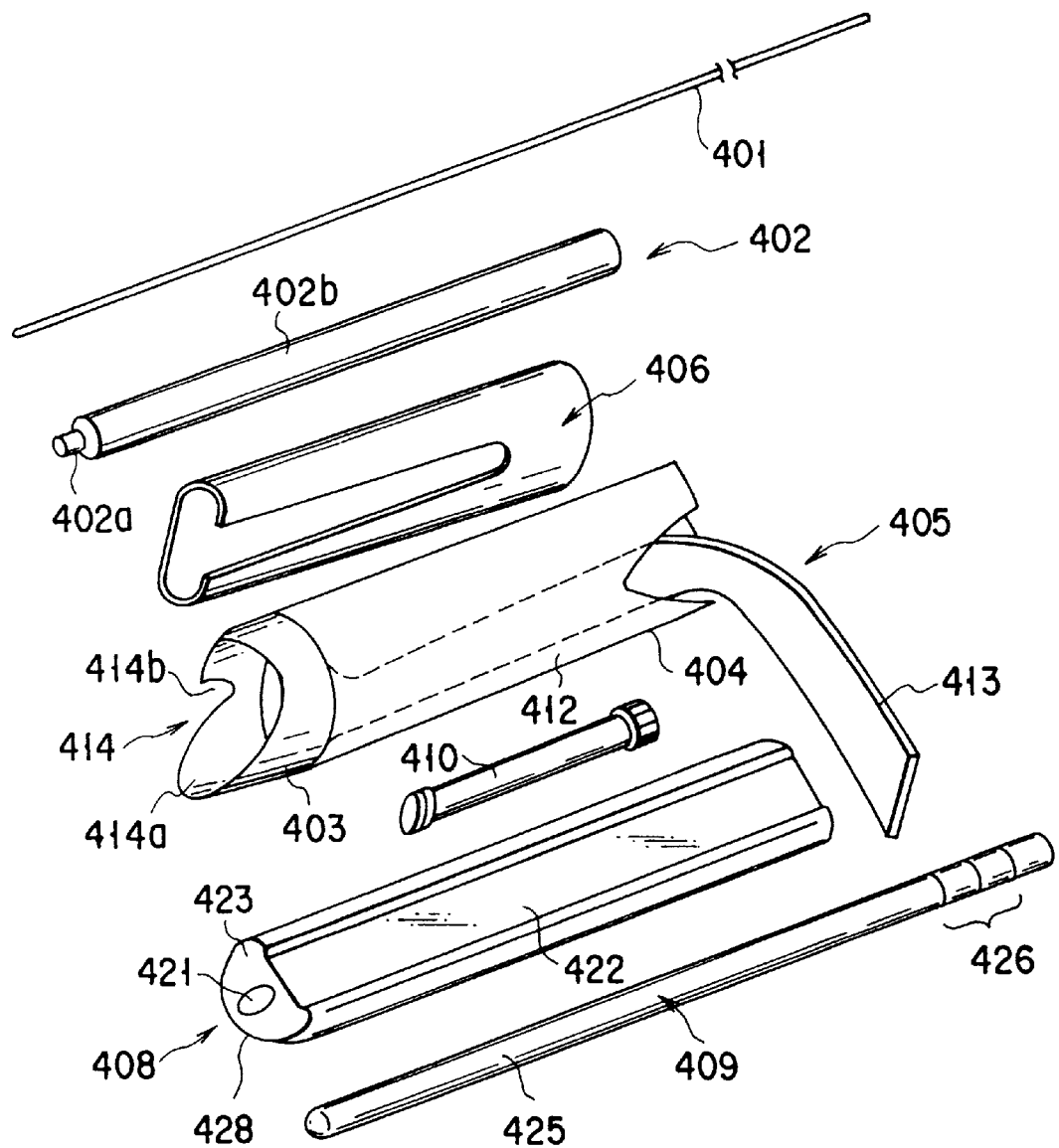

The 44th embodiment of the present invention will be described with reference to FIG. 106. This embodiment includes a modification of the system of the 38th embodiment. A cavity securing tool system of this embodiment comprises a guidewire 401, a dilator 402, an operation sheath 405, a pusher 406, a mandrin 408, a probe 409, and a port 410, as in the 38th embodiment. Of these tools, the dilator 402 and the mandrin 408 have the following structures. The dilator 402 has a small number of tubes, i.e., a tube 402*a* and a tube 402*b* for guiding the mandrin 408. The tubes 402*a* and 402*b* are longer than the operation sheath 405 and the mandrin 408. As in the 39th embodiment, a sharp portion 428 is formed on a portion of the edge of one end portion of the mandrin 408. The other end portion of the mandrin 408 is formed into a blunt convex surface.

Since there are many common points between an operation using the cavity securing tool system of the 44th embodiment and the operation in the 38th embodiment, an operation procedure will be described below by mainly referring to the characteristic features of the 44th embodiment. First of all, an incision reaching the fascia is made in the skin portion to be perforated, and the guidewire 401 and the dilator 402 are inserted into the skin portion in the order named in accordance with the procedure described in the 38th embodiment. After this process, the mandrin 408 is fitted on the tube 402*b* of the dilator 402, with the blunt end portion going first, and is pushed into the vital tissue. As a result, the mandrin 408 can be inserted deep to a region of surgical object while the blunt end portion of the mandrin 408 tears the muscle. Since the incision reaching the fascia is made, the dilator 402 can form a perforation without using a thick tube. In addition, the mandrin 408 can be directly inserted from the incision in the skin without using the guidewire 401 and the dilator 402.

The mandrin 408 is then pulled out. The mandrin 408 is inserted into the body again along the perforation formed in advance, with the sharp portion 428 going first. The sharp portion 428 is used to abrade tissue such as muscle off the vertebral arch portion. The mandrin 408 is properly positioned to the treatment site by using the probe 409. The subsequent operation is performed in the same procedure as in the 38th embodiment.

In this embodiment, the dilator 402 need not be used, or any thick tube need not be used when the dilator 402 is to be used. This facilitates a perforating process.

[45th Embodiment]

The 45th embodiment of the present invention will be described with reference to FIGS. 107A to 107C. This embodiment includes a modification of the cavity securing tool in the 13th embodiment. A cavity securing tool in this embodiment includes a ring-like member 452 forming part of a cavity securing portion 451 and a pair of arm members 453*a* and 453*b* coupled to the ring-like member 452. The pair of arm members 453*a* and 453*b* constitute a tool insertion guide means for guiding an operation tool. The pair of arm members 453*a* and 453*b* are made of a hard material, e.g., a metal material, which is different from the material for the ring-like member 452. The upper end portions of the pair of arm members 453*a* and 453*b* are formed into operating portions 454*a* and 454*b* bend outward at right angles in opposite directions. The ring-like member 452 is made of a material that is hard enough to secure an operation cavity in tissue but soft enough to deform to displace the pair of arm members 453*a* and 453*b*. As in the 38th embodiment, an engaging means 455 that is specially shaped to be engaged with a bone portion is formed on the distal end edge of the ring-like member 452.

When this cavity securing tool is inserted into tissue, the pair of arm members 453*a* and 453*b* are pushed by the tissue and compressed upon deformation of the ring-like member 452, as shown in FIG. 107B. When an operation tool is to be introduced into the tissue, the operating portions 454*a* and 454*b* are pulled in opposite directions to spread the pair of arm members 453*a* and 453*b*, as shown in FIG. 107C. An operation tool 456 is then introduced into the tissue through the gap between the pair of arm members 453*a* and 453*b*.

[46th Embodiment]

Figure 108:
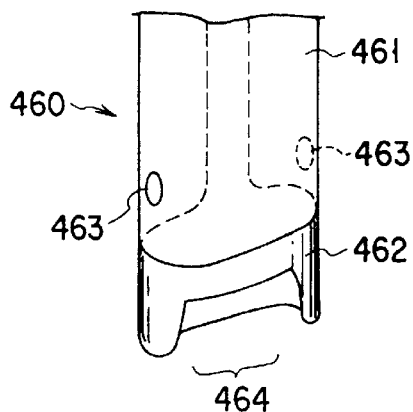

The 46th embodiment of the present invention will be described with reference to FIG. 108. This embodiment includes a modification of the operation sheath. An operation sheath 460 in this embodiment has a flat, ring-like cavity securing portion 462 formed continuously with the distal end of a cylindrical soft sheet portion 461. Two port coupling holes 463 are formed in the circumferential wall of the lower portion of the soft sheet portion 461 at positions along the major axis direction. An engaging means for a bone is formed on the distal end edge of the cavity securing portion 462. This distal end edge has no projection portion and is flat as a whole. A recess portion 464 to be engaged with the proximal end portion of a spina is formed in part of the distal end edge. This recess portion 464 is wider than the recess portion in the 40th embodiment. Note that the size of the recess portion on the spina side in the direction of height is preferably set to about 1 to 10 mm from the horizontal plane of the distal end.

Since the recess portion 464 of the engaging means for a bone, which is engaged with the proximal end portion of a spina, is wide, the operation sheath 460 can be used on either the right side or the left side of a vertebral body. In addition, since the engaging means for a bone has no projection process, and the recess portion 464 is wide, the operation sheath 460 can be easily moved in the head/tail direction.

[47th Embodiment]

The 47th embodiment of the present invention will be described with reference to FIGS. 109A and 109B. This embodiment includes a modification of the operation sheath in the 46th embodiment. An operation sheath 460 in this embodiment has a recess portion 464*b*, located on the articular process side, on the distal end edge of a cavity securing portion 462, in addition to a recess portion 464*a* on the spina side. These portions constitute an engaging means for a bone. Since the recess portion 464*b* is also formed on the articular process side, the operation sheath 460 can be stably fitted on a bone portion in an operation site, and can be easily positioned to a predetermined site. If, for example, the operation sheath 460 needs to be moved to the articular process side, movement in the corresponding direction is facilitated.

[48th Embodiment]

The 48th embodiment of the present invention will be described with reference to FIG. 110. In this embodiment, for example, a search portion (probe) 465 is integrally formed with the reference surface 423 on the distal end of the mandrin 408 in the 38th embodiment. According to the 48th embodiment, a probe made of a member different from the member for the mandrin 408 need not be prepared. In addition, since a probe made of a different member need not be used, there is no need to insert/remove the probe, and the operator can search for a site of operation by using only the mandrin 408. Therefore, the above process is simplified.

[49th Embodiment]

The 49th embodiment of the present invention will be described with reference to FIGS. 111A to 114. FIGS. 111A and 111B are views for explaining a cavity securing tool 470. FIG. 112 is a perspective view of an indicator member 480. FIG. 113 is a perspective view of a combination of the cavity securing tool 470 and the indicator member 480. FIG. 114 is a perspective view of a dilator 490 for dilating a cavity in tissue.

As shown in FIG. 111, the cavity securing tool 470 includes a rigid cylindrical member 473 serving as a main body member and having a cavity securing portion 471 serving as a cavity securing means for securing a cavity in vital tissue and a tool insertion guide portion 472 serving as a tool insertion guide means continuous with the cavity securing portion 471. The cylindrical member 473 is isoparametric throughout the length and has an oval or elliptic cross-section. An engaging means for a bone is formed on the distal end edge of the cavity securing portion 471. This engaging means is constituted by a flat reference surface 474 and a recess portion 475 formed in part of the reference surface 474 and serving as a coupling means that is brought into contact with the proximal end portion of a spina and is coupled to a bone. A port insertion hole 476 is formed in a side wall of the cylindrical member 473. An operating gripping portion 477 is integrally formed on a wall portion of the upper end of the cylindrical member 473 to extend toward the articular process side. This cavity securing tool 470 also serves as a dilator to be lastly inserted into the tissue.

As shown in FIG. 112, the indicator member 480 has a cross-section with the same shape and area as those of the hole of the cavity securing portion 471 of the cavity securing tool 470, and can be tightly inserted into the hole of the cavity securing tool 470. A central portion of a reference surface 481 that is the distal end face of the indicator member 480 protrudes. This protrusion forms a search portion 483 to be brought into contact with the tissue. In addition, an indicator portion 484 is formed on the outer surface of the proximal end portion of the indicator member 480. The indicator member 480 and the cavity securing tool 470 can be combined with each other, as shown in FIG. 113.

As shown in FIG. 114, the dilator 490 has a plurality of tubes 491*a* to 491*c* combined into a so-called multi-tube antenna type structure. The outer surface of tube 491*c* that can be combined with the cavity securing tool 470 has the same shape as that of the hole of the cavity securing portion 471.

The system of this embodiment is used as follows. A perforation in the tissue is sequentially dilated by the tubes 491*a* to 491*c* of the dilator 490 in FIG. 114. The cavity securing tool 470 in FIGS. 111A and 111B is then fitted on the tube 491*c* of the dilator 490, which has the same outer surface shape as the hole of the cavity securing tool 470. The cavity securing tool 470 is inserted into the tissue until it comes into contact with the region of surgical object. After the cavity securing tool 470 is inserted, the tubes 491*a* to 491*c* of the dilator 490 are removed, while the cavity securing tool 470 is left.

Subsequently, the operator inserts the indicator member 480 in FIG. 112 into the hole of the cavity securing tool 470, and moves the cavity securing tool 470 while holding the operating gripping portion 477 with his/her hand, thereby searching for the region of surgical object with the search portion 483 of the indicator member 480. When the search portion 483 is located at the desired position, the indicator portion 484 of the indicator member 480 comes below the proximal end of the cavity securing portion 471. With this, the region of surgical object can be detected. Since the distal end portions of the cavity securing tool 470 and the indicator member 480 are larger than the hole between vertebral arches, they do not enter the hole, assuring safety. The indicator member 480 is removed from the cavity securing tool 470, and a treatment tool is inserted into the tool insertion guide portion 472. Subsequently, a surgical operation is performed on the tissue.

According to this embodiment, a region of surgical object can be easily detected, and the cavity securing tool 470 can be indwelled at a proper position.

[50th Embodiment]

The 50th embodiment of the present invention will be described with FIGS. 115 to 122. FIG. 115 shows the tools belonging to a cavity securing tool system according to the 50th embodiment. This cavity securing tool system includes a guidewire 501, a dilator 502 serving as an insertion tool, a mandrin 503, an operation sheath 504, a pusher 505, and a port 506.

The guidewire 501 is used to make a perforation in a vital portion to determine an insertion path for an insertion tool, thereby guiding the insertion tool into the body. The dilator 502 is of the so-called multi-tube antenna type, in which a plurality of tubes 502*a* to 502*d* having different diameters are sequentially fitted on each other. Of these tubes, the thinnest tube 502*a* allows the guidewire 501 to be inserted therein. The guidewire 501 is longer than any of the remaining tools. All the distal end edges of the tubes 502*a* to 502*d* located on the insertion side are chamfered. The thinnest tube 502*a* of the dilator **502* is fitted on the guidewire 501 inserted into the body in advance, and the tubes 502*b* to 502*d* are sequentially fitted on each other in the order of increasing diameter. With this process, the perforation made by the guidewire 501 is dilated. The tubes 502*a* to 502*d* have different lengths. The thinnest tube 502*a* is longest. The tubes become shorter with an increase in diameter. The thickest tube 502*d* is shortest. One of the thin tubes, e.g., the tube 502*b*, serves as a guide when the mandrin 503 is to be inserted into vital tissue. A combination of the tube 502*b* and the mandrin 503 can serve as the probe of an extracorporeal detection means for externally detecting the region of surgical object by the touch. The circumference of the tube 502*d* of the dilator 502, which has the largest outer diameter, is almost equal to the outer circumference of the distal end portion of the operation sheath 504. In this embodiment, the outer diameter of the tube 502*d* having the largest outer diameter is set to 17 mm.

The operation sheath 504 includes a cavity securing portion 507 for securing a cavity above the region of surgical object and a cylindrical soft sheet member 508 that is formed continuously with the cavity securing portion 507 and serves as an operation tool guide means. The soft sheet member 508 serves as a tool insertion communicating member for allowing a tool to be inserted into a cavity from outside the body. The soft sheet member 508 has a substantially cylindrical shape. The operation sheath 504 is pushed into the body by the pusher 505 using the mandrin 503 as a guide. A flat operating member 510 is formed continuously with the cavity securing portion 507 to extend to the outside of the body through the soft sheet member 508. The operating member 510 is made of a plate-like (belt-like) member, located on the articular process side, and formed continuously with a ring member 511 forming the cavity securing portion 507. The end portion of the operating member 510, which extends to the outside of the body, bends and protrudes toward the articular process side. This portion protruding laterally serves as an operating gripping portion 512. The operating gripping portion 512 is especially made wide to allow the operator to easily hold it.

The ring member 511 forming the cavity securing portion 507 is made of a hard belt-like member and has an endless, oval or elliptic, flat, ring-like cross-section. The distal end edge of this belt-like, ring-like member is specially shaped to be engaged with a bone portion. That is, an engaging means 516 for a bone is formed on the distal end edge of the ring-like member.

Note that the region A surrounded with the dashed line in FIG. 90A is the region of surgical object in this embodiment, and a large opening portion 516a formed in the engaging means 516 is engaged with the inclined portion C between the spina and the vertebral arch portion in FIG. 90A. Each projection portion 516b of the engaging means 516 is inserted in and engaged with the relatively large indentation located in the vertical direction with respect to the region of surgical object. In addition, a recess portion 516c of the engaging means 516 is engaged with the prominence on the articular process side in the region of surgical object. As shown in FIG. 90B, which is a view obtained when viewed from the direction of the arrow B in FIG. 90A, in general, the portions between vertebral arches greatly undulate, as indicated by the arrow D. In addition, the portions between the vertebral arches and the spinae have certain slopes.

The hole of the cavity securing portion 507 of the operation sheath 504 has an oval or elliptic cross-section, i.e., a flat cross-section. The circumference of the cavity securing portion 507 is almost equal to that of the cavity securing portion in the form of a perfect circle in the previous embodiment. For this reason, as shown in FIGS. 118A and 118B, the treatment cavity becomes a long region. The reasons why such an elliptic cavity is formed will be described below. A treatment in an operation often proceeds from the portion between vertebral arches to the head and tail sides. In this case, the region of surgical object is a region elongated in the head/tail direction (the region indicated by the dashed line in FIG. 90A). If, therefore, the circumference of the cavity securing portion 507 is set to be equal to that of a cavity securing portion in the form of a perfect circle, and the hole of the cavity securing portion 507 is made elliptic or oval, a larger treatment region can be covered in the hole of the cavity securing portion 507 with substantially the same pushing effect as that given by the cavity securing portion in the form of a perfect circle. In addition, as shown in FIG. 89C, the cavity in the form of a perfect circle comes into contact with the spinae, and hence cannot be moved to the spina side. For this reason, the treatment region A cannot be fully covered in the cavity. In contrast to this, the oval or elliptic cavity can cover a larger part of the treatment region A than the cavity in the form of a perfect circle. In addition, if the vertebral arch between an articular process and a spina is narrow (which differs among individuals or depending on the vertebral body level), the region of surgical object cannot be positioned in substantially the center of the cavity in the form of a perfect circle in some case. In contrast to this, since the elliptic or oval cavity is short in the minor axis direction, no unnecessary portion enters the cavity, and the region of surgical object can be positioned in substantially the center of the cavity. For the above reasons, when the circumference of an elliptic cavity is made equal to that of a cavity in the form of a perfect circle, the region of surgical object can be efficiently covered in the cavity with substantially the same pushing effect as that given by the cavity in the form of a perfect circle.

In this embodiment, the cavity securing portion 507 has an oval shape having a major axis length of 19 mm and a minor axis length of 13.5 mm. The outer circumference of the cavity securing portion 507 is almost equal to the outer circumference of the tube 502d of the dilator 502, which has the largest outer diameter.

As shown in FIG. 117C, which is a view taken from the direction of an arrow E in FIG. 117A, the cavity securing portion 507 has the engaging means 516 as an engaging means for a bone. This engaging means 516 has the large opening portion 516a, the projection portions 516b, and the recess portion 516c. This large opening portion 516a is shaped to be fitted on the slope from a vertebral arch portion to a spina. This slope is steep in some person or depending on the vertebral body level. If the cavity securing portion 507 has no large opening portion serving as an engaging means for a spina, the distal end of the cavity securing portion 507 comes into contact with the slope. When the cavity securing portion 507 is pushed inside, the portion moves toward the articular process along the slope. As a result, the region of surgical object cannot be positioned in the cavity. In contrast to this, according to the cavity securing portion 507 in this embodiment, since the large opening portion 516a on the spina side, which serves as an engaging means, is fitted on the slope, even if the slope is steep, the region of surgical object can be positioned in the cavity. In addition, since the slope is fitted in the large opening portion 516a when the operation sheath 504 is inserted into the body, the cavity securing portion 507 can be easily positioned. Furthermore, since the projection portions 516b and the recess portion 516c, which serve as an engaging means, almost conform to the shape of the portion around the region of surgical object, entrance of unnecessary muscle tissue into the cavity can be prevented. By properly setting a height D from the opening portion 516a to the recess portion 516c, this engaging means can be engaged with either a vertebral body with a steep slope or a vertebral body with a gradual slope. This allows the region of surgical object to be locate in the cavity.

This shape will be described in more detail. A large gap is set between the large opening portion 516a and the projection portions 516b, and the distal end portion has a symmetrical shape and is adaptable to both the right and left vertebral arches. For example, in a case of a left vertebral arch, when a treatment cavity is located with respect to a target site as shown in FIG. 118A, the best visual field is obtained. In this case, the swelling bone portion on the portion between the spina and the vertebral arch almost coincides with a portion A in FIG. 118A, and the edge of the vertebral arch portion on the articular process side almost coincides with a portion B in FIG. 118A. The portions (portions C and D) on the two sides of these portions A and B are recessed. The shape of the distal end of the cavity securing portion 507 substantially conforms to this bone shape. The portion A enters the large opening portion 516a of the cavity securing portion 507, which is elongated vertically. The projection portions 516b enter the recess portions C and D. The portion B enters the recess portion 516c.

The above case is associated with the left site. In a case of a right site, the above tools are placed in positions opposite to those in the above case. In this case, as shown in FIG. 118B, the positions where the large opening portion 516a, the projection portion 516b, and the recess portion 516c of the above cavity securing portion 507 are brought into contact with the bones are opposite to those in the above case. That is, the cavity securing portion 507 has the large opening portion 516a, the wide recess portion 516c, and the wide gap between the projection portions 516b, and hence is not influenced by the positions of the prominences of the portions A and B. The cavity securing portion 507 can therefore be adapted for the right and left cases.

In addition, with the large opening portion 516a, the wide recess portion 516c, and the wide gap between the projection portions 516b, when a wide site of operation is to be checked, the cavity securing portion 507 can be easily moved especially in the head/tail direction while the cavity securing portion 507 is engaged with the contact portion of a bone. Furthermore, since the projection portions 516b prevent unnecessary muscle tissue from entering the cavity, the operator can easily move the site of operation while securing a stable visual field, thereby widely checking an anatomical operation and the like.

In consideration of the above cases, for the human lumbar vertebrae, as shown in FIG. 117B, the curve extending from the large opening portion 516a on the spina side to the projection portion 516b is preferably set such that the oblique line (Z—Z) extending from the large opening portion 516a on the spina side crosses an intersection O of a center axis (X—X) along the minor axis length of the cavity securing portion 507 and an extended line (Y—Y) passing through the distal end of the projection portion 516b in the horizontal direction. In this embodiment, as shown in FIG. 117C, a width B of the opening portion 516a is about 14 mm; and the height D from the opening portion 516a to the recess portion 516c, about 6 mm. The height from the recess portion 516c to the distal end of the cavity securing portion 507 (the height of the projection portion 516b) is about 1.5 mm.

As described above, since the cavity securing portion 507 includes the large opening portion 516a, the projection portions 516b, and the recess portion 516c, which serve as an engaging means for engaging the elliptic hole with a bone, a treatment region can be efficiently caught and kept in the cavity. Even if, therefore, the vertebral arch portion is narrow and the slope is steep, which depends on individuals or the vertebral body level, a good cavity can be held. Obviously, the cavity securing portion 507 can be used without posing any problem even if the vertebral arch is wide and the slope is not very steep.

The belt-like ring member of the cavity securing portion 507 is not limited to an oval or elliptic shape, and an odd-shaped ring member such as a rectangular or round rhomboid ring member can be used. In addition, since the cavity securing portion 507 can be adapted for the right and left bone shapes, different operation sheaths need not be prepared. Furthermore, since the cavity securing portion 507 can be easily moved, a site of operation can be checked in a wide range.

The soft sheet member 508 of the operation sheath 504 is flexible enough to be easily collapsed by the pressure from surrounding tissue when it is indwelled in the tissue. The soft sheet member 508 is made of a transparent material that allows the operator to see the movement of tissue or a tool located outside a cavity from the cavity side with an endoscope.

In addition, an antireflection means such as a means using a satin material is preferably applied to at least the inner surface of the operation sheath 504 in a region positioned in vital tissue. One or a plurality of port coupling holes 517 in which the distal end portions of ports 506 can be inserted are formed in portions of the wall of the soft sheet member 508. Markings 518 are formed on the edges of the port coupling holes 517 to allow the operator to easily check the positions of the holes 517 from inside the cavity side.

The position of each port coupling hole 517 will be described below. In this embodiment, an endoscope having a field angle of 90° is used. Assume that the port 506 is inserted into the port coupling hole 517, the endoscope is inserted into the port 506, and the entire treatment region of the cavity for the cavity securing portion 507 is to be covered within the visual field of the endoscope. In this case, in consideration of interference between a treatment tool and the endoscope, the protrusion amount of the distal end of the endoscope from the distal end of the port 506 is preferably minimized. In this embodiment, since the cavity securing portion 507 has the large opening portion 516a serving as an engaging means for a bone, a tissue surface is located at a level of about 6 mm from the recess portion 516c. To cover the entire treatment region including this tissue surface within the visual field, since the major axis length of the hole of the cavity securing portion 507 is about 17 mm, an image in a range having a diameter of about 20 mm, which is slightly larger than the major axis length of the hole, is required. Therefore, a level of about 10 mm from the tissue surface corresponds to the insertion position where an image in a range having a diameter of about 20 mm can be obtained with the endoscope having a field angle of 90°, and the protrusion amount of the distal end of the endoscope into the hole can be reduced. In this case, since the distal end portion 535 of the port 506 slightly protrudes downward from the port coupling hole 517, the distal end of the endoscope is located at a position below the port coupling hole 517. In consideration of this, the level of the port coupling hole 517 is preferably set to about 12 mm from the tissue surface that protrudes into the hole owing to the engaging means 516. For the above reason, in this embodiment, the port coupling hole 517 is formed at a position (C) about 18 mm away from the recess portion 516c (see FIG. 117C). When a hernia is to be removed, the treatment region is located at a depth of about 20 mm, at most, from the engaging means 516 of the cavity securing portion 507. For this reason, the endoscope preferably has a depth of focus of about 10 mm to 40 mm or more so as to obviate the necessity for focusing. When a deeper treatment region is to be observed, the endoscope may be inserted into a cavity. In this case, however, the endoscope protrudes into the hole of the cavity securing portion 507 and tends to interfere with a treatment tool. If, therefore, an endoscope having a magnifying function is used, the protrusion amount of the endoscope decreases. As a result, the interference between the treatment tool and the endoscope can be reduced, and a good treatment region at a deep position can be obtained.

The mandrin 503 serves as a cavity securing tool guide member for guiding the above cavity securing tool into vital tissue. As shown in FIG. 116, the outer surface of the mandrin 503 is shaped such that the mandrin 503 is almost tightly fitted in the cavity securing portion 507. Obviously, the cavity securing portion 507 has a flat cross-section such as an elliptic or oval cross-section that is identical to a cross-section of the cavity securing portion 507. The outer circumference of the mandrin 503 is therefore shorter than that of the tube 502d of the dilator 502 which has the largest outer diameter (the outer circumference the tube 502d is longer than the inner circumference of the cavity securing portion 507).

The major axis length of an oval cross-section of the mandrin 503 is almost equal to the diameter of the tube 502d having the largest outer diameter. In this embodiment, the mandrin 503 has a major axis length of 17 mm and a minor axis length of 11.5 mm. The outer circumference of the mandrin 503 is almost equal to the inner circumference of the cavity securing portion 507.

An insertion hole 521 is formed as a through hole in the center of the mandrin 503 along the axial direction. For example, the tube 502b of the dilator 502 can be fitted in the insertion hole 521 in a relatively tight state. An operating portion relief groove 522 is formed in the outer surface of the mandrin 503. This groove 522 also serves as a guide in which the operating member 510 is fitted when the operation sheath 504 is fitted on the mandrin 503. The mandrin 503 has a distal end like the one shown in FIG. 116B (a view taken in the direction of an arrow A). This distal end has a blade portion 523 parallel to the major axis direction of a flat cross-section of the mandrin 503. The blade edge line of the blade portion 523 is perpendicular to the direction of length of the mandrin 503. The blade portion 523 serves as a means for abrading vital tissue off a bone. The length of the blade portion 523 is smaller than the maximum outer diameter of the dilator 502. The ridge of the distal end of the mandrin 503 is round except for the blade portion 523. A proximal end 524 of the mandrin 503 is formed into a smooth, curved surface. This curved surface starts from a position corresponding to a position inside the inner diameter of the pusher 505. The major axis length of a cross-section of the mandrin 503 is 17 mm. The mandrin 503 is formed to have a size that inhibits the mandrin 503 from entering the portion between vertebral arches (hole between the vertebral arches) and stops it to a bone portion. The distal end of the mandrin 503 serves as a reference position when a search is performed to detect the shape of the region of surgical object from outside the body with the small-diameter tubes 502a and 502b of the dilator 502. The operator uses the mandrin 503 as a reference member to perform a search to detect the shape of the region of surgical object from outside the body using the small-diameter tubes 502a and 502b of the dilator 502 as search members.

As shown in FIGS. 119A and 119B, the pusher 505 has a cylindrical shape. A notched portion 531 is formed in the outer surface of the pusher 505 to extend along the axial direction from a midway portion to the distal end. The notched portion 531 is open at the distal end of the pusher 505. An outer circumference C of the pusher 505 is smaller than the outer circumference of the cavity securing portion 507 of the operation sheath 504. An inner circumference B of the pusher 505 is almost equal to the outer circumference of the mandrin 503. The pusher 505 is made of Teflon or the like and can deform into a flat shape, as shown in FIG. 119C. The total length of the pusher 505 is set such that the sum of the protrusion amount of a bone portion (in the region of surgical object) protruding into the cavity securing portion 507 and the total length of the mandrin 503 from the position where the bone portion protrudes when the pusher 505 is engaged with the bone portion in the cavity securing portion 507 is almost equal to the sum of the height of the cavity securing portion 507 and the total length of the pusher 505. That is, the proximal end of the mandrin 503 almost coincides with the proximal end of the pusher 505 when the operation sheath 504 is inserted using the mandrin 503 as a guide until the distal end is inserted deepest and comes into contact with the bone.

As shown in FIGS. 120A and 120B, the port 506 includes a distal end portion 535 inserted into a body cavity, a proximal end portion 536 to be located outside the body, and a channel portion 537 for connecting the distal end portion 535 to the proximal end portion 536. The port 506 has an insertion hole 538 for causing the distal end portion 535 to communicate with the proximal end portion 536. The outer diameter of the distal end portion 535 is larger than that of the channel portion 537. A stepped portion is therefore formed between the distal end portion 535 and the channel portion 537. The distal end edge of the distal end portion 535 is constituted by an inclined surface 539a inclined with respect to the center axis of the insertion hole 538 and a vertical relief portion 539b. The proximal end edge of the distal end portion 535 has an inclined surface 539c that is inclined with respect to the center axis (the axis of the hole) of the insertion hole 538 and parallel to the inclined surface 539a. The proximal end portion 536 has a flat portion 536a on part of its outer surface. When this flat portion 536a faces up, the inclined surface 539a of the distal end portion 535 also faces up.

The cavity securing system has the above structure. This system may be used in combination with a scope holder 542 capable of holding an endoscope 541, as shown in FIG. 121. It is preferable that the endoscope 541 is held in the scope holder 542 to be rotatable about the optical axis, and is also maintained in a position where the operator releases the endoscope 541. With a combination of the scope holder 542 and the above system, the operator need not hold the endoscope 541. Since no person needs to always hold the endoscope 541, the load on the operator reduces, and the operability improves.

In addition, a holding tool (not shown) for holding the operation sheath 504 may be added to this system.

A procedure in a surgical operation method using the cavity securing tool system according to this embodiment will be described next. In this case, the operator is to remove a hernia by approaching a treatment region, almost straight, from the back side of the body.

As shown n FIG. 121, the operator lays the patient on a bed 543 with his/her face down. The operator anesthetizes the patient first, and then makes an incision in the skin immediately above the region of surgical object with a scalpel or the like. In this case, the operator may make an incision reaching the fascia. The operator pierces the guidewire 501 from the incision into the muscle toward the treatment site. The operator inserts the distal end of the guidewire 501 toward the bone portion of the proximal end portion of a spina to make the distal end come into contact with the bone portion. The operator checks this state by X-ray fluoroscopy or the like. As is obvious, the operator may perform this process under X-ray fluoroscopy. The dilator 502 is then fitted on the guidewire 501.

The distal end of the guidewire 501 is in contact with the bone portion, and the dilator 502 is inserted along the guidewire 501 until the dilator 502 comes into contact with the bone portion. The guidewire 501 is preferably pulled out when the tube 502a of the dilator 502, which has the smallest outer diameter, is inserted.

When the tubes 502a to 502d of the dilator 502 are sequentially fitted on each other, the vital tissue around the perforation made by the guidewire 501 is spread. As a result, the perforation is dilated. The guidewire 501 is pulled out immediately after the thinnest tube 502a is inserted. After a necessary number of tubes, i.e., the tubes 502a to 502d, of the dilator 502 are inserted, for example, only the thin tubes 502a and 502b are left, and the remaining tubes 502c and 502d are pulled out. At this time, since the length of the dilator 502 decreases with an increase in diameter, only an unnecessary tube can be easily picked up and removed.

The mandrin 503 is pushed into the tissue by using the tube 502b as a guide while adjustment is made to insert the tubes 502a and 502b of the dilator 502 into the insertion hole 521 of the mandrin 503. With this process, the circular hole dilated by the circular dilator 502 is formed into an elliptic hole. The mandrin 503 is inserted until its distal end comes into contact with the bone portion. The perforation to be accessed has been dilated by the dilator 502. In addition, the outer circumference of the tube 502d of the dilator 502, which has the largest outer diameter, is larger than that of the mandrin 503, and the diameter of the tube 502d of the dilator 502, which has the largest outer diameter, is almost equal to the major axis length of the mandrin 503. For these reasons, the mandrin 503 can be inserted relatively easily without further spreading the tissue around the perforation made in advance. In addition, the length of the blade portion 523 of the distal end of the mandrin 503 is smaller than the diameter of the tube 502d of the dilator 502 which has the largest diameter, and the blade portion 523 is smoothly continuous with the side surfaces. This prevents the sharp portion from coming into contact with the perforation made by the dilator 502 and unnecessarily damaging the tissue.

The operator then abrades tissue such as muscle off the vertebral arch portion by using the blade portion 523 of the mandrin 503. In manipulating the mandrin 503, the operator aligns the blade edge of the blade portion 523 with the head/tail direction, and moves the blade portion 523 from the spina to the articular process. That is, the blade edge is located in the head/tail direction and is moved in a direction almost perpendicular to the head/tail direction to abrade the tissue. The size of the distal end portion of the mandrin 503 is set such that the distal end does not enter the portion between the vertebral arches. This prevents the blade portion 523 of the mandrin 503 from accidentally entering the portion between the vertebral arches and damaging the tissue or the like on an unnecessary portion.

With this abrading process, the operator can feel the region of surgical object, and can know which part of the region of surgical object is accessed. If the operator can satisfactorily know the position of surgical object by the above feel, the next step can be started. If, however, the operator is uncertain about the position of the region of surgical object by only the feel obtained by the abrading process using the mandrin 503, the operator may search for the region of surgical object by the following process.

As in the case shown in FIGS. 92A and 92B, the operator searches for the target region of surgical object by using the thin tubes 502a and 502b of the dilator 502, inserted into the insertion hole 521 of the mandrin 503, as probes. Since the thin tubes 502a and 502b of the dilator 502 are longer than the mandrin 503, these tubes are easy to manipulate. The operator pushes the distal end of the dilator 502 as a probe out of the reference surface of the distal end of the mandrin 503, and searches for the portion between the vertebral arches with the distal end. By repeatedly inserting the distal end of the dilator 502 as the probe, the operator searches for a position where the distal end enters the hole between the vertebral arches relatively deep. The operator can easily know, from outside the body, on the basis of the movement and feel of the dilator 502 that the distal end of the dilator 502 is inserted into the indentation between the vertebral arches relatively deep. That is, the operator can know the protrusion amount of the distal end of the dilator 502 from the protrusion length of the dilator 502 as the probe on the proximal end face of the mandrin 503, and hence can check the shape and position of the region of surgical object.

When the position of the portion between the vertebral arches is detected in this manner, the mandrin 503 follows the positioned dilator 502, and the reference surface on the distal end of the mandrin 503 is positioned to the region of surgical object. Since the diameter of the mandrin 503 is larger than the width of the portion between the vertebral arches, and the reference surface is a relatively wide surface, the mandrin 503 is safely positioned without entering the portion between the vertebral arches. In this manner, the mandrin 503 can be easily positioned in the region of surgical object, and the reference surface of the mandrin 503 can be reliably positioned to the predetermined region of surgical object.

When the mandrin 503 is positioned, the tubes 502a and 502b of the dilator 502 are pulled out from the insertion hole 521 while the mandrin 503 is left. Since both the tubes 502a and 502b of the dilator 502 are longer than the mandrin 503, these tubes can be easily manipulated. The operator fits the operating member 510 of the operation sheath 504 in the operating portion relief groove 522 of the mandrin 503, and fits the operation sheath 504 on the mandrin 503. The operator then inserts the pusher 505 into the hole of the soft sheet member 508 of the operation sheath 504 while positioning the notched portion 531 of the pusher 505 to the operating gripping portion 512 of the operation sheath 504. The operator pushes the operation sheath 504 into the tissue while pushing the proximal end of the pusher 505 using the mandrin 503 as a guide.

Since the pusher 505 is made of a deformable material, it deforms in conformity with the outer shape of the odd-shaped mandrin 503. The operation sheath 504 can therefore be pushed into the body cavity relatively smoothly. The proximal end 524 of the mandrin 503 has the smooth curved surface, and the curved surface starts from a position corresponding to a position within the hole of the pusher 505. For this reason, when the pusher 505 is pushed into the cavity, the pusher 505 can smoothly deform along the outer diameter. This facilitate insertion of the pusher 505. Furthermore, since the pusher 505 is made of a deformable material, the hole and outer surface of the pusher 505 need not be odd-shaped in advance and may have circular shapes. The pusher 505 can therefore be manufactured at low cost.

Subsequently, the operator inserts the operation sheath 504 by using the mandrin 503 as a guide until the distal end is inserted deepest and comes into contact with the bone. By checking whether the proximal end of the mandrin 503 coincides with the proximal end of the pusher 505, the operator can determine that the distal end of the operation sheath 504 is inserted deepest. As shown in FIG. 118A, the operator then engages the engaging means 516 of the cavity securing portion 507 with the bone portion around the region of surgical object.

The distal end of the cavity securing portion 507 is shaped to be engaged with the bone portion. In addition, the length of the pusher 505 is set such that the proximal end of the mandrin 503 coincides with the proximal end of the pusher 505 when the distal end of the cavity securing portion 507 is inserted deepest. For these reasons, inserting the distal end of the cavity securing portion 507 until the proximal ends of the mandrin 503 and the pusher 505 coincide with each other is an indicator for checking whether the cavity securing portion 507 is inserted to a proper position. In addition, the operator knows the position of the region of surgical object by abrading tissue and the like off the upper surface of a vertebral arch portion with the mandrin 503. In some case, the position of the region of surgical object is detected by using a combination of the dilator 502 and the mandrin 503, and the mandrin 503 guided to a proper position is used as a guide, thereby indwelling the operation sheath 504 in a body cavity using the engaging means 516. By combining the above steps, the cavity securing portion 507 of the operation sheath 504 can be left at a proper position more easily.

Since the outer circumference of the tube 502d of the dilator 502, which has the largest outer diameter, is almost equal to that of the cavity securing portion 507 of the operation sheath 504, the size of the hole formed in tissue which is dilated by the tube 502d to allow the operation sheath 504 to be inserted therein corresponds to the diameter of the cavity securing portion 507. When the operation sheath 504 is inserted along the mandrin 503, the hole formed in the tissue by the circular dilator 502 is formed into an oval shape conforming to the oval shape of the cavity securing portion 507. However, since the outer circumferences of the mandrin 503 and the dilator 502 are almost equal to each other, the insertion of the operation sheath 504 hardly spreads the tissue. In addition, since the operation sheath 504 can be inserted with little force, no excessive force works on the operation sheath 504. Therefore, the sheath 504 is not damaged.

That is, a treatment region can be efficiently caught in the operation sheath 504 as compared with the circular operation sheath 504 with the uniform outer circumference, with the same invasive effect on tissue.

When the operator determines from outside the body that the proximal end of the mandrin 503 and proximal end of the pusher 505 coincide with each other, he/she pulls out the mandrin 503 and the pusher 505 while leaving the operation sheath 504 in the cavity. Thereafter, the operator inserts an operation tool such as an endoscope or a treatment tool into the hole of the soft sheet member 508 of the operation sheath 504, and starts treatment. When the endoscope 541 is fixed to the scope holder 542, the operator need not hold the endoscope 541 with his/her hand, and hence becomes free from a cumbersome task.

The operator removes muscle left near the vertebral arch portion, and checks whether the cavity securing portion 507 is properly indwelled in the treatment region. In this case, since the tissue such as the muscle has been abraded off the vertebral arch portion by the blade portion 523 of the mandrin 503, only little muscle is left in the hole of the cavity securing portion 507, and the operator can clearly observe a site of operation after the sheath is left.

If the exposed portion of the soft sheet member 508, located outside the body, interferes with an operation, a plurality of cuts are formed in the exposed portion to split it into a plurality of tongue-like portions, and these portions are stitched to the skin of the body or fixed thereto with an adhesive tape, as shown in FIG. 94. Alternatively, as shown in FIG. 95, the exposed portion of the soft sheet member 508, located outside the body, may cut away.

Subsequently, an operation similar to a general operation of removing the hernia of intervertebral disc is performed by using the endoscope.

The port 506 is used when the operator determines the necessity to use it as in case in which the treatment site is to be observed from another angle; many treatment tools are to be used at once; or a relatively thick treatment tool or an odd-shaped treatment tool is to be used. In such a case, the operator selects the port coupling hole 517 of the soft sheet member 508, and inserts the lower end 135 of the port 506 into the selected hole. This allows a lateral approach to the treatment region. More specifically, a new incision is made in the skin, and the guidewire 501 is inserted from the incision into the body toward the port coupling hole 517 of the soft sheet member 508. At this time, the distal end of the guidewire 501 can be observed with the endoscope inserted into the soft sheet member 508. In addition, since the markings 518 that can be observed from inside the hole of the soft sheet member 508 with the endoscope are formed around the port coupling hole 517, the distal end of the guidewire 501 can be easily guided into the port coupling hole 517. Thereafter, the thinnest tube 502a of the dilator 502 is fitted on the guidewire 501 and is inserted into the port coupling hole 517. The guidewire 501 is then removed. The port 506 is inserted by using the dilator 502 as a guide. The operator checks whether the distal end portion 535 of the port 506 completely protrudes from the soft sheet member 508 into the hole, and adjusts the distal end portion 535 of the port 506 to cause the inclined surface 539a to face up in accordance with the position of the flat portion 536a of the proximal end portion 536 of the port 506. After this, the operator inserts the endoscope or the like into the port 506, and performs a normal operation.

FIG. 122 shows a state in which the port 506 is coupled to the operation sheath 504, and the endoscope 541 is inserted into the port 506. The port 506 is inserted into the port coupling hole 517, and the endoscope 541 extends through the hole of the port 506. Since the above members are positioned such that the entire treatment region can be covered in a good visual field when the treatment region is observed with the endoscope 541 without causing the endoscope 541 to protrude much into the cavity, the interference between the endoscope 541 and treatment tools can be reduced, and a good visual field can be obtained.

In addition, since no unnecessary portion of the distal end portion 535 of the port 506 protrudes into the cavity owing to the inclined surface 539a, the interference between the distal end portion 535 and forceps in the cavity can be reduced. Furthermore, owing to the relief portion 539b, a visual field A of the endoscope 541 is not interfered, and the distal end of the port 506 is inserted into the port coupling hole 517 of the soft sheet member 508 to a position C in FIG. 117C. With this arrangement, when the endoscope 541 is inserted into the port 506, the entire region of surgical object can be obtained as an endoscopic image. For this reason, a sufficiently good visual field can be obtained without causing the endoscope 541 to protrude much, and the distal end of the endoscope does not protrude into the cavity. This reduces the interference between the endoscope and forceps and allows the operator to have a good visual field.

Although the treatment site becomes deeper as the treatment proceeds, the deepest portion can be observed by using an endoscope having a magnifying function without causing the endoscope to protrude into the cavity.

Since the diameter of the port coupling hole is smaller than the outer diameter of the distal end portion of the port and the coupling portion, when the distal end portion of the port is inserted into the port coupling hole, the port and the soft sheet can be coupled to each other by the elastic force of the soft sheet member. Even if a force acts in the direction in which the port is removed upon movement of the sheath or insertion/removal of the endoscope into/from the port, since the inclined surface of the distal end portion of the port is almost parallel to the soft sheet portion, into which the port is inserted, the elastic force of the soft sheet acts on the entire surface of the distal end portion of the port, and the coupling portion is not easily detached from the soft sheet.

[51st Embodiment]

The 51st embodiment of the present invention will be described with reference to FIG. 123. This embodiment includes a modification of the operation sheath 504 as the cavity securing tool in the 50th embodiment. Graduations 551 are added to all or part of the outer surface of a translucent soft sheet member 508. The 51st embodiment is the same as the 50th embodiment except for this. Since the soft sheet member 508 is translucent, the graduations 551 can be read and checked from inside the hole.

With the addition of the graduations 551 to the soft sheet member 508, the operator can know how much the operation sheath 504 is inserted into a body cavity.

[52nd Embodiment]

The 52nd embodiment of the present invention will be described with reference to FIGS. 124 and 125. This includes a modification of the cavity securing tool in the 50th embodiment. In this embodiment, perforations 560a to 560d are formed in the outer surface of the proximal end portion of a soft sheet member 508 in advance. The 52nd embodiment is the same as the 50th embodiment except for this.

When the exposed portion of the soft sheet member 508, located outside the body, interferes with an operation, the exposed portion is torn along the perforations 560a to 560d, as shown in FIG. 125. Tongue-like portions 561a to 561d formed in this manner may be stitched to the skin of the body or fixed thereto with an adhesive tape.

By forming the perforations 560a to 560d in the soft sheet member 508 in advance, an unnecessary portion of the soft sheet member 508, which is outside thee body, can be easily cut without using scissors.

[53rd Embodiment]

The 53rd embodiment of the present invention will be described with reference to FIGS. 126A and 126B. This embodiment includes a modification of the operation sheath 504 as the cavity securing tool in the 50th embodiment. In this embodiment, a soft sheet member 508 is fixed to an operating member 510. The 53rd embodiment is the same as the 50th embodiment except for this. The soft sheet member 508 is made of one sheet-like member. The upper end edge of a cavity securing portion 507 and a side edge of the operating member 510 are fixed to an end edge of the member with, for example, an adhesive. As a result, a cylindrical tool is formed as a whole by one sheet-like member and the operating member 510.

By fixing the member of the soft sheet member 508 and the operating member 510 with an adhesive, the member of the soft sheet member 508 need not be formed into a cylindrical member as in the above embodiment. This facilitates the manufacturing process. In addition, no treatment tool is caught or inserted between the operating member 510 and the soft sheet member 508.

[54th Embodiment]

The 54th embodiment of the present invention will be described with reference to FIGS. 127 and 128. This embodiment includes a modification of the operation sheath 504 as the cavity securing tool in the 50th embodiment described above. In this embodiment, a hard or semi-hard, cylindrical member 571 is connected to the end of a soft sheet member 508 which is exposed to the outside of the body. The 54th embodiment is the same as the 50th embodiment except for this.

Since the hard or semi-hard, cylindrical member 571 is connected to the end of the soft sheet member 508 which is exposed to the outside of the body, the end portion of the soft sheet member 508, which is exposed to the outside of the body, hardly collapses even after an operation sheath 504 is inserted into a body cavity, as shown in FIG. 128. An endoscope or treatment tool can therefore be easily guided into the hole of the soft sheet member 508.

[55th Embodiment]

The 55th embodiment of the present invention will be described with reference to FIGS. 129A to 129C. This embodiment is a modification of the operation sheath 504 as the cavity securing tool in the 50th embodiment. As shown in FIG. 129B, an engaging means 516 (to be engaged with a bone) on the distal end of a cavity securing portion 507 is an inclined surface with an angle A with respect to a line perpendicular to the center axis of the cavity securing portion 507. The inclined surface on the opening side comes into contact with the slope portion extending from a spina to a vertebral arch portion in a region of surgical object, and the tip of the cavity securing portion 507 comes into contact with an articular process. The 55th embodiment is the same as the 50th embodiment except for this. The angle of this inclined surface is preferably 5° to 50°.

Since the engaging means 516 for a bone has only the inclined surface, this cavity securing tool can be used for both right and left cases. In addition, the tool is easily manufactured at low cost.

[56th Embodiment]

The 56th embodiment of the present invention will be described with reference to FIGS. 130A and 130B. This embodiment is a modification of the dilator 502 in the 50th embodiment. An anchor means 575 is formed on the distal end of a tube 502a of a dilator 502 which has the smallest diameter. The 56th embodiment is the same as the 50th embodiment except for this.

For example, the anchor means 575 has sharp-pointed projections formed on the distal end. The anchor means 575 is used as follows. As in the case of the tube 502a of the dilator 502 which has the smallest diameter in the 50th embodiment, the tube 502a having the anchor means 575 is fitted on a guidewire 501 and inserted into tissue. When the operator determines by the feel that the distal end of the tube 502a is in contact with a vertebral arch in the region of surgical object, he/she lightly hits the proximal end of the tube 502a with a hammer to fix the anchor means 575 formed on the distal end of the tube 502a to the vertebral arch portion. Thereafter, tubes are sequentially fitted on each other in the order of increasing diameter to spread the tissue as in the above embodiments.

Since the anchor means 575 is formed on the distal end of the tube 502a of the dilator 502, which has the smallest diameter, and is fixed to a vertebral arch, a shift of the dilator 502 from a place where the tissue is to be spread can be prevented when the dilator 502 is inserted afterward. Since the tube 502b and the subsequent tubes of the dilator 502 always come into contact with the upper surface of the bone, the dilator 502 can be safely inserted afterward.

[57th Embodiment]

The 57th embodiment of the present invention will be described with reference to FIGS. 131A to 131C and 132. A cavity securing tool in this embodiment differs from the tools in the previous embodiments in target (bone) sites. An engaging means 516 serving as an engaging means and formed on the distal end edge of a cavity securing portion 507 of an operation sheath 504 is shaped to be engaged with a bone portion of tissue around an articular process in a region of surgical object when the engaging means 516 reaches it. More specifically, as shown in FIGS. 131A to 131C, the engaging means 516 for a bone is constituted by a recess portion 516a to be brought into contact with the articular process, a projection portion 516c on the spina side, and a projection portion 516b on the transverse process side. The projection portion 516b on the transverse process side is longer than the projection portion 516c on the spina side. According to an access method in this embodiment, as shown in FIG. 132, the access path is located closer to the abdomen side than the one in the 50th embodiment. After the engaging means 516 of the operation sheath 504 is engaged with a bone in a treatment site, a treatment on an intervertebral foramen is mainly performed. This tool can be used to remove the hernia of intervertebral disc that protrudes laterally. The 57th embodiment is the same as the 50th embodiment except for this.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalent.

We claim:

1. A surgical operation system for percutaneously securing a working cavity for a surgical operation in a body, comprising:

a cavity securing tool including cavity securing means that is inserted into a living body through a skin to secure a working cavity in vital tissue and has a hole with an odd-shaped cross-section, and tool insertion channel means that allows a tool to be inserted into the cavity;

an insertion tool for forming an insertion path for introducing said cavity securing tool into the vital tissue through the skin; and a cavity securing tool guide tool on which said cavity securing tool can be mounted, and which can be mounted on said insertion tool.

2. A system according to claim 1, wherein said insertion tool has a plurality of tubular members whose diameters increase stepwise, said tubular members being sequentially fitted on each other to be combined in the order of increasing diameter.

3. A system according to claim 2, wherein said cavity securing tool guide tool can be fitted on one of said tubular members of said insertion tool.

4. A system according to claim 3, wherein said cavity securing tool guide tool has an outer circumference smaller than that of one of said tubular members of said insertion tool which has the largest outer diameter.

5. A system according to claim 1, wherein said cavity securing tool guide tool has an elliptic or oval cross-section.

6. A system according to claim 1, wherein said cavity securing tool guide tool is a deformable, cylindrical member.

7. A system according to claim 6, wherein said cavity securing tool guide tool is transparent.

8. A system according to claim 6, wherein at least part of said cavity securing tool has a mesh structure.

9. A surgical operation system for percutaneously securing a working cavity for a surgical operation in a body, comprising:

a cavity securing tool including cavity securing means that is inserted into a living body through the skin to secure a cavity in vital tissue and has a hole, and tool insertion channel means that allows a tool to be inserted into the cavity; and a cavity securing tool guide member including abrasion means formed on a distal end to abrade tissue from a bone, and guide means for guiding said cavity securing tool into the vital tissue.

10. A system according to claim 9, further comprising an insertion tool for forming an insertion path for introducing said cavity securing tool into the vital tissue through the skin.

11. A system according to claim 9, wherein said cavity securing tool guide member also serves as said insertion tool.

12. A system according to claim 10, wherein said insertion tool comprises a plurality of tubular members whose diameters increase stepwise.

13. A system according to claim 10, wherein said cavity securing tool guide member can be fitted on one of said tubular members of said insertion tool.

14. A system according to claim 10, wherein said cavity securing tool guide member has an outer circumference smaller than that of one of said tubular members of said insertion tool which has the largest outer diameter.

15. A system according to claim 10, wherein a length of a blade edge line of said abrasion means is smaller than half the circumference of one of said tubular members of said insertion tool which has the largest outer diameter.

16. A system according to claim 9, wherein said cavity securing tool guide member has an elliptic or oval cross-section.

17. A system according to claim 16, wherein said abrasion means has a blade edge line extending along a major axis direction of the cross-section of said cavity securing guide member.

18. A system according to claim 9, wherein said tool insertion guide member is made of a deformable member.

19. A system according to claim 9, wherein said tool insertion guide member is made of a transparent member.

20. A system according to claim 9, wherein said tool insertion guide member is made of a member having a mesh structure.

21. An insertion tool to be inserted into a living body through the skin, comprising a plurality of tubular members, each having a different inner diameter and a different outer diameter, and anchor means formed on a distal end of at least one of the tubular members and designed to engage with a bone.

22. A tool according to claim 21, further comprising a surgical cavity securing tool that can be fitted on one of said tubular members of said insertion tool.

23. A surgical operation cavity securing tool percutaneously inserted and used in a body, comprising:

cavity securing means that is inserted into a living body through a skin to secure a cavity in vital tissue;

deformable tool insertion guide means that communicates with the cavity secured by said cavity securing means to cause the cavity to communicate with the outside of the body;

a rigid portion coupled to said cavity securing means and extending outside the body; and a gripping portion coupled to said rigid portion, wherein a cross-sectional shape of a hole of said cavity securing means has major and minor axes, and said rigid portion is coupled to said cavity securing means at a position parallel to the major axis.

24. A surgical operation cavity securing tool that is used near a spina after being placed therenear through a skin of a back, comprising:

cavity securing means that is inserted into a living body through an incision to secure a cavity in vital tissue;

deformable tool insertion guide means that communicates with the cavity secured by said cavity securing means to cause the cavity to communicate with the outside of the body;

a rigid portion that is coupled to said cavity securing means, placed laterally with respect to a set treatment cavity, and extends outside the body; and a gripping portion coupled to said rigid portion.

25. A surgical operation cavity securing tool percutaneously inserted and used in a body, comprising cavity securing means that is inserted into a living body through an skin to secure a cavity in vital tissue, said cavity securing means having engaging means for a bone, wherein said engaging means for a bone comprises an opening portion to be engaged with a vertebral arch portion, the opening portion having a substantially symmetrical shape with respect to a plane passing through a center axis.

26. A tool according to claim 25, wherein the opening portion includes at least two opening portions, the two opening portions being located at opposing positions.

27. A surgical operation cavity securing tool to be inserted into vital tissue through a skin so as to secure a working cavity for a surgical operation in a body, comprising:

a cavity securing portion for securing a working cavity for a surgical operation in vital tissue; and a deformable tool insertion guide portion that communicates with a cavity secured by said cavity securing portion to cause the cavity to communicate with the outside of the body, wherein a surgical operation is performed upon insertion of an endoscope and an operation tool into the cavity secured by said cavity securing portion through said tool insertion guide portion, and said tool insertion guide portion comprises at least one deformable plate structure.

28. A surgical operation cavity securing tool to be inserted into a body from a back portion of the body so as to perform a surgical treatment on a spine, comprising:

a cavity securing portion for securing a working cavity in the body, and a tool insertion guide portion connected to said cavity securing portion and extending to the outside of the body, wherein said tool insertion guide portion has a guide surface communicating with the cavity formed by said cavity securing portion, and is constituted by a soft, tubular member to be positioned in tissue, and a semi-hard member formed continuously with said soft, tubular member and located outside the body.

29. A surgical operation system for securing a working space for a surgical operation in a body, and performing a surgical operation by using an endoscope, comprising:

an endoscope serving as an observation means;

a cavity securing tool including a cavity securing means that is inserted into vital tissue through a skin portion to secure a working space in the body, and a wall member having a hole for causing the cavity to communicate with the outside of the body, said wall member having at least a transparent portion;

at least one port that is inserted into the vital tissue through another skin portion and guided to the cavity;

port insertion means for forming an insertion path for said port; and means for coupling said port to said cavity securing tool in the cavity.

30. A surgical operation system for securing a working space for a surgical operation in a body, and performing a surgical operation by using an endoscope, comprising:

an endoscope serving as observation means;

a cavity securing tool including cavity securing means that is inserted into vital tissue through a skin portion to secure a working space in the body, and a wall member having a hole for causing the cavity to communicate with the outside of the body;

at least one port that is inserted into the vital tissue through another skin portion and guided to the cavity; and port insertion means for forming an insertion path for said port, wherein said cavity securing tool and said port insertion means are made of titanium and can be observed by magnetic resonance imaging means (MRI).

31. An endoscope surgical operation system for securing a working space for a surgical operation in a body, said system using an endoscope, comprising:

a cavity securing tool for securing a cavity in a region of surgical object; and cavity securing tool guide means having insertion position detection means that is arranged on a distal end to detect a position where said cavity securing tool is to be inserted, said guide means being used to insert said cavity securing tool into vital tissue.

32. A system according to claim 31, wherein said insertion position detection means detects a shape of the region of surgical object.

33. A system according to claim 32, wherein said shape detection means comprises:

a reference member that is formed on a distal end of said means and brought into contact with a portion near the region of surgical object; and an indicator member having a cross-sectional area smaller than that of said reference member, said reference member and said indicator member are arranged parallel to each other to be movable in a major axis direction, and the shape of the region of surgical object is detected from change amounts of said indicator member and said reference member.

34. A system according to claim 32, wherein said shape detection means comprises:

a reference member that is formed on a distal end of said means and brought into contact with a portion near the region of surgical object; and an indicator member having a cross-sectional area smaller than that of said reference member, said reference member and said indicator member are arranged parallel to each other to be movable in a major axis direction, a total length of said indicator member is larger than that of said reference member, and change amounts of said indicator member and said reference member and a difference between a length of a proximal end of said indicator member and a length of a proximal end of said reference member change depending on an insertion position, thereby detecting the shape of the region of surgical object.

35. A system according to claim 33, wherein said indicator member also serves as an insertion tool for forming an insertion path for said cavity securing tool.

36. A system according to claim 31, wherein said insertion position detecting means comprises transfer means for transferring a shape of a portion around the region of surgical object as a shape of a portion located outside the body.

37. A system according to claim 36, wherein said transfer means comprises:

detection means for detecting a shape of a portion around a region of surgical object;

reflection means for reflecting the detected shape in a shape of a portion located outside the body; and transfer means for transferring the shape detected by said detection means to said reflection means.

38. A system according to claim 37, wherein said detection means, said reflection means, and said transfer means are continuously and systematically arranged, and are constituted by a bundle of rod-like members having the same total length.

39. An endoscopic operation system comprising:

a cavity securing tool having a surface on a distal end which is brought into contact with a portion near a region of surgical object, the surface serving as a reference surface;

a cavity securing tool guide member having an indicator portion on a distal end which has a cross-sectional area smaller than that of the reference surface; and insertion position detection means for detecting an insertion position of said cavity securing tool by combining said cavity securing tool and said cavity securing tool guide member, wherein said cavity securing tool and said cavity securing tool guide member are arranged parallel to each other to be movable in a major axis direction, and a shape is detected from change amounts of said cavity securing tool and said cavity securing tool guide member.

40. An endoscopic operation system comprising a cavity securing tool for securing a working cavity in tissue, said tool having engaging means to be engaged with a region of surgical object, cavity securing tool guide means serving as a guide for inserting said cavity securing tool into a body, and means for detecting an insertion position of said cavity securing tool by combining said cavity securing means and said cavity securing tool guide means, wherein said insertion position detection means is formed such that when said cavity securing tool is engaged with the region of surgical object, a sum of a protrusion amount of a bone portion into a cavity securing portion and a total length of said cavity securing tool guide means is almost equal to a total length of said cavity securing means, and detects the insertion position of said cavity securing means on the basis of coincidence between a proximal end of said cavity securing means and a proximal end of said cavity securing tool guide means.

41. An endoscopic operation system according to claim 40, wherein said cavity securing tool comprises:

a ring-like cavity securing portion that has engaging means to be engaged with a region of surgical object and forms a working cavity in tissue; and a pusher for pushing said ring-like cavity securing portion, and said insertion position detection means is formed such that when said cavity securing tool is engaged with the region of surgical object, a sum of a protrusion amount of a bone portion into a cavity securing portion and a total length of said cavity securing tool guide means is almost equal to a sum of a height of said cavity securing portion and a total length of said pusher, and detects the insertion position of said cavity securing means on the basis of coincidence between a proximal end of said pusher and a proximal end of said cavity securing tool guide means.

42. A treatment method using a system including a discectomy cavity securing tool that is inserted into tissue to form a working cavity, said tool having means for observing the cavity, tool insertion guide means through which a treatment tool is inserted, and engaging means having a distal end to be engaged with a posterior spine vertebral arch of a spine, and extracorporeal detection means for detecting a position of a region of surgical object, comprising the steps of:

(a) forming an insertion path in vital tissue at a predetermined position and angle;

(b) inserting said detecting means into the path and detecting the region of surgical object;

(c) inserting said discectomy cavity securing tool by using said detection means as a guide;

(d) engaging said discectomy cavity securing tool with the posterior spine vertebral arch;

(e) observing the cavity with said observation means; and (f) inserting a treatment tool into said tool insertion guide means, and performing a treatment on a bone under observation.

43. A method according to claim 42, further comprising: the step of abrading tissue before said cavity securing tool is inserted into the body.

44. A treatment method using a system including a discectomy cavity securing tool that is inserted into tissue to form a working cavity, said tool having means for observing the cavity, tool insertion guide means through which a tool is inserted, engaging means to be engaged with a posterior spine vertebral arch of a spine, and abrasion means for abrading vital tissue from a bone, comprising the steps of:

(a) forming an insertion path in vital tissue at a predetermined position and angle;

(b) inserting said discectomy cavity securing tool guide member into the path, and abrading tissue around a region of surgical object with a distal end of said guide member;

(c) inserting said discectomy cavity securing tool, along said discectomy cavity securing tool guide member, into a place where abrasion is performed;

(d) engaging said discectomy cavity securing tool with the posterior spine vertebral arch;

(e) observing the cavity with said observation means; and (f) inserting a treatment tool into said tool insertion guide means, and performing a treatment on a bone under observation.

45. A system according to claim 14, wherein a length of a blade edge line of said abrasion means is smaller than the largest diameter of the edrity securing tool guide member.

46. A system according to claim 15, wherein a length of a blade edge line of said abrasion means is smaller than the largest diameter of the diameters of said tubular member of said insertion tool.

47. A system according to claim 11, wherein said insertion tool comprises a plurality of tubular members whose diameters increase stepwise.

48. A system according to claim 11, wherein said cavity securing tool guide member can be fitted on one of said tubular members of said insertion tool.

49. A system according to claim 34, wherein said indicator member also serves as an insertion tool for forming an insertion path for said cavity securing tool.

* * * * *